(12) United States Patent
Gentles et al.

(10) Patent No.: US 7,547,690 B2
(45) Date of Patent: Jun. 16, 2009

(54) COMPOUNDS FOR THE TREATMENT OF HEPATITIS C

(75) Inventors: Robert G. Gentles, Wallingford, CT (US); Xiaofan Zheng, Cheshire, CT (US); Min Ding, Glastonbury, CT (US); Yong Tu, Cheshire, CT (US); Ying Han, Cheshire, CT (US); Piyasena Hewawasam, Middletown, CT (US); John F. Kadow, Wallingford, CT (US); John A. Bender, Middletown, CT (US); Kap-Sun Yeung, Madison, CT (US); Katharine A. Grant-Young, Madison, CT (US); Thomas W. Hudyma, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/039,239

(22) Filed: Feb. 28, 2008

(65) Prior Publication Data

US 2008/0227769 A1     Sep. 18, 2008

Related U.S. Application Data

(60) Provisional application No. 60/989,474, filed on Nov. 21, 2007, provisional application No. 60/894,887, filed on Mar. 14, 2007.

(51) Int. Cl.
*A61P 31/00*     (2006.01)
*A61K 31/55*     (2006.01)
*C07D 223/14*    (2006.01)

(52) U.S. Cl. .................. 514/214.01; 540/576
(58) Field of Classification Search ............ 514/214.01; 540/576
See application file for complete search history.

(56) References Cited

U.S. PATENT DOCUMENTS

| 7,153,848 | B2 | 12/2006 | Hudyma et al. | 514/214.01 |
| 7,348,425 | B2 | 3/2008 | Hudyma et al. | 540/576 |
| 2007/0060565 | A1 | 3/2007 | Meanwell et al. | 514/214.01 |
| 2007/0078122 | A1 | 4/2007 | Bergstrom et al. | 514/214.01 |
| 2007/0184024 | A1 | 8/2007 | Meanwell et al. | 424/85.2 |
| 2007/0185083 | A1 | 8/2007 | Bergstrom et al. | 514/214.01 |
| 2007/0270405 | A1 | 11/2007 | Bender et al. | 514/214.01 |
| 2007/0270406 | A1 | 11/2007 | Gentles et al. | 514/214.01 |
| 2007/0275930 | A1 | 11/2007 | Gentles et al. | 514/79 |
| 2007/0275947 | A1 | 11/2007 | Bergstrom | 514/211.15 |
| 2007/0287694 | A1 | 12/2007 | Yeung et al. | 514/210.21 |

FOREIGN PATENT DOCUMENTS

| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 12/022,541, filed Jan. 30, 2008, Kap-Sun Yeung et al.
U.S. Appl. No. 12/046,030, filed Mar. 11, 2008, Kap-Sun Yeung et al.
U.S. Appl. No. 12/045,874, filed Mar. 11, 2008, Robert G. Gentles et al.
U.S. Appl. No. 12/045,766, filed Mar. 11, 2008, John A. Bender et al.
U.S. Appl. No. 12/041,072, filed Mar. 3, 2008, Kap-Sun Yeung et al.
U.S. Appl. No. 12/031,844, filed Feb. 15, 2008, Andrew Nickel et al.
U.S. Appl. No. 12/046,286, filed Mar. 11, 2008, Piyasena Hewawasam et al.
U.S. Appl. No. 11/942,285, filed Nov. 19, 2007, John A. Bender et al.
U.S. Appl. No. 11/971,362, filed Jan. 9, 2008, John A. Bender et al.

*Primary Examiner*—Brenda L Coleman
(74) *Attorney, Agent, or Firm*—James Epperson

(57) ABSTRACT

The invention encompasses compounds of formula I, including pharmaceutically acceptable salts, as well as compositions and methods of using these compounds. The compounds have activity against hepatitis C virus (HCV) and are useful in treating those infected with HCV.

13 Claims, No Drawings

COMPOUNDS FOR THE TREATMENT OF HEPATITIS C

CROSS REFERENCE TO RELATED APPLICATIONS

This application claims the benefit of U.S. provisional application Ser. Nos. U.S. Ser. No. 60/894,887 filed Mar. 14, 2007 and 60/989,474 filed Nov. 21, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242).

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

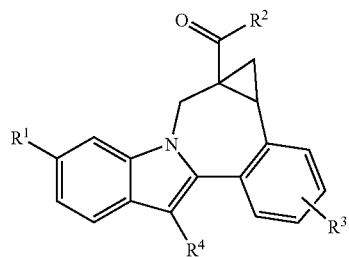

where:
$R^1$ is $CO_2R^5$ or $CONR^6R^7$;
$R^2$ is

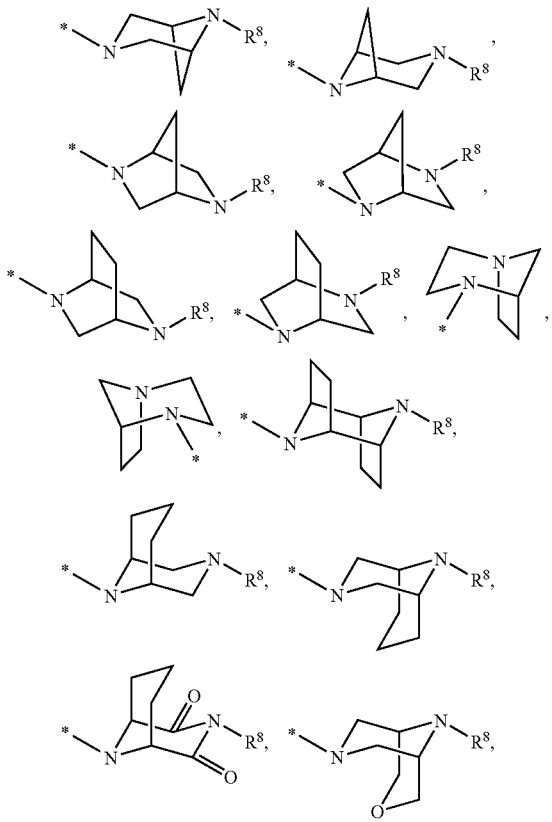

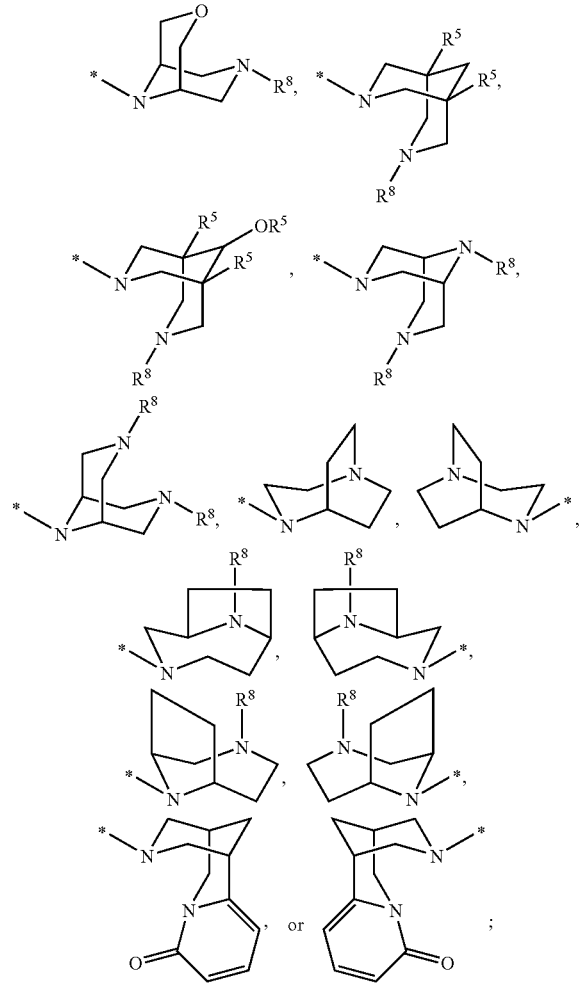

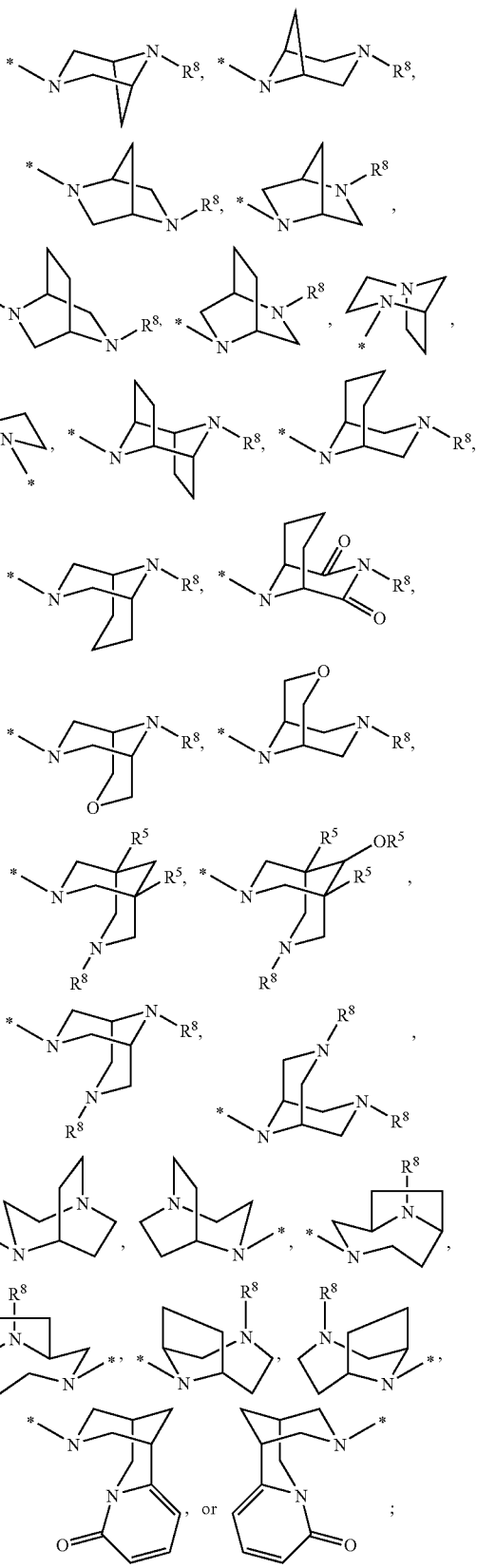

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, alkenylSO$_2$, cycloalkylSO$_2$, (cycloalkyl)alkylSO$_2$, haloalkylSO$_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, hydroxyalkyl, alkoxyalkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, N—($R^{12}$)piperazinyl, morpholinyl, thiomorpholinyl, homopiperidinyl, homomorpholinyl, tetrahydrofuranyl, tetrahydropyranyl, (tetrahydrofuranyl)alkyl, or (tetrahydropyranyl)alkyl; and $R^{12}$ is hydrogen or alkyl;

or a pharmaceutically acceptable salt thereof.

Another aspect of the invention is a compound of formula I where $R^1$ is $CO_2R^5$ or $CONR^6R^7$;

$R^2$ is

R³ is hydrogen, halo, alkyl, alkenyl, hydroxy, benzyloxy, or alkoxy;
R⁴ is cycloalkyl;
R⁵ is hydrogen or alkyl;
R⁶ is hydrogen, alkyl, alkylSO₂, alkenylSO₂, cycloalkylSO₂, (cycloalkyl)alkylSO₂, haloalkylSO₂, (R⁹)(R¹⁰)NSO₂, or (R¹¹)SO₂;
R⁷ is hydrogen or alkyl;
R⁸ is hydrogen, alkyl, cycloalkyl, (cycloalkyl)alkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, benzyl, benzyloxycarbonyl, or pyridinyl;
R⁹ is hydrogen or alkyl;
R¹⁰ is hydrogen or alkyl;
R¹¹ is azetidinyl, pyrrolidinyl, piperidinyl, N—(R¹²)piperazinyl, morpholinyl, thiomorpholinyl, homopiperidinyl, homomorpholinyl, tetrahydrofuranyl, tetrahydropyranyl, (tetrahydrofuranyl)alkyl, or (tetrahydropyranyl)alkyl; and
R¹² is hydrogen or alkyl;

or a pharmaceutically acceptable salt thereof.

Another aspect of the invention is a compound of formula I where
R¹ is CO₂R⁵ or CONR⁶R⁷;
R² is

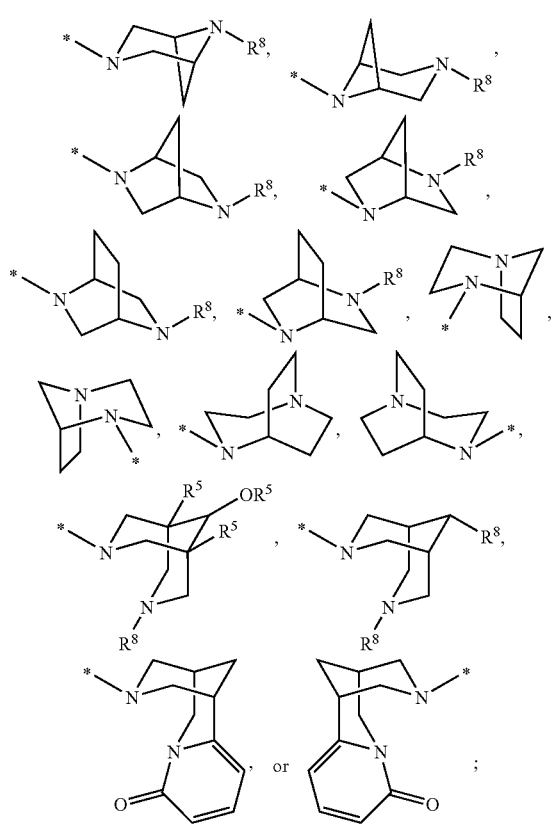

R³ is hydrogen, halo, alkyl, alkenyl, hydroxy, benzyloxy, or alkoxy;
R⁴ is cycloalkyl;
R⁵ is hydrogen or alkyl;
R⁶ is hydrogen, alkyl, alkylSO₂, cycloalkylSO₂, haloalkylSO₂, (R⁹)(R¹⁰)NSO₂, or (R¹¹)SO₂;
R⁷ is hydrogen or alkyl;
R⁸ is hydrogen, alkyl, cycloalkyl, (cycloalkyl)alkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, benzyl, benzyloxycarbonyl, or pyridinyl;
R⁹ is hydrogen or alkyl;
R¹⁰ is hydrogen or alkyl;
R¹¹ is azetidinyl, pyrrolidinyl, piperidinyl, N—(R¹²)piperazinyl, morpholinyl, thiomorpholinyl, homopiperidinyl, or homomorpholinyl; and
R¹² is hydrogen or alkyl.

Another aspect of the invention is a compound of formula I where R¹ is CONR⁶R⁷; R⁶ is alkylSO₂, cycloalkylSO₂, haloalkylSO₂, (R⁹)₂NSO₂, or (R¹⁰)SO₂; and R⁷ is hydrogen.

Another aspect of the invention is a compound of formula I where R³ is hydrogen.

Another aspect of the invention is a compound of formula I where R³ is methoxy.

Another aspect of the invention is a compound of formula I where R⁴ is cyclohexyl.

Another aspect of the invention is a compound of formula I where R⁶ is (R⁹)(R¹⁰)NSO₂ or (R¹¹)SO₂.

Another aspect of the invention is a compound of formula I according to the following stereochemistry.

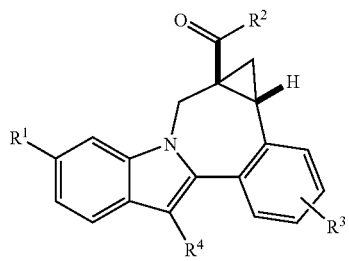

Another aspect of the invention is a compound of formula I according to the following stereochemistry.

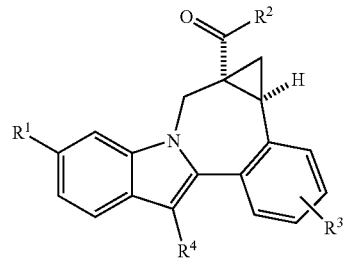

Any scope of any variable, including R¹, R², R³, R⁴, R⁵, R⁶, R⁷, R⁸, R⁹, R¹⁰, R¹¹, or R¹², can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl"

includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art.

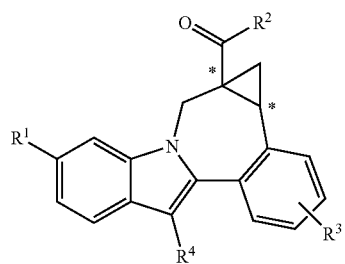

Synthetic Methods

The compounds may be made by methods known in the art including those described below. Some reagents and intermediates are known in the art. Other reagents and intermediates can be made by methods known in the art using readily available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Methyl 2-bromo-3-cyclohexyl-1H-indole-6-carboxylate can be hydrolyzed to 2-bromo-3-cyclohexyl-1H-indole-6-carboxylic acid (See Scheme 1). This compound can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions with a diversity of 2-formyl boronic acids or esters, using for example, Suzuki coupling conditions, to provide cyclic hemiaminal intermediates of the type depicted. These compounds can be converted to indolobenzazepines derivatives by treatment with methyl 2-(dimethoxyphosphoryl)acrylate under the influence of cesium carbonate in DMF via consecutive Michael and Horner Emmons reactions.

Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed and the product acids can be condensed with a variety of alkyl-bridged diamines. For example, O-(1H-benzotriazol-1-yl)-N,N,N',N'-tetramethyluronium tetrafluoroborate and diisopropyl ethyl amine in DMSO can give alkyl bridged diamine carboxamides.

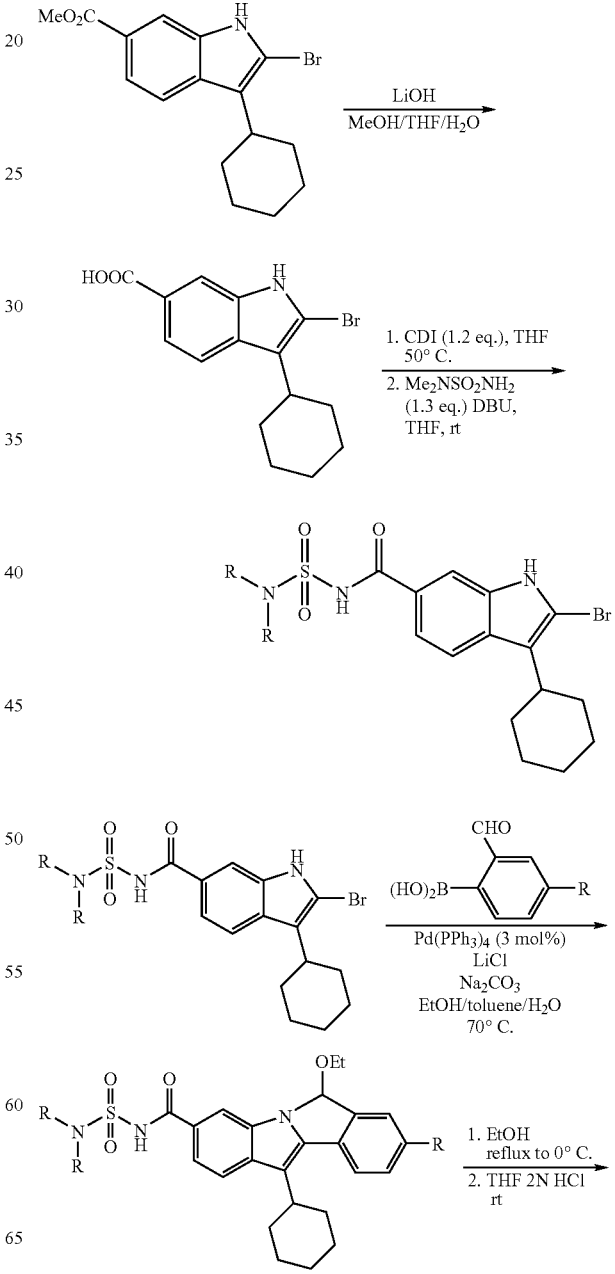

Scheme 1.

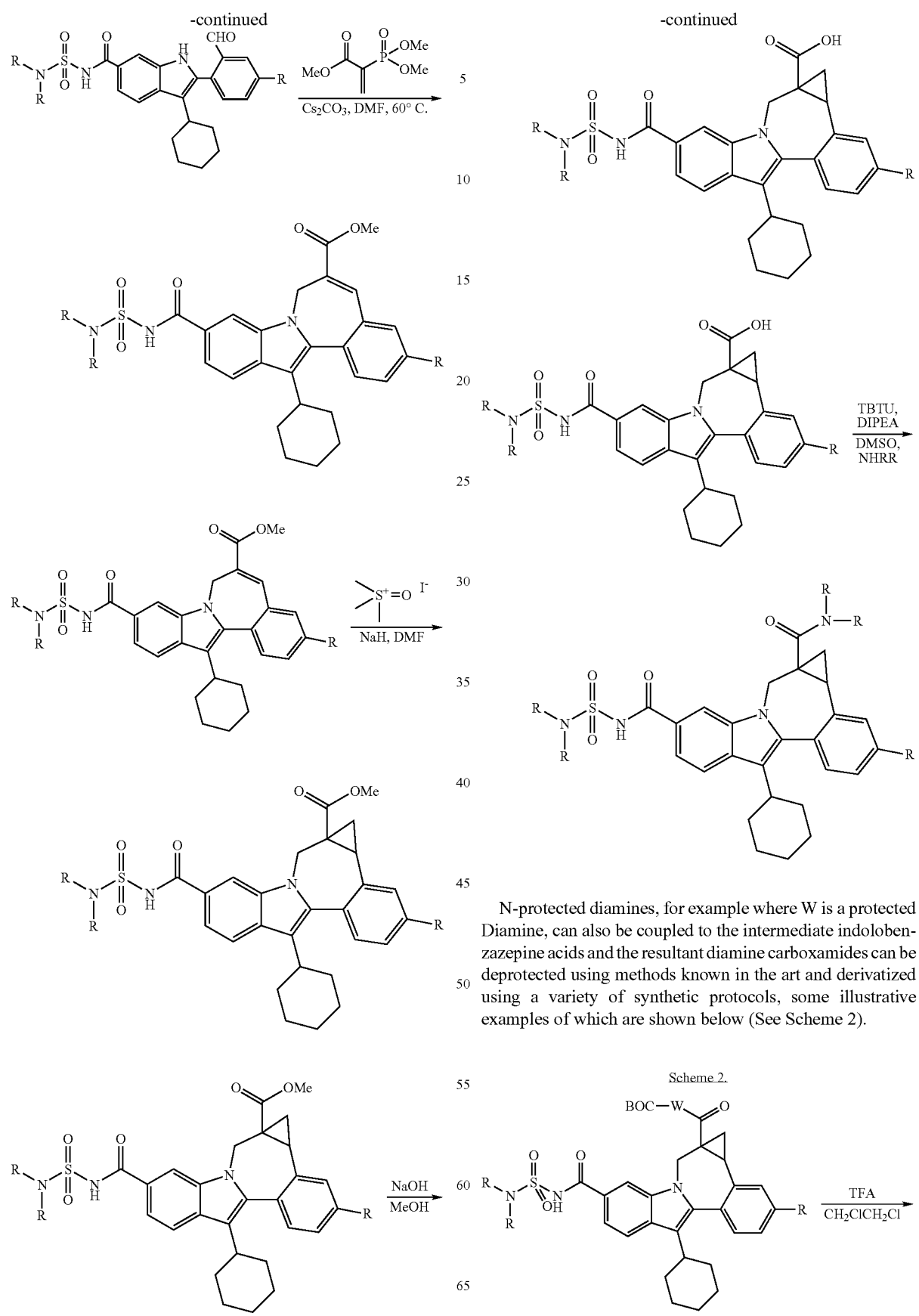
N-protected diamines, for example where W is a protected Diamine, can also be coupled to the intermediate indolobenzazepine acids and the resultant diamine carboxamides can be deprotected using methods known in the art and derivatized using a variety of synthetic protocols, some illustrative examples of which are shown below (See Scheme 2).
Scheme 2.

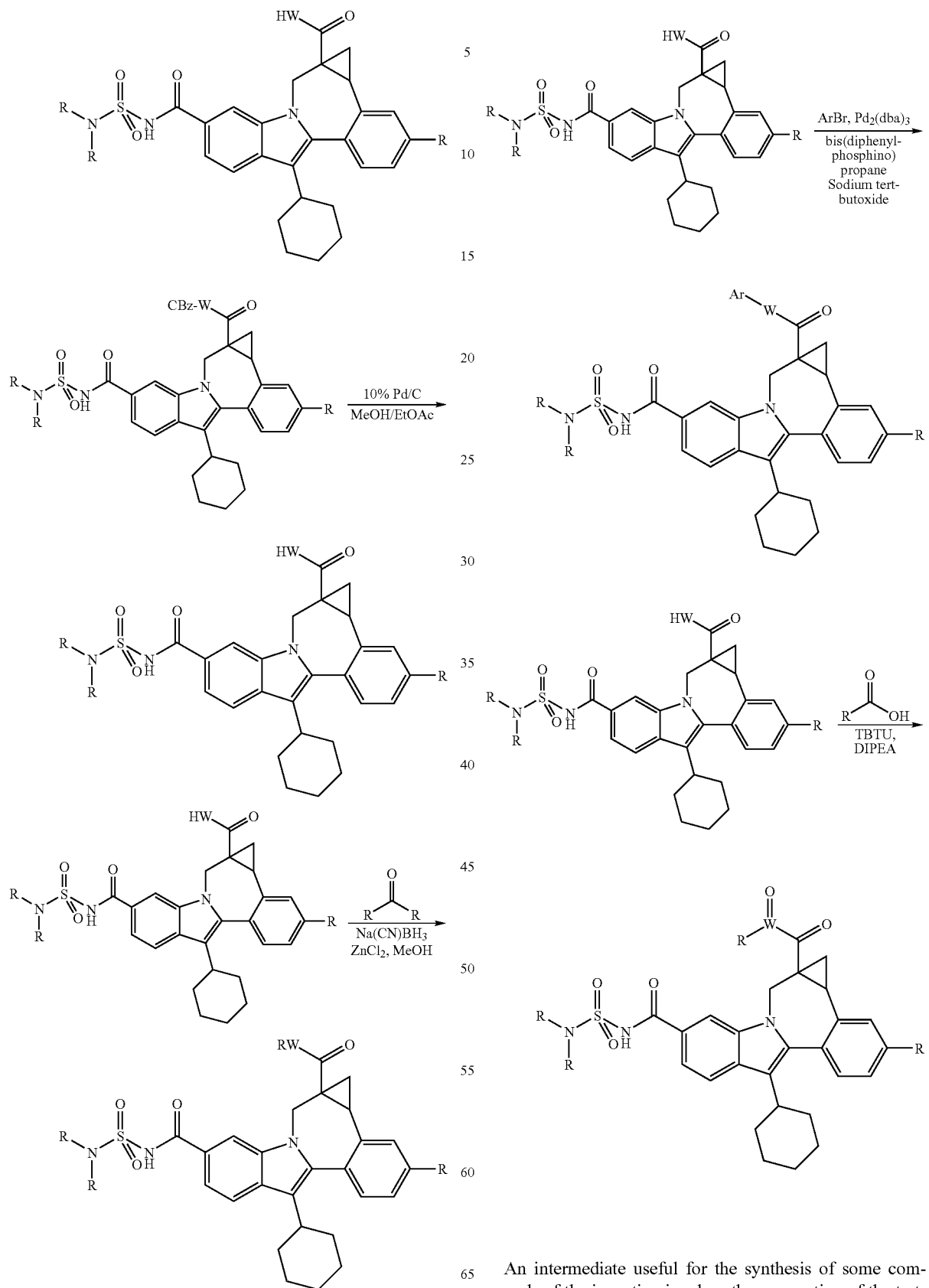
An intermediate useful for the synthesis of some compounds of the invention involves the preparation of the tert-butyl ester indolobenzazepine shown in Scheme 3.

Scheme 3.

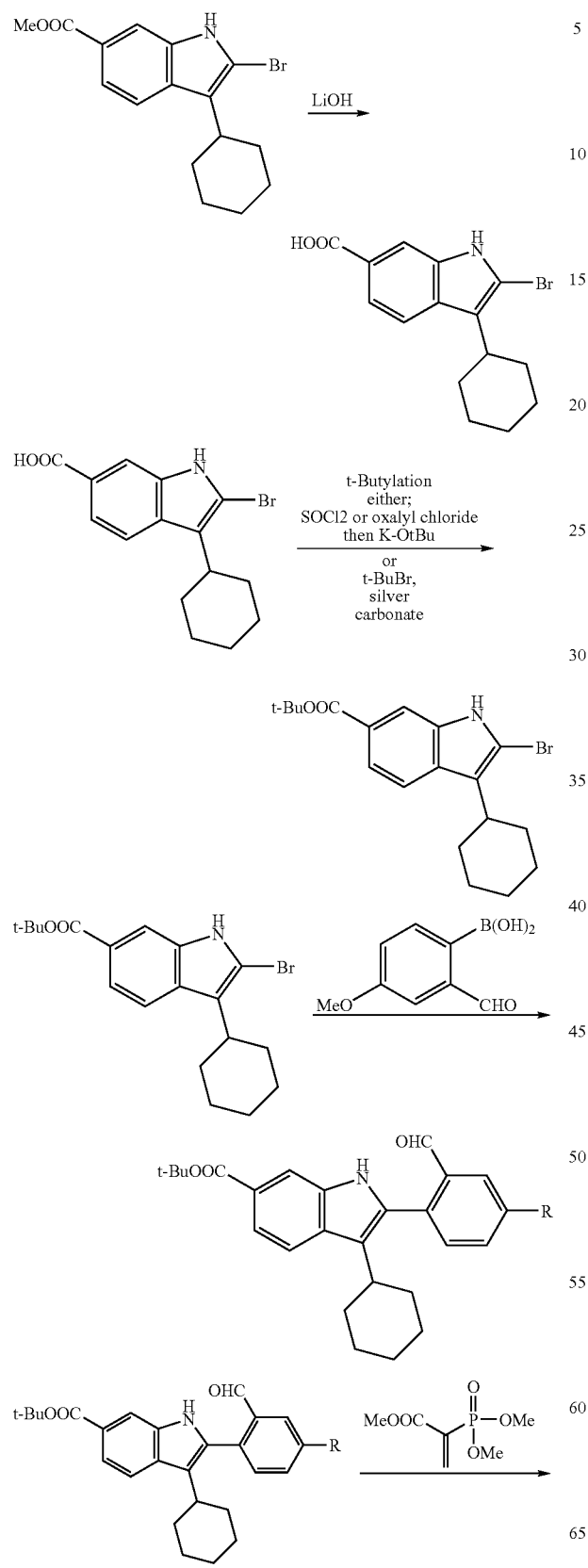

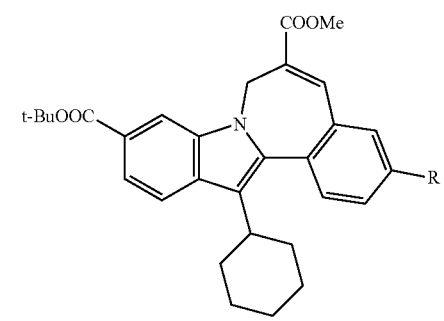

-continued

This methodology involves base catalyzed hydrolysis of the indole methyl ester shown, followed by its reaction with either thionyl chloride and potassium tertiary butoxide, or alkylation with silver carbonate and tertiary butyl bromides. The resultant compound can be transformed using chemistry analogous to that outlined previously to provide the mixed ester indolobenzazepines shown above.

These intermediates are useful in an alternative procedure that can be employed for the preparation of acylsulfamide and acylsulfonamide alkyl-bridged diamines, as shown in Scheme 4. Cyclopropanation of an intermediate t-butyl ester indolobenzazepine and subsequent cleavage of the t-butyl ester group can generate the acid which can be coupled to a diversity of sulfonamides and sulfonylureas. Subsequent hydrolysis affords the related aliphatic acid, which can be coupled with a diversity of alkyl-bridged diamines. For example, O-(1H-benzotriazol-1-yl)-N,N, N',N'-tetramethyluronium tetrafluoroborate and diisopropyl ethyl amine in DMSO can give the alkyl bridged diamine carboxamides.

Scheme 4.

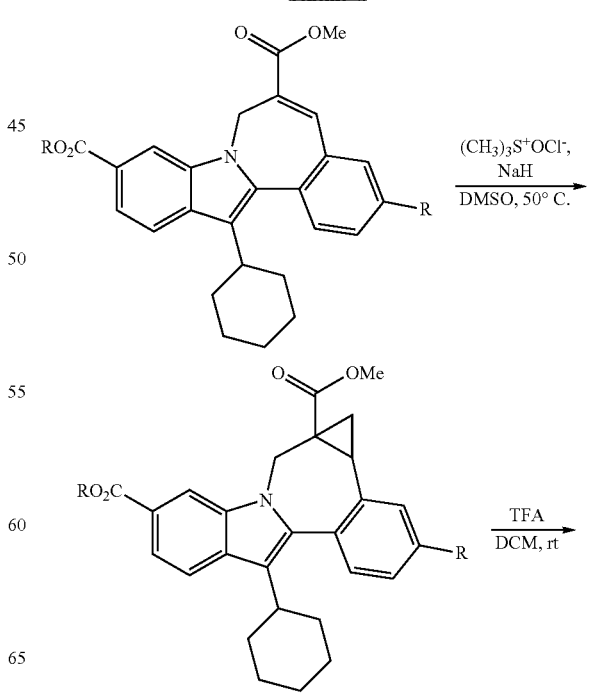

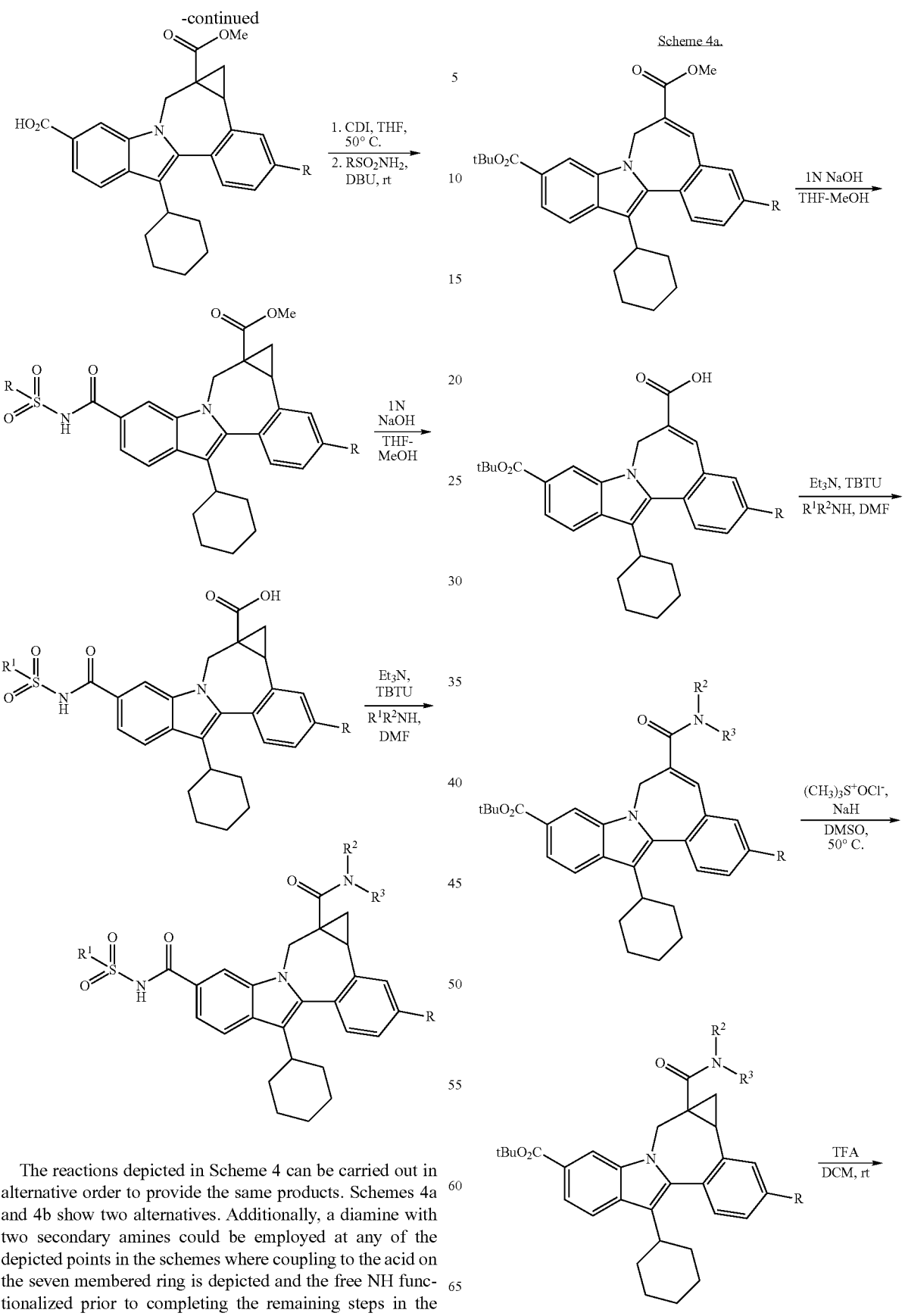

The reactions depicted in Scheme 4 can be carried out in alternative order to provide the same products. Schemes 4a and 4b show two alternatives. Additionally, a diamine with two secondary amines could be employed at any of the depicted points in the schemes where coupling to the acid on the seven membered ring is depicted and the free NH functionalized prior to completing the remaining steps in the scheme.

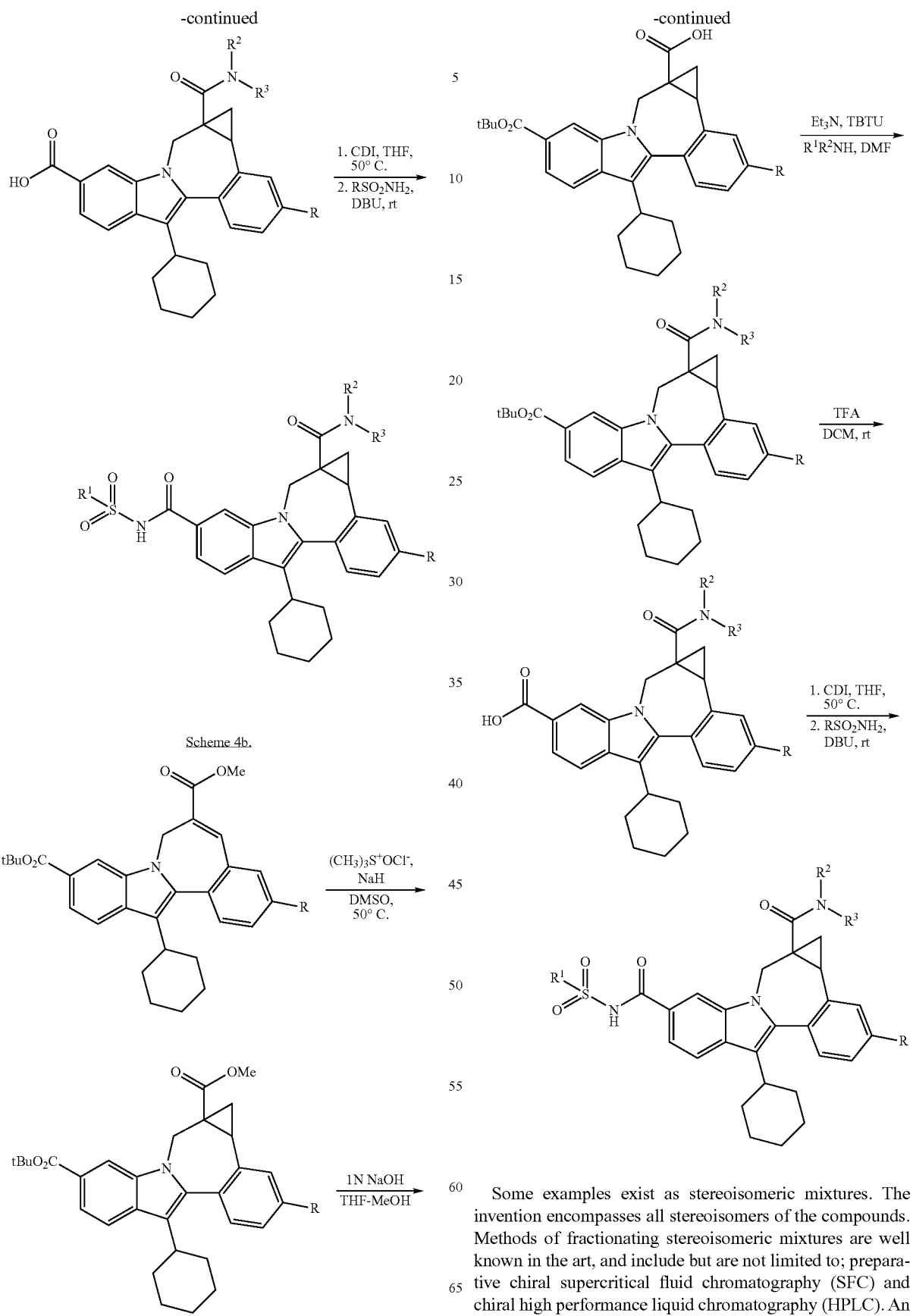

Some examples exist as stereoisomeric mixtures. The invention encompasses all stereoisomers of the compounds. Methods of fractionating stereoisomeric mixtures are well known in the art, and include but are not limited to; preparative chiral supercritical fluid chromatography (SFC) and chiral high performance liquid chromatography (HPLC). An example using this approach is shown in scheme 5.

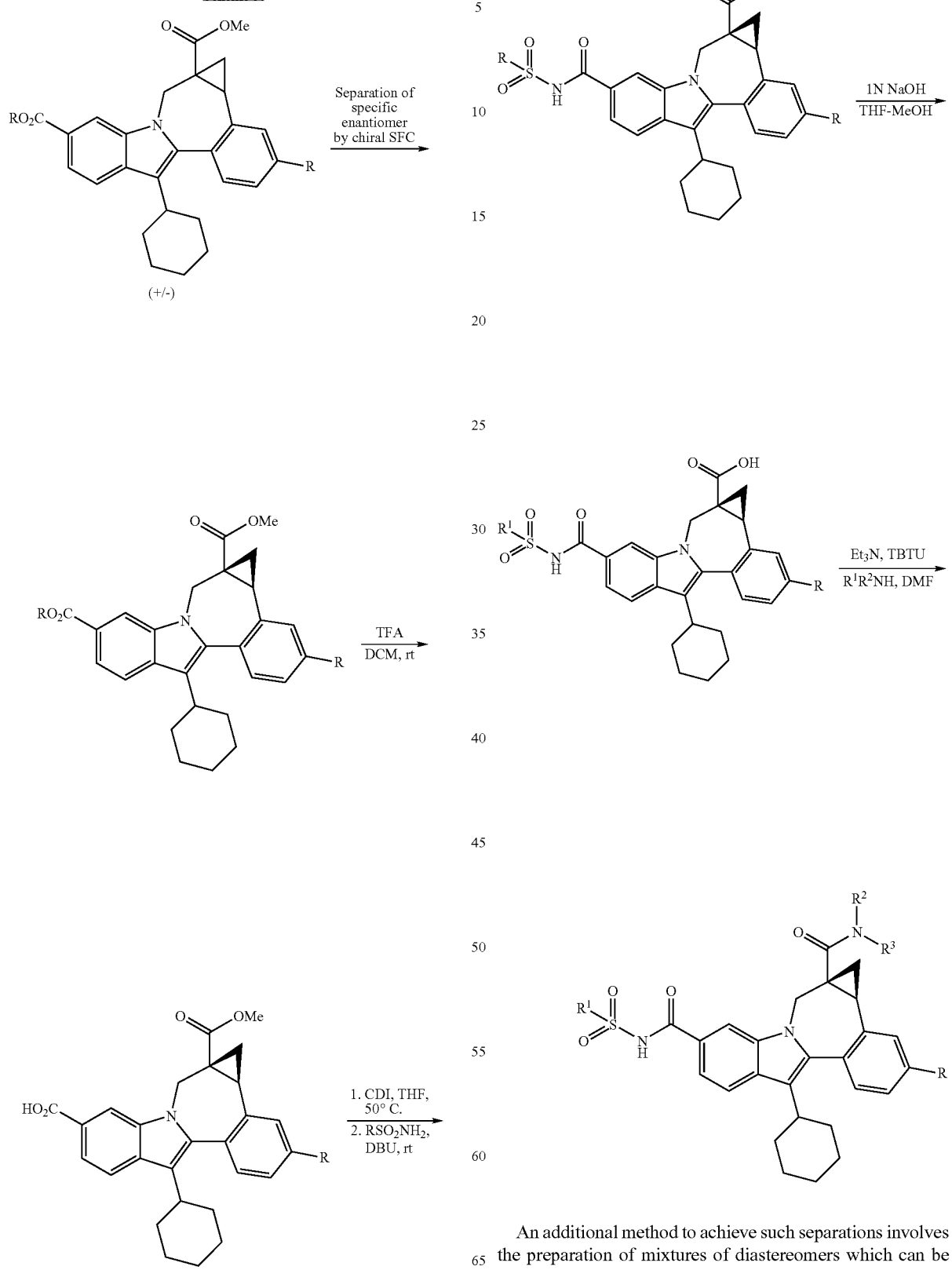
An additional method to achieve such separations involves the preparation of mixtures of diastereomers which can be separated using a variety of methods known in the art. One example of this approach is shown below (Scheme 6).

Scheme 6.

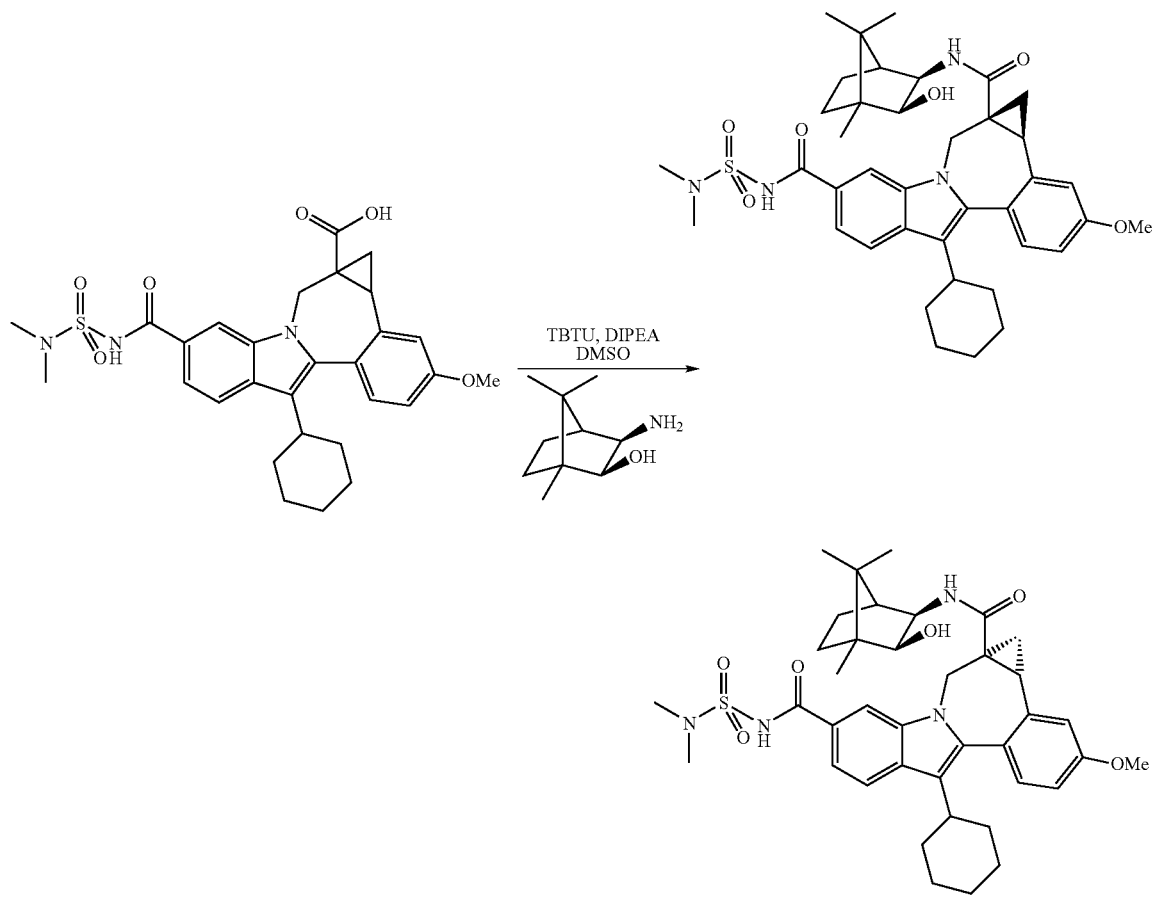

Diastereomers separated by reverse phase HPLC

Some diastereomeric amides can be separated using reverse phase HPLC. After hydroysis, the resultant optically active acids can be coupled with bridged diamines derivatives (Scheme 7). For example, O-(1H-benzotriazol-1-yl)-N,N,N', N'-tetramethyluronium tetrafluoroborate and diisopropyl ethyl amine in DMSO can be used to give the alkyl bridged carboxamides. Other standard acid amine coupling methods can also be used to give optically active carboxamides.

Scheme 7.

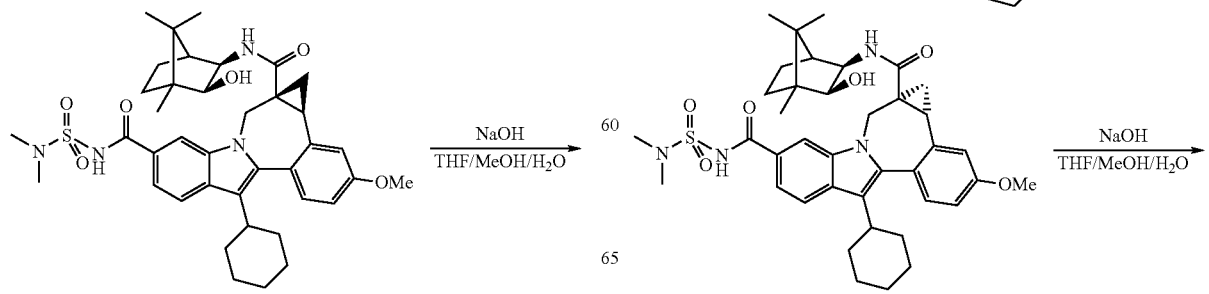

-continued

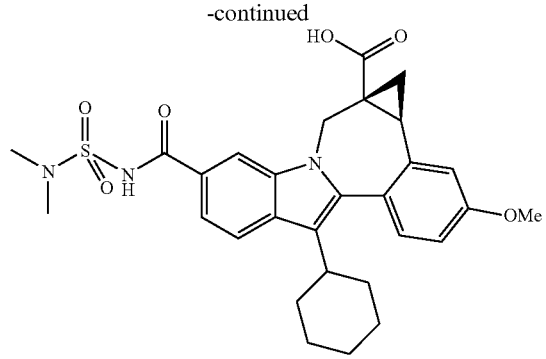

-continued

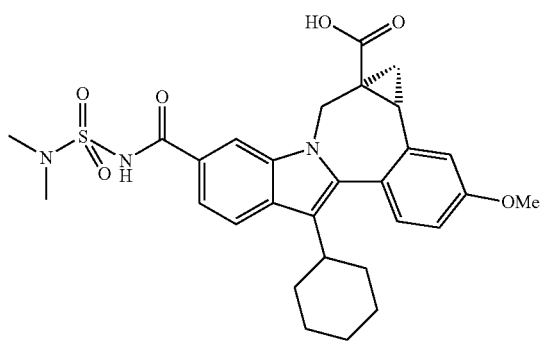

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using two sequential chromatography steps: Heparin sepharose CL-6B and polyU sepharose 4B (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Corning 3600). The assay buffer is composed of 20 mM Hepes, pH 7.5, 2.5 mM KCl, 2.5 mM MgCl2, 1 mM DTT, 1.6 U RNAse inhibitor (Promega N2515), 0.01 mg/ml BSA (Sigma B6917), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (1.75 nM) was added to diluted compound followed by the addition of a mixture of template (0.36 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. The HCV FRET screening assay was performed in 96-well cell culture plates. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 μM final from a 2 mM stock.

To prepare plates, HCV replicon cells, with or without a Renilla luciferase reporter gene, were trypsinized and plated in a 96-well plate with titrated test compounds added in columns 3 through 12; columns 1 and 2 contained a control compound (HCV control inhibitor), and the bottom row contained cells with DMSO only. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added to measure cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for up to 20 cycles and the plate read in a kinetic mode. Typically, the signal to noise using an endpoint analysis after the reads was at least three-fold. Alternatively, after Alamar blue reading, plates were rinsed with PBS, then used for luciferase assay using the Promega Dual-Glo Luciferase Assay System or the Promega EnduRen Live Cell Substrate assay.

Compound analysis was performed by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV control inhibitor at the end of the assay period. These numbers were similar to those obtained from naïve Huh-7 cells. The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values were calculated as the concentration which caused a 50% reduction in FRET or luciferase activity. The two numbers generated for the compound plate, percent cytoxicity and percent activity, were used to determine compounds of interest for further analysis.

Representative data for compounds are reported in Table 1.

TABLE 1

| Structure | $IC_{50}$ | $EC_{50}$ |
|---|---|---|
| 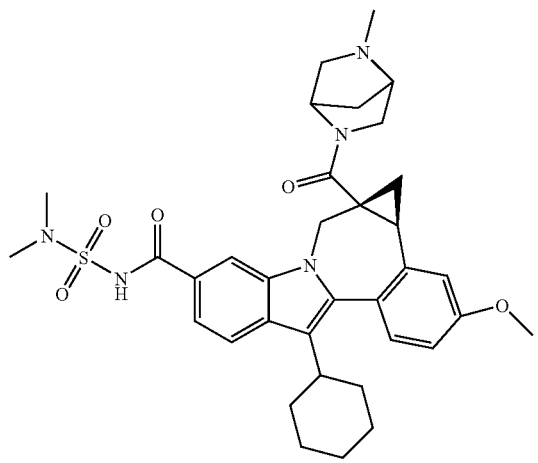 | C | B |
| 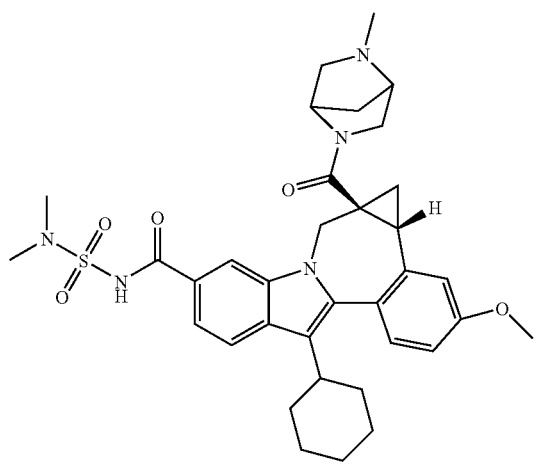 | B | B |

TABLE 1-continued
| Structure | IC$_{50}$ | EC$_{50}$ |
|---|---|---|
| 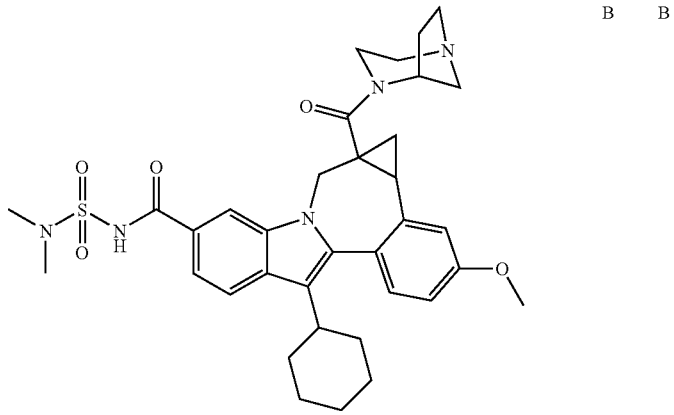 | B | B |
| 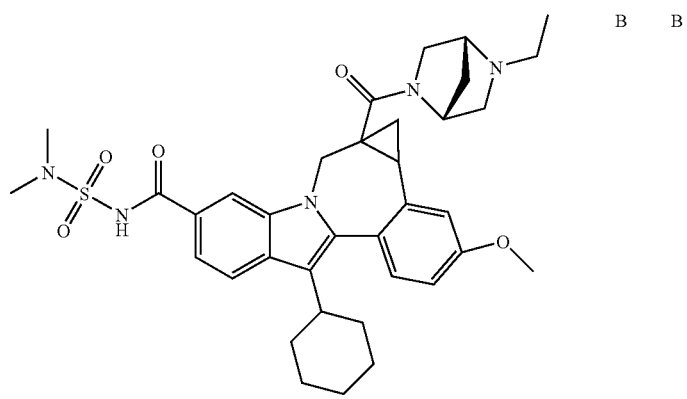 | B | B |
| 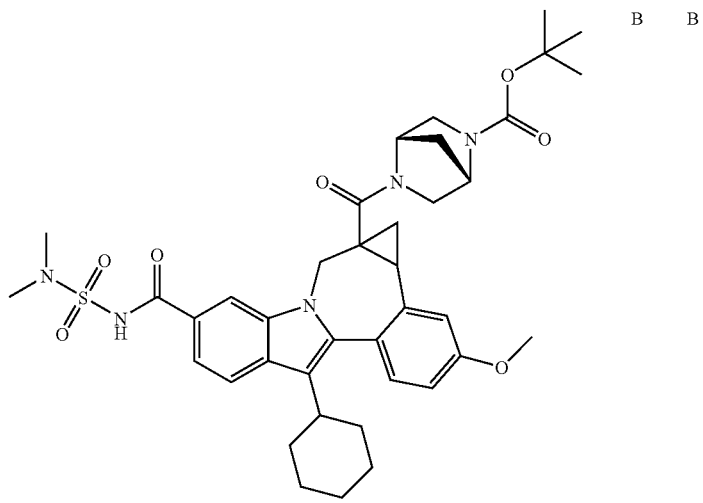 | B | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
| --- | --- | --- |
| 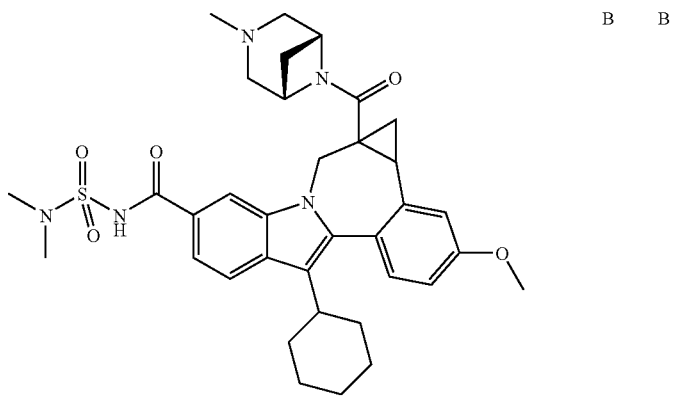 | B | B |
| 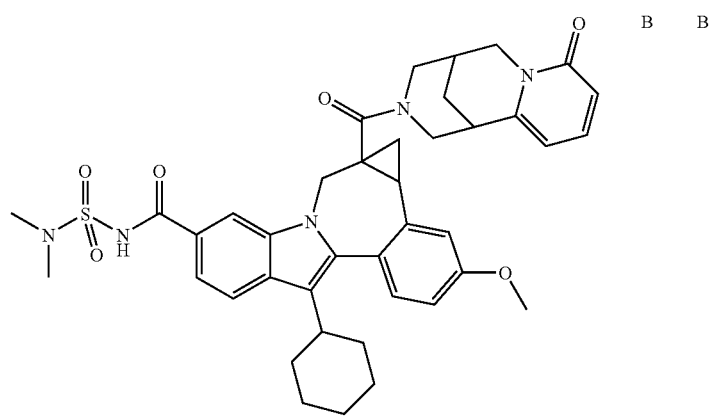 | B | B |
| 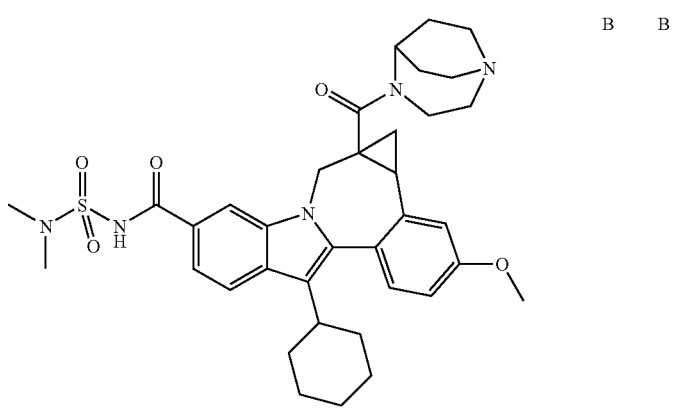 | B | B |

TABLE 1-continued
| Structure | IC$_{50}$ | EC$_{50}$ |
|---|---|---|
| 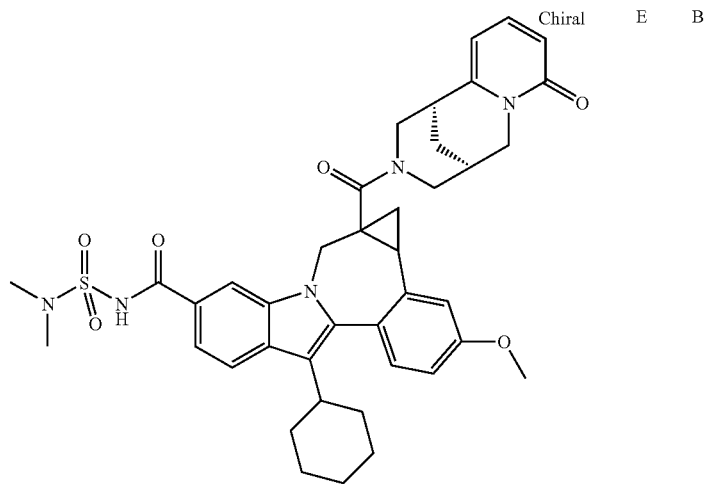 | E | B |
| 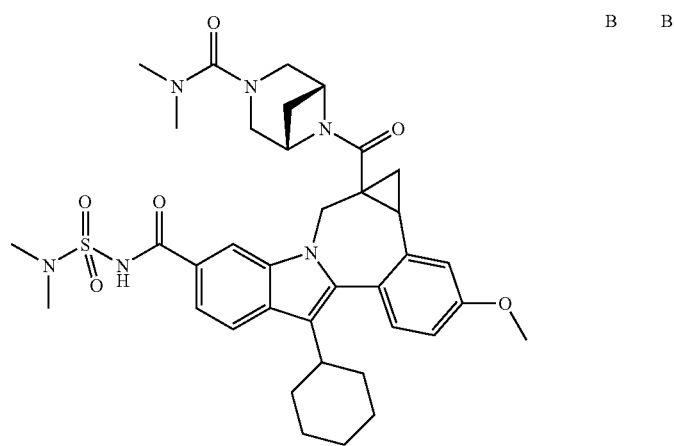 | B | B |
| 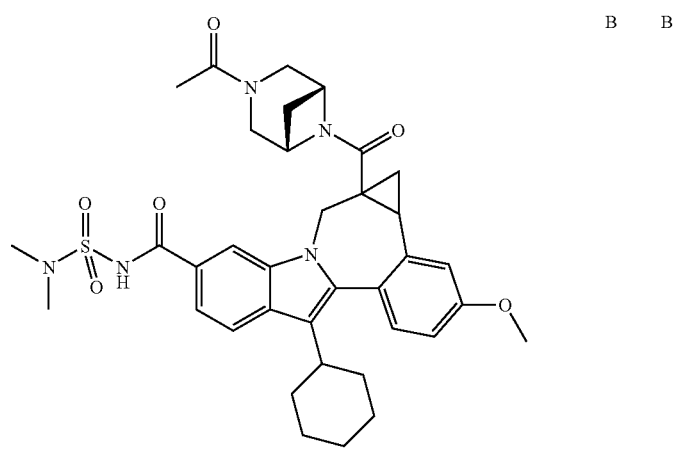 | B | B |

TABLE 1-continued
| Structure | IC$_{50}$ | EC$_{50}$ |
|---|---|---|
| 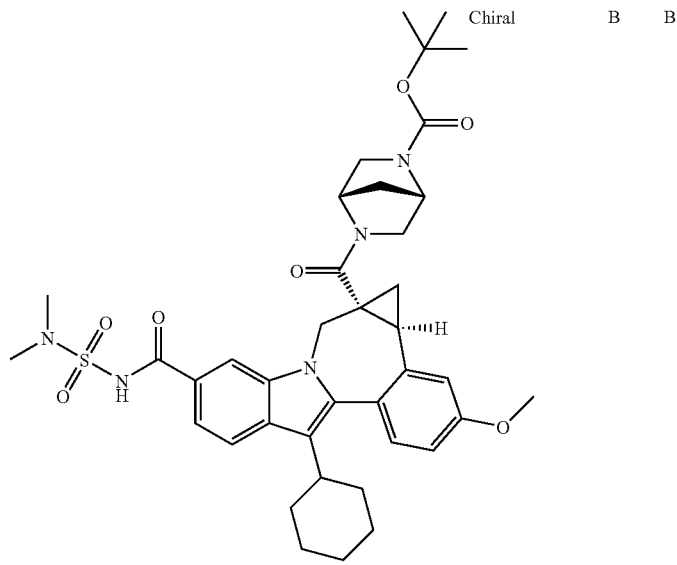 | B | B |
| 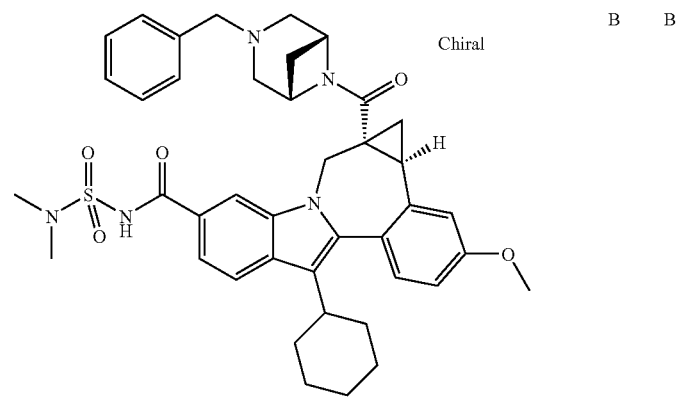 | B | B |
| 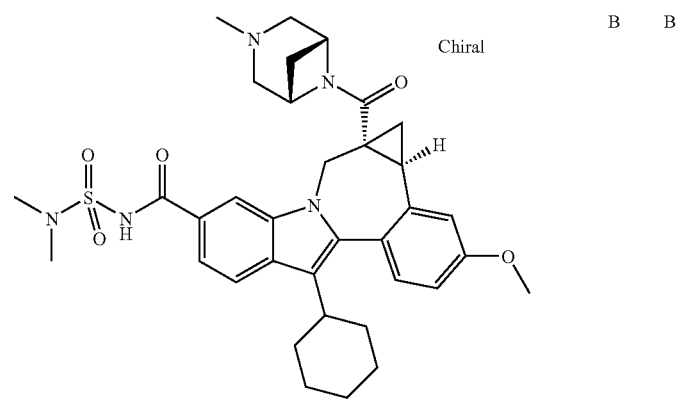 | B | B |

TABLE 1-continued
| Structure | IC$_{50}$ | EC$_{50}$ |
|---|---|---|
| 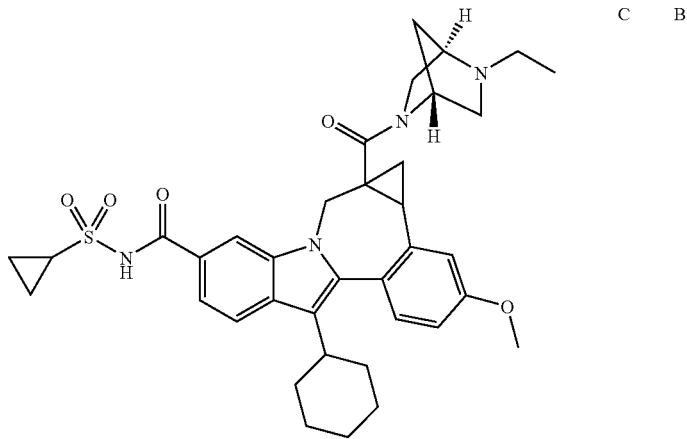 | C | B |
| 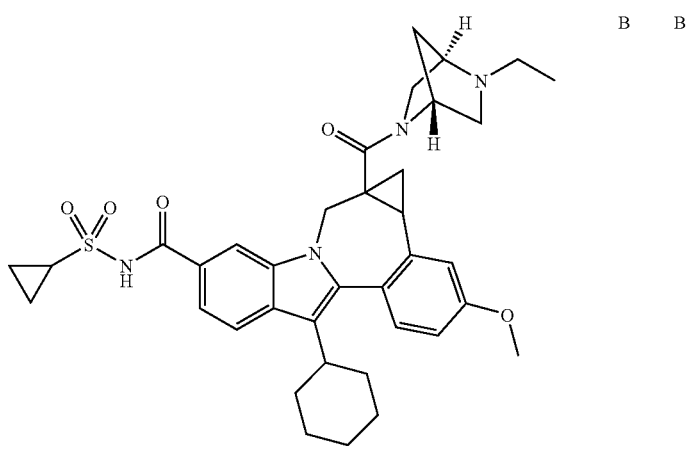 | B | B |
| 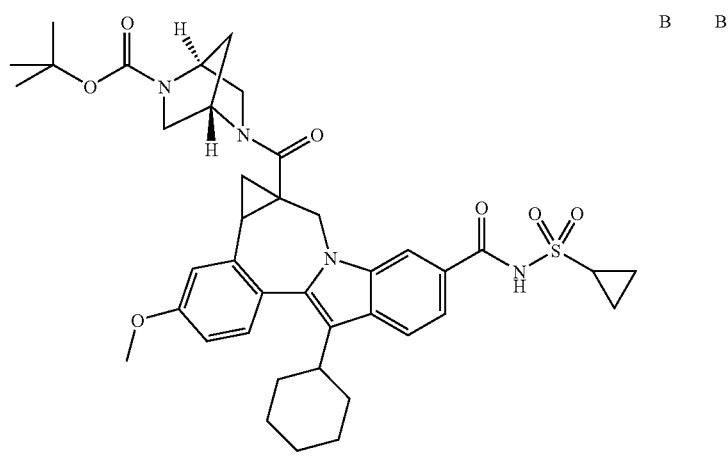 | B | B |

TABLE 1-continued
| Structure | IC$_{50}$ | EC$_{50}$ |
| --- | --- | --- |
| 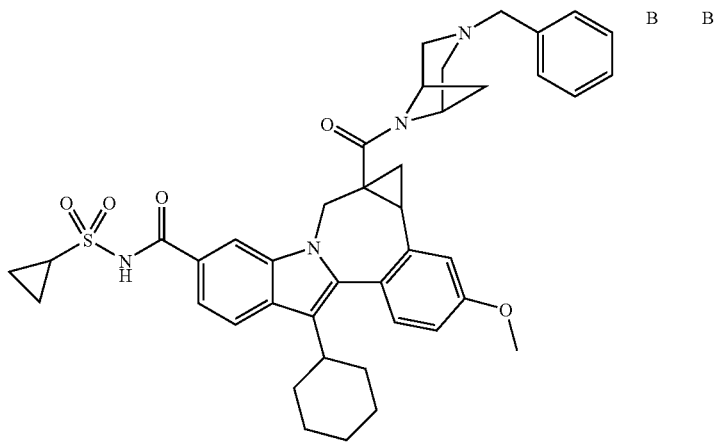 | B | B |
| 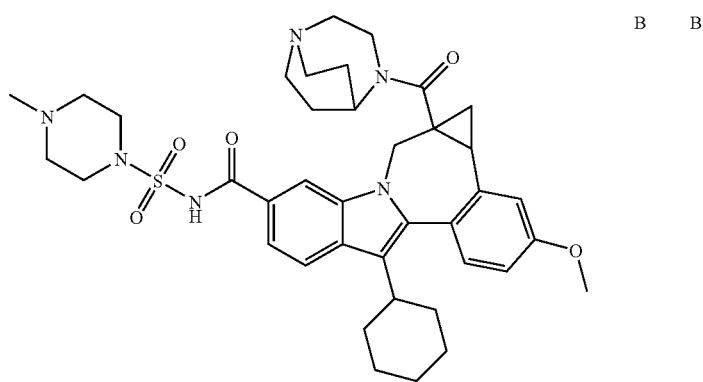 | B | B |
| 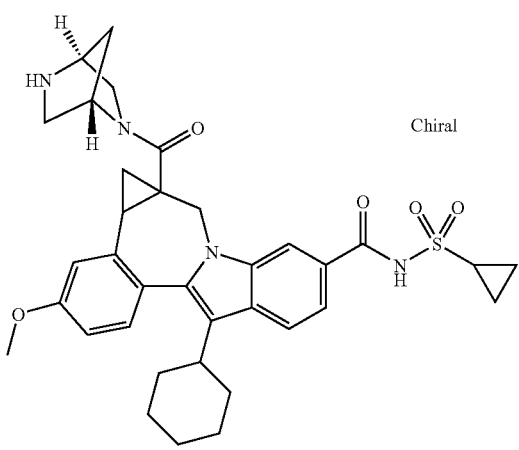 Chiral | | |

TABLE 1-continued
| Structure | IC$_{50}$ | EC$_{50}$ |
|---|---|---|
| 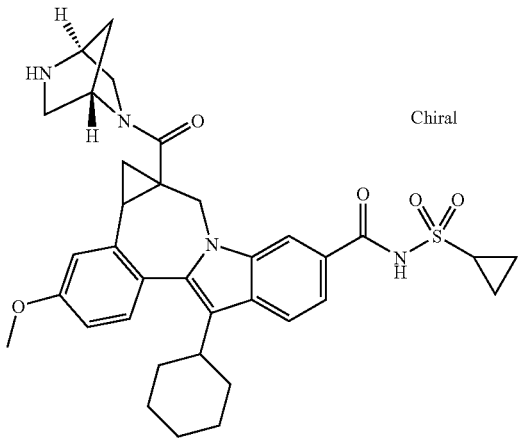 Chiral | B | |
| 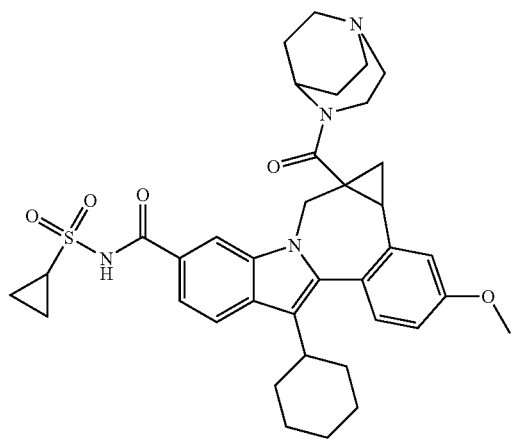 | B | B |
| 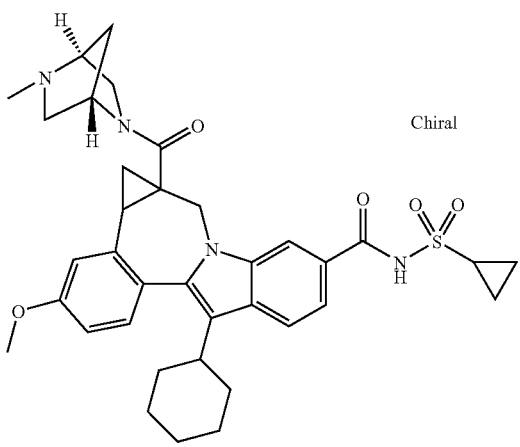 Chiral | B | A |

TABLE 1-continued
| Structure | IC$_{50}$ | EC$_{50}$ |
|---|---|---|
| 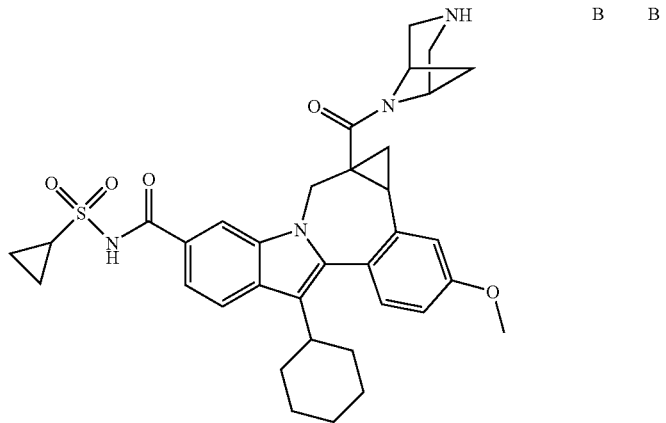 | B | B |
| 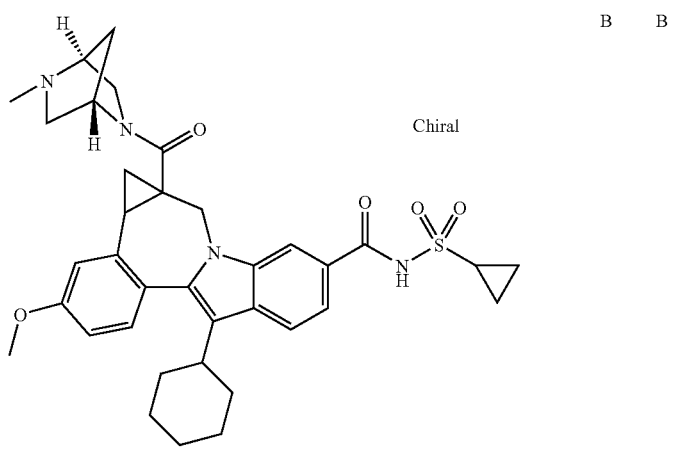 Chiral | B | B |
| 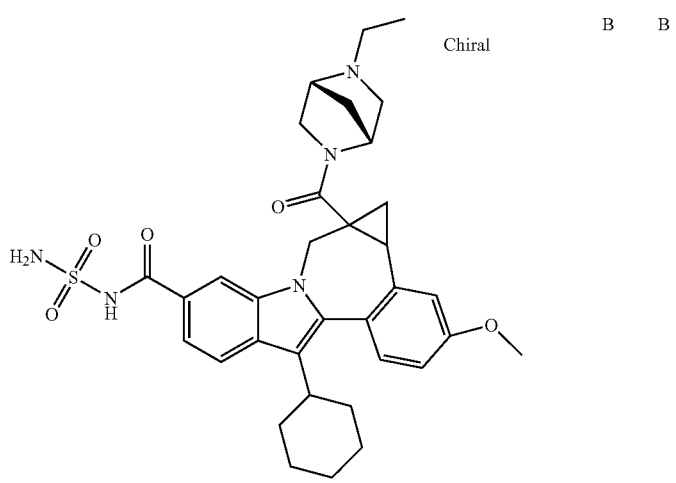 Chiral | B | B |

TABLE 1-continued
| Structure | IC$_{50}$ | EC$_{50}$ |
|---|---|---|
| 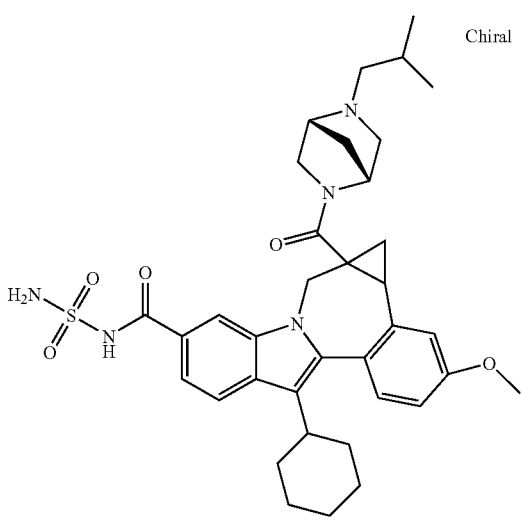 Chiral | B | B |
| 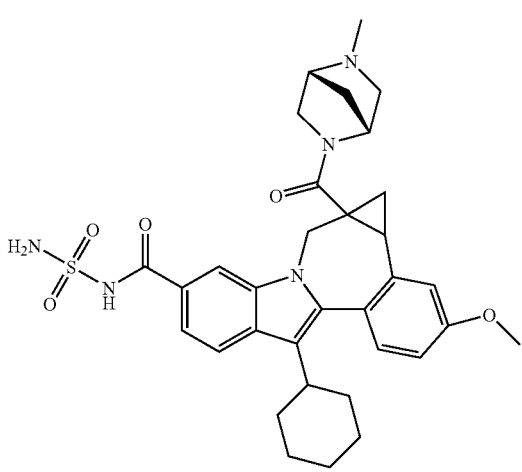 Chiral | B | B |
| 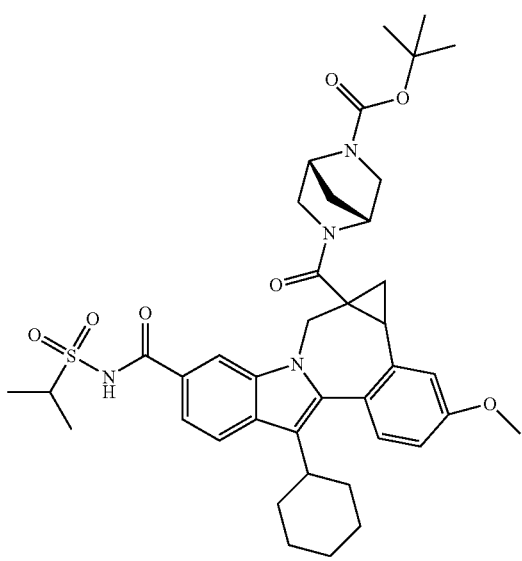 | B | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
|---|---|---|
| 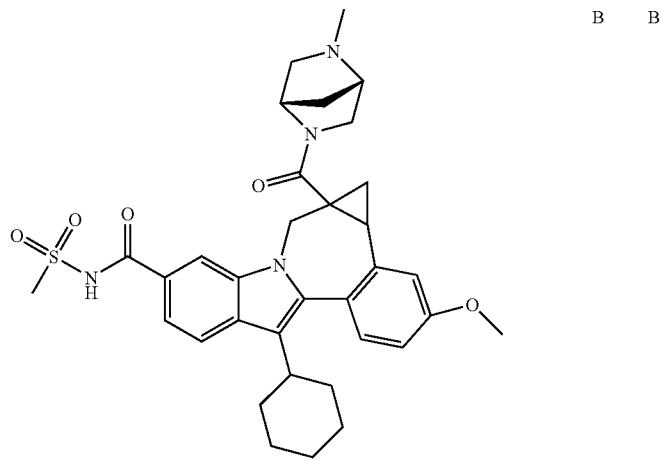 | B | B |
| 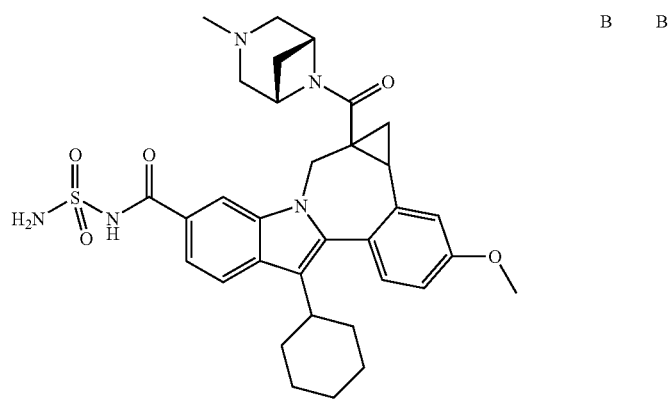 | B | B |
| 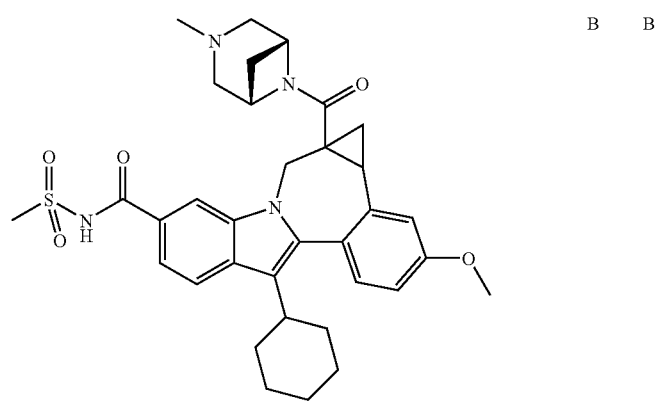 | B | B |

TABLE 1-continued

| Structure | IC$_{50}$ | EC$_{50}$ |
|---|---|---|
| | B | B |
| | B | B |
| | B | B |

TABLE 1-continued

| Structure | IC$_{50}$ | EC$_{50}$ |
|---|---|---|
| | B | B |
| | B | B |
| Chiral | B | B |

TABLE 1-continued
| Structure | IC$_{50}$ | EC$_{50}$ |
|---|---|---|
| 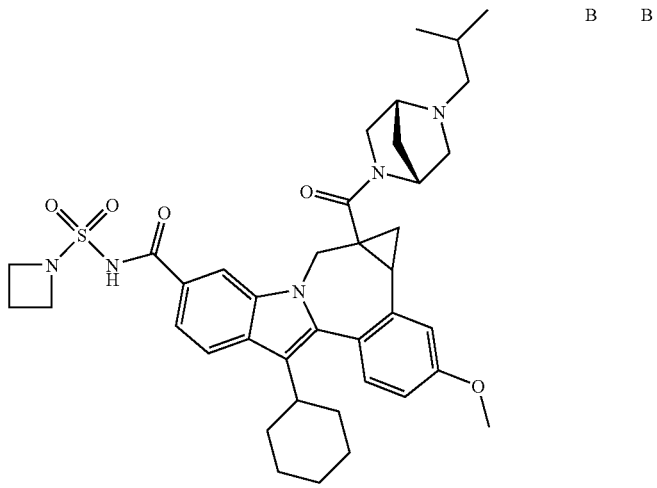 | B | B |
| 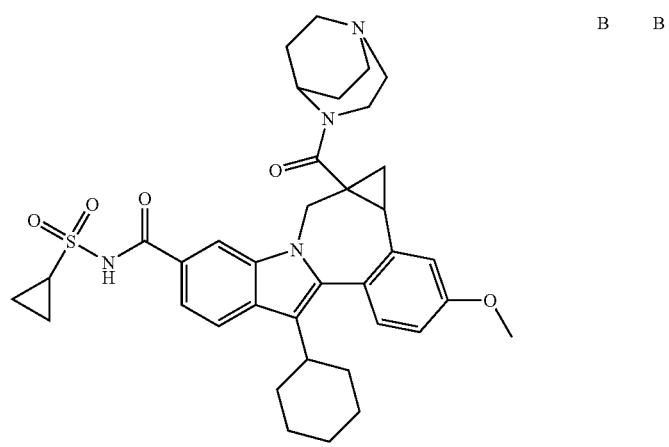 | B | B |
| 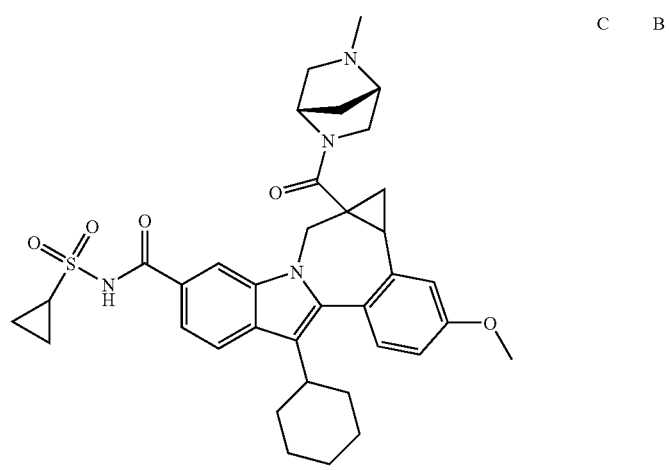 | C | B |

TABLE 1-continued
| Structure | IC$_{50}$ | EC$_{50}$ |
|---|---|---|
| 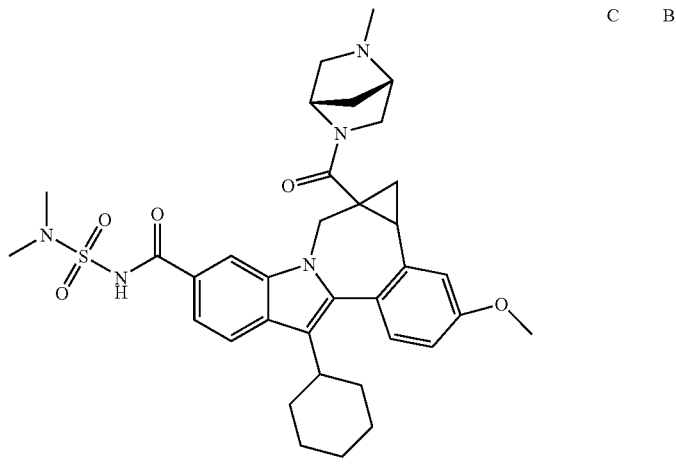 | C | B |
| 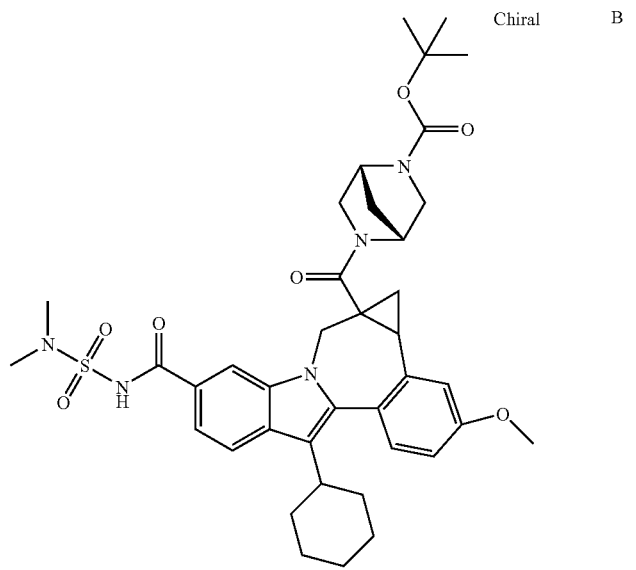 Chiral | B | |
| 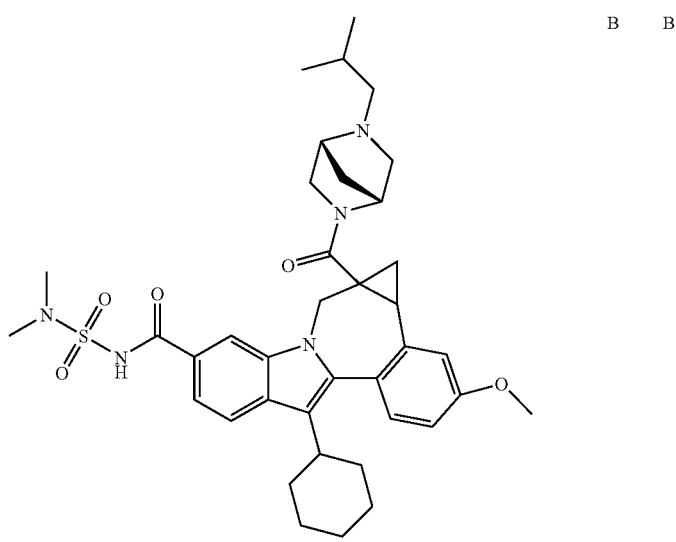 | B | B |

TABLE 1-continued

| Structure | IC$_{50}$ | EC$_{50}$ |
|---|---|---|
| | B | B |
| 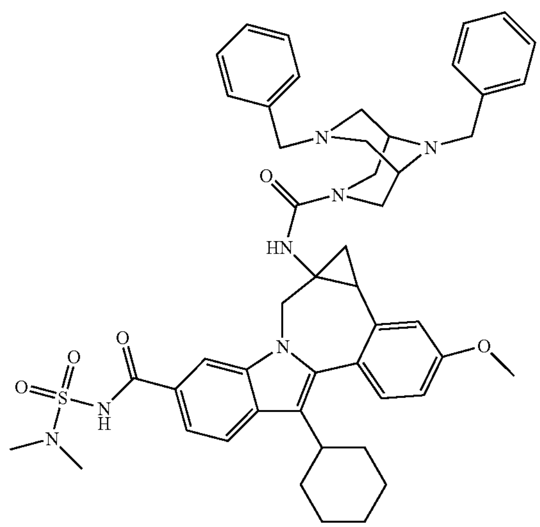 | G | |
| | B | B |

TABLE 1-continued
| Structure | IC$_{50}$ | EC$_{50}$ |
|---|---|---|
| 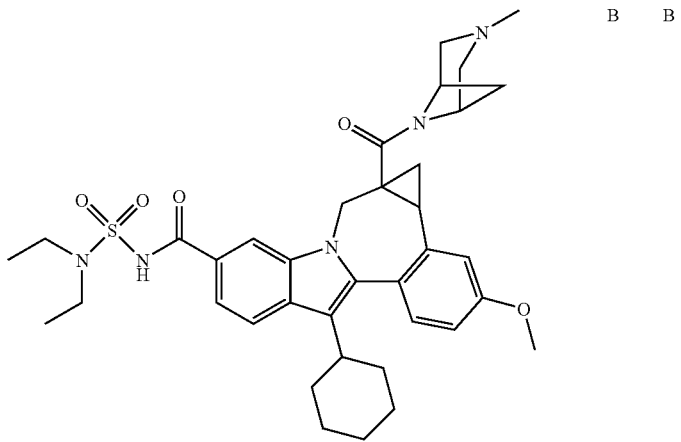 | B | B |
| 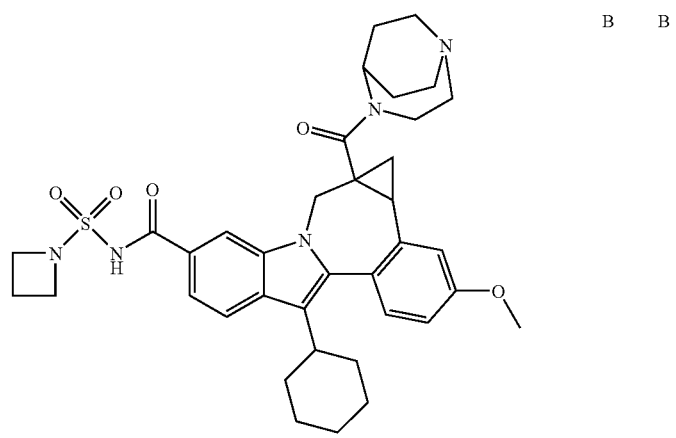 | B | B |
| 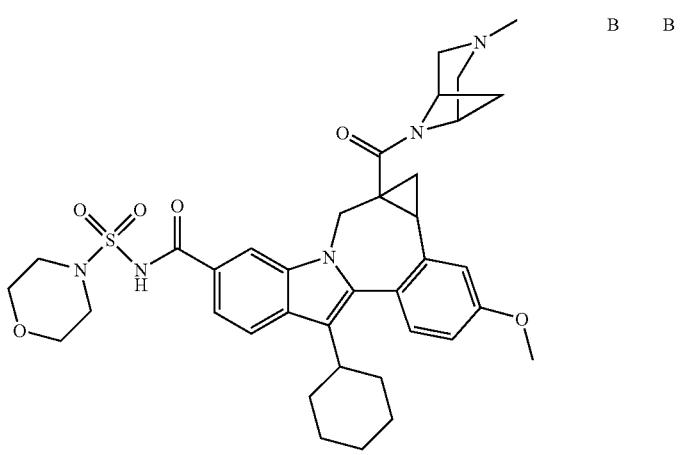 | B | B |

TABLE 1-continued
| Structure | IC$_{50}$ | EC$_{50}$ |
| --- | --- | --- |
| 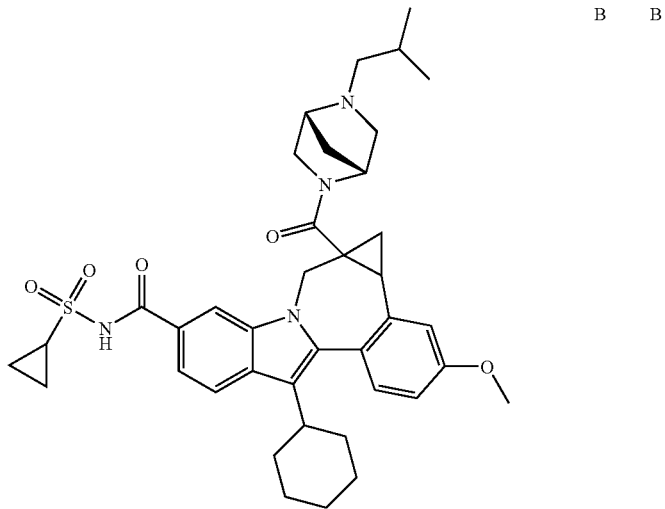 | B | B |
| 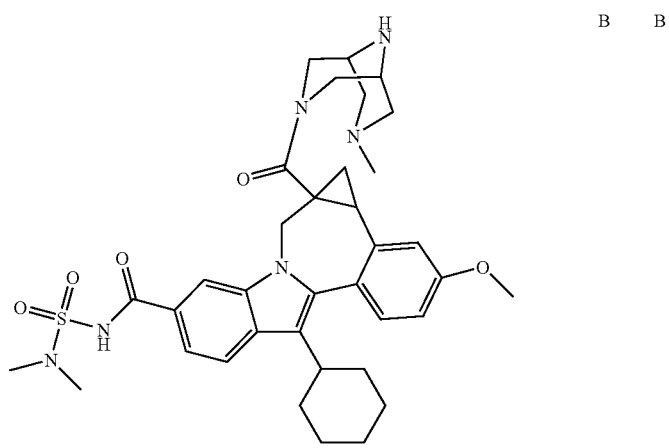 | B | B |
| 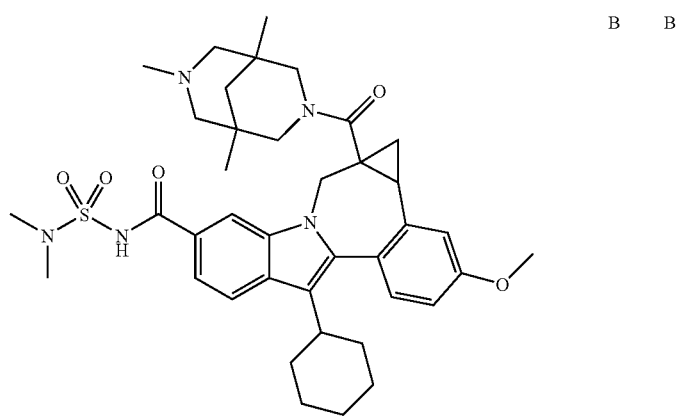 | B | B |

TABLE 1-continued
| Structure | IC$_{50}$ | EC$_{50}$ |
|---|---|---|
| 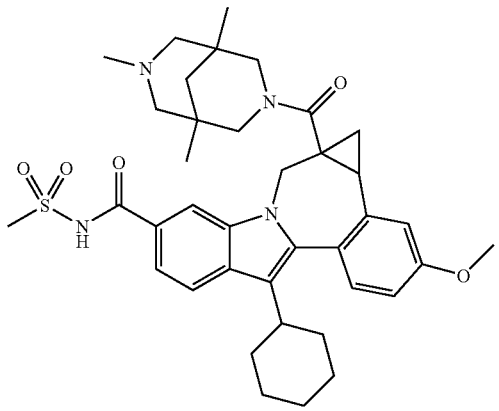 | B | B |
| 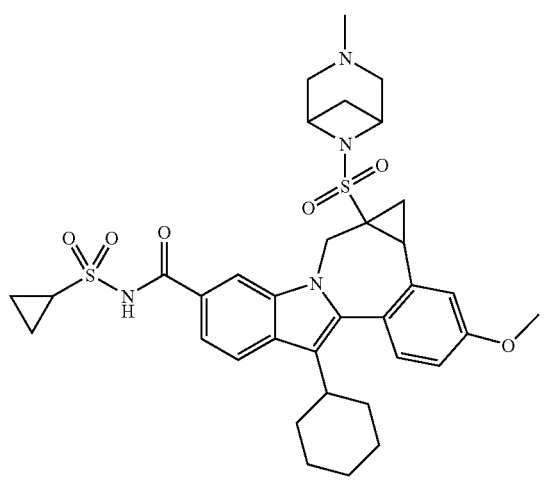 | B | B |
| 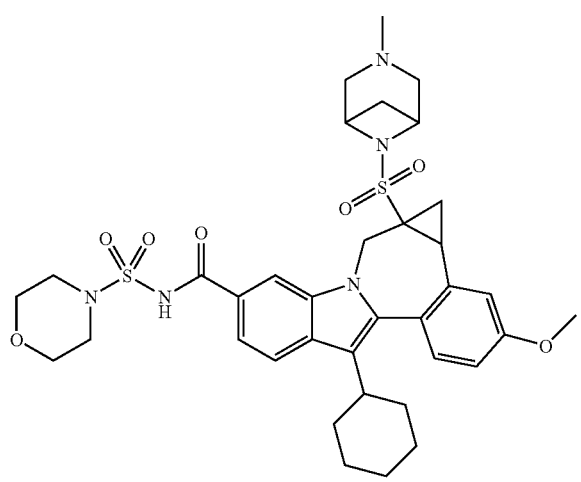 | B | B |

TABLE 1-continued

| Structure | IC$_{50}$ | EC$_{50}$ |
|---|---|---|
| | B | B |
| | B | G |
| | B | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
|---|---|---|
| 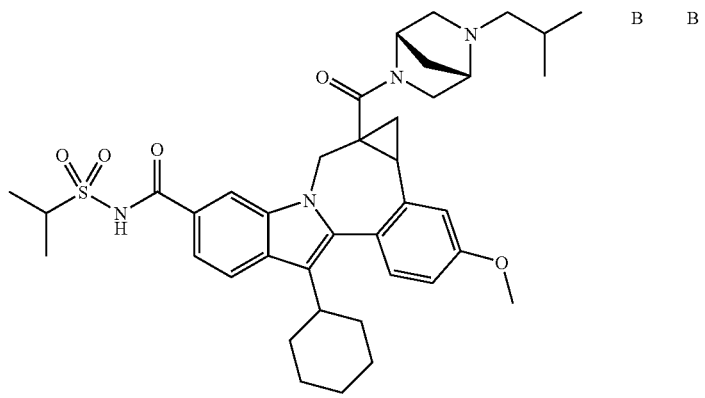 | B | B |
| 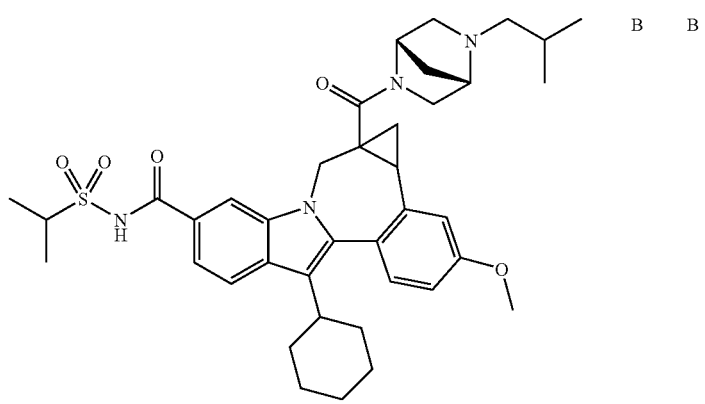 | B | B |
| 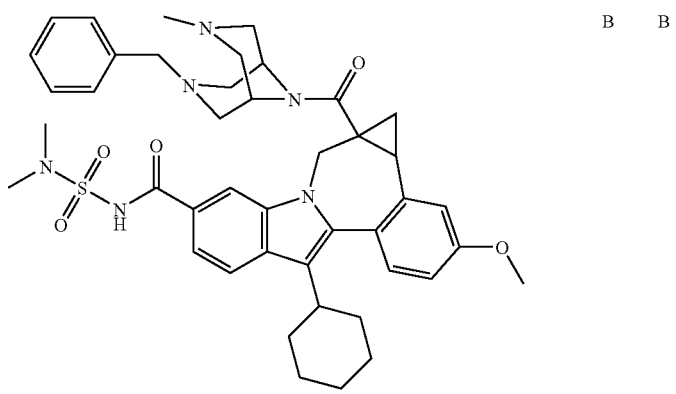 | B | B |

TABLE 1-continued
| Structure | IC$_{50}$ | EC$_{50}$ |
| --- | --- | --- |
| 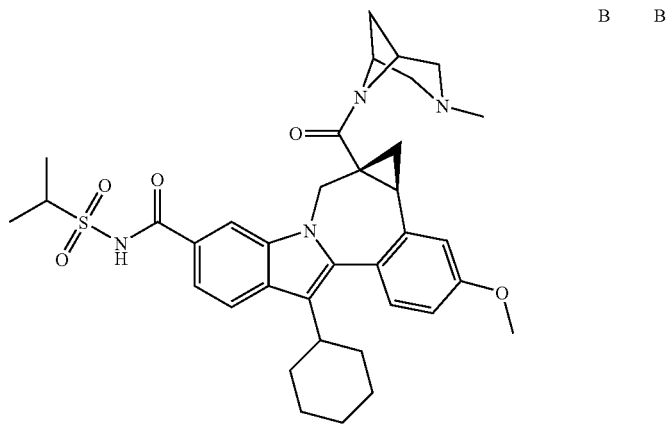 | B | B |
| 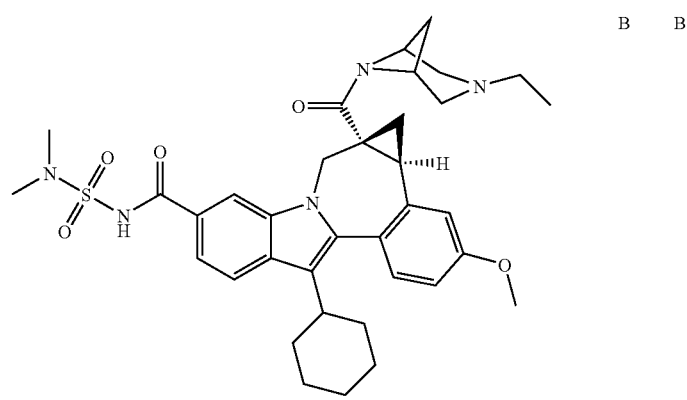 | B | B |
| 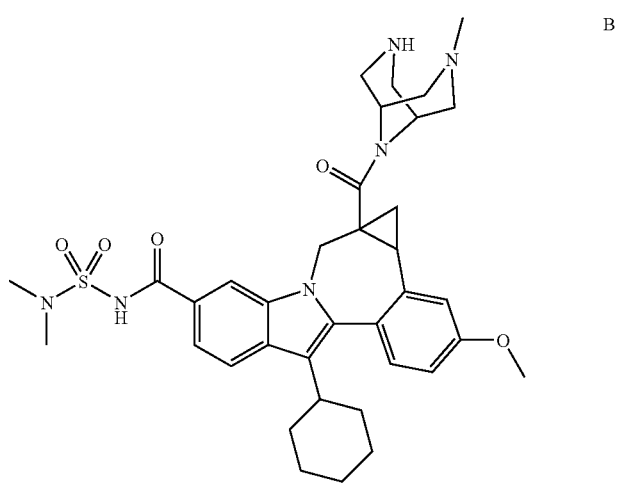 | B | |

TABLE 1-continued
| Structure | IC$_{50}$ | EC$_{50}$ |
|---|---|---|
| 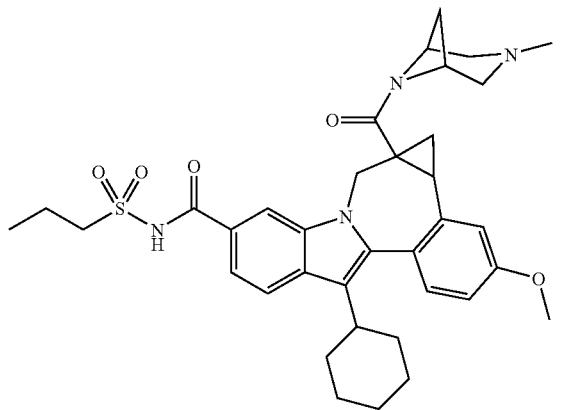 | B | B |
| 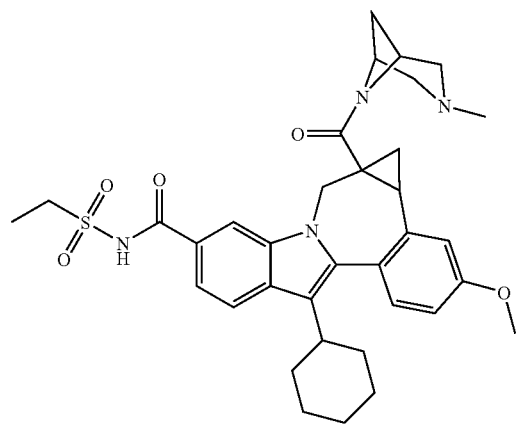 | | |
| 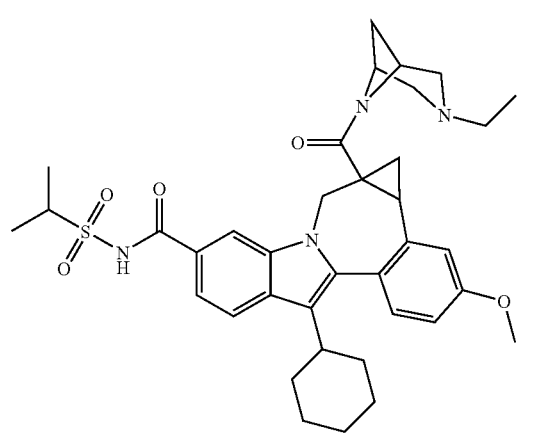 | B | B |

TABLE 1-continued
| Structure | IC$_{50}$ | EC$_{50}$ |
|---|---|---|
| 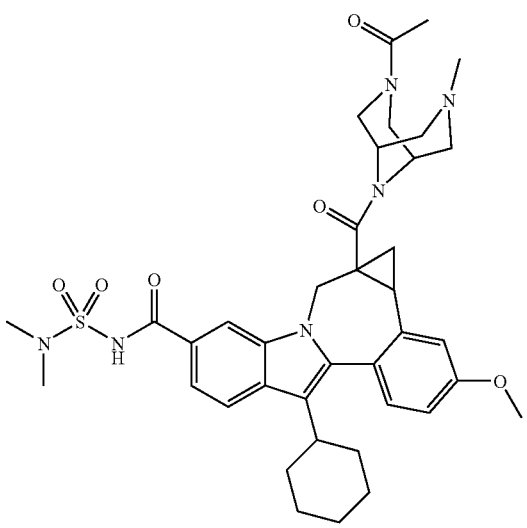 | B | B |
| 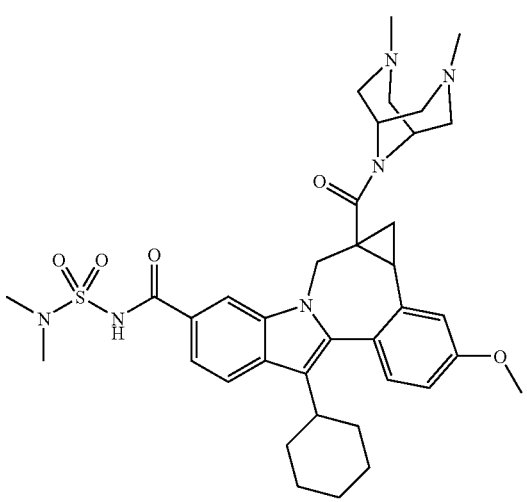 | B | B |
| 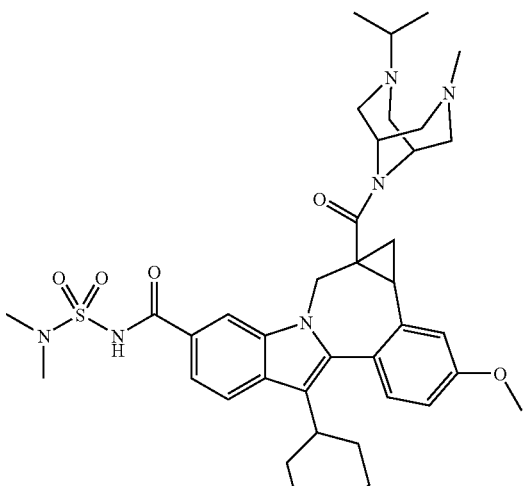 | B | B |

TABLE 1-continued
| Structure | IC$_{50}$ | EC$_{50}$ |
|---|---|---|
| 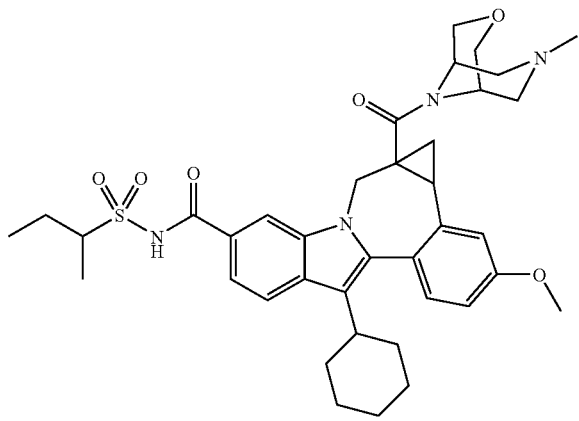 | B | |
| 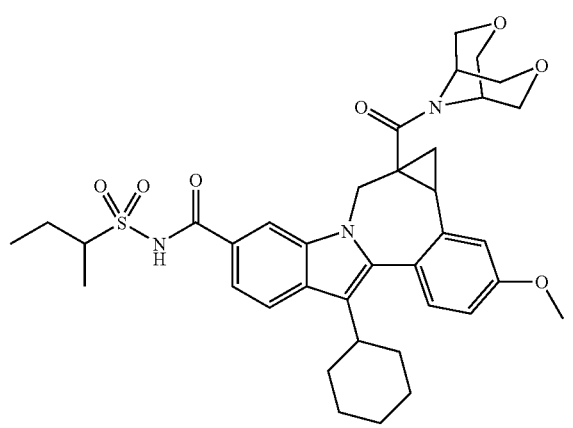 | B | B |
| 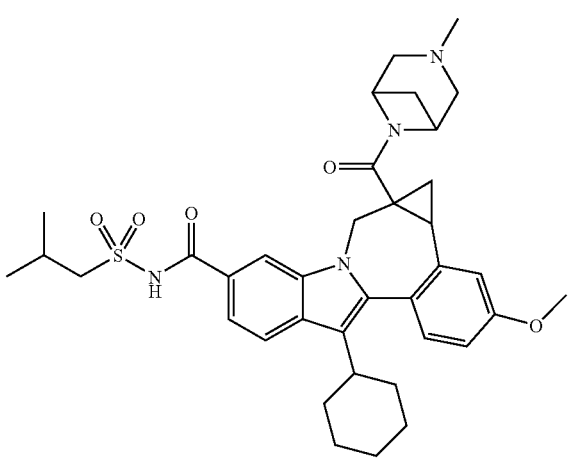 | B | B |

TABLE 1-continued
| Structure | IC$_{50}$ | EC$_{50}$ |
| --- | --- | --- |
| 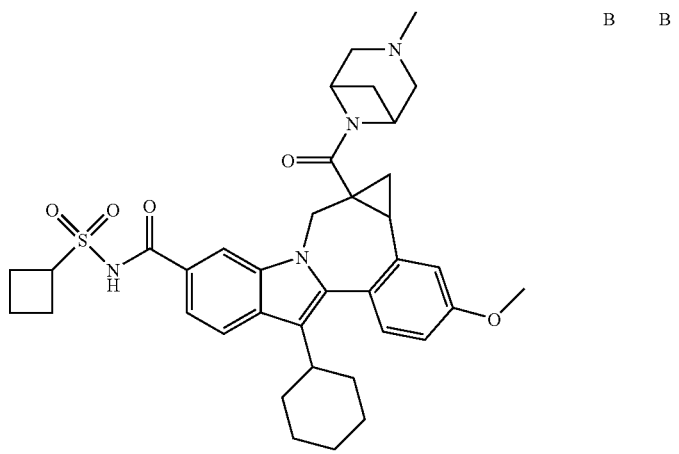 | B | B |
| 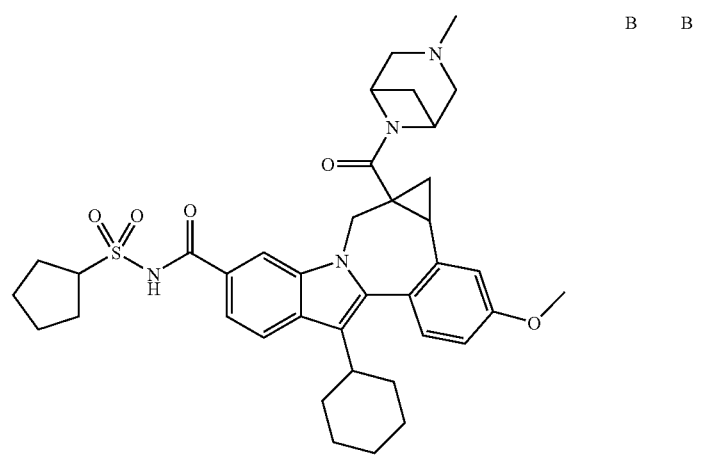 | B | B |
| 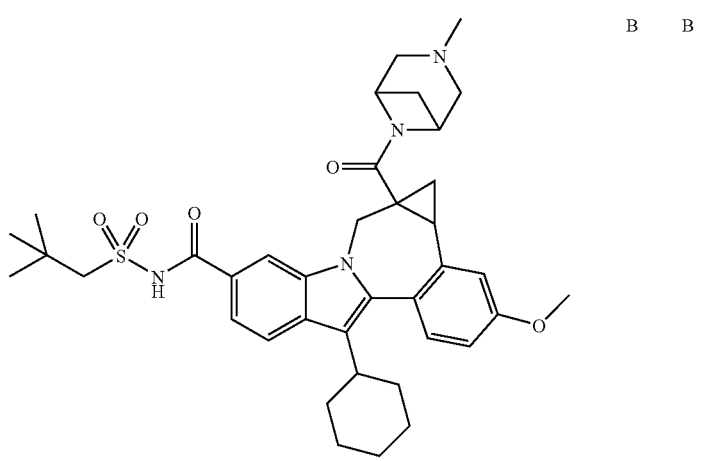 | B | B |

TABLE 1-continued
| Structure | IC$_{50}$ | EC$_{50}$ |
|---|---|---|
| 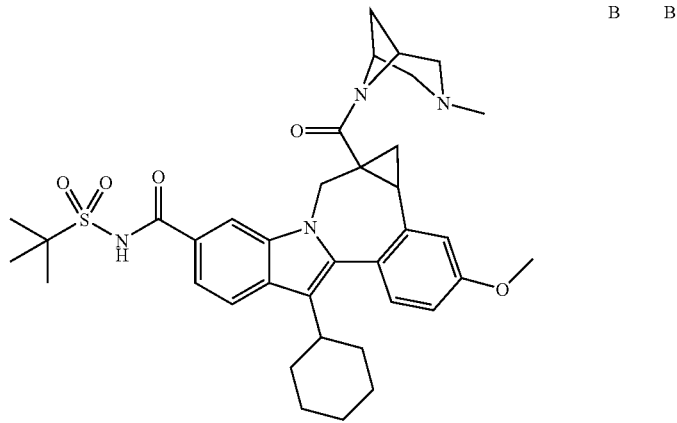 | B | B |
| 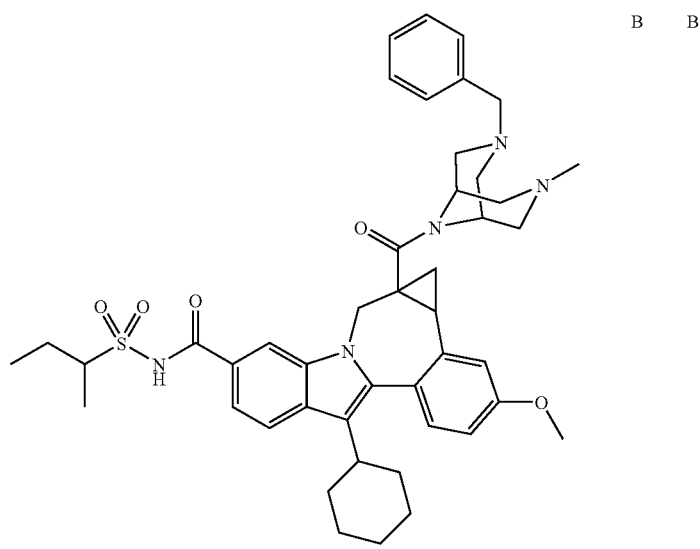 | B | B |
| 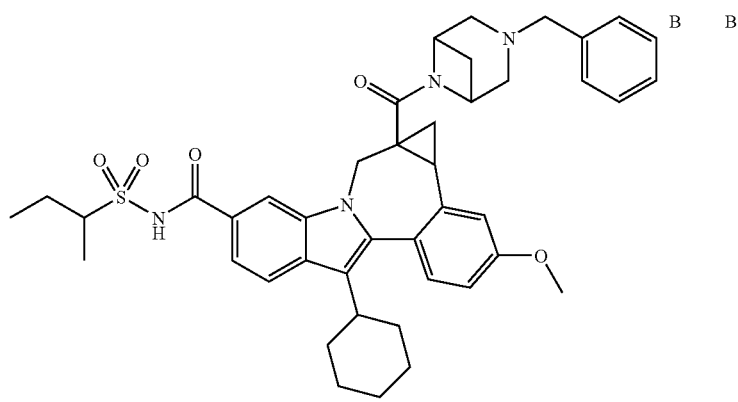 | B | B |

TABLE 1-continued

| Structure | IC$_{50}$ | EC$_{50}$ |
|---|---|---|
| | B | B |
| | B | B |
| | B | G |
| | B | G |

TABLE 1-continued
| Structure | IC$_{50}$ | EC$_{50}$ |
|---|---|---|
| 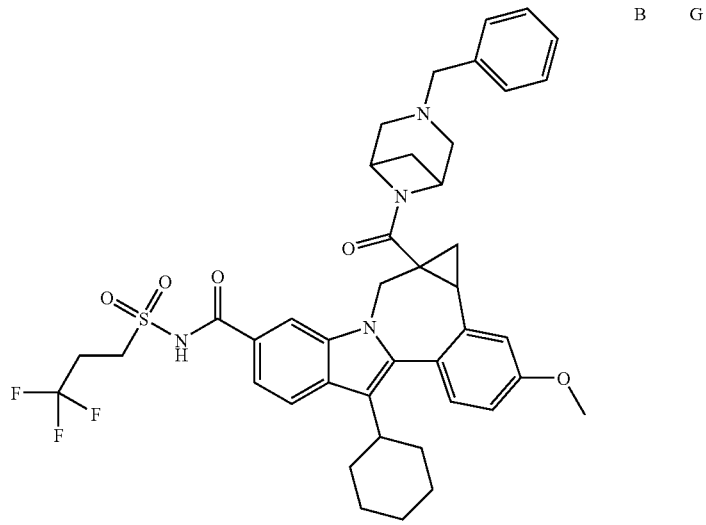 | B | G |
| 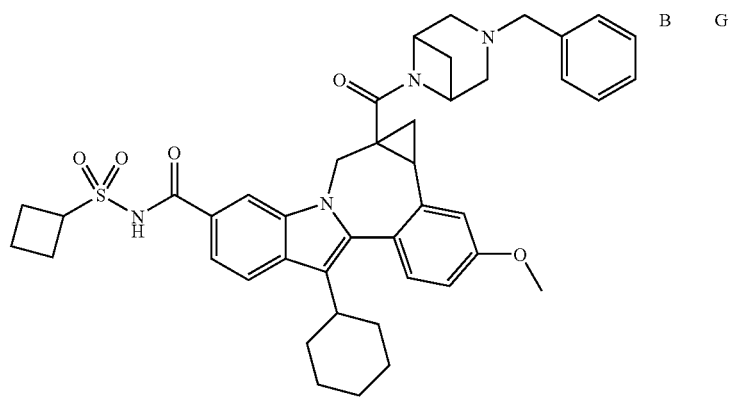 | B | G |
| 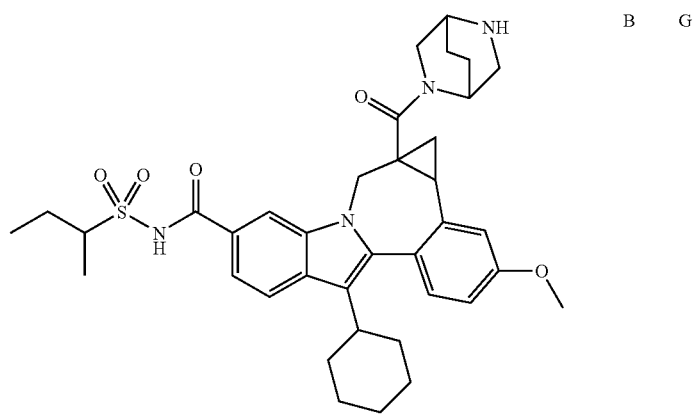 | B | G |

TABLE 1-continued
| Structure | IC$_{50}$ | EC$_{50}$ |
|---|---|---|
| 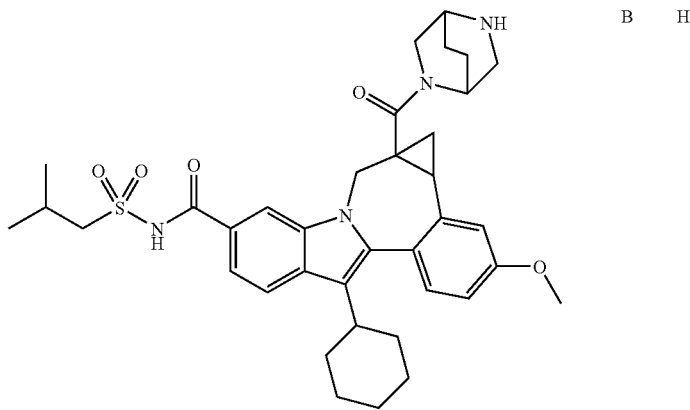 | B | H |
| 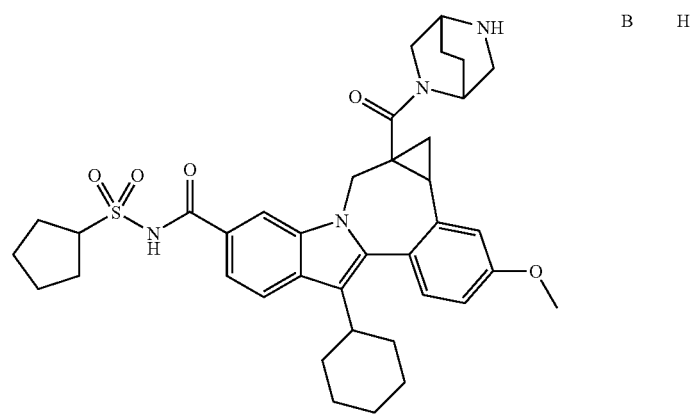 | B | H |
| 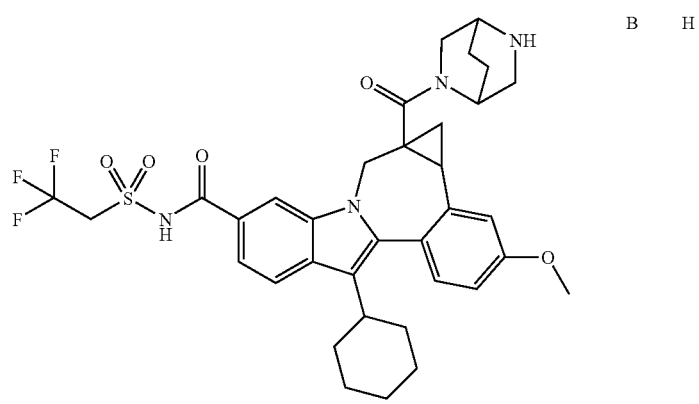 | B | H |

TABLE 1-continued
| Structure | IC$_{50}$ | EC$_{50}$ |
|---|---|---|
| 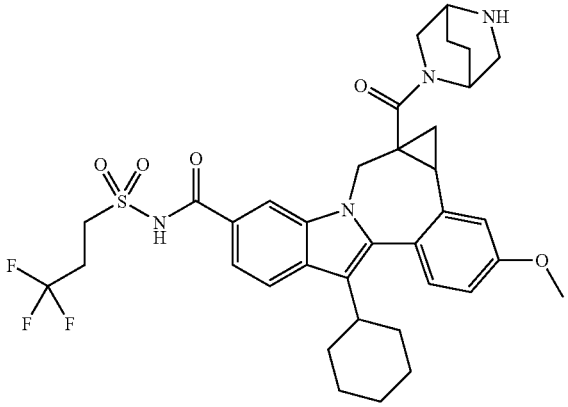 | B | H |
| 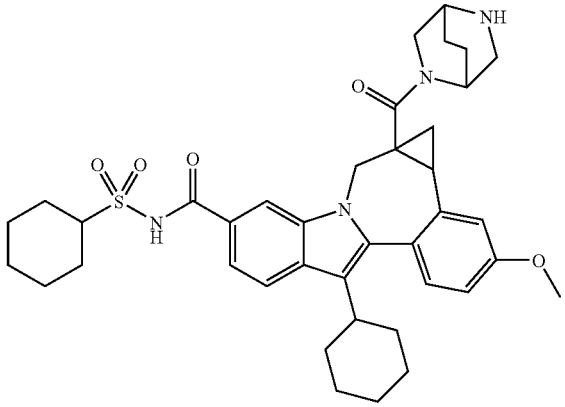 | B | H |
| 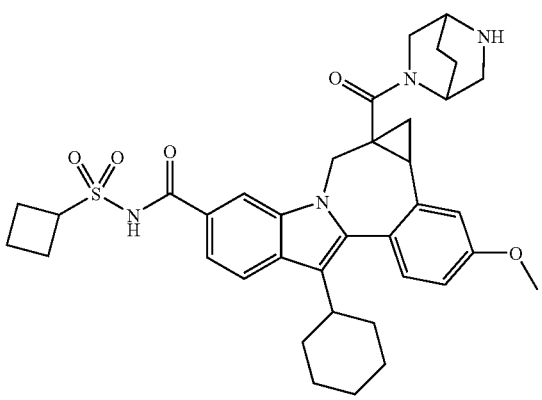 | B | B |
| 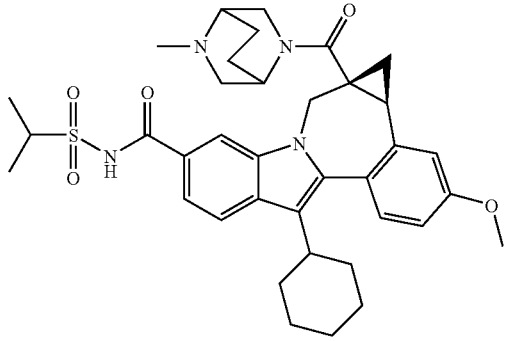 | | B |

TABLE 1-continued
| Structure | IC$_{50}$ | EC$_{50}$ |
|---|---|---|
| 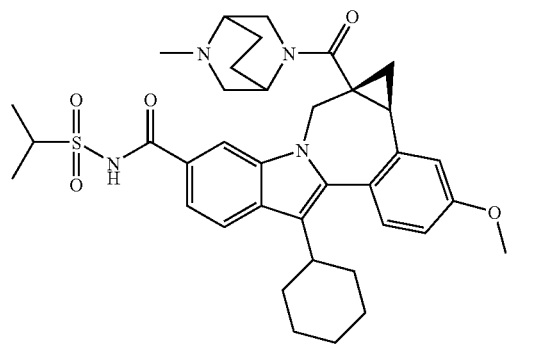 | | B |
| 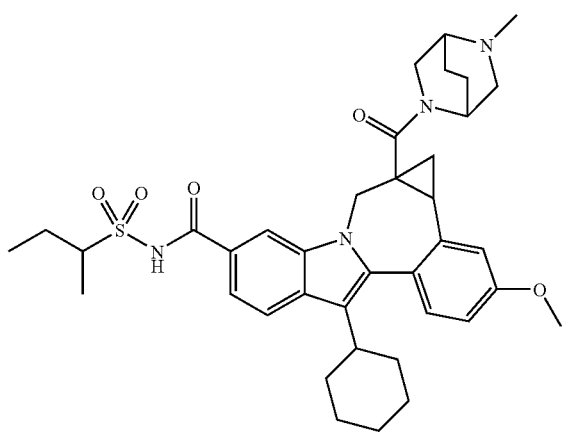 | | |
| 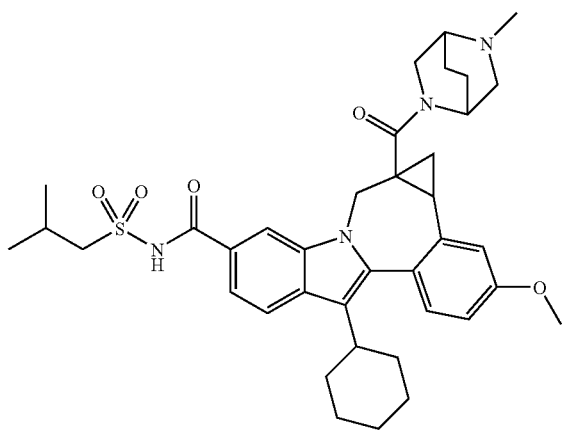 | | |

TABLE 1-continued
| Structure | IC$_{50}$ | EC$_{50}$ |
|---|---|---|
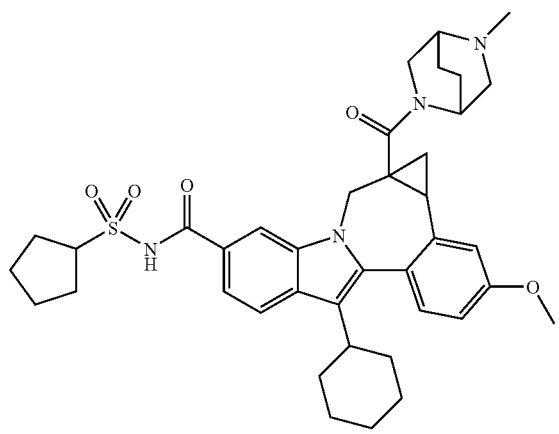
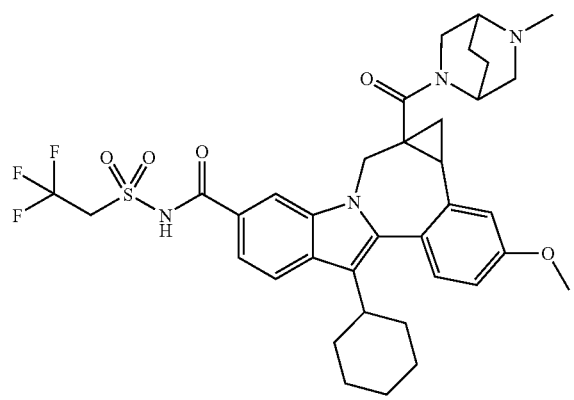
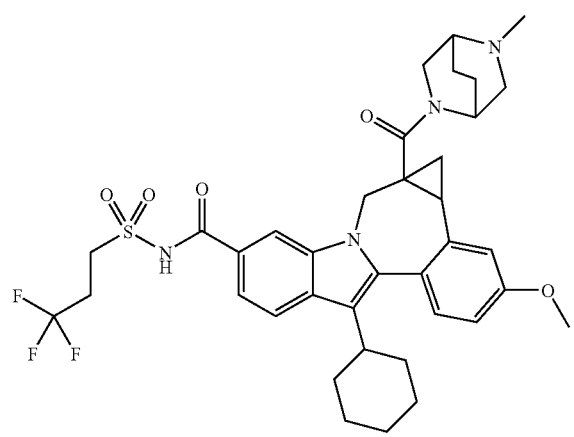

TABLE 1-continued
| Structure | IC$_{50}$ | EC$_{50}$ |
|---|---|---|
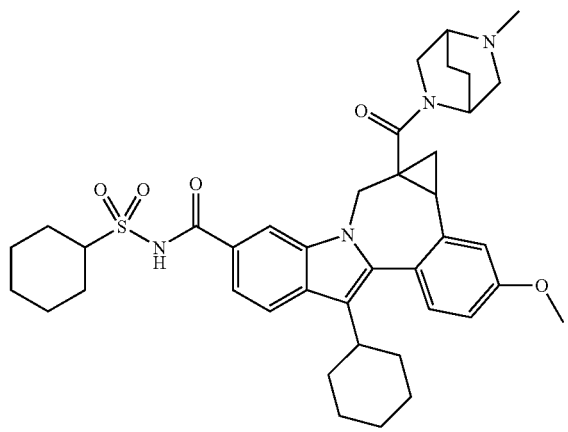
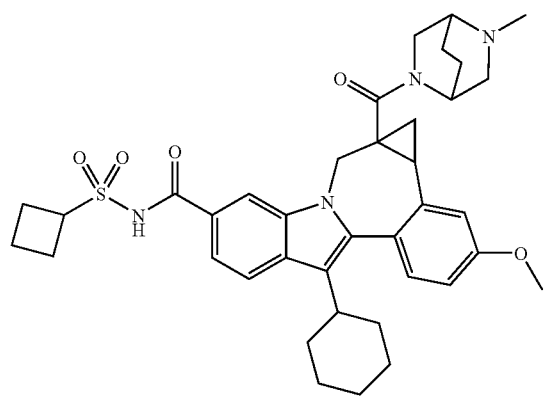
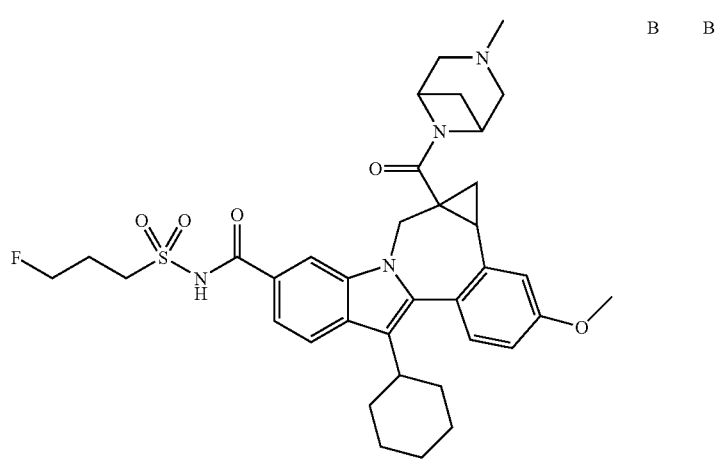
B   B TABLE 1-continued
| Structure | IC$_{50}$ | EC$_{50}$ |
|---|---|---|
| 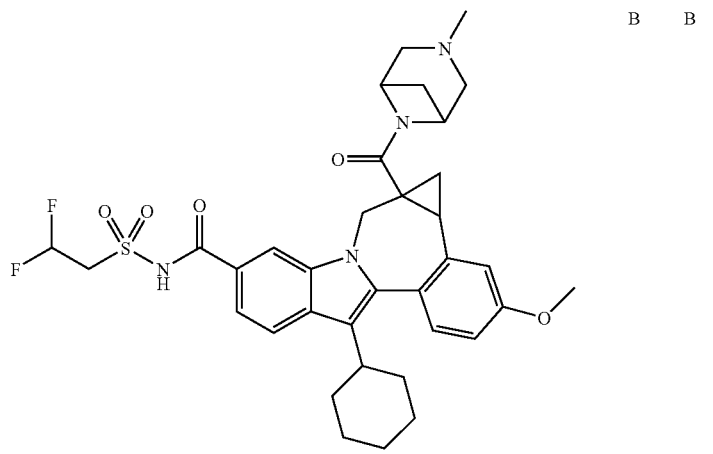 | B | B |
| 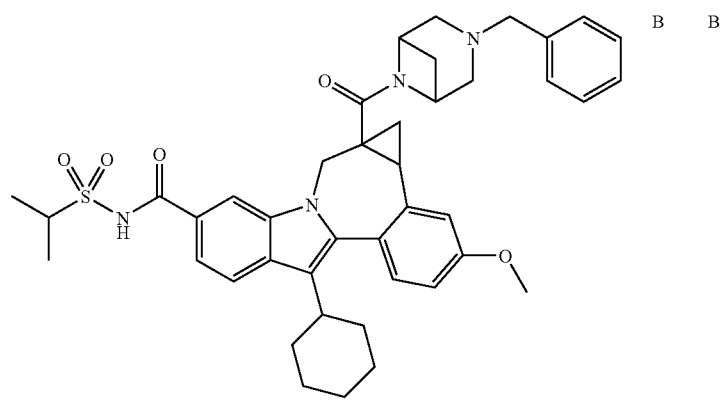 | B | B |
| 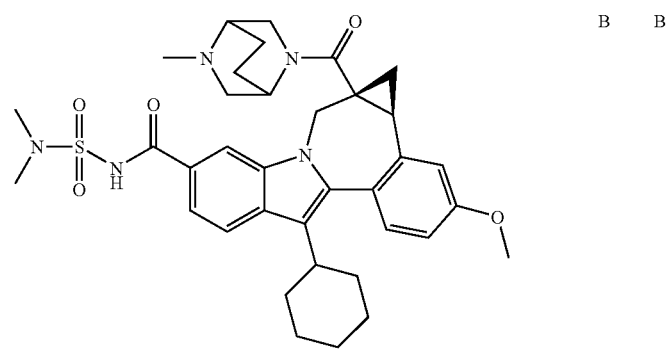 | B | B |

TABLE 1-continued
| Structure | IC$_{50}$ | EC$_{50}$ |
|---|---|---|
| 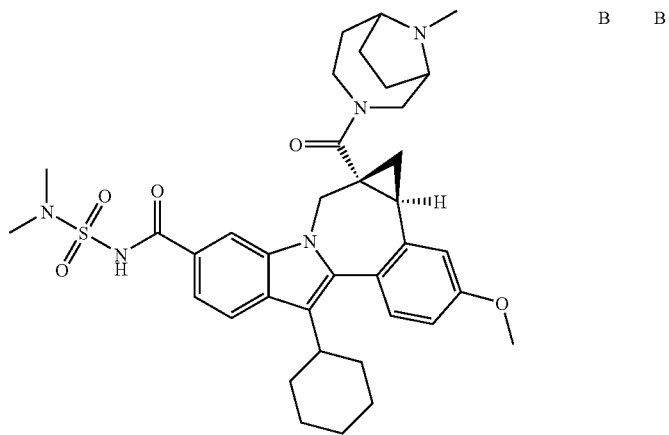 | B | B |
| 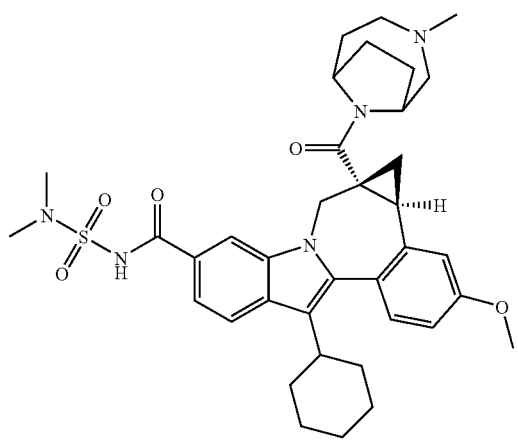 | | |
| 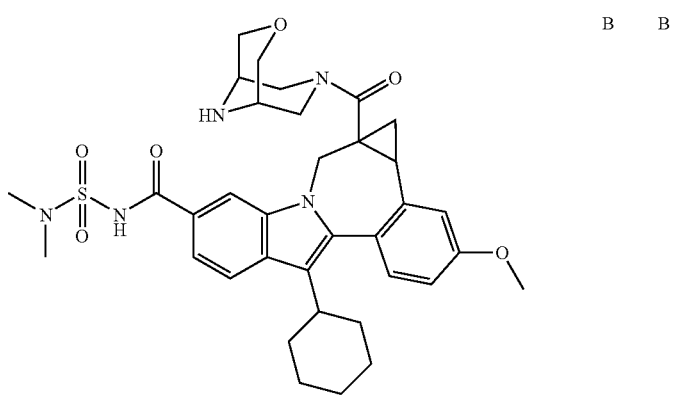 | B | B |

TABLE 1-continued
| Structure | IC$_{50}$ | EC$_{50}$ |
|---|---|---|
| 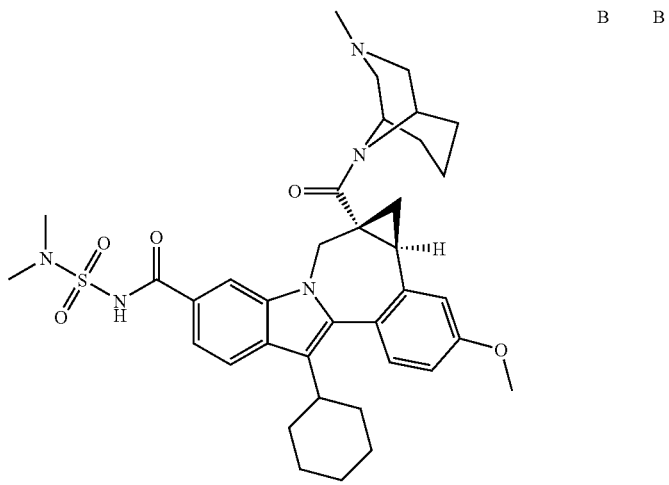 | B | B |
| 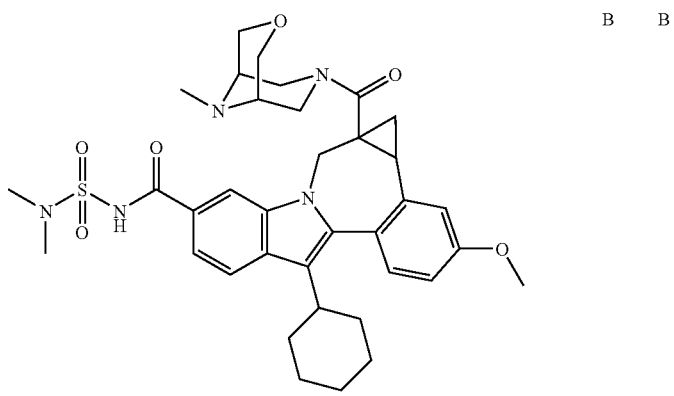 | B | B |
| 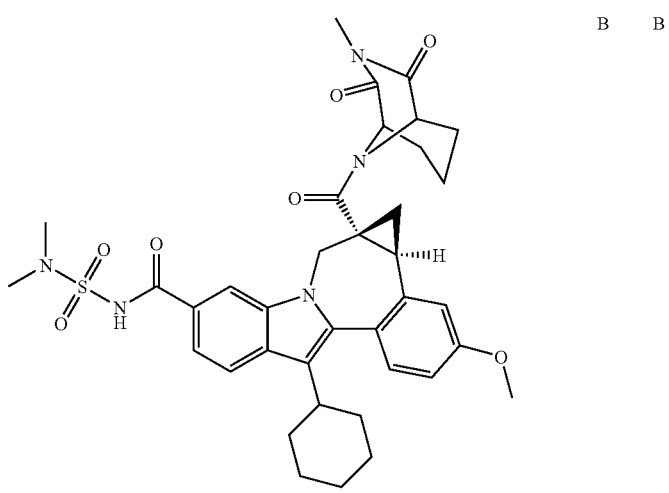 | B | B |

TABLE 1-continued
| Structure | IC$_{50}$ | EC$_{50}$ |
|---|---|---|
| 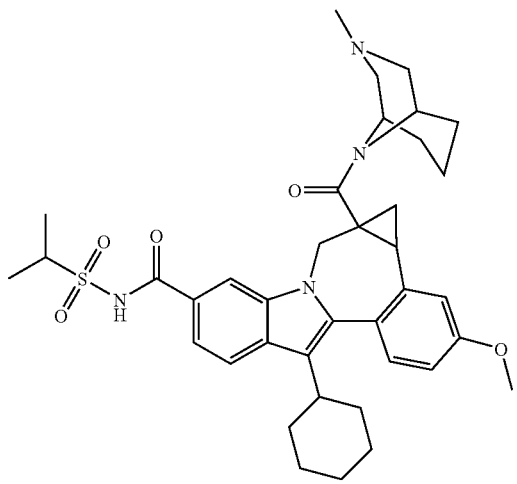 | B | B |
| 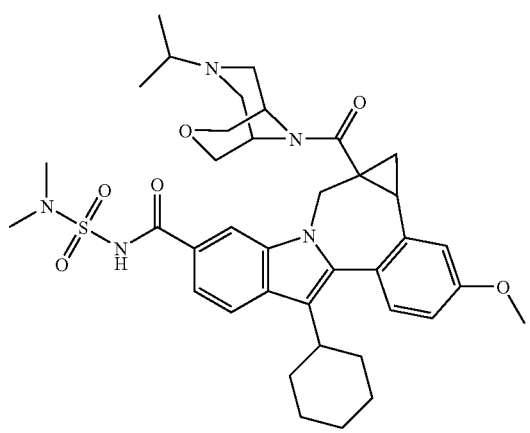 | B | B |
| 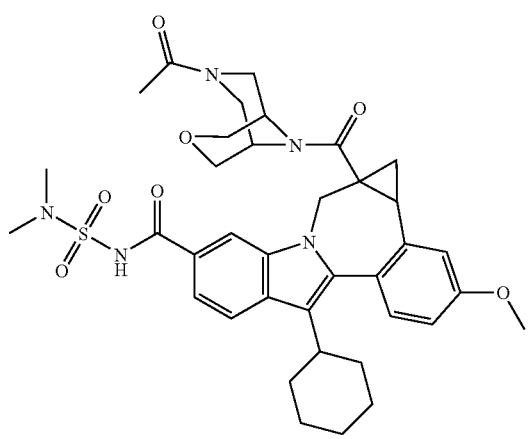 | B | B |

TABLE 1-continued
| Structure | IC$_{50}$ | EC$_{50}$ |
|---|---|---|
| 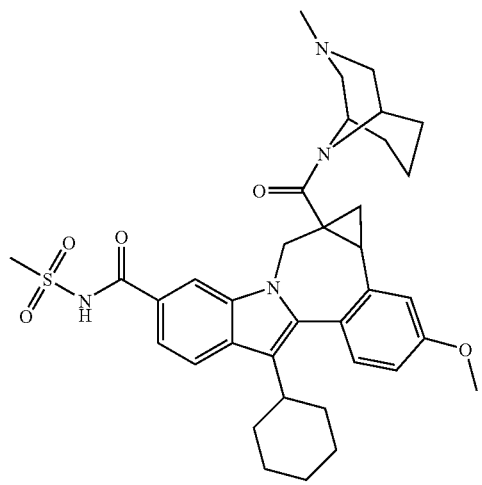 | B | B |
| 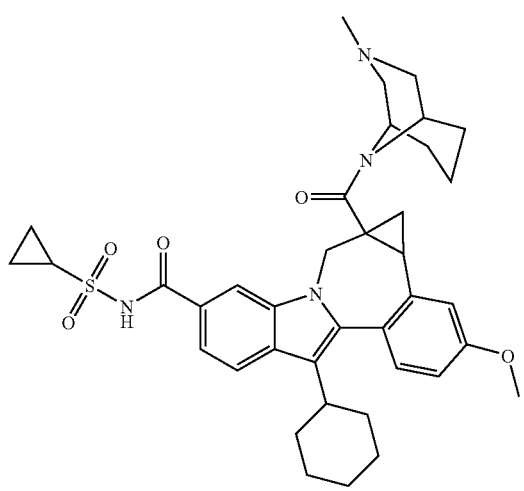 | B | B |
| 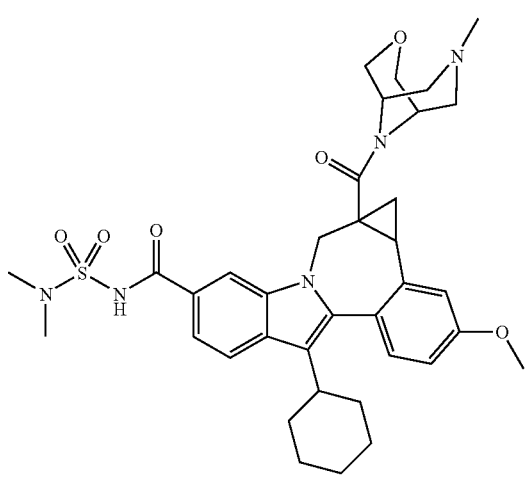 | B | B |

TABLE 1-continued
| Structure | IC$_{50}$ | EC$_{50}$ |
|---|---|---|
| 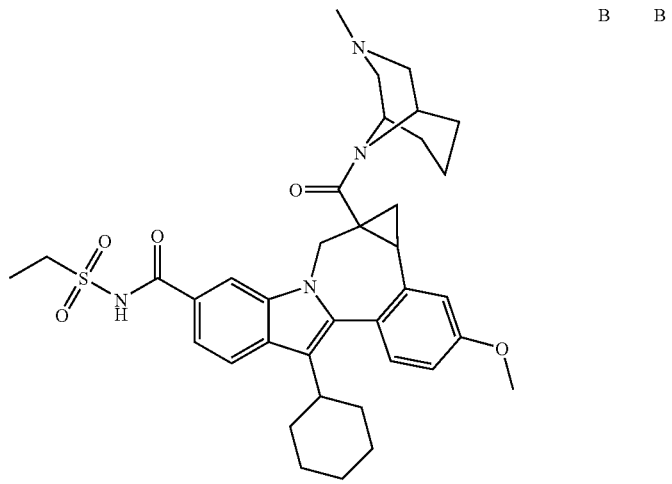 | B | B |
| 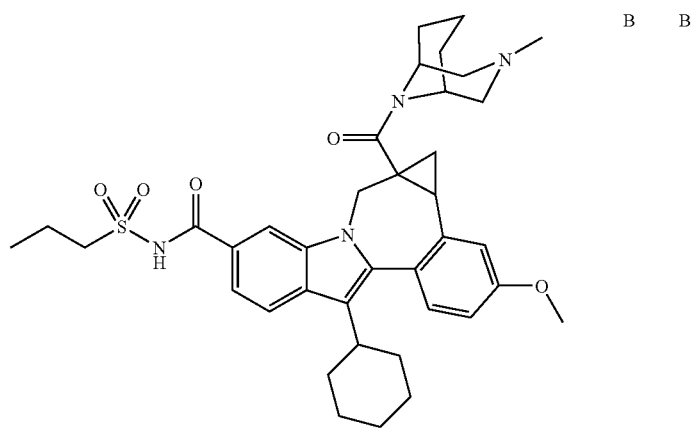 | B | B |
| 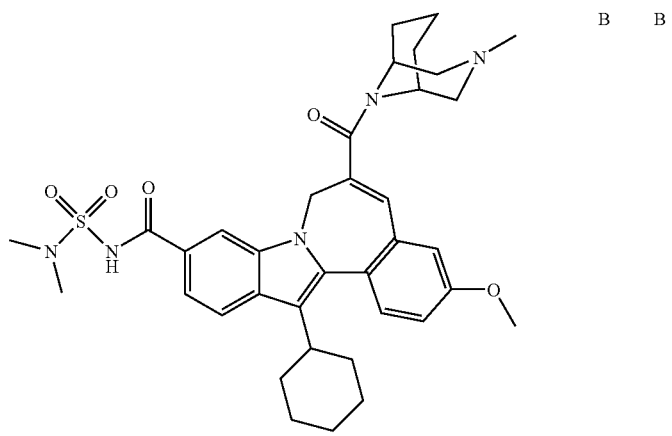 | B | B |

TABLE 1-continued
| Structure | IC$_{50}$ | EC$_{50}$ |
|---|---|---|
| 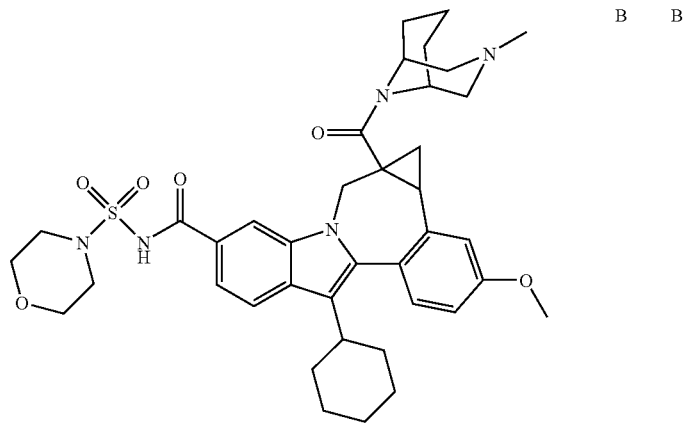 | B | B |
| 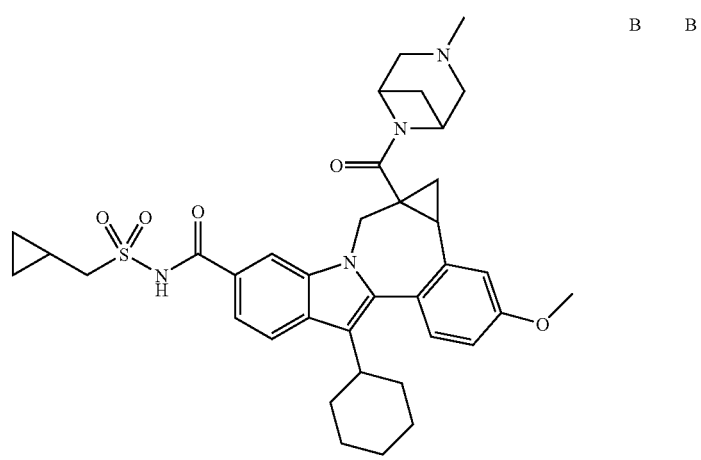 | B | B |
| 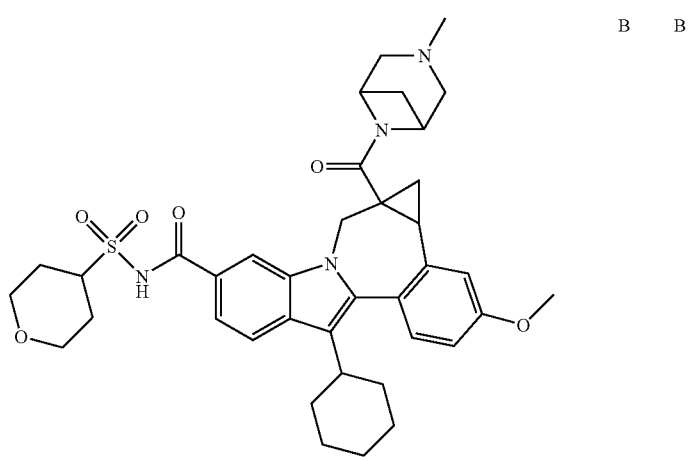 | B | B |

TABLE 1-continued

| Structure | IC$_{50}$ | EC$_{50}$ |
|---|---|---|
| | B | B |
| | B | B |
| | B | B |

TABLE 1-continued

| Structure | IC$_{50}$ | EC$_{50}$ |
|---|---|---|
| | B | B |
| | B | B |
| | B | B |
| | B | B |

TABLE 1-continued
| Structure | IC$_{50}$ | EC$_{50}$ |
|---|---|---|
| 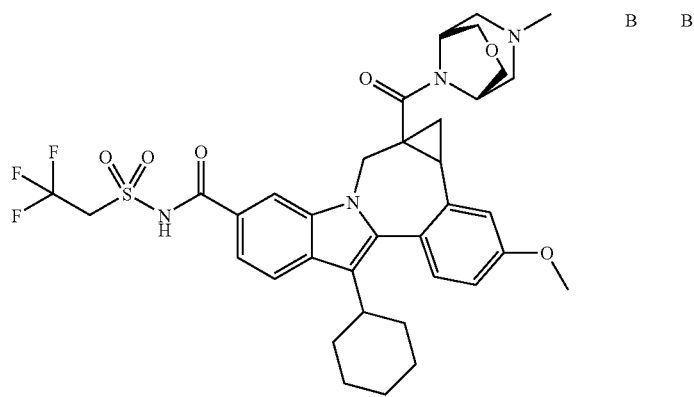 | B | B |
| 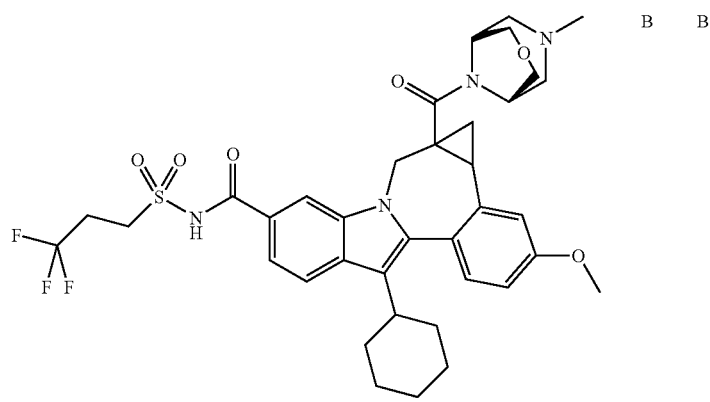 | B | B |
| 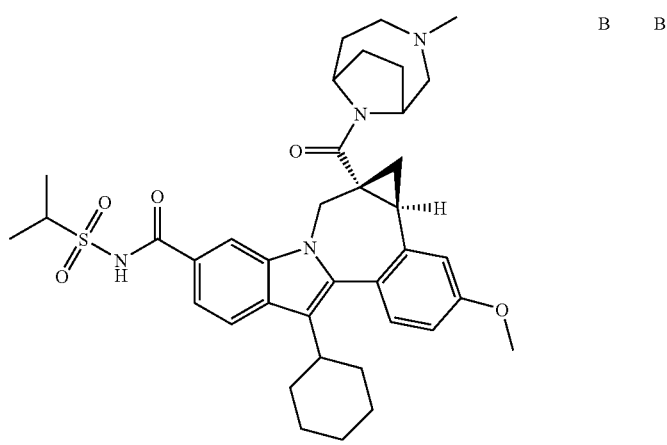 | B | B |

TABLE 1-continued
| Structure | IC$_{50}$ | EC$_{50}$ |
|---|---|---|
| 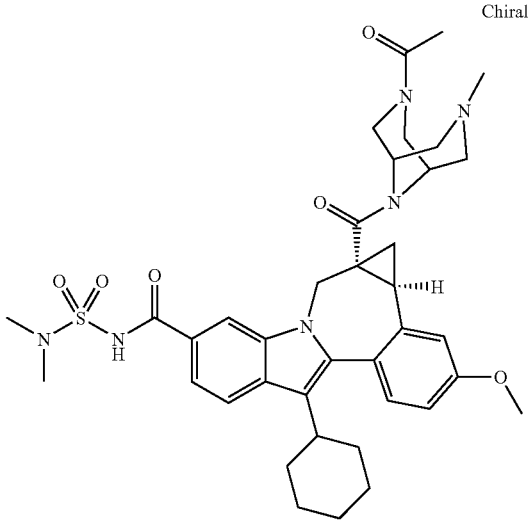 | B | B |
| 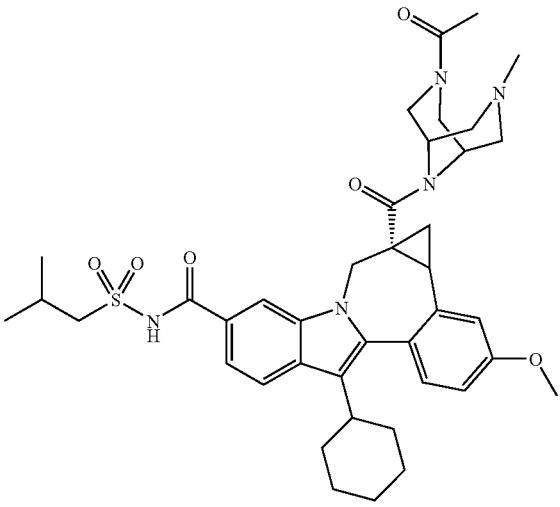 | | |
| 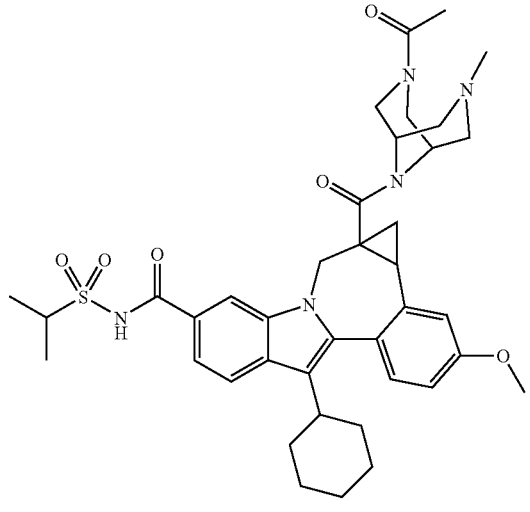 | | |

TABLE 1-continued

| Structure | IC$_{50}$ | EC$_{50}$ |
|---|---|---|
| 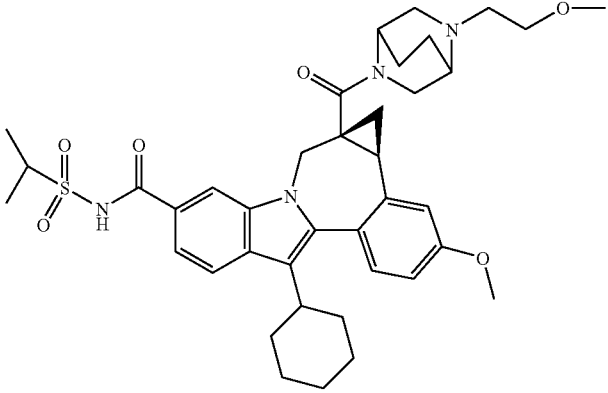 | B | B |

A > 0.5 µM;
B 0.0024 µM-0.5 µM;
C < 0.02 µM but an exact value was not determined;
D > 0.04 µM but an exact value was not determined;
E < 0.07 µM but an exact value was not determined;
G > 0.5 µM to 5.0 µM;
H > 1.0 µM but an exact value was not determined.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgment.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |

TABLE 2-continued

| Brand Name | Type of Inhibitor or Target | Source Company |
|---|---|---|
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Unless otherwise specified, analytical LCMS data on the following intermediates and examples were acquired using the following columns and conditions. Stop time: Gradient time+1 minute; Starting conc: 0% B unless otherwise noted; Eluent A: 5% $CH_3CN$/95% $H_2O$ with 10 mM $NH_4OAc$ (for columns A, D and E); 10% MeOH/90% $H_2O$ with 0.1% TFA (for columns B and C); Eluent B: 95% $CH_3CN$/5% $H_2O$ with 10 mM $NH_4OAc$ (for columns A, D and E); 90% MeOH/10% $H_2O$ with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18.

As as artifact of the software used, some chemical structures have some hydrogen atoms omitted.

Intermediate 1

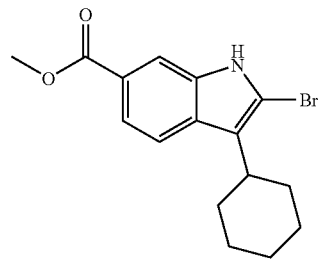

1H-Indole-6-carboxylic acid, 2-bromo-3-cyclohexyl-, methyl ester. Freshly recrystallized pyridinium tribromide (recrystallization from hot AcOH (5 mL per 1 g), rinsed with cold AcOH and dried under high vacuum over KOH) was added in portions (over 10 min.) to a stirring solution of methyl 3-cyclohexyl-1H-indole-6-carboxylate (60 g, 233 mmol) (prepared using procedures describe in WO2004/065367) in $CHCl_3$/THF (1:1, 1.25 L) at 2° C. The reaction solution was stirred at 0-5° C. for 2.5 h, and washed with sat. aq. $NaHSO_3$ (1 L), 1 N HCl (1 L) and brine (1 L). The organic layer was dried ($MgSO_4$) and concentrated. The resulting red oil was diluted with $Et_2O$ and concentrated. The resulting pink solid was dissolved into $Et_2$ O (200 mL) treated with hexanes (300 mL) and partially concentrated. The solids were collected by filtration and rinsed with hexanes. The mother liquor was concentrated to dryness and the procedure repeated. The solids were combined to yield 1H-indole-6-carboxylic acid, 2-bromo-3-cyclohexyl-, methyl ester (64 g, 190 mmol, 82%) as a fluffy pink solid, which was used without further purification. 1HNMR (300 MHz, $CDCl_3$) δ 8.47 (br s, 1H), 8.03 (d, J=1.4 Hz, 1H), 7.74 (dd, J=1.4, 8.8 Hz, 1H), 7.69 (d, J=8.8 Hz, 1H), 3.92 (s, 3H), 2.82 (tt, J=3.7, 11.7 Hz, 1H), 1.98-1.72 (m, 7H), 1.50-1.27 (m, 3H). 13CNMR (75 MHz, CDCl3) δ 168.2, 135.6, 130.2, 123.1, 120.8, 120.3, 118.7, 112.8, 110.7, 52.1, 37.0, 32.2(2), 27.0 (2), 26.1. LCMS: m/e 334 (M−H)⁻, ret time 3.34 min, column A, 4 minute gradient.

Intermediate 2

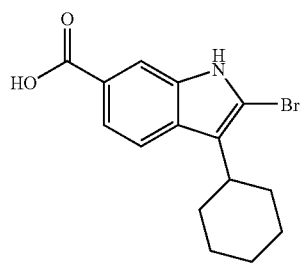

1H-Indole-6-carboxylic acid, 2-bromo-3-cyclohexyl-. A solution of methyl 2-bromo-3-cyclohexyl-1H-indole-6-carboxylate (20 g, 60 mmol) and LiOH (3.8 g, 160 mmol) in MeOH/THF/$H_2O$ (1:1:1, 300 mL) was heated at 90° C. for 2 h. The reaction mixture was cooled in an ice/$H_2O$ bath, neutralized with 1M HCl (~160 mL) diluted with H₂O (250 mL) and stirred for 1 h at rt. The precipitates were collected by filtration rinse with H₂O and dried to yield 1H-indole-6-carboxylic acid, 2-bromo-3-cyclohexyl-(quant.) which was used without further purification.

An alternative procedure that can by used to provide 1H-indole-6-carboxylic acid, 2-bromo-3-cyclohexyl- is described below:

A solution of methyl 2-bromo-3-cyclohexyl-1H-indole-6-carboxylate (117 g, 349 mmol) and LiOH.H₂O (26.4 g, 629 mmol) in MeOH/THF/H2O (1:1:1, 1.8 L) was heated at reflux for 3 h. The reaction mixture was cooled in an ice/H2O bath to ~2° C., neutralized with 1M HCl (~650 mL) (added at such a rate that temperature did not exceed 5° C.), diluted with H2O (1 L) and stirred while warming to ambient temperature. The precipitates were collected by filtration rinsed with H₂O and dried to yield the mono THF solvate of 1H-indole-6-carboxylic acid, 2-bromo-3-cyclohexyl-(135.5 g, 345 mmol, 99%) as a yellow solid, which was used without further purification. 1HNMR (300 MHz, CDCl₃) δ 11.01 (br s, 1H), 8.77 (s, 1H), 8.07 (d, J=1.5 Hz, 1H), 7.82 (dd, J=1.5, 8.8 Hz, 1H), 7.72 (d, J=8.8 Hz, 1H), 3.84 -3.74 (m, 4H), 2.89 (m, 1H), 1.98-1.72 (m, 11H), 1.50-1.24 (m, 3H). 13CNMR (75 MHz, CDCl3) δ 172.7, 135.5, 130.7, 122.3, 120.9(2), 118.8, 113.3, 111.1, 67.9(2), 37.0, 32.2(2), 27.0(2), 26.1, 25.5(2). LCMS: m/e 320 (M–H)⁻, ret time 2.21 min, column A, 4 minute gradient.

Intermediate 3

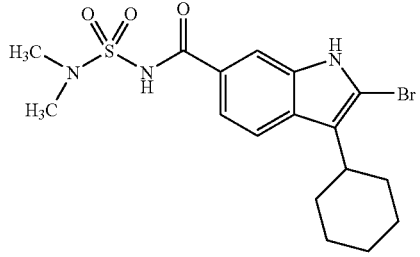

1H-Indole-6-carboxamide, 2-bromo-3-cyclohexyl-N-[(dimethylamino)sulfonyl]-. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of CO₂ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g ,8.8 mmol) in THF (4 mL). Stirring was continued for 24 hr. The mixture was partitioned between ethyl acetate and dilute HCl. The ethyl acetate layer was washed with water followed by brine and dried over Na₂SO₄. The extract was concentrated to dryness to leave the title product as a pale yellow friable foam, (2.0 g, 74%, >90% purity, estimated from NMR). ¹H NMR (300 MHz, DMSO-D6) δ ppm 1.28-1.49 (m, 3H) 1.59-2.04 (m, 7H) 2.74-2.82 (m, 1H) 2.88 (s, 6H) 7.57 (dd, J=8.42, 1.46 Hz, 1H) 7.74 (d, J=8.78 Hz, 1H) 7.91 (s, 1H) 11.71 (s, 1H) 12.08 (s, 1H).

An alternative method for the preparation of 1H-indole-6-carboxamide, 2-bromo-3-cyclohexyl-N-[(dimethylamino) sulfonyl]- is described below.

To a 1 L four necked round bottom flask equipped with a mechanical stirrer, a temperature controller, a N2 inlet, and a condenser, under N2, was added 2-bromo-3-cyclohexyl-1H-indole-6-carboxylic acid (102.0 g, 0.259 mol) and dry THF (300 mL). After stirring for 10 min, CDI (50.3 g, 0.31 mol) was added portion wise. The reaction mixture was then heated to 50° C. for 2 h. After cooling to 30° C., N,N-dimethylaminosulfonamide (41.7 g, 0.336 mol) was added in one portion followed by addition of DBU (54.1 mL, 0.362 mol) drop wise over a period of 1 h. The reaction mixture was then stirred at rt for 20 h. The solvent was removed in vacuo and the residue was partitioned between EtOAc and 1 N HCl (1:1, 2 L). The organic layer was separated and the aqueous layer was extracted with EtOAc (500 mL). The combined organic layers were washed with brine (1.5 L) and dried over MgSO4. The solution was filtered and concentrated in vacuo to give the crude product (111.0 g). The crude product was suspended in EtOAc (400 mL) at 60° C. To the suspension was added heptane (2 L) slowly. The resulting suspension was stirred and cooled to 0° C. It was then filtered. The filter cake was rinsed with small amount of heptane and house vacuum air dried for 2 days. The product was collected as a white solid (92.0 g, 83%). ¹H NMR (MeOD, 300 MHz) δ 7.89 (s, H), 7.77 (d, J=8.4 Hz, 1H), 7.55 (dd, J=8.4 and 1.8 Hz, 1H), 3.01 (s, 6H), 2.73-2.95 (m, 1H), 1.81-2.05 (m, 8H), 1.39-1.50 (m, 2H); m/z 429 (M+H)+.

Intermediate 4

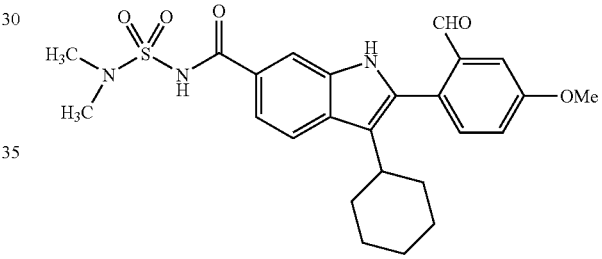

1H-Indole-6-carboxamide, 3-cyclohexyl-N-[(dimethylamino)sulfonyl]-2-(2-formyl-4-methoxyphenyl)-. A mixture of the 2-Bromo-3-cyclohexyl-N-[(dimethylamino)sulfonyl]-1H-indole-6-carboxamide (4.28 g, 0.01 mol), 4-methoxy-2-formylphenyl boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

An alternative procedure for the preparation of 1H-indole-6-carboxamide, 3-cyclohexyl-N-[(dimethylamino)sulfonyl]-2-(2-formyl-4-methoxyphenyl)- is provided below:

To a slurried solution of 2-bromo-3-cyclohexyl-N-[(dimethylamino)sulfonyl]-indole-6-carboxamide (54.0 g, 126 mmol), 4-methoxy-2-formylphenylboronic acid (29.5 g, 164 mmol) and LiCl (13.3 g, 315 mmol) in EtOH/toluene (1:1, 1

L) was added a solution of $Na_2CO_3$ (40.1 g, 379 mmol) in water (380 mL). The reaction mixture was stirred 10 min. and then Pd(PPh3)4 (11.3 g, 10.0 mmol) was added. The reaction solution was flushed with nitrogen and heated at 70° C. (internal monitoring) overnight and then cooled to rt. The reaction was diluted with EtOAc (1 L) and EtOH (100 mL), washed carefully with 1N aqueous HCl (1 L) and brine (500 mL), dried (MgSO4), filtered and concentrated. The residual solids were stirred with Et2O (600 mL) for 1 h and collected by filtration to yield 1H-indole-6-carboxamide, 3-cyclohexyl-N-[(dimethylamino)sulfonyl]-2-(2-formyl-4-methoxyphenyl)- (52.8 g, 109 mmol, 87%) as a yellow powder which was used without further purification. 1HNMR (300 MHz, d6-DMSO) δ 11.66 (s, 1H), 8.17 (s, 1H), 7.75 (d, J=8.4 Hz, 1H), 7.74 (d, J=8.4 Hz, 1H), 7.59 (dd, J=1.4, 8.4 Hz, 1H), 7.23-7.16 (m, 2H), 7.08 (dd, J=2.6, 8.4 Hz, 1H), 6.54 (d, J=8.8 Hz, 1H), 3.86 (s, 3H), 3.22-3.08 (m, 1H), 2.91 (s, 6H), 2.00-1.74 (m, 7H), 1.60-1.38 (m, 3H). 13CNMR (75 MHz, CDCl3) δ 165.7, 158.8, 147.2, 139.1, 134.3, 132.0, 123.4, 122.0, 119.2, 118.2, 114.8, 112.3, 110.4, 109.8, 79.6, 45.9, 37.2(2), 34.7, 32.0(2), 25.9(2), 24.9. LCMS: m/e 482 (M–H)⁻, ret time 2.56 min, column A, 4 minute gradient.

Intermediate 5

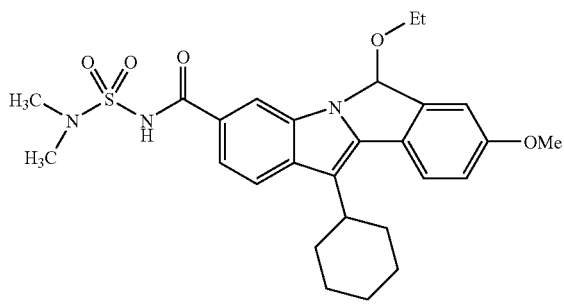

6H-Isoindolo[2,1-a]indole-3-carboxamide, 11-cyclohexyl-N-[(dimethylamino)sulfonyl]-6-ethoxy-8-methoxy-. To a 5 L four necked round bottom flask equipped with a temperature controller, a condenser, a N2 inlet and a mechanical stirrer, was charged toluene (900 mL), EtOH (900 mL), 2-bromo-3-cyclohexyl-N-(N,N-dimethylsulfamoyl)-1H-indole-6-carboxamide (90 g, 0.21 mol), 2-formyl-4-methoxyphenylboronic acid (49.2 g, 0.273 mol) and LiCl (22.1 g, 0.525 mol). The resulting solution was bubbled with $N_2$ for 15 mins. A solution of $Na_2CO_3$ (66.8 g, 0.63 mol) in $H_2O$ (675 mL) was added and the reaction mixture was bubbled with $N_2$ for another (10 mins). Pd(PPh$_3$)$_4$ (7.0 g, 6.3 mmol) was added and the reaction mixture was heated to 70° C. for 20 h. After cooling to 35° C., a solution of 1 N HCl (1.5 L) was added slowly. The resulting mixture was transferred to a 6 L separatory funnel and extracted with EtOAc (2×1.5 L). The combined organic extracts were washed with brine (2 L), dried over MgSO4, filtered and concentrated in vacuo to give a yellow solid, which was triturated with 20% EtOAc in hexane (450 mL, 50° C. to 0° C.) to give 3-cyclohexyl-N-(N,N-dimethylsulfamoyl)-2-(2-formyl-4-methoxyphenyl)-1H-indole-6-carboxamide(65.9 g) as a yellow solid. HPLC purity, 98%.

The mother liquid from the trituration was concentrated in vacuo. The residue was refluxed with EtOH (50 mL) for 3 h. The solution was then cooled to 0° C. The precipitates were filtered and washed with cooled TBME (5° C.) (20 mL). The filter cake was house vacuum air dried to give a further quantity of the title compound as a white solid (16.0 g). HPLC purity, 99%. ¹H NMR (CDCl3, 300 MHz) δ 8.75 (s, 1H), 7.96 (s, 1H), 7.73 (d, J=8.4 Hz, 1H), 7.67 (d, J=8.4 Hz, 1H), 7.45 (dd, J=8.4 and 1.4 Hz, 1H), 7.09 (d, J=2.2 Hz, 1H), 6.98 (dd, J=8.4 and 2.2 Hz, 1H), 6.50 (s, 1H), 3.86 (s, 3H), 3.05 (s, 6H), 2.92-3.13 (m, 3H), 1.85-1.93 (m, 7H), 1.40-1.42 (m, 3H), 1.05 (t, J=7.1 Hz, 3H). m/z 512 (M+H)+.

Intermediate 6

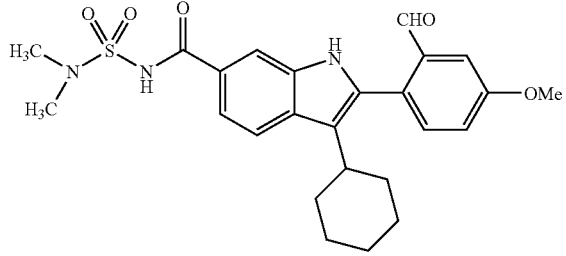

1H-indole-6-carboxamide, 3-cyclohexyl-N-[(dimethylamino)sulfonyl]-2-(2-formyl-4-methoxyphenyl)-. 11-cyclohexyl-N-(N,N-dimethylsulfamoyl)-6-ethoxy-8-methoxy-6H-isoindolo[2,1-a]indole-3-carboxamide was dissolved in THF was vigorously stirred under N2 at rt for 16 h. The resulting suspension was filtered and washed with cooled TBME (2×30 mL). the filer cake was vacuum air dried overnight to give the title compound as a yellow solid. HPLC purity, 99% ¹H NMR (DMSO-d6, 300 MHz) δ 11.65 (s 1H), 8.16 (s, 1H), 7.76 (d, J=5.9 Hz, 1H), 7.73 (d, J=5.9 Hz, 1H), 7.58 (dd, J=8.5 and 1.5 Hz, 1H), 7.17-7.20 (m, 2H), 7.08 (dd, J=8.5 and 1.4 Hz, 1H), 6.55 (d, J=8.6 Hz, 1H), 3.86 (s, 3H), 3.14-3.18 (m, 1H), 2.91 (s, 6H), 1.75-1.99 (m, 7H), 1.48-1.60 (m, 3H); m/z 484 (M+H)+.

Intermediate 7

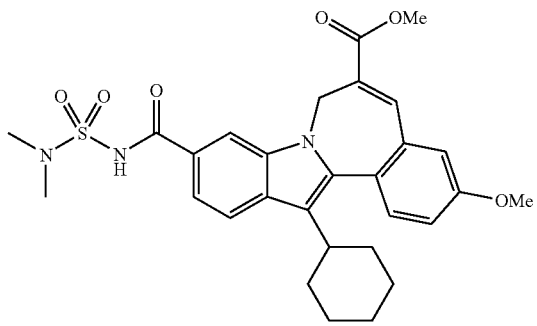

7H-Indolo[2,1-a][2]benzazepine-6-carboxylic acid, 13-cyclohexyl-10-[[[(dimethylamino)sulfonyl]amino]carbonyl]-3-methoxy-, methyl ester. A mixture of the 3-cyclohexyl-N-(N,N-dimethylsulfamoyl)-2-(2-formyl-4-methoxyphenyl)-1H-indole-6-carboxamide (4.8 g, 0.01 mol), methyl 2-(dimethoxyphosphoryl)acrylate (9.7 g, 0.02 mol) and cesium carbonate (7.1 g, 0.02 mol) in DMF (28 mL) was stirred for 20 hr at an oil bath temperature of 55° C. The mixture was poured into ice-water and acidified with dilute HCl to precipitate the crude product. The solid was collected, dried and flash chromatographed on SiO$_2$ (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

An alternate procedure for the preparation of 7H-indolo[2,1-a][2]benzazepine-6-carboxylic acid, 13-cyclohexyl-10-[[[(dimethylamino)sulfonyl]amino]carbonyl]-3-methoxy-, methyl ester is provided below.

A solution of 11-cyclohexyl-N-[(dimethylamino)sulfonyl]-6-hydroxy-8-methoxy-6H-isoindolo[2,1-a]indole-3-carboxamide (cyclic hemiaminal) (63.0 g, 130 mmol), methyl 2-(dimethoxyphosphoryl)acrylate (60 g, 261 mmol), cesium carbonate (106 g, 326 mmol) in DMF (400 mL) was heated at 60° C. (bath temp) for 4.5 h. Additional methyl 2-(dimethoxyphosphoryl)acrylate (15 g, 65 mmol) and cesium carbonate (21.2 g, 65 mmol) were added and the reaction was heated at 60° C. overnight then and cooled to rt. The stirring reaction mixture was diluted with H$_2$O (1 L), slowly neutralized with 1N aqueous HCl (800 mL), stirred 3 h, and then the precipitates were collected by filtration. The solids were triturated with Et2O (800 mL) and dried to yield methyl 7H-indolo[2,1-a][2]benzazepine-6-carboxylic acid, 13-cyclohexyl-10-[[[(dimethylamino)sulfonyl]amino]carbonyl]-3-methoxy-, methyl ester (70.2 g, 127 mmol, 98%) as a yellow solid which was used without further purification. 1HNMR (300 MHz, CDCl3) δ 8.67 (s, 1H), 8.09 (s, 1H), 7.86 (d, J=8.4 Hz, 1H), 7.80 (s, 1H), 7.50 (d, J=8.4 Hz, 1H), 7.42 (d, J=8.8 Hz, 1H), 7.08 (dd, J=2.6, 8.8 Hz, 1H), 6.98 (d, J=2.6 Hz, 1H), 5.75-5.51 (m, 1H), 4.29-4.01 (m, 1H), 3.89 (s, 3H), 3.82 (s, 3H), 3.05 (s, 6H), 2.87-2.73 (m, 1H), 2.11-1.12 (m, 10H). LCMS: m/e 550 (M−H)−, ret time 3.21 min, column A, 4 minute gradient.

Intermediate 8

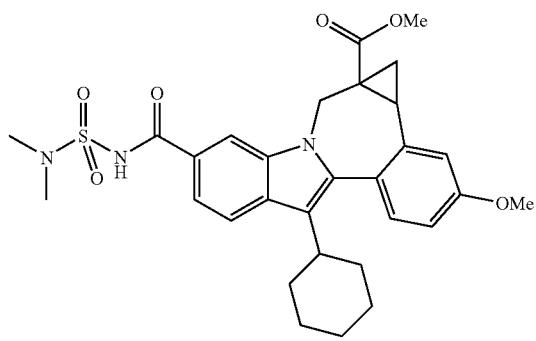

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (+/−)-. DMSO (5 mL) was added to a mixture of trimethylsulfoxonium iodide (199 mg, 0.906 mmol) and NaH (38 mg in 60% oil dispersion, 0.953 mmol) in a round-bottomed flask. The reaction mixture was stirred at rt for 0.5 hr. 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (125 mg, 0.227 mmol) was then added and the reaction mixture was stirred at rt. for 3 hr., and then at 50° C. for a further 3 hr. The reaction was then quenched with water and acidified with 1N HCl solution. The crude product then precipitated as a light yellow solid which was collected by filtration and air dried, (106 mg, 83% yield). 6 mg of this material was then purified by Prep. HPLC to afford the title compound as a light yellow solid (1.8 mg). MS m/z 566(MH+), Retention time: 3.850 min.1H NMR (500 MHz, MeOD) δ ppm 0.28 (m, 0.36H) 1.19-2.20 (m, 11.64H) 2.70-3.02 (m, 2H) 3.03 (s, 2.16H) 3.05 (s, 3.84H) 3.49 (d, J=15.26 Hz, 0.64H) 3.54 (s, 1.92H) 3.83 (s, 1.08H) 3.91 (s, 3H) 4.08 (d, J=15.26 Hz, 0.36H) 5.29 (d, J=15.26 Hz, 0.36H) 5.50 (d, J=14.95 Hz, 0.64H) 6.98-7.06 (m, 1H) 7.16 (d, J=2.44 Hz, 0.36H) 7.23 (d, J=2.44 Hz, 0.64H) 7.30 (d, J=8.55 Hz, 0.64H) 7.34 (d, J=8.55 Hz, 0.36H) 7.56 (dd, J=8.55, 1.53 Hz, 0.64H) 7.63 (dd, J=8.55, 1.53 Hz, 0.36H) 7.88 (d, J=8.55 Hz, 0.64H) 7.91 (d, J=8.55 Hz, 0.36H) 8.12 (s, 0.36H) 8.33 (d, J=1.53 Hz, 0.64H).

An alternative procedure for the preparation of the title compounds is provided below.

To a flame dried, four necked, 1 L round bottom flask equipped with a mechanical stirrer, N2 inlet and a thermometer, under N2, was charged sodium hydride (95%) (3.09 g, 129.2 mmol) and dry DMF (200 mL). With vigorous stirring, trimethylsulfoxonium iodide (32.5 g, 147.3 mmol) portion wise during which time the temperature rose to 30° C. After stirring for 30 mins, a solution of 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (33.8 g, 61.3 mmol) in dry DMF (70 mL) was added quickly. The reaction mixture was stirred below 30° C. for 30 mins and then poured into an ice cold solution of 1 N HCl (130 mL) in H2O (2 L) portion wise. After the resulting suspension was mechanically stirred for 1 h, the precipitates were filtered and the filter cake was washed with H2O (100 mL). The filter cake was partitioned between EtOAc and 0.5 N HCl (1:1, 4 L). The organic phase was separated, washed with H2O (1 L) and brine (1 L), dried over MgSO$_4$, filtered and concentrated in vacuo. The residue was dissolved in EtOAc (150 mL), and the solution was filtered through a silica gel pad (300 g in hexane) and rinsed with 50% EtOAc in hexane (5 L). The filtrate was concentrated in vacuo to give a slightly yellow solid which was triturated with 10% EtOAc in TBME (220 mL) from 50° C. to 0° C. to give cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (+/−)- as a white solid (26.1 g, 75% yield). HPLC purity, 100%. $^1$H NMR (DMSO-d$_6$, 300 MHz) δ 11.61 (s, 1H), 8.47 (s, 0.5H), 8.25 (s, 0.5H), 7.81-7.88 (m, 1H), 7.57-7.63 (m, 1H), 7.23-7.29 (m, 2H), 7.01-7.07 (m, 1H), 5.43 (d, J=15.0 Hz, 0.5H), 5.22 (d, J=15 Hz, 0.5H), 4.04 (dd, J=15.4 and 6.6 Hz, 0.5H), 3.83 (s, 3H), 3.75 (s, 1H), 3.08-3.47 (m, 0.5H), 3.29 (s, 3H), 2.73-2.92 (m, 8H), 1.11-1.99 (m, 10.5H), 0.20 (m, 0.5H); m/z 566 (M+H)$^+$.

Intermediate 9

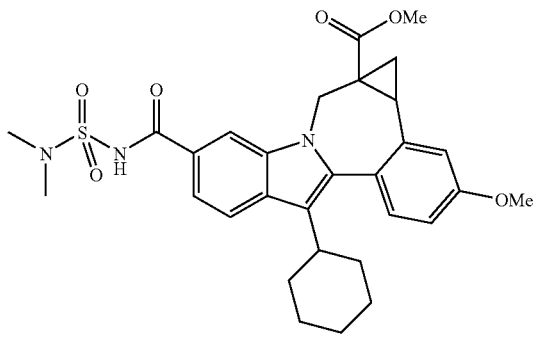

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)-. A sample of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-methyl ester was dissolved in EtOH/CH$_3$CN 1/1+0.5% DEA at a concentration of 50 mg/ml. [The addition of DEA ensures the compound remains in solution during the injection process]. This solution was then injected onto a Thar SFC-350 preparative SFC under the conditions shown below.

Preparative conditions on Thar SFC-350: Column: Chiralcel OJ-H 5×25 cm; mobile phase: 25% MeOH/CH3CN (1/1) in CO2; pressure (bar): 100; flow rate (ml/min): 240; solution concentration (mg/ml): 50; injection amount (ml): 4.5-5; Cycle time (min/inj): 6.5-7; Temperature (° C.): 45; throughput (g/hr): ~2; Detector wavelength (nm): 254.

From 371.4 g of racemic starting material, a total of 177.3 g of the desired second eluting (−) isomer was obtained, containing ~1 Meq of diethylamine. This material was purified using the following procedure. The mixture (24.7 g) dissolved in dichloromethane (800 mL)) was washed sequentially with; 0.5 N HCl (1×400 mL, 1×240 mL), H$_2$O (2×240 mL), and brine (2×240 mL). The organic layer was then dried (Anhy. Na$_2$SO$_4$), filtered and evaporated to give 22.33 g of (cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)- as a yellow solid (92% recovery). HPLC$^1$>99% (Rt 2.38 min); LC/MS (ES$^+$) 566.51 (M+H, 100); [α]$_D^{25}$ $^C$ -194.64° (c 1.03, MeOH). Anal. Calcd for C$_{30}$H$_{35}$N$_3$O$_6$S.0.33H$_2$O: C, 63.04; H, 6.29; N, 7.35; S, 5.61; H$_2$O, 1.04. Found: C, 63.07; H, 6.01; N, 7.24; S, 5.58; H$_2$O, 1.03. The NMR shows the absence of Et$_2$NH. The EE of this material was determined to be >99% using the following analytical HPLC procedure.

Analytical conditions of ee determination on Thar analytical SFC. Analytical Column: Chiralcel OJ (0.46×25 cm, 10 μl); BPR pressure: 100 bars; Temperature: 35° C.; Flow rate: 3.0 ml/min; Mobile Phase: 15% MeOH/CH$_3$CN (1/1) in CO$_2$; Detector Wavelength: 254 nm; Retention time (min): 4, 6.5.

Intermediate 10

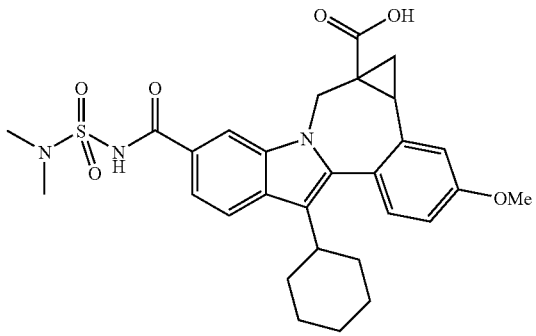

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. To a solution of (−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester (22.33 g, 39.5 mmol) in MeOH (300 mL) was added 1 N NaOH (120 mL) slowly over 20 min., while maintaining the reaction temperature <30° C. The mixture was stirred at rt under N$_2$ for 18 h. The HPLC indicated the reaction was complete. To the reaction solution was added 1 N HCl (130 mL). After addition was complete, the pH of the reaction mixture was about 2. The methanol in the reaction mixture was evaporated. Water (300 mL) was added to the mixture which was then extracted with CH$_2$Cl$_2$ (1×600 mL, 1×200 mL). The combined extracts were washed with H$_2$O (2×300 mL), brine (2×300 mL), dried (Na$_2$SO$_4$) and evaporated to give 20.82 g (96% yield) of the title compound as a yellow solid. HPLC conditions column: Phenomenoex Synergi Polar-RP 4 um 4.6×50 mm; UV: 220 nm; gradient time: 4 min; flow rate: 4 mL/min, 75-100% B; solvent A: 10% MeOH/90% H$_2$O with 0.2% H$_3$PO$_4$, solvent B: 90% MeOH/10% H$_2$O with 0.2% H$_3$PO$_4$. HPLC >99% (Rt 1.80 min.) LC/MS (ES$^+$) 552.25 (M+H, 100); [α]$_D^{25}$ $^C$-166.99° (c 1.00, MeOH). GC analysis: CH$_2$Cl$_2$ 4.94%; Anal. Calcd for C$_{29}$H$_{33}$N$_3$O$_6$S.0.16 H$_2$O.0.35 CH$_2$Cl$_2$: C, 60.37; H, 5.87; N, 7.20; S, 5.49; H$_2$O, 0.49; CH$_2$Cl$_2$, 5.02. Found: C, 59.95; H, 5.89; N, 7.03; S, 5.38; H$_2$O, 0.47; CH$_2$Cl$_2$, 4.94.

Intermediate 11

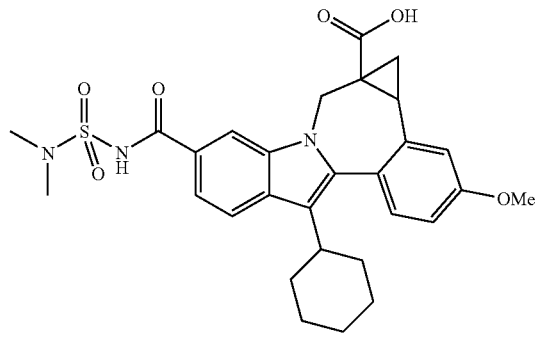

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+/−)-. To a solution of ((+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester (100 mg, 0.177 mmol) in THF/Methanol mixture (2.0 mL/2.0 mL), 2N NaOH solution (1.0 mL) was added. The reaction mixture was heated at 90° C. under microwave conditions for 5 min. It was then concentrated, acidified with 1N HCl solution and extracted with ethyl acetate (2×20 mL). The organic layers were combined, dried (MgSO$_4$), filtered and concentrated. The residue was purified by preparative HPLC to afford the desired product as a light yellow solid, (59 mg, 60% yield). MS m/z 552(MH$^+$), Retention time: 3.850 min. 1H NMR (300 MHz, MeOD) δ ppm 0.25 (m, 0.38H) 1.14-2.22 (m, 11.62H) 2.69-2.98 (m, 2H) 3.02 (s, 2.28H) 3.02 (s, 3.72H) 3.41 (d, J=15.00 Hz, 0.62H) 3.88 (s, 3H) 4.01 (d, J=15.00 Hz, 0.38H) 5.26 (d, J=15.00 Hz, 0.38H) 5.45 (d, J=14.64 Hz, 0.62H) 6.94-7.02 (m, 1H) 7.13 (d, J=2.56 Hz, 0.38H) 7.21 (d, J=2.20 Hz, 0.62H) 7.26 (d, J=8.42 Hz, 0.62H) 7.30 (d, J=8.78 Hz, 0.38H) 7.53 (dd, J=8.42, 1.46 Hz, 0.62H) 7.61 (dd, J=8.60, 1.65 Hz, 0.38H)

7.85 (d, J=8.42 Hz, 0.62H) 7.89 (d, J=8.42 Hz, 0.38H) 8.10 (s, 0.38H) 8.28 (d, J=1.46 Hz, 0.62H).

Intermediate 12

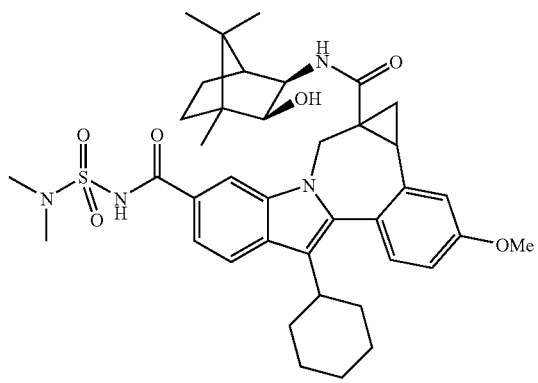

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aR)-[partial]-. TBTU (437 mg, 1.36 mmol) and DIPEA (0.95 mL, 5.436 mmol) were added to a solution of ((+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-(500 mg, 0.906 mmol) in DMSO (20.0 mL). The reaction mixture was stirred at rt for 15 min. (2S,3R)-3-Amino-1,7,7-trimethylbicyclo[2.2.1]heptan-2-ol (280 mg, 1.36 mmol) was then added and the reaction mixture was stirred at rt overnight. The reaction mixture was quenched with water and acidified with 1N HCl solution. A brown solid separated which was collected by filtration. This material was then fractionated by Preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aR)-[partial]-elutes before Cycloprop[d]indolo[2,1-a][2]benzazepine-1a,5(2H)-dicarboxamide, 8-cyclohexyl-N$^5$-[sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]-under the HPLC conditions described above. Product obtained as a light yellow solid, 230 mg, 36% yield). MS m/703(MH$^+$), Retention time: 3.936 min. 1H NMR (500 MHz, MeOD) δ ppm 0.14-0.24 (m, 2.64H) 0.51 (s, 2.46H) 0.72-2.21 (m, 20.9H) 2.49 (m, 0.18H) 2.62 (m, 0.82H) 2.85 (m, 0.18H) 2.96 (m, 0.82H) 3.03 (s, 6H) 3.39 (m, 0.82H) 3.49-3.58 (m, 1.64H) 3.71-3.80 (m, 0.36H) 3.90 (s, 3H) 4.17 (d, J=14.65 Hz, 0.18H) 5.06 (d, J=14.65 Hz, 0.18H) 5.37 (d, J=14.95 Hz, 0.82H) 6.73 (d, J=5.49 Hz, 0.82H) 6.98-7.05 (m, 1H) 7.08 (d, J=4.58 Hz, 0.18H) 7.10 (d, J=2.44 Hz, 0.18H) 7.21 (d, J=2.44 Hz, 0.82H)

7.31 (d, J=8.55 Hz, 0.82H) 7.34 (d, J=8.55 Hz, 0.18H) 7.59-7.64 (m, 1H) 7.87-7.93 (m, 1H) 7.99 (s, 0.18H) 8.09 (d, J=1.22 Hz, 0.82H).

Intermediate 13

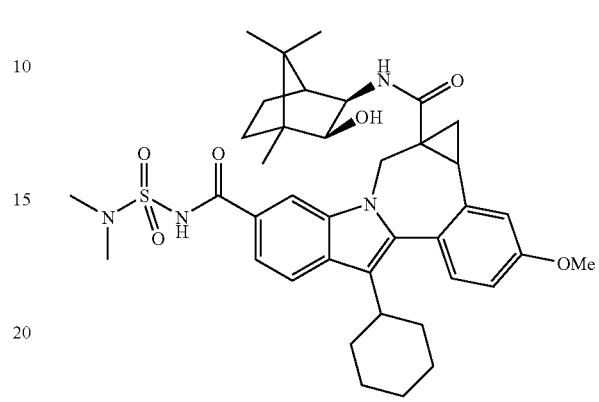

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]-. TBTU (437 mg, 1.36 mmol) and DIPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-(500 mg, 0.906 mmol) in DMSO (20.0 mL). The reaction mixture was stirred at rt for 15 min. Then (2S, 3R)-3-amino-1,7,7-trimethylbicyclo[2.2.1]heptan-2-ol (280 mg, 1.36 mmol) was added, and the reaction mixture was stirred at rt overnight. The reaction mixture was quenched with water and then acidified with 1N HCl solution. A brown colored solid separated that was collected by filtration. This material was then fractionated by preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]- elutes after cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1 ]hept-2-yl]-11-methoxy-, (1aR)-[partial]- under the HPLC conditions described above. Product obtained as a light yellow solid, 215 mg, 34% yield). MS m/703(MH$^+$), Retention time: 4.038 min. 1H NMR (500 MHz, MeOD) δ ppm 0.20 (m, 0.38H) 0.75 (s, 1.86H) 0.76 (s, 1.86H) 0.84 (s, 1.86H) 0.85 (s, 1.14H) 0.89-2.18 (m, 18.9H) 2.52 (m, 0.38H) 2.70 (m, 0.62H) 2.85 (m, 0.38H) 2.97 (m, 0.62H) 3.03 (s, 2.28H) 3.04 (s, 3.72H) 3.33-3.39 (m, 0.62H) 3.43-3.51 (m, 1.24H) 3.73-3.77 (m, 0.38H) 3.78-3.84 (m, 0.38H) 3.90 (s, 1.86H) 3.90 (s, 1.14H) 4.14 (d, J=14.65 Hz, 0.38H) 5.11 (d, J=14.65 Hz, 0.38H) 5.44 (d, J=15.26 Hz, 0.62H) 6.68 (d, J=4.88 Hz, 0.62H) 6.96-7.03 (m, 1H) 7.07 (d, J=5.19 Hz, 0.38H) 7.12 (d, J=2.44 Hz, 0.38H) 7.23 (d, J=2.14 Hz, 0.62H) 7.27 (d, J=8.54 Hz, 0.62H) 7.33 (d, J=8.54 Hz, 0.38H) 7.55

(dd, J=8.39, 1.68 Hz, 0.62H) 7.62 (dd, J=8.55, 1.53 Hz, 0.38H) 7.87 (d, J=8.54 Hz, 0.62H) 7.91 (d, J=8.55 Hz, 0.38H) 8.08 (d, J=1.22 Hz, 0.38H) 8.10 (d, J=1.22 Hz, 0.62H).

Intermediate 14

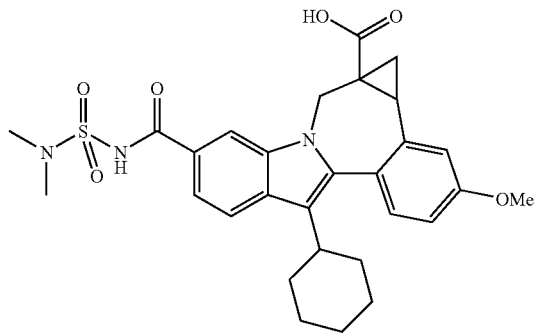

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. 10 N NaOH (2.0 mL, 20 mmol) solution and 4 mL of water were added to a solution of cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aR)-[partial]- (160 mg, 0.228 mmol) in THF/MeOH (7 mL/7 mL). The reaction mixture was heated at 120° C. under microwave conditions for 1 hr. It was then concentrated, acidified with conc. HCl solution and extracted with ethyl acetate twice (2×30 mL). The organic layers were combined, dried (MgSO$_4$), filtered and concentrated in vacuo to an orange oil. The crude product was then purified by Prep. HPLC column to afford the product a light yellow solid, (80 mg, 64% yield). Average specific rotation −130.85°; Solvent MeOH; Wavelength 589 nm; 50 cm cell. MS m/552(MH$^+$), Retention time: 3.760 min. 1H NMR (500 MHz, MeOD) δ ppm 0.27 (m, 0.38H) 1.14-2.22 (m, 11.62H) 2.76 (m, 0.38H) 2.80-2.92 (m, 1H) 2.92-3.09 (m, 6.62H) 3.45 (d, J=14.95 Hz, 0.62H) 3.90 (s, 1.86H) 3.91 (s, 1.14H) 4.04 (d, J=15.26 Hz, 0.38H) 5.28 (d, J=15.26 Hz, 0.38H) 5.47 (d, J=15.26 Hz, 0.62H) 6.95-7.05 (m, 1H) 7.15 (d, J=2.75 Hz, 0.38H) 7.23 (d, J=1.83 Hz, 0.62H) 7.28 (d, J=8.55 Hz, 0.62H) 7.33 (d, J=8.54 Hz, 0.38H) 7.54 (dd, J=8.39, 1.68 Hz, 0.62H) 7.63 (dd, J=8.55, 1.53 Hz, 0.38H) 7.86 (d, J=8.55 Hz, 0.62H) 7.91 (d, J=8.55 Hz, 0.38H) 8.11 (d, J=1.22 Hz, 0.62H) 8.29 (d, J=1.22 Hz, 0.38H).

Intermediate 15

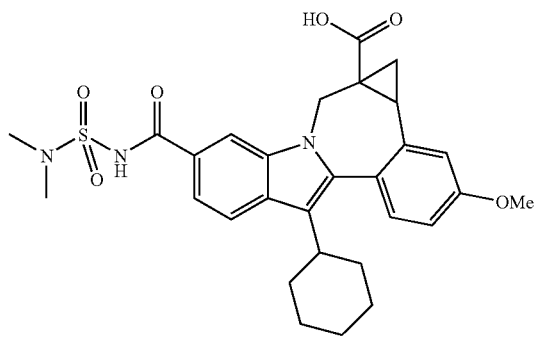

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+)-. 10 N NaOH (1.8 mL, 18 mmol) solution and 4 mL of water were added to a solution of cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]- (130 mg, 0.185 mmol) in bTHF/MeOH (7 mL/7 mL). The reaction mixture was heated at 120° C. under microwave conditions for 1 hr. It was concentrated, acidified with conc. HCl solution and extracted with ethyl acetate twice (2×30 mL). The organic layers were combined, dried (MgSO$_4$), filtered and concentrated in vacuo to give an orange oil. The crude product was then purified by Prep. HPLC column to afford the product as a light yellow solid, (68 mg, 67% yield). Average specific rotation+174.73°; Solvent MeOH; Wavelength 589 nm; 50 cm cell MS m/552(MH$^+$), Retention time: 3.773 min. 1H NMR (500 MHz, MeOD) δ ppm 0.27 (m, 0.38H) 1.14-2.22 (m, 11.62H) 2.76 (m, 0.38H) 2.80-2.92 (m, 1H) 2.92-3.09 (m, 6.62H) 3.45 (d, J=14.95 Hz, 0.62H) 3.90 (s, 1.86H) 3.91 (s, 1.14H) 4.04 (d, J=15.26 Hz, 0.38H) 5.28 (d, J=15.26 Hz, 0.38H) 5.47 (d, J=15.26 Hz, 0.62H) 6.95-7.05 (m, 1H) 7.15 (d, J=2.75 Hz, 0.38H) 7.23 (d, J=1.83 Hz, 0.62H) 7.28 (d, J=8.55 Hz, 0.62H) 7.33 (d, J=8.54 Hz, 0.38H) 7.54 (dd, J=8.39, 1.68 Hz, 0.62H) 7.63 (dd, J=8.55, 1.53 Hz, 0.38H) 7.86 (d, J=8.55 Hz, 0.62H) 7.91 (d, J=8.55 Hz, 0.38H) 8.11 (d, J=1.22 Hz, 0.62H) 8.29 (d, J=1.22 Hz, 0.38H).

Intermediate 16

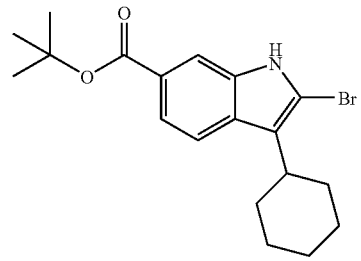

1H-Indole-6-carboxylic acid, 2-bromo-3-cyclohexyl-, 1,1-dimethylethyl ester. To a mechanically stirred solution of 2-bromo-3-cyclohexyl-1H-indole-6-carboxylic acid (80 g, 0.24 m) in dry methylene dichloride(1.2 L) and THF (100 mL) were added activated molecular sieves (4A, 80 g) and silver carbonate (275 g, 0.99 m). The reaction mixture was cooled to 0° C. and t-Butyl bromide (142 g, 1.04 m) was added drop wise. The mixture was stirred overnight at rt and monitored by TLC (Hexane-Ethyl acetate 80:20, R$_f$ (Product)= 0.7). If any bromo acid was left unconverted a further 10% of silver carbonate was added and stirring was continued for an addition 2-4 h. On completion, the reaction mixture was filtered through a thin bed of celite. The filtrand was washed with methylene dichloride (500 mL). The combined filtrates were concentrated in-vacuo, and the crude product thus obtained was purified by silica gel chromatography: (230-400 mesh, eluted with a gradient of ethyl acetate in pet ether 0-2%). Homogeneous fractions were combined and evaporated under reduced pressure to give 80 g (85%) of the title compound. HPLC: 90.1% (RT=6.56 min), Column: C18 BDS, (50×4.6 mm), Mobile Phase: Gradient of 0.1% TFA in water: ACN (30→100→30), Flow rate 0.8 mL/min. LCMS:

99.8% (RT=4.44 min), Column: Geneis, C18 50×4.6 mm Mobile Phase: Gradient of 0.1% Formic acid in water: ACN (70→95→70), Flow rate: 0.8 mL/min; M−1=376.5; $^1$H NMR CDCl$_3$) (400 MHz) δ 1.37-1.40 (m, 3H, cyc.Hexyl), 1.62 (s, 9H, t-Bu), 1.80-1.94 (two sets of m, 3H, & 4H respectively, cyc.Hexyl part), 2.81 (m, 1H, CH of cyc.Hexyl-benzylic), 7.70-7.75 (m, 2H, Indole-H$_{4\&5}$), 8.04 (s, 1H, Indole-H$_7$), 8.52 (s, 1H, Indole-NH).

Intermediate 17

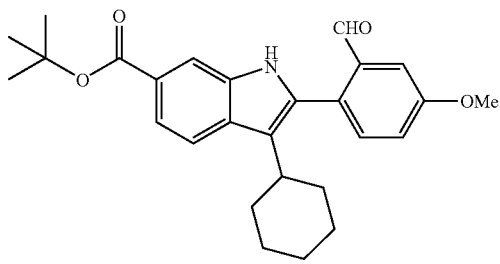

1H-Indole-6-carboxylic acid, 3-cyclohexyl-2-(2-formyl-4-methoxyphenyl)-,1,1-dimethylethyl ester. tert-Butyl 2-bromo-3-cyclohexyl-1H-indole-6-carboxylate (72 g, 0.19 m) was dissolved in a 1:1 mixture of toluene and ethanol (720 mL) and degasified. LiCl (23.9 g, 0.51 m) was then added, followed by sodium carbonate (720 mL, 1.0 M solution degasified separately,) and Pd-tetrakis (13.1 g, 0.011 m). After stirring for 0.25 h, 2-formyl-4-methoxyphenylboronic acid (41.1 g, 0.22 m) was added and the reaction mixture was heated to 85° C. for 4 h. The reaction was then monitored by TLC, (Hexane-Ethyl acetate 80:20, R$_f$ (Product)=0.55). On completion, the reaction mixture was cooled to rt and water (1.0 L) was added followed by ethyl acetate (1.0 L). The organic layer was washed with brine, and dried and concentrated under vacuum to afford the title compound as a yellow solid. Yield 75 g (74%). HPLC: 99.7% (RT=6.30 min), Column: C18 BDS (4.6×50 mm), SC-307, Mobile Phase: Gradient of 0.1% TFA in water: ACN (30→100→30), Flow rate 0.8 mL/min. LCMS: 98.0% (RT=5.28 min), Column: Geneis, C18 (50×4.6 mm), Mobile Phase: Gradient of 0.1% Formic acid in water: ACN (70→95→70), Flow rate: 0.8 mL/min; M−1=432.2; $^1$H NMR (DMSO-d$_6$) (400 MHz) δ 1.40-1.48 (m, 3H, cyc.Hexyl), 1.57 (s, 9H, t-Bu), 1.84-1.90 (m, 7H, cyc.Hexyl part), 3.09 (m, 1H, CH of cyc.Hexyl-benzylic), 3.84 (s, 3H, OCH$_3$), 6.55 (d, J=4 Hz, 1H, aryl H$_2$), 7.06 (d, 1H, aryl H$_3$), 7.08 (s, 1H, aryl H$_6$), 7.23 (d, 1H Indole-H$_5$), 7.53 (d, J=8 Hz, 1H, Indole-H$_4$), 7.70-7.75 (m, 2H, NH+Indole-H$_7$), 8.06 (s, 1H, CHO).

Intermediate 18

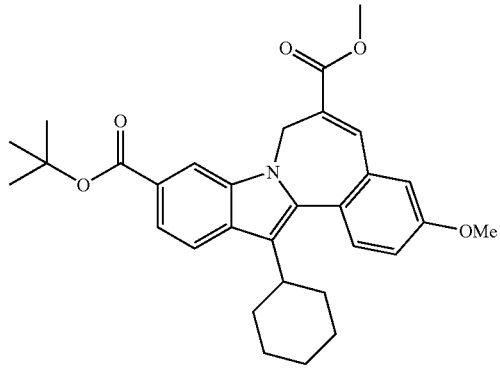

7H-Indolo[2,1-a][2]benzazepine-6,10-dicarboxylic acid, 13-cyclohexyl-, 10-(1,1-dimethylethyl) 6-methyl ester. tert-Butyl 3-cyclohexyl-2-(2-formyl-4-methoxyphenyl)-1H-indole-6-carboxylate (62.5 g, 0.144 m) was dissolved in dry DMF (1.2 L) and stirred mechanically. Cesium carbonate (84 g, 0.17 m) and methyl 2-(dimethoxyphosphoryl)acrylate (65-70% GC pure, 56.2 g, 0.18 m) were then added and the reaction mixture was heated to 65° C. for 4 h, and the reaction was monitored by TLC (Hexane-Ethyl acetate 80:20, R$_f$ (Product)=0.7). On completion, the mixture was cooled to rt, then quenched with water (1.0 L). A yellow solid precipitated, which was collected by filtration and air dried. This material was then slurried in methanol, filtered, and dried under vacuum to give the product as a yellow powder, (70 g, 90%). HPLC: 99.1% (RT=6.45 min), Column: C18 BDS (4.6×50 mm), Mobile Phase: Gradient of 0.1% TFA in water: ACN (30→100→30), Flow rate 0.8 mL/min. LCMS: 100% (RT=7.00 min), Column: Geneis, C18 (50×4.6 mm), Mobile Phase: Gradient of 0.1% Formic acid in water: ACN (70→95→70), Flow rate: 0.8 mL/min; M+1=502.2; $^1$H NMR (CDCl$_3$) (400 MHz) δ 1.10-1.30 (m, 3H, cyc.Hexyl), 1.64 (s, 9H, t-Bu), 1.77-2.07 (m, 7H, cyc.Hexyl part), 2.80 (m, 1H, CH of cyc.Hexyl-benzylic), 3.84 (s, 3H, OCH$_3$), 3.93 (s, 3H, COOCH$_3$), 4.15 & 5.65 (two br. peak., 1H each, allylic CH$_2$), 6.95 (s, 1H, aryl H$_{6'}$), 7.01 (d, 1H, aryl H$_{2'}$), 7.53 (d, J=8 Hz, 1H, aryl H$_{3'}$), 7.70 (d, J=4 Hz, 1H, Indole-H$_5$), 7.84 (s+d, 2H, olefinic H+Indole-H$_4$), 8.24 (s, 1H, indole-H$_7$); $^{13}$C NMR (CDCl$_3$) (100.0 MHz) δ 166.92, 165.71, 158.96, 142.28, 136.47, 13.50, 134.61, 132.43, 132.01, 129.73, 124.78, 124.68, 120.33, 119.39, 119.04, 115.62, 115.05, 111.27, 80.27, 55.49, 52.50, 39.09, 36.81, 33.40, 28.38, 27.15, 26.28.

Intermediate 19

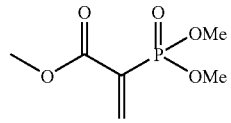

2-Propenoic acid, 2-(dimethoxyphosphinyl)-, methyl ester. To a 5 L four necked round bottom flask equipped with a mechanical stirrer, a condenser, a temperature controller and a N2 inlet, was charged paraformaldehyde (40.5 g, 1.35 mol), MeOH (2 L) and piperidine (2 mL). The reaction mixture was heated to reflux under N2 for 3 h. After cooling to 50° C., 2-(dimethoxyphosphoryl)acetate (150 g, 0.824 mol) was added in one portion. The reaction mixture was continued to reflux for 18 h. After cooling to rt, the reaction solution was concentrated in vacuo to give a clear colorless oil. The above oil was dissolved in dry toluene (1 L) in a 3 L four necked round bottom flask equipped a temperature controller, a N$_2$ inlet, a magnetic stirrer and a Dean-Stark apparatus. To the solution was added TsOH.H$_2$O (5.2 g). The reaction mixture was then refluxed azeotropically to remove methanol for 18 h. After cooling to rt, the solution was concentrated in vacuo to give a yellow oil which was vacuum distilled at 150-155° C./0.2 mmHg to afford the product as a colorless oil (135.0 g). Purity, 90% based on 1H NMR. $^1$H NMR (CDCl3, 300 MHz)

δ 7.0 (dd, J=42.4 and 1.5 Hz, 1H), 6.73 (dd, J=20.5 and 1.8 Hz, 1H), 3.80 (s, 6H), 3.76 (s, 3H).

Intermediate 20

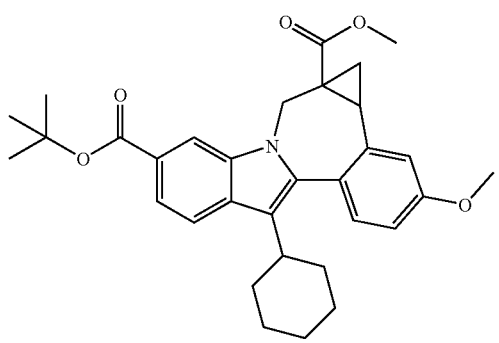

Cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, ((+/−). Sodium hydride (96 mg, 4 mmol) was added to a stirred suspension of trimethylsulfoxonium chloride (567 mg, 4.4 mmol) in anhydrous DMSO (10 mL) under nitrogen. The resultant mixture was stirred at rt for 30-45 min and then neat 7H-indolo[2,1-a][2]benzazepine-6,10-dicarboxylic acid, 13-cyclohexyl-3-methoxy-, 10-(1,1-dimethylethyl) 6-methyl ester (1.0, 2 mmol) was added in small portions. The suspension was diluted with DMSO (5 mL) and heated at 50° C. for 3-4 h. The reaction mixture was allowed to cool to rt and water was added. A solid separated, which was collected by filtration and washed with water and then air dried overnight to afford 1.15 g of crude product. This material was purified by flash column chromatography (silica gel, 3% MeOH in DCM) to provide pure title compound (0.96 g): LC/MS: Retention time 3.816 min; m/e 516 (MH$^+$). $^1$H NMR (400 MHz, CDCl$_3$): The product was observed to exist as inter-converting rotamers, as evidenced from the compound's NMR spectrum.

The following procedure is an example of a method to effect the resolution of racemic cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−). A sample of cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−)- was dissolved in a mixture of isopropanol and acetonitrile (8:2) to give a final concentration of 20 mg/mL. This mixture was injected on a preparative chiral SFC chromatography system using the following conditions: Chiralcel OJ-H column, 4.6×250 mm, 5 μm; Mobile Phase: 8% MeOH in CO$_2$; Temp: 35° C.; Flow rate: 2 mL/min for 16 min; UV monitored @260 nm; Injection: 5 μl of ~20.0 mg/mL in IPA:ACN (8:2).

Intermediate 21

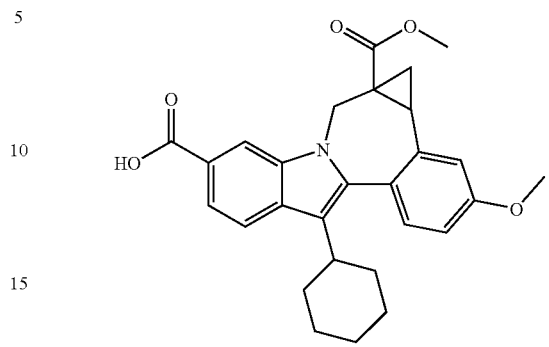

Cycloprop[d]indolo[2,1-a][2]benzazepine-1a,5(2H)-dicarboxylic acid, 8-cyclohexyl-1,12b-dihydro-11-methoxy-, 1a-methyl ester, (+/−)-. TFA (5 mL) was added to a solution of (+/−) 8-Cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester (515 mg, 1 mmol) in anhydrous DCM (10 mL). The resultant solution was stirred at rt for approximately 8 to 12 hr. The reaction was then evaporated to dryness to afford the title compound (0.47 g, 100%). LC/MS: Retention time 2.245 min; m/e 460 (MH$^+$). $^1$H NMR (400 MHz, CDCl$_3$): From the compounds NMR spectrum, the product was observed to exist as a mixture of interconverting rotamers.

Intermediate 22

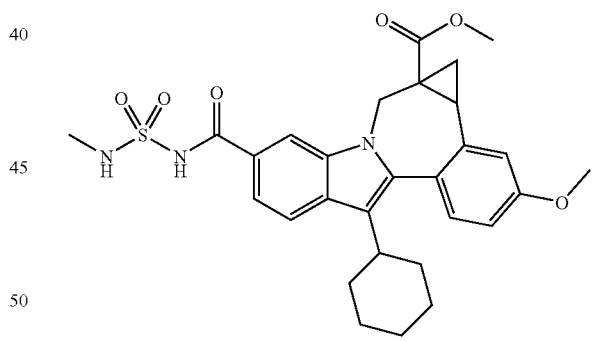

Cycloprop[d]indolo[2,1-a][2]benzazepine-1a(2H)-carboxylic acid, 8-cyclohexyl-1,12b-dihydro-11-methoxy-5-[[[(methylamino)sulfonyl]amino]carbonyl]-, methyl ester. A solution of 8-Cyclohexyl-1,1a,2,12b-tetrahydro-11-methoxy-1a-(methoxycarbonyl)-cycloprop[d]indolo[2,1-a][2]benzazepine-5-carboxylic acid (140 mg, 0.31 mmol) and CDI (64 mg, 0.40 mmol) in THF (3 mL) was stirred for 1 hr at 60° C. N-methylsulfamide (68 mg, 0.62 mmol) and DBU (71.6 mg, 0.47 mmol) were added and the mixture was stirred at 60° C. overnight. The reaction was then poured into cold water, acidified with dilute hydrochloric acid and extracted into ethyl acetate. The extracts were washed sequentially with dilute hydrochloric acid (0.1 N), and brine, and then dried (anhy. sodium sulfate), filtered and evaporated to provide the title compound as a brown solid. ESI-MS m/e 552 (MH⁺). This material was used without further purification.

Intermediate 23

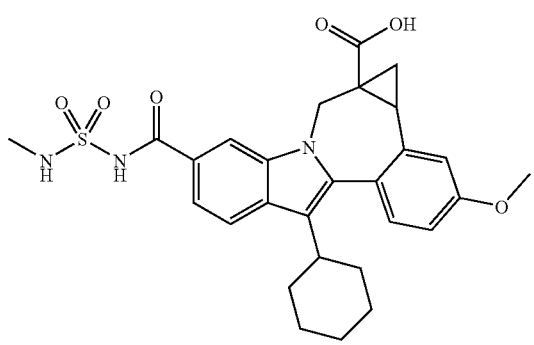

Cycloprop[d]indolo[2,1-a][2]benzazepine-1a(2H)-carboxylic acid, 8-cyclohexyl-1,12b-dihydro-11-methoxy-5-[[[(methylamino)sulfonyl]amino]carbonyl]-. Cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy-, methyl ester was dissolved in THF, MeOH mixture ( 2 mL,2 mL). 2.5 M NaOH (aq.) (1.2 mL, 3 mmol) was then added and the reaction was shaken at 22° C. for 2 hr. The solution was then neutralized with 1M HCl (aq.) (3 mL) and concentrated to remove the organic solvents. The residue was slurried with H₂O and the solids were collected by filtration, washed with H₂O and dried to yield compound the title compound (160 mg, 0.30 mmol). ESI-MS m/e 538 (MH⁺). This material was used without further purification.

Intermediate 24

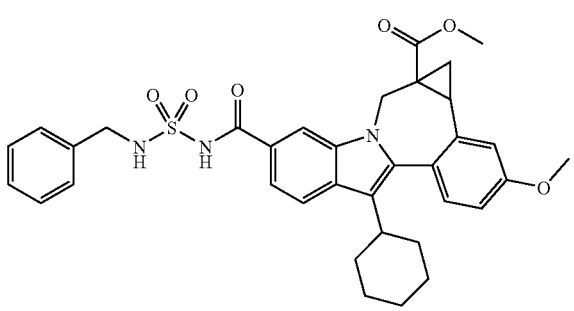

Cycloprop[d]indolo[2,1-a][2]benzazepine-1a(2H)-carboxylic acid, 8-cyclohexyl-5-[[[(benzylamino)sulfonyl]amino]carbonyl]-1,12b-dihydro-11-(methoxy)-12-(methoxy)-, methyl ester, (+/−)-. A solution of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (200 mg, 0.44 mmol) and CDI (92 mg, 0.57 mmol) in THF (5 mL) was stirred for 1 hr at 60° C. N-benzylsulfamide (164 mg, 0.88 mmol) and DBU (100 mg, 0.66 mmol) were then added and the resultant mixture was stirred at 60° C. overnight. The reaction was then poured into cold water, acidified with dilute hydrochloric acid and extracted into ethyl acetate. The organic phase was washed hydrochloric acid (0.1 N), brine and dried (sodium sulfate) and evaporated in vacuo to provide the title compound as a brown solid. ESI-MS m/e 628 (MH⁺).

Intermediate 25

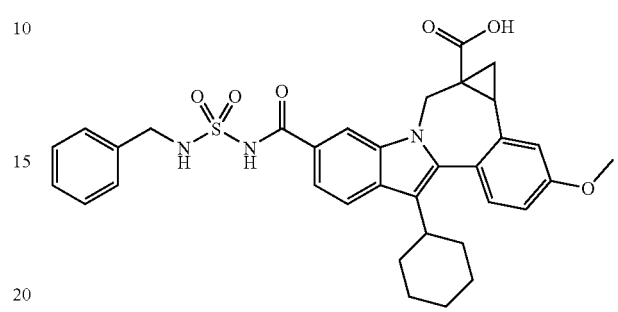

Cycloprop[d]indolo[2,1-a][2]benzazepine-1a(2H)-carboxylic acid, 8-cyclohexyl-1,12b-dihydro-11-methoxy-5-[[[[(phenylmethyl)amino]sulfonyl]amino]carbonyl]-, (+/−)-. The title compound was prepared using a similar procedure to that described for cycloprop[d]indolo[2,1-a][2]benzazepine-1a(2H)-carboxylic acid, 8-cyclohexyl-5-[[[(methylamino)sulfonyl]amino]carbonyl]-1,12b-dihydro-11-methoxy-cycloprop [d]indolo[2,1-a][2]benzazepine-1a(2H)-carboxylic acid starting from (+/−) 8-cyclohexyl-1,1a,2,12b-tetrahydro-11-methoxy-1a-(methoxycarbonyl)-cycloprop [d]indolo[2,1-a][2]benzazepine-5-carboxylic acid. ESI-MS m/e 613 (MH+), 1H NMR (500 MHz, MeOD) δ ppm 1.22-2.20 (m, 13H) 3.27-3.31 (m, 1H) 3.47 (d, J=14.95 Hz, 0.6H) 3.92 (d, J=2.44 Hz, 3H) 4.04 (d, 0.4H) 4.31 (d, J=2.75 Hz, 2H) 5.24 (d, 0.4H) 5.48 (d, 0.6H) 7.02 (d, 1H) 7.17 (d, J=2.75 Hz, 1H) 7.19-7.35 (m, 5H) 7.39 (t, J=7.48 Hz, 2H) 7.45-7.52 (m, 1H) 7.80 (d, J=1.53 Hz, 0.4H) 7.85 (dd, J=8.39, 6.87 Hz, 1H) 8.22 (d, J=1.53 Hz, 0.6H).

Intermediate 26

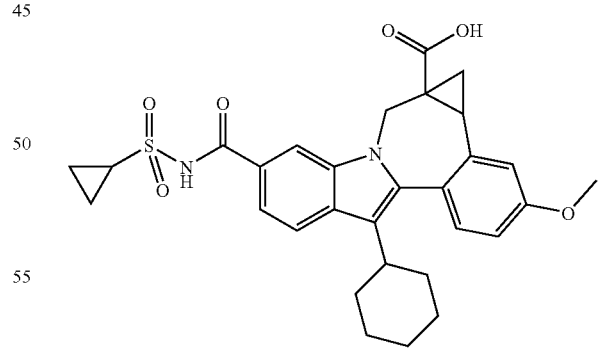

Cycloprop[d]indolo[2,1-a][2]benzazepine-1a(2H)-carboxylic acid, 8-cyclohexyl-5-[[[(cyclopropylsulfonyl)amino]carbonyl]-1,12b-dihydro-11-methoxy-, ((+/−)-. A mixture of ((+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (1 equiv), and carbonyldiimidazole (1.5 equiv) in anhydrous THF was heated at 50° C. for 30 min and allowed to cool to rt. Then 1 equiv of cyclopropanesulfonamide and 1,8-diazabicyclo[5.4.0]undec-7-ene (2 equiv) were added consecutively. The resultant mixture was stirred at rt overnight. After acidic aqueous workup, the isolated crude product was purified by prep. HPLC. The intermediate ester was then hydrolyzed using 1N NaOH in THF-MeOH to afford the title compound. LC/MS: Retention time: 2.030 min; m/e 549 (MH+). ¹H NMR (400 MHz, CDCl₃): The product was observed to exist as inter-converting rotamers, as evidenced from the compound's NMR spectrum.

Intermediates 26-37 use the experimental procedures that follow until otherwise noted. LCMS data: Stop time: Gradient time +1 minute; Starting conc: 0% B unless otherwise noted; Ending conc: 100% B unless otherwise noted; Eluent A: 5% CH₃CN/95% H₂O with 10 mM NH₄OAc (for columns A, D and E); 10% MeOH/90% H₂O with 0.1% TFA (for columns B and C); Eluent B: 95% CH₃CN/5% H₂O with 10 mM NH₄OAc (for columns A, D and E); 90% MeOH/10% H₂O with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18; Preparative HPLC data: Conditions for H₂O/CH₃CN with 10 mM NH₄OAc buffer; Gradient: Linear over 20 min. unless otherwise noted; Starting conc: 15% B unless otherwise noted; Ending conc: 100% B; Eluent A: 5% CH₃CN/95% H₂O with 10 mM NH₄OAc; Eluent B:95% CH₃CN/5% H₂O with 10 mM NH₄OAc; Column: Sunfire Prep C₁₈ OBD 5μ 30×100 mm; Conditions for H₂O/MeOH with 0.1% TFA buffer; Gradient: Linear over 20 min. unless otherwise noted; Starting conc: 30% B unless otherwise noted; Ending conc: 100% B; Eluent A: 10% MeOH/90% H₂O with 0.1% TFA; Eluent B: 90% MeOH/10% H₂O with 0.1% TFA; Column: phenomenex 21×100 mmC18 H₂O.

Intermediate 26

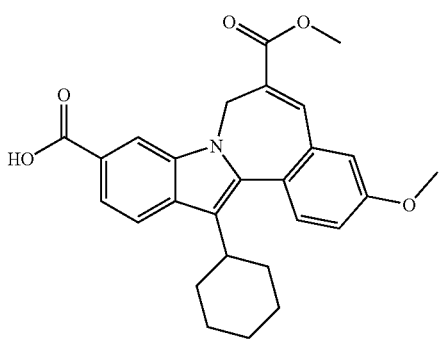

13-Cyclohexyl-3-methoxy-6-(methoxycarbonyl)-7H-indolo[2,1-a][2]benzazepine-10-carboxylic acid. Trifluoroacetic acid (30 mL) was added dropwise to a stirring slurry of 10-tert-butyl 6-methyl 13-cyclohexyl-3-methoxy-7H-indolo[2,1-a][2]benzazepine-6,10-dicarboxylate (10 g, 20 mmol) in dichloroethane (30 mL) under N₂. The clear dark green solution was stirred at rt for 2.5 h, concentrated to dryness and stirred with EtOAc (100 mL) overnight. The solids were collected by filtration, washed with EtOAc and Et₂O to yield 13-cyclohexyl-3-methoxy-6-(methoxycarbonyl)-7H-indolo[2,1-a][2]benzazepine-10-carboxylic acid (8.35 g, 18.8 mmol, 94%) was as a yellow solid which was used without further purification. ¹HNMR (300 MHz, CDCl₃) δ 1.13-2.16 (m, 10H), 2.74-2.88 (m, 1H), 3.84 (s, 3H), 3.89 (s, 3H), 4.06-4.19 (m, 1H), 5.54-5.76 (m, 1H), 6.98 (d, J=2.6 Hz, 1H), 7.08 (dd, J=8.4, 2.6 Hz, 1H), 7.52 (d, J=8.4 Hz, 1H), 7.78 (dd, J=8.8, 1.1 Hz, 1H), 7.80 (s, 1H), 7.86 (d, J=8.8 Hz, 1H), 8.34 (d, J=1.1 Hz, 1H). LCMS: m/e 446 (M+H)+, ret time 3.21 min, column B, 4 minute gradient.

Intermediate 27

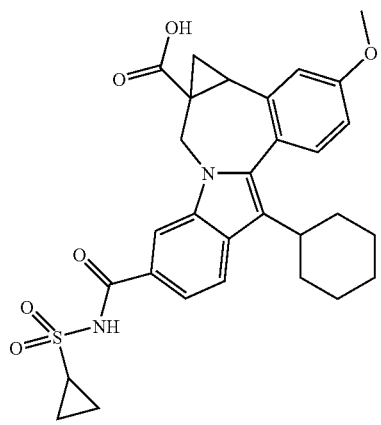

Methyl 13-cyclohexyl-10-((cyclopropylsulfonyl)carbamoyl)-3-methoxy-7H-indolo[2,1-a][2]benzazepine-6-carboxylate. 1,1'-Carbonyldiimidazole (1.82 g, 11.2 mmol) was added to a slurry of 13-cyclohexyl-3-methoxy-6-(methoxycarbonyl)-7H-indolo[2,1-a][2]benzazepine-10-carboxylic acid (3.85 g, 8.65 mmol) in THF (15 mL). The reaction mixture was heated at 60° C. for 1.5 h, cooled to rt, treated with cyclopropanesulfonamide (1.36 g, 11.2 mmol), stirred 10 min and then treated with the dropwise addition of a solution of DBU (2.0 mL, 13 mmol) in THF (3 mL). The reaction mixture was stirred at rt overnight, diluted with EtOAc (100 mL) and washed with H₂O (~30 mL), 1N HCl (aq.) (2×50 mL) and brine (~30 mL). The combined aqueous layers were extracted with EtOAc (100 mL) and the organic layer was washed with 1N HCl (aq.) (~50 mL). The combined organic layers were washed with brine (~30 mL), dried (MgSO₄), filtered and concentrated. The residue was stirred with Et₂O (~100 mL) for 2 h and the solids were collected by filtration, rinsed with Et₂O and dried to yield methyl 13-cyclohexyl-10-((cyclopropylsulfonyl)carbamoyl)-3-methoxy-7H-indolo[2,1-a][2]benzazepine-6-carboxylate (4.24 g, 7.73 mmol, 89%) as a pale yellow solid which was used without further purification. ¹HNMR (300 MHz, CDCl₃) δ 1.08-2.13 (m, 14H), 2.73-2.87 (m, 1H), 3.13-3.24 (m, 1H), 3.82 (s, 3H), 3.89 (s, 3H), 4.04-4.27 (m, 1H), 5.50-5.71 (m, 1H), 6.98 (d, J=2.6 Hz, 1H), 7.08 (dd, J=8.8, 2.6 Hz, 1H), 7.44 (dd, J=8.4, 1.1 Hz, 1H), 7.50 (d, J=8.8 Hz, 1H), 7.80 (s, 1H), 7.86 (d, J=8.4 Hz, 1H), 8.11 (br s, 1H), 8.78 (br s, 1H). LCMS: m/e 549 (M+H)+, ret time 3.79 min, column B, 4 minute gradient.

Intermediate 28

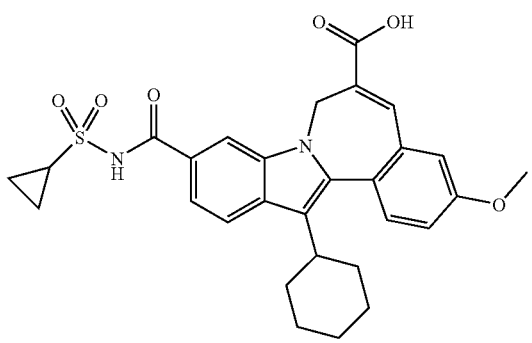

13-Cyclohexyl-10-((cyclopropylsulfonyl)carbamoyl)-3-methoxy-7H-indolo[2,1-a][2]benzazepine-6-carboxylic acid. Methyl 13-cyclohexyl-10-((cyclopropylsulfonyl)carbamoyl)-3-methoxy-7H-indolo[2,1-a][2]benzazepine-6-carboxylate (1.0 g, 1.8 mmol) was dissolved into MeOH//THF (1:1, 24 mL) and treated with 1M aqueous NaOH (5 mL). The reaction mixture was stirred and heated at 60° C. for 1.5 h and cooled to rt. The clear solution was neutralized with 1M aqueous HCl (5 mL) and concentrated to remove organic solvents. The resultant solids were collected by filtration, washed with $H_2O$ and dried under vacuum to yield 13-cyclohexyl-10-((cyclopropylsulfonyl)carbamoyl)-3-methoxy-7H-indolo[2,1-a][2]benzazepine-6-carboxylic acid (1.0 g, 1.7 mmol, 94%) as a bright yellow solid (with 0.75 equiv. of THF) which was used without further purification. $^1$HNMR (300 MHz, $CD_3OD$) δ 1.11-2.24 (m, 17H, 3H from THF), 2.81-2.96 (m, 1H), 3.17-3.28 (m, 1H), 3.69-3.79 (m, 3H, from THF), 3.94 (s, 3H), 4.07-4.33 (m, 1H), 5.55-5.81 (m, 1H), 7.14-7.24 (m, 2H), 7.55-7.64 (m, 2H), 7.88-7.94 (m, 2H), 8.20 (br s, 1H). LCMS: m/e 535 (M+H)$^+$, ret time 3.73 min, column B, 4 minute gradient.

Intermediate 29

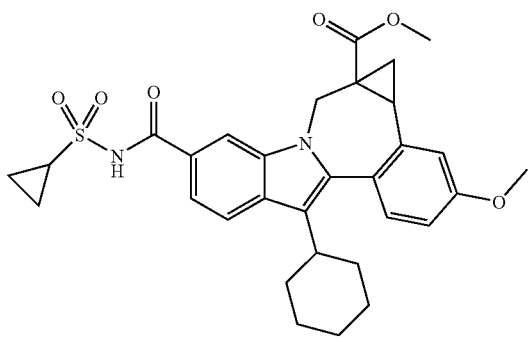

Methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate. To slurry of sodium hydride (60% dispersion in mineral oil, 370 mg, 9.2 mmol) in DMSO (8 mL) stirring under $N_2$ was added trimethylsulfoxonium iodide (2.03 g, 9.2 mmol). The reaction mixture was stirred for 45 min and then methyl 13-cyclohexyl-10-((cyclopropylsulfonyl)carbamoyl)-3-methoxy-7H-indolo[2,1-a][2]benzazepine-6-carboxylate (2.2 g, 4.0 mmol) in DMSO (5 mL) was added (flask rinsed with DMSO (2×3 mL)). The reaction mixture was stirred 1 h, poured into 0.25N HCl (100 mL), and extracted with EtOAc (150 mL). The organic layer was washed with brine (20 mL) and the combined aqueous layers were extracted with EtOAc (100 mL). The combine organic layers were washed with brine (~20 mL), dried ($MgSO_4$), filtered and concentrated to dryness. The residue was stirred with EtOAc/$Et_2O$ (1:3, 50 mL) and the solids were removed by filtration. The motherliquor was concentrated and dried under high vacuum to yield methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (1.92 g, 3.4 mmol, 85%) as a yellow solid which was used without further purification. Presents as a ~2:1 mixture of rotamers or atrope isomers. $^1$HNMR (300 MHz, $CD_3OD$) δ 0.19-0.26 (m, 0.4H), 0.78-2.19 (m, 15.6H), 2.64-3.02 (m, 2H), 3.16-3.28 (m, 1H), 3.41 (d, J=15.0 Hz, 0.6H), 3.51 (s, 1.8H), 3.80 (s, 1.2H), 3.88 (s, 3H), 4.00 (d, J=15.0 Hz, 0.4H), 5.22 (d, J=15.0 Hz, 0.4H), 5.42 (d, J=15.0 Hz, 0.6H), 6.93-7.01 (m, 1H), 7.12 (d, J=2.6 Hz, 0.4H), 7.19 (d, J=2.6 Hz, 0.6H), 7.25 (d, J=8.8 Hz, 0.6H), 7.29 (d, J=8.8 Hz, 0.4H), 7.55 (dd, J=8.8, 1.5 Hz, 0.6H), 7.63 (dd, J=8.8, 1.5 Hz, 0.4H), 7.85 (d, J=8.8 Hz, 0.6H), 7.88 (d, J=8.8 Hz, 0.4H), 8.08 (d, J=1.5 Hz, 0.4H), 8.31 (d, J=1.5 Hz, 0.6H). LCMS: m/e 563 (M+H)$^+$, ret time 3.75 min, column B, 4 minute gradient.

Intermediate 30

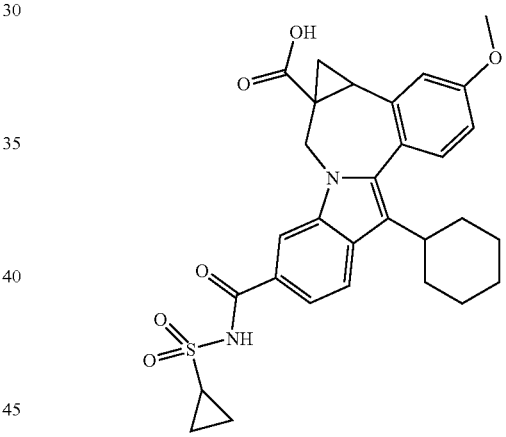

8-Cyclohexyl-5-((cyclopropylsulfonyl)carbamoyl)-11-methoxy-1,12b-dihydrocyclopropa[d]indolo[2,1-a][2]benzazepine-1a(2H)-carboxylic acid. Methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (1.92 g, 3.41 mmol) was dissolved into MeOH//THF (1:1, 40 mL) and treated with 1M aqueous NaOH (8 mL). The reaction mixture was stirred and heated at 60° C. for 2 h and cooled to rt. The clear solution was neutralized with 1M aqueous HCl (8 mL) and concentrated to remove organic solvents. The resultant solids were collected by filtration, washed with $H_2O$ and dried under vacuum to yield 8-cyclohexyl-5-((cyclopropylsulfonyl)carbamoyl)-11-methoxy-1,12b-dihydrocyclopropa[d]indolo[2,1-a][2]benzazepine-1a(2H)-carboxylic acid (1.66 g, 3.03 mmol, 89%) as a yellow powder which was used without further purification. Presents as a 1:1 mixture of rotamers or atrope isomers. $^1$HNMR (300 MHz, $CDCl_3$) δ 0.32 (t, J=6.2 Hz, 0.5H), 0.71-2.12 (m, 15.5H), 2.61-2.94 (m, 2H), 3.16-3.27 (m, 1H), 3.41 (d, J=15.0 Hz, 0.5H), 3.82 (s, 1.5H), 3.86 (s, 1.5H), 3.99 (d, J=15.0 Hz, 0.5H), 5.28 (d, J=15.0 Hz, 0.5H), 5.49 (d, J=15.0 Hz, 0.5H), 6.85 (dd, J=8.4, 2.6 Hz, 0.5H), 6.91 (dd, J=8.4, 2.6 Hz, 0.5H), 6.96 (d, J=2.6 Hz, 0.5H), 7.08 (d, J=2.6 Hz, 0.5H), 7.19 (d, J=8.4 Hz, 0.5H), 7.24 (d, J=8.4 Hz, 0.5H), 7.61 (d, J=8.4 Hz, 0.5H), 7.67 (d, J=8.4 Hz, 0.5H), 7.83 (d, J=8.4 Hz, 0.5H), 7.85 (d, J=8.4 Hz, 0.5H), 8.06 (s, 0.5H), 8.35 (s, 0.5H), 9.31-10.35 (m, 1H). LCMS: m/e 547 (M−H)$^-$, ret time 2.06 min, column A, 4 minute gradient.

Intermediate 31

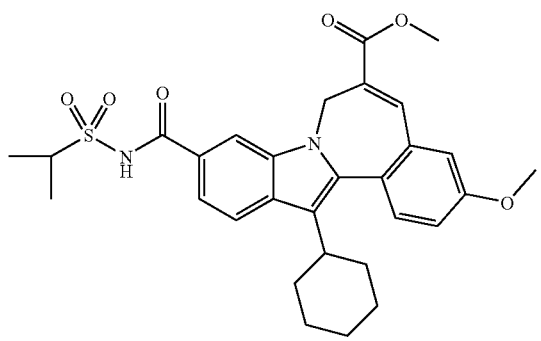

Methyl 13-cyclohexyl-10-((isopropylsulfonyl)carbamoyl)-3-methoxy-7H-indolo[2,1-a][2]benzazepine-6-carboxylate. 1,1'-Carbonyldiimidazole (262 mg, 1.62 mmol) was added to a slurry of 13-cyclohexyl-3-methoxy-6-(methoxycarbonyl)-7H-indolo[2,1-a][2]benzazepine-10-carboxylic acid (603 mg, 1.36 mmol) in THF (3 mL). The reaction mixture was heated at 60° C. for 1.5 h, cooled to rt, treated with propane-2-sulfonamide (200 mg, 1.62 mmol), stirred 10 min and then treated with the dropwise addition of a solution of DBU (0.27 mL, 1.8 mmol) in THF (0.75 mL). The reaction mixture was stirred at rt overnight, diluted with EtOAc (15 mL) and washed with H$_2$O (~5 mL), 1N HCl (aq.) (2×10 mL) and brine (~5 mL). The combined aqueous layers were extracted with EtOAc (15 mL) and the organic layer was washed with 1N HCl (aq.) (~10 mL). The combined organic layers were washed with brine (~5 mL), dried (MgSO$_4$), filtered and concentrated. The residue was stirred with Et$_2$O (~15 mL) for 2 h and the solids were collected by filtration, rinsed with Et$_2$O and dried to yield methyl 13-cyclohexyl-10-((isopropylsulfonyl)carbamoyl)-3-methoxy-7H-indolo[2,1-a][2]benzazepine-6-carboxylate (640 mg, 1.2 mmol, 85%) as a bright yellow solid which was used without further purification. $^1$HNMR (300 MHz, CDCl$_3$) δ 1.12-2.13 (m, 10H), 1.47 (d, J=7.0 Hz, 6H), 2.73-2.86 (m, 1H), 3.82 (s, 3H), 3.89 (s, 3H), 4.06-4.26 (m, 1H), 4.09 (septet, J=7.0 Hz, 1H), 5.51-5.71 (m, 1H), 6.98 (d, J=2.6 Hz, 1H), 7.08 (dd, J=8.4, 2.6 Hz, 1H), 7.44 (dd, J=8.4, 1.5 Hz, 1H), 7.50 (d, J=8.4 Hz, 1H), 7.80 (s, 1H), 7.87 (d, J=8.4 Hz, 1H), 8.10 (d, J=1.5 Hz, 1H), 8.57 (s, 1H). LCMS: m/e 551 (M+H)$^+$, ret time 3.87 min, column B, 4 minute gradient.

Intermediate 32

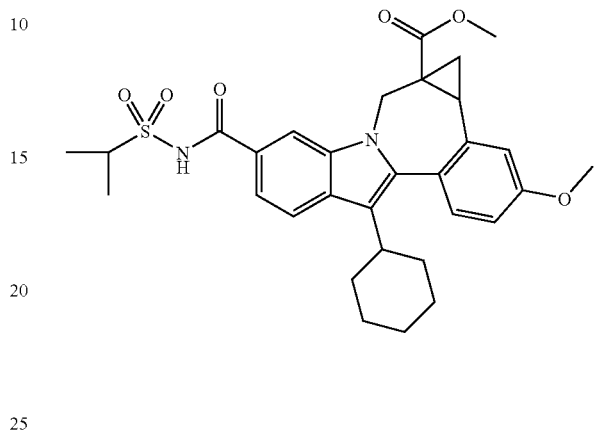

Methyl 8-cyclohexyl-5-((isopropylsulfonyl)carbamoyl)-11-methoxy-1,12b-dihydrocyclopropa[d]indolo[2,1-a][2]benzazepine-1a(2H)-carboxylate. To slurry of sodium hydride (60% dispersion in mineral oil, 97 mg, 2.4 mmol) in DMSO (2 mL) stirring under N$_2$ was added trimethylsulfoxonium iodide (530 g, 2.4 mmol). The reaction mixture was stirred for 45 min and then methyl 13-cyclohexyl-10-((isopropylsulfonyl)carbamoyl)-3-methoxy-7H-indolo[2,1-a][2]benzazepine-6-carboxylate (578 g, 1.05 mmol) in DMSO (1.5 mL) was added (flask rinsed with DMSO (2×0.75 mL)). The reaction mixture was stirred 1 h, poured into 0.25N HCl (25 mL), and extracted with EtOAc (40 mL). The organic layer was washed with brine (10 ml) and the combined aqueous layers were extracted with EtOAc (25 mL). The combine organic layers were washed with brine (~10 mL), dried (MgSO$_4$), filtered and concentrated to dryness. The residue was stirred with EtOAc/Et$_2$O (1:4, 10 mL) and the solids were removed by filtration. The motherliquor was concentrated and dried under high vacuum to yield methyl 8-cyclohexyl-5-((isopopylsulfonyl)carbamoyl)-11-methoxy-1,12b-dihydrocyclopropa[d]indolo[2,1-a][2]benzazepine-1a(2H)-carboxylate (620 mg, 1.0 mmol, quant.) as a yellow solid which was used without further purification. Presents as a ~2:1 mixture of rotamers or atrope isomers. $^1$HNMR (300 MHz, CDCl$_3$) δ 0.32-0.39 (m, 0.4H), 0.77-2.09 (m, 17.6H), 2.60-2.96 (m, 2H), 3.41 (d, J=15.0 Hz, 0.6H), 3.53 (s, 1.8H), 3.79 (s, 1.2H), 3.87 (s, 3H), 4.02-4.14 (m, 1.4H), 5.14 (d, J=15.0 Hz, 0.4H), 5.39 (d, J=15.0 Hz, 0.6H), 6.89 (dd, J=8.4, 2.6 Hz, 0.4H), 6.91 (dd, J=8.4, 2.6 Hz, 0.6H), 7.00 (d, J=2.6 Hz, 0.4H), 7.11 (d, J=2.6 Hz, 0.6H), 7.23 (d, J=8.4 Hz, 0.6H), 7.25 (d, J=8.4 Hz, 0.4H), 7.38 (dd, J=8.4, 1.5 Hz, 0.6H), 7.43 (dd, J=8.4, 1.5 Hz, 0.4H), 7.83 (d, J=8.4 Hz, 0.6H), 7.86 (d, J=8.4 Hz, 0.4H), 7.96 (d, J=1.5 Hz, 0.4H), 8.20 (d, J=1.5 Hz, 0.6H), 8.39 (s, 0.4H), 8.43 (s, 0.6H). LCMS: m/e 563 (M−H)$^-$, ret time 3.00 min, column A, 4 minute gradient.

Intermediate 33

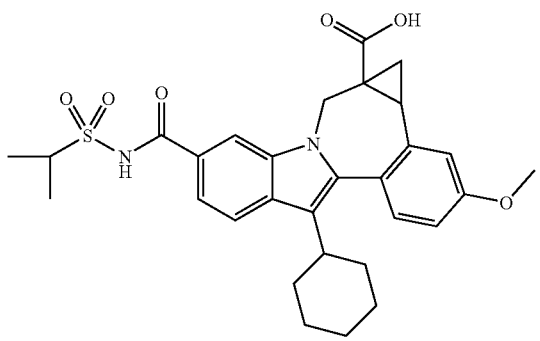

8-Cyclohexyl-5-((isopropylsulfonyl)carbamoyl)-11-methoxy-1,12b-dihydrocyclopropa[d]indolo[2,1-a][2]benzazepine-1a(2H)-carboxylic acid. Methyl 8-cyclohexyl-5-((isopropylsulfonyl)carbamoyl)-11-methoxy-1,12b-dihydrocyclopropa[d]indolo[2,1-a][2]benzazepine-1a(2H)-carboxylate (606 mg, 1.07 mmol) was dissolved into MeOH//THF (1:1, 14 mL) and treated with 1M aqueous NaOH (2.5 mL). The reaction mixture was stirred and heated at 60° C. for 2 h and cooled to rt. The clear solution was neutralized with 1M aqueous HCl (2.5 mL) and concentrated to remove organic solvents. The residue was stirred with $H_2O$ (10 mL) overnight and the resultant solids were collected by filtration, washed with $H_2O$ and dried under vacuum to yield 8-cyclohexyl-5-((isopropylsulfonyl)carbamoyl)-11-methoxy-1,12b-dihydrocyclopropa[d]indolo[2,1-a][2]benzazepine-1a(2H)-carboxylic acid (530 mg, 0.96 mmol, 90%) as a bright yellow solid which was used without further purification. Presents as a ~2:1 mixture of rotamers or atrope isomers. $^1$HNMR (300 MHz, $CD_3OD$) δ 0.23-0.30 (m, 0.4H), 0.80-2.24 (m, 17.6H), 2.70-3.11 (m, 2H), 3.46 (d, J=15.0 Hz, 0.6H), 3.95 (s, 3H), 3.93-4.10 (m, 1.4H), 5.29 (d, J=15.0 Hz, 0.4H), 5.48 (d, J=15.0 Hz, 0.6H), 6.98-7.05 (m, 1H), 7.16 (d, J=2.6 Hz, 0.4H), 7.23 (d, J=2.6 Hz, 0.6H), 7.29 (d, J=8.8 Hz, 0.6H), 7.33 (d, J=8.8 Hz, 0.4H), 7.56 (dd, J=8.8, 1.5 Hz, 0.6H), 7.64 (dd, J=8.4, 1.5 Hz, 0.4H), 7.87 (d, J=8.8 Hz, 0.6H), 7.92 (d, J=8.4 Hz, 0.4H), 8.13 (d, J=1.5 Hz, 0.4H), 8.31 (d, J=1.5 Hz, 0.6H). LCMS: m/e 551 (M+H)$^+$, ret time 3.74 min, column B, 4 minute gradient.

Intermediate 34

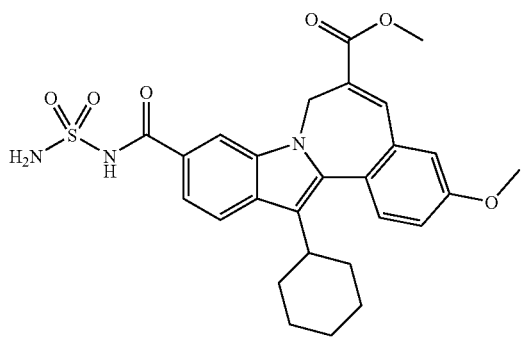

Methyl 10-((aminosulfonyl)carbamoyl)-13-cyclohexyl-3-methoxy-7H-indolo[2,1-a][2]benzazepine-6-carboxylate.

1,1'-Carbonyldiimidazole (1.23 g, 7.60 mmol) was added to a slurry of 13-cyclohexyl-3-methoxy-6-(methoxycarbonyl)-7H-indolo[2,1-a][2]benzazepine-10-carboxylic acid (2.6 g, 5.8 mmol) in THF (11 mL). The reaction mixture was heated at 60° C. for 1.5 h, cooled to rt, treated with sulfamide (1.12 g, 11.7 mmol), stirred 10 min and then treated with the dropwise addition of a solution of DBU (1.8 mL, 11.7 mmol) in THF (3 mL). The reaction mixture was stirred at rt for 3 h, diluted with EtOAc (80 mL) and $CH_2Cl_2$ (100 mL) and concentrated to dryness. The residue was diluted with $CH_2Cl_2$ (100 mL) and washed with 1N HCl (aq.) (2×100 mL). The combined aqueous layers were extracted with $CH_2Cl_2$ (100 mL) and the combined organic layers were washed with ½ saturated brine (~50 mL), dried ($MgSO_4$), filtered and concentrated. The residue was stirred with $Et_2O$ (~75 mL) for 1 h and the solids were collected by filtration, rinsed with $Et_2O$ and dried to yield methyl 10-((aminosulfonyl)carbamoyl)-13-cyclohexyl-3-methoxy-7H-indolo[2,1-a][2]benzazepine-6-carboxylate (2.8 g, 5.3 mmol, 91%) as a bright yellow solid which was used without further purification. $^1$HNMR (300 MHz, $CDCl_3$) δ 1.08-2.10 (m, 10H), 2.71-2.84 (m, 1H), 3.79 (s, 3H), 3.89 (s, 3H), 4.00-4.18 (m, 1H), 5.50-5.64 (m, 1H), 5.68 (s, 2H), 6.97 (d, J=2.6 Hz, 1H), 7.07 (dd, J=8.8, 2.6 Hz, 1H), 7.46 (dd, J=8.4, 1.5 Hz, 1H), 7.49 (d, J=8.8 Hz, 1H), 7.78 (s, 1H), 7.82 (d, J=8.4 Hz, 1H), 8.10 (br s, 1H), 9.49 (s, 1H). LCMS: m/e 524 (M+H)$^+$, ret time 3.60 min, column B, 4 minute gradient.

Intermediate 35

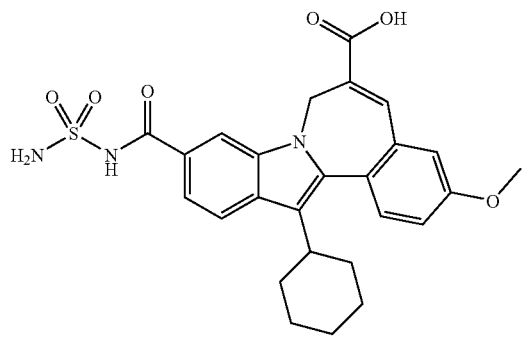

10-((Aminosulfonyl)carbamoyl)-13-cyclohexyl-3-methoxy-7H-indolo[2,1-a][2]benzazepine-6-carboxylic acid. Methyl 10-((aminosulfonyl)carbamoyl)-13-cyclohexyl-3-methoxy-7H-indolo[2,1-a][2]benzazepine-6-carboxylate (725 mg, 1.39 mmol) was dissolved into MeOH//THF (1:1, 16 mL) and treated with 1M aqueous NaOH (3 mL). The reaction mixture was stirred and heated at 60° C. for 0.5 h and cooled to rt. The reaction solution was diluted with MeOH/$H_2O$ (2:1, 15 mL), neutralized with 1M aqueous HCl (3 mL) and concentrated to remove organic solvents. The resultant solids were collected by filtration, washed with $H_2O$ and dried under vacuum to yield 10-((aminosulfonyl)carbamoyl)-13-cyclohexyl-3-methoxy-7H-indolo[2,1-a][2]benzazepine-6-carboxylic acid (650 g, 1.3 mmol, 92%) as a bright yellow solid which was used without further purification. $^1$HNMR (300 MHz, $CDCl_3$) δ 1.16-2.22 (m, 10H), 2.82-2.96 (m, 1H), 3.94 (s, 3H), 4.07-4.29 (m, 1H), 5.57-5.80 (m, 1H), 7.14-7.23 (m,

Intermediate 36

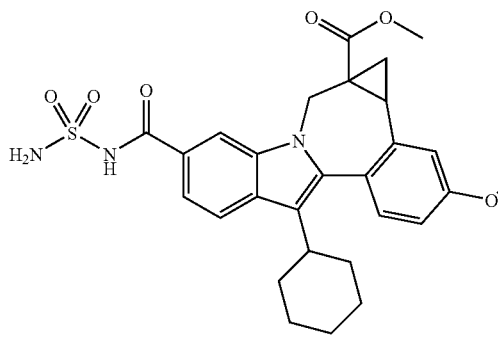

Methyl 5-((aminosulfonyl)carbamoyl)-8-cyclohexyl-11-methoxy-1,12b-dihydrocyclopropa[d]indolo[2,1-a][2]benzazepine-1a(2H)-carboxylate. To slurry of sodium hydride (60% dispersion in mineral oil, 350 mg, 8.8 mmol) in DMSO (8 mL) stirring under N₂ was added trimethylsulfoxonium iodide (1.93 g, 8.8 mmol) in three portions. The reaction mixture was stirred for 0.5 h and then methyl 10-((aminosulfonyl)carbamoyl)-13-cyclohexyl-3-methoxy-7H-indolo[2,1-a][2]benzazepine-6-carboxylate (2.0 g, 3.8 mmol) in DMSO (8 mL) was added (flask rinsed with DMSO (2×2 mL)). The reaction mixture was stirred 1 h, poured into 0.25N HCl (100 mL), and diluted with CH₂Cl₂ (100 mL). The solution was filtered to collect solids, and the organic layer of the motherliquor was separated and concentrated to dryness. The residue was dissolved into EtOAc (~150 mL) was washed with H₂O (~50 mL) and brine (~50 mL) dried (MgSO₄), filtered and concentrated to dryness. The residue was stirred with EtOAc/Et₂O (4:1, 50 mL) and the solids were collected by filtration and washed with EtOAc. These solids were combined with the initially collected solids to yield methyl 5-((aminosulfonyl)carbamoyl)-8-cyclohexyl-11-methoxy-1,12b-dihydrocyclopropa[d]indolo[2,1-a][2]benzazepine-1a(2H)-carboxylate (1.39 g, 2.6 mmol, 68%) as a tan solid which was used without further purification. Presents as a 1:1 mixture of rotamers or atrope isomers. ¹HNMR (300 MHz, DMSO-d₆) δ 0.13-0.21 (m, 0.5H), 1.06-2.12 (m, 11.5H), 2.64-2.94 (m, 2H), 3.46 (s, 1.5H), 3.49 (d, J=15.0 Hz, 0.5H), 3.75 (s, 1.5H), 3.85 (s, 3H), 4.02 (d, J=15.0 Hz, 0.5H), 5.21 (d, J=15.0 Hz, 0.5H), 5.42 (d, J=15.0 Hz, 0.5H), 6.99-7.09 (m, 1H), 7.17-7.31 (m, 1H), 7.41 (s, 0.5H), 7.43 (s, 0.5H), 7.66-7.56 (m, 1H), 7.82 (d, J=8.4 Hz, 0.5), 7.87 (d, J=8.8 Hz, 0.5H), 8.25 (s, 0.5H), 8.47 (s, 0.5H), 11.62 (s, 0.5H), 11.69 (s, 0.5H). LCMS: m/e 538 (M+H)⁺, ret time 3.56 min, column B, 4 minute gradient.

Intermediate 37

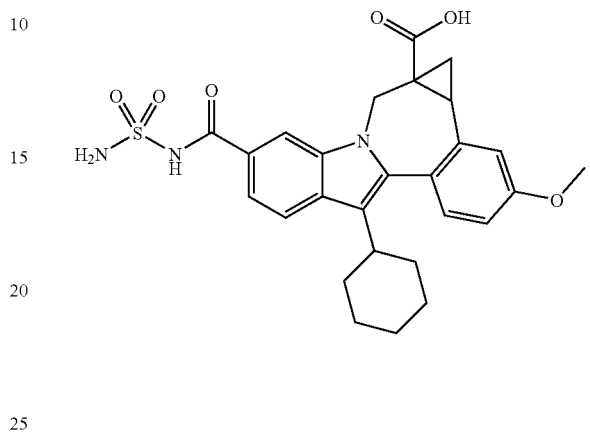

5-((Aminosulfonyl)carbamoyl)-8-cyclohexyl-11-methoxy-1,12b-dihydrocyclopropa[d]indolo[2,1-a][2]benzazepine-1a(2H)-carboxylic acid. Methyl 5-((aminosulfonyl)carbamoyl)-8-cyclohexyl-11-methoxy-1,12b-dihydrocyclopropa[d]indolo[2,1-a][2]benzazepine-1a(2H)-carboxylate (1.1 mg, 2.0 mmol) was dissolved into MeOH// THF (1:1, 24 mL) and treated with 1M aqueous NaOH (5 mL). The reaction mixture was stirred and heated at 60° C. for 2 h and cooled to rt. The clear solution was neutralized with 1M aqueous HCl (5 mL) and concentrated to remove organic solvents. The residue was stirred with H₂O (10 mL) for 1 h and the resultant solids were collected by filtration, washed with H₂O and dried under vacuum to yield 5-((aminosulfonyl)carbamoyl)-8-cyclohexyl-11-methoxy-1,12b-dihydrocyclopropa[d]indolo[2,1-a][2]benzazepine-1a(2H)-carboxylic acid (1.05 mg, 2.0 mmol, 98%) as a light yellow solid which was used without further purification. Presents as a 1:1 mixture of rotamers or atrope isomers. ¹HNMR (300 MHz, DMSO-d₆) δ 0.08-0.17 (m, 0.5H), 0.79-2.13 (m, 11.5H), 2.65-2.94 (m, 2H), 3.44 (d, J=14.6 Hz, 0.5H), 3.85 (s, 3H), 3.96 (d, J=14.6 Hz, 0.5H), 5.20 (d, J=14.6 Hz, 0.5H), 5.40 (d, J=14.6 Hz, 0.5H), 6.98-7.08 (m, 1H), 7.17-7.46 (m, 4H), 7.58 (d, J=8.1 Hz, 0.5H), 7.62 (d, J=8.1 Hz, 0.5H), 7.81 (d, J=8.8 Hz, 0.5H), 7.87 (d, J=8.8 Hz, 0.5H), 8.25 (s, 0.5H), 8.44 (s, 0.5H), 11.48-13.19 (m, 2H). LCMS: m/e 524 (M+H)⁺, ret time 3.51 min, column B, 4 minute gradient.

Intermediate 38 was analyzed by the following LC/MS method: Column: PHENOMENNEX-LUNA 3.0×50 mm S10; Mobile Phase:(A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

155

Intermediate 38

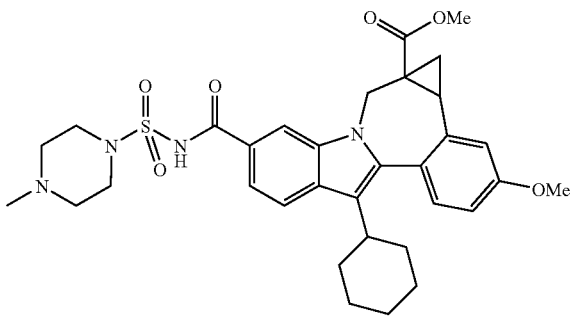

((+/−)-8-Cyclohexyl-N-4-(4-methylpiperazin-1-ylsulfonyl)-1,1a,2,12b-tetrahydro-11-methoxy-1a-(methoxycarbonyl)cycloprop[d]indolo[2,1-a][2]benzazepine-5-carboxamide. To a stirred solution of the acid (1.15 g, 2.5 mmol) in an THF (5 mL), neat CDI (0.61 g, 3.75 mmol) was added and the mixture was heated at 50° C. for 30 min. Then reagent the amine and DBU were added and the resultant mixture was stirred at rt overnight. Reaction was quenched with satd. NH4Cl and then extracted with EtOAc (2×50 mL). Organic layer was washed with water and then dried (Na2SO4). Crude product was purified by flash column chromatography (silica gel, 8-10% MeOH in DCM) to afford the product (1.03 g, 66%) as a beige solid. LC/MS: Retention time: 2.913 min; m/e 621 (MH$^+$). The product was observed to exist as interconverting rotamers by 1H NMR (400 MHz, CHLOROFORM-D): δ ppm 0.31-0.41 (m, 1H), 1.16-1.28 (m, 2H), 1.29-1.48 (m, 2H), 1.50-1.61 (m, 1H), 1.63-1.84 (m, 3H), 1.85-2.10 (m, 6H), 2.28-2.39 (m, 3H), 2.38-2.50 (m, 1H), 2.51-2.61 (m, 4H), 2.61-2.82 (m, 1H), 2.82-2.96 (m, 1H), 3.36-3.48 (m, 1H), 3.50-3.62 (m, 3H), 3.77-3.92 (m, 3H), 5.10-5.44 (m, 1H), 6.69 (s, 1H), 6.86-7.04 (m, 1H), 7.08-7.15 (m, 1H), 7.21-7.28 (m, 1H), 7.33-7.55 (m, 1H), 7.77-7.88 (m, 1H), 7.94-8.25 (m, 1H).

Intermediate 39 and Examples 1-11 the experimental procedures that follow until otherwise noted. HPLC method: Method A: Start % B=0; Final % B=100; Gradient time=3 min; Flow Rate=4 ml/min; Wavelength=220; Solvent A=10% MeOH-90% H2O-0.1% TFA; Solvent B=90% MeOH-10% H2O-0.1% TFA; Column: Peneomenex-Luna 3.0×50 mm S10; Method B: Start % B=0; Final % B=100; Gradient time=3 min; Flow Rate=4 ml/min; Wavelength=220; Solvent A=5% Acetonitril-95% H2O-10 Mm Ammonium Acetate; Solvent B=95% Acetonitril-5% H2O-10 Mm Ammonium Acetate; Column=Phenomenex-Luna 3.0×50 mm S10. Compounds for which LC/MS data was obtained with method B are noted. Unless noted LC/MS was obtained using Method A.

Intermediate 39

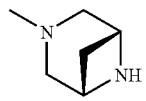

(1R,5S)-3-methyl-3,6-diazabicyclo[3.1.1]heptane. To a solution of (1R,5S)-tert-butyl 3,6-diazabicyclo[3.1.1]heptane-6-carboxylate (1.0 g, 5.04 mmol) in MeOH (25 mL), paraformaldehyde (0.227 g, 7.57 mmol) and zinc chloride (1.03 g, 7.57 mmol) were added. Then sodium cyanoborohydride (0.475 g, 7.57 mmol) was added in portions. The reaction mixture was stirred at rt. for overnight. Then insoluble solid was filtered out and the filtrated was concentrated. The residue was participated between 10% NaHCO$_3$ solution and ethyl acetate (2×50 mL). The organic layers were combined, dried (MgSO$_4$) and concentrated to give a colorless oil. It was then dissolved in CH$_2$Cl$_2$ (10 mL) and TFA (2.5 mL) was added. The reaction mixture was stirred at rt. for overnight. TFA and solvent were evaporated to give a white solid as final product as diTFA salt. (1.14 g, 66% yield). MS m/113(MH$^+$). $^1$H NMR (500 MHz, MeOD) δ ppm 2.25 (d, J=11.90 Hz, 1H) 3.01-3.06 (m, 3H) 3.08-3.18 (m, 1H) 3.80 (d, J=13.73 Hz, 2H) 4.13 (d, J=14.34 Hz, 2H) 4.47 (d, J=6.10 Hz, 2H).

EXAMPLE 1

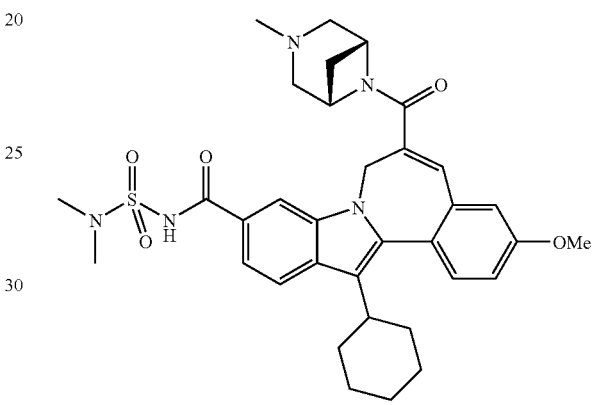

7H-Indolo[2,1-a][2]benzazepine-10-carboxamide, 13-cyclohexyl-N-[(dimethylamino)sulfonyl]-3-methoxy-6-[[(1R,5S)-3-methyl-3,6-diazabicyclo[3.1.1]hept-6-yl]carbonyl]-. MS m/z 632(MH$^+$), Retention time: 2.510 min. $^1$H NMR (500 MHz, MeOD) δ ppm 1.12-1.61 (m, 4H) 1.65-2.22 (m, 7H) 2.28-3.09 (m, 12H) 3.51-3.88 (m, 3 ) 3.95 (s, 3H) 4.20 (d, J=13.42 Hz, 1H) 4.63 (s, br, 2H) 5.51 (d, J=13.43 Hz, 1H) 7.17-7.25 (m, 2H) 7.43 (s, 1H) 7.54-7.62 (m, 2H) 7.93 (d, J=8.24 Hz, 1H) 8.18 (s, 1H)

EXAMPLE 2

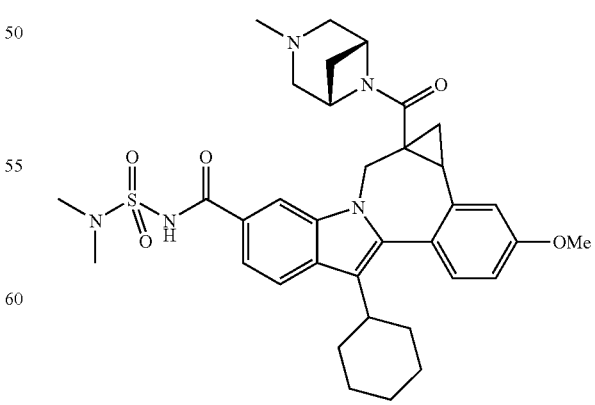

Cycloprop[d]indolo[2,1-a][2]benzazepine-5-carboxamide, 8-cyclohexyl-N-[(dimethylamino)sulfonyl]-1,1a,2,12b- tetrahydro-11-methoxy-1a-[[(1R,5S)-3-methyl-3,6-diazabicyclo[3.1.1]hept-6-yl]carbonyl]-. MS m/z 644(MH+), Retention time: 2.057 min (Method B). $^1$H NMR (500 MHz, MeOD) δ ppm 0.14 (m, 0.2H) 1.12-2.19 (m, 14.8H) 2.39-3.08 (m, 12H) 3.44-3.95 (m, 7.4 ) 4.15 (d, J=14.65 Hz, 0.2H) 4.57 (s, br, 0.4H) 5.01 (d, J=14.65 Hz, 0.2H) 5.31 (s, br, 0.8H) 6.98-7.04 (m, 1H) 7.19 (s, 1H) 7.30 (d, J=8.55 Hz, 0.8H) 7.33 (d, J=8.55 Hz, 0.2H) 7.59 (d, J=8.24 Hz, 1H) 7.88 (d, J=8.55 Hz, 0.2H) 7.93 (d, J=8.54 Hz, 0.8H) 8.08 (s, 0.2H) 8.10 (s, 0.8H).

EXAMPLE 3

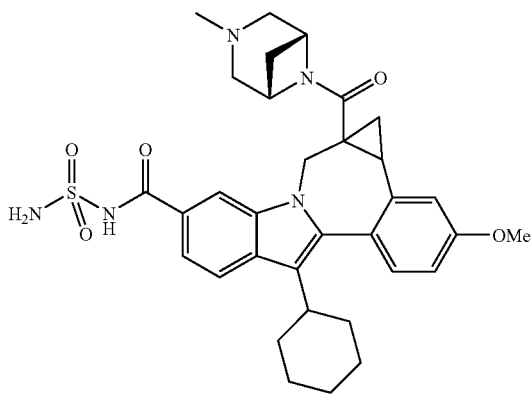

Cycloprop[d]indolo[2,1-a][2]benzazepine-5-carboxamide, N-(aminosulfonyl)-8-cyclohexyl-1,1a,2,12b-tetrahydro-11-methoxy-1a-[[(1R,5S)-3-methyl-3,6-diazabicyclo[3.1.1]hept-6-yl]carbonyl]-. MS m/z 618(MH+), Retention time: 2.292 min. $^1$H NMR (500 MHz, MeOD) δ ppm 0.18 (m, 0.17H) 1.20-2.23 (m, 14.83H) 2.55-3. 3.99 (m, 13.49H) 4.19 (d, J=14.95 Hz, 0.17H) 4.62 (s, br, 0.34H) 5.05 (d, J=14.65 Hz, 0.17H) 5.35 (s, br, 0.83H) 7.01-7.09 (m, 1H) 7.21-7.27 (m, 1H) 7.30-7.38 (m, 1H) 7.60-7.69 (m, 1H) 7.91 (d, J=8.55 Hz, 0.17H) 7.97 (d, J=8.55 Hz, 0.83H) 8.12 (s, 0.17H) 8.15 (s, 0.83H).

EXAMPLE 4

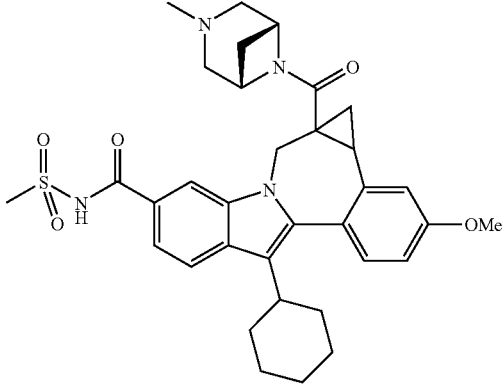

Cycloprop[d]indolo[2,1-a][2]benzazepine-5-carboxamide, 8-cyclohexyl-1,1a,2,12b-tetrahydro-11-methoxy-1a-[[(1R,5S)-3-methyl-3,6-diazabicyclo[3.1.1]hept-6-yl]carbonyl]-N-(methylsulfonyl)-. MS m/z 617(MH+), Retention time: 2.383 min. $^1$H NMR (500 MHz, MeOD) δ ppm 0.18 (m, 0.19H) 1.17-2.25 (m, 14.81H) 2.54-4.04 (m, 16.43H) 4.19 (d, J=14.65 Hz, 0.19H) 4.62 (s, br, 0.38H) 5.06 (d, J=14.34 Hz, 0.19H) 5.35 (s, br, 0.81H) 7.01-7.10 (m, 1H) 7.22-7.25 (m, 1H) 7.32-7.39 (m, 1H) 7.60-7.68 (m, 1H) 7.93 (d, J=8.55 Hz, 0.19H) 7.98 (d, J=8.55 Hz, 0.81H) 8.14 (s, 0.19H) 8.17 (s, 0.81H).

EXAMPLE 5

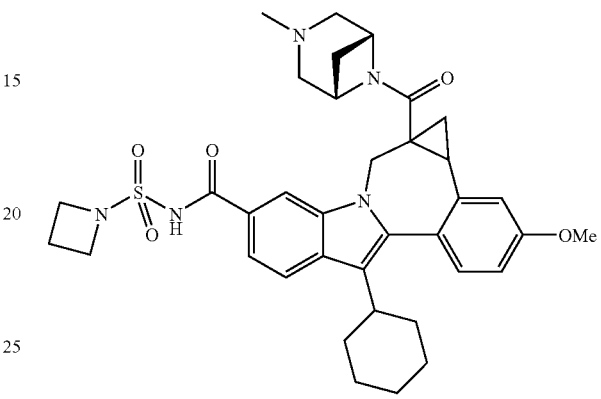

Cycloprop[d]indolo[2,1-a][2]benzazepine-5-carboxamide, N-(1-azetidinylsulfonyl)-8-cyclohexyl-1,1a,2,12b-tetrahydro-11-methoxy-1a-[[(1R,5S)-3-methyl-3,6-diazabicyclo[3.1.1]hept-6-yl]carbonyl]-. MS m/z 658(MH+), Retention time: 2.467 min. $^1$H NMR (500 MHz, MeOD) δ ppm 0.20 (m, 0.18H) 1.18-2.23 (m, 14.82H) 2.24-2.37 (m, 2H) 2.53-3.99 (m, 13.46H) 4.16-4.30 (m, 4.18H) 4.62 (s, br, 0.36H) 5.07 (d, J=14.65 Hz, 0.18H) 5.36 (s, br, 0.82H) 7.02-7.10 (m, 1H) 7.22-7.25 (m, 1H) 7.31-7.39 (m, 1H) 7.66 (d, J=8.24 Hz, 1H) 7.94 (d, J=8.55 Hz, 0.18H) 7.99 (d, J=8.55 Hz, 0.82H) 8.15 (s, 0.18H) 8.19 (s, 0.82H).

EXAMPLE 6

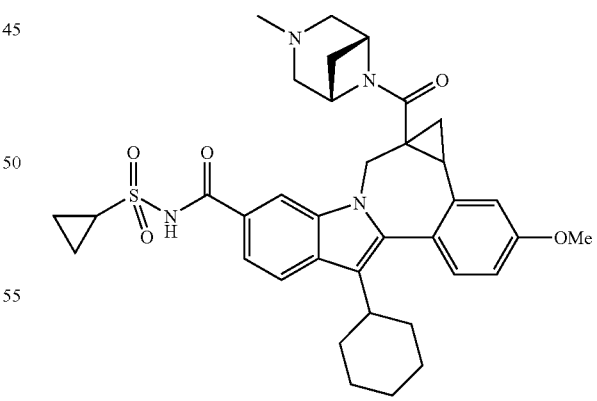

Cycloprop[d]indolo[2,1-a][2]benzazepine-5-carboxamide, 8-cyclohexyl-N-(cyclopropylsulfonyl)-1,1a,2,12b-tetrahydro-11-methoxy-1a-[[(1R,5S)-3-methyl-3,6-diazabicyclo[3.1.1]hept-6-yl]carbonyl]-. MS m/z 643(MH+), Retention time: 2.438 min. $^1$H NMR (500 MHz, MeOD) δ ppm 0.14-0.23 (m, 0.16H) 1.11-2.25 (m, 18.84H) 2.51-4.01 (m, 14.52H) 4.19 (d, J=14.95 Hz, 0.16H) 4.62 (s, br, 0.32H)

5.06 (d, J=14.95 Hz, 0.16H) 5.37 (s, br, 0.84H) 7.00-7.11 (m, 1H) 7.19-7.27 (m, 1H) 7.32-7.41 (m, 1H) 7.60-7.69 (m, 1H) 7.94 (d, J=8.55 Hz, 0.16H) 7.99 (d, J=8.55 Hz, 0.84H) 8.13 (s, 0.16H) 8.17 (s, 0.84H).

EXAMPLE 7

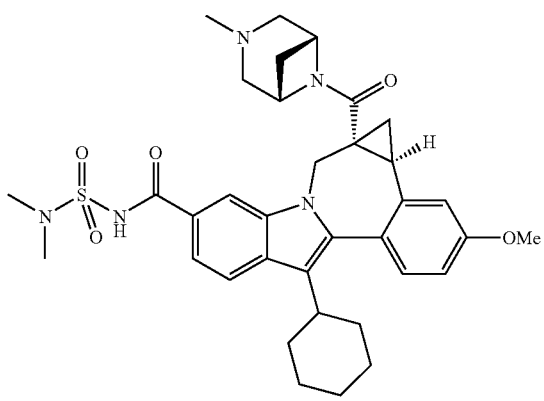

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(1R,5S)-3-methyl-3,6-diazabicyclo[3.1.1]hept-6-yl]carbonyl]-, (1aR,12bS)-. MS m/z 644 (MH+), Retention time: 2.175 min(Method B). $^1$H NMR (500 MHz, MeOD) δ ppm 0.14 (m, 0.2H) 1.12-2.19 (m, 14.8H) 2.39-3.08 (m, 12H) 3.44-3.95 (m, 7.4H) 4.15 (d, J=14.65 Hz, 0.2H) 4.57 (s, br, 0.4H) 5.01 (d, J=14.65 Hz, 0.2H) 5.31 (s, br, 0.8H) 6.98-7.04 (m, 1H) 7.19 (s, 1H) 7.30 (d, J=8.55 Hz, 0.8H) 7.33 (d, J=8.55 Hz, 0.2H) 7.59 (d, J=8.24 Hz, 1H) 7.88 (d, J=8.55 Hz, 0.2H) 7.93 (d, J=8.54 Hz, 0.8H) 8.08 (s, 0.2H) 8.10 (s, 0.8H).

EXAMPLE 8

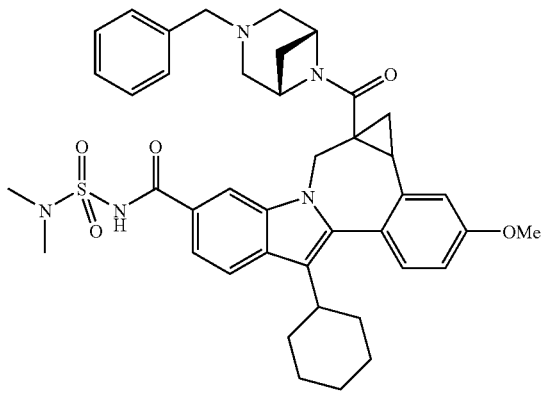

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(1R,5S)-3-(phenylmethyl)-3,6-diazabicyclo[3.1.1]hept-6-yl]carbonyl]-. To a solution of cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (300 mg, 0.544 mmol) in DMSO (10 mL), TBTU (262 mg, 0.816 mmol) and DIPEA (0.47 mL, 2.72 mmol) were added. The reaction mixture was stirred at rt for 15 min. Then (1R,5S)-3-benzyl-3,6-diazabicyclo[3.1.1]heptane (154 mg, 0.816 mmol) was added and the reaction mixture was stirred at rt. for overnight. It was then concentrated and the residue was purified by Prep. HPLC column to give a light yellow solid as final product. (373 mg, 82% yield). MS m/z 722(MH+), Retention time: 3.500 min (Method B). $^1$H NMR (500 MHz, MeOD) δ ppm 0.13 (m, 0.24H) 1.14-2.25 (m, 14.76H) 2.49-4.03 (m, 18.28H) 4.13 (d, J=14.65 Hz, 0.24H) 4.45-4.66 (m, 0.48H) 4.98 (d, J=14.95 Hz, 0.24H) 5.36 (s, br, 0.76H) 7.03 (dd, J=8.39, 2.59 Hz, 1H) 7.16-7.64 (m, 8H) 7.90 (d, J=8.54 Hz, 0.24H) 7.92 (d, J=8.55 Hz, 0.76H) 8.08 (s, 0.24H) 8.19 (s, br, 0.76H).

EXAMPLE 9

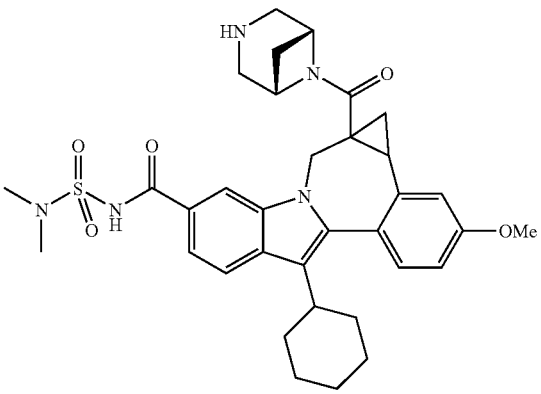

Cycloprop[d]indolo[2,1-a][2]benzazepine-5-carboxamide, 8-cyclohexyl-1a-[(1R,5S)-3,6-diazabicyclo[3.1.1]hept-6-ylcarbonyl]-N-[(dimethylamino)sulfonyl]-1,1a,2,12b-tetrahydro-11-methoxy-. To a solution of cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(1R,5S)-3-(phenylmethyl)-3,6-diazabicyclo[3.1.1]hept-6-yl]carbonyl]- (60 mg, 0.072 mmol) in ethanol (5 mL), Pd(OH)$_2$ (60 mg) and 1N HCl solution (0.072 mL, 0.072 mmol) were added. The reaction mixture was shaken under a hydrogenator at 30-40 psi for 6 hr. Catalyst was filtered off celite and the filtrate was concentrated to give a yellowish solid as crude product. It was then purified by Prep. HPLC column to give a light yellow solid as final product as TFA salt. (42 mg, 78% yield). MS m/z 632(MH+), Retention time: 1.795 min (Method B). ¹H NMR (500 MHz, MeOD) δ ppm 0.17 (m, 0.26H) 1.15-2.25 (m, 14.74H) 2.45-4.01 (m, 16.22H) 4.20 (d, J=14.34 Hz, 0.26H) 4.57 (s, br, 0.52H) 5.00-5.04 (m, 0.26H) 5.23 (d, J=14.95 Hz, 0.74H) 7.01-7.09 (m, 1H) 7.22 (s, 1H) 7.33 (d, J=8.55 Hz, 0.74H) 7.36 (d, J=8.54 Hz, 0.26H) 7.63 (dd, J=8.55, 1.53 Hz, 1H) 7.89-7.98 (m, 1H) 8.14 (s, 1H).

EXAMPLE 10

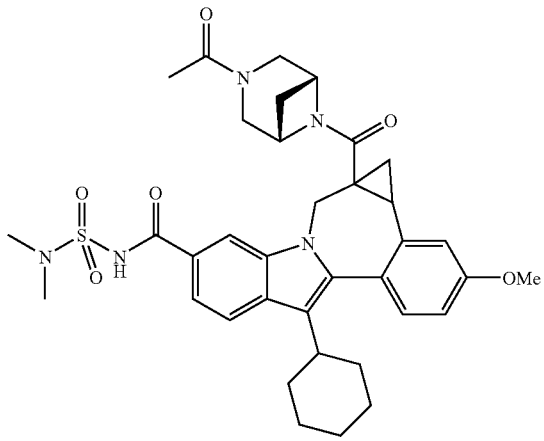

Cycloprop[d]indolo[2,1-a][2]benzazepine-5-carboxamide, 1a-[[(1R,5S)-3-acetyl-3,6-diazabicyclo[3.1.1]hept-6-yl]carbonyl]-8-cyclohexyl-N-[(dimethylamino)sulfonyl]-1,1a,2,12b-tetrahydro-11-methoxy-. To a solution of acetic acid (0.002 mL, 0.040 mmol) in DMSO (1.0 mL), TBTU (16.1 mg, 0.050 mmol) and DIPEA (0.029 mL, 0.128 mmol) were added. The reaction mixture was stirred at rt. for 10 min. Then cycloprop[d]indolo[2,1-a][2]benzazepine-5-carboxamide, 8-cyclohexyl-1a-[(1R,5S)-3,6-diazabicyclo[3.1.1]hept-6-ylcarbonyl]-N-[(dimethylamino)sulfonyl]-1,1a,2,12b-tetrahydro-11-methoxy- (25 mg, 0.0335 mmol) was added. Ther reaction mixture was then stirred at rt. for overnight. It was then purified by Prep. HPLC column. Fractions were collected and concentrated to give a light yellow solid as final product. (16.5 mg, 73% yield). MS m/z 674(MH+), Retention time: 2.718 min. ¹H NMR (500 MHz, MeOD) δ ppm 0.09 (m, 0.3H) 0.49-2.28 (m, 17.7H) 2.31-4.52 (m, 16.4H) 4.66-5.43 (m, 1.6H) 6.92-7.05 (m, 1H) 7.06-7.21 (m, 1H) 7.25-7.35 (m, 1H) 7.45-7.69 (m, 1H) 7.76-8.00 (m, 1H) 8.02-8.16 (m, 1H).

EXAMPLE 11

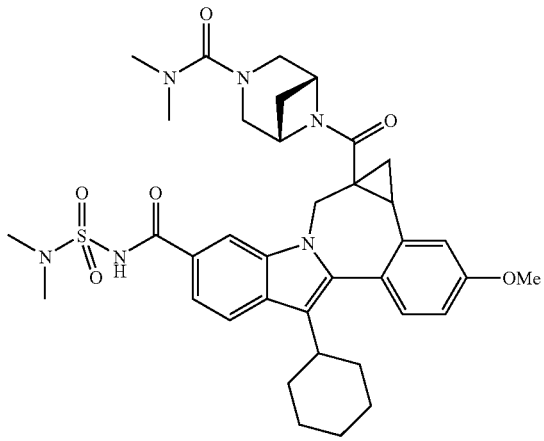

Cycloprop[d]indolo[2,1-a][2]benzazepine-5-carboxamide, 8-cyclohexyl-1a-[[(1R,5S)-3-[(dimethylamino)carbonyl]-3,6-diazabicyclo[3.1.1]hept-6-yl]carbonyl]-N-[(dimethylamino)sulfonyl]-1,1a,2,12b-tetrahydro-11-methoxy-. To a solution of cycloprop[d]indolo[2,1-a][2]benzazepine-5-carboxamide, 8-cyclohexyl-1a-[(1R,5S)-3,6-diazabicyclo[3.1.1]hept-6-ylcarbonyl]-N-[(dimethylamino)sulfonyl]-1,1a,2,12b-tetrahydro-11-methoxy- (50 mg, 0.067 mmol) in CH2Cl2 (3 mL), DIPEA (0.052 mL, 0.3 mmol) and dimethylcarbamy chloride (0.009 mL, 0.1 mmol) were added. The reaction mixture was stirred at rt. for overnight. It was then concentrated and the residue was purified by Prep. HPLC column. The fractions were collected and concentrated to give a yellow solid as final product. (18.5 mg, 39% yield). MS m/z 703(MH+), Retention time: 2.771 min. ¹H NMR (500 MHz, MeOD) δ ppm 0.08 (m, 0.4H) 0.53-2.22 (m, 14.6H) 2.29-4.43 (m, 22.2H) 4.55-5.46 (m, 1.8H) 6.93-7.04 (m, 1H) 7.16 (d, J=2.44 Hz, 0.4H) 7.19 (d, J=2.45 Hz, 0.6H) 7.25-7.34 (m, 1H) 7.44-7.70 (m, 1H) 7.76-7.99 (m, 1H) 8.00-8.16 (m, 0.6H) 8.42 (s, br, 0.4H).

Examples 12-16 use the experimental procedures that follow until otherwise noted. All the compounds described below were analyzed by following LC/MS method: Start % B: 0; Final % B: 100; Gradient time: 3 min; Stop time: 4 min; Flow rate: 4 ml/min; Wavelenth:220; Solvent A: 10% MeOH/ 90% H₂O/0.1% Trifluoroacetic Acid; Solvent B: 10% H₂O/ 90% MeOH/0.1% Trifluoroacetic Acid; Column: XBridge 4.6×50 mm S5.

EXAMPLE 12

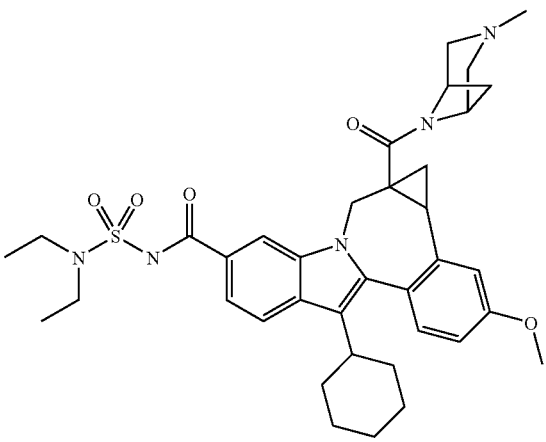

(+/−)-8-Cyclohexyl-N-(N,N-diethylaminosulfonyl)-1,1a,2,12b-tetrahydro-11-methoxy-1a-(1-(3-methyl-3,6-diazabicyclo[3.1.1]heptan-6-yl))-8-carbonyl)-cycloprop[d]indolo[2,1-a][2]benzazepine-5-carboxamide. To a mixture of the compound acid (0.050 g, 0.86 mmol) and 3-methyl-3,6-diazabicyclo[3.1.1]heptane bis(2,2,2-trifluoroacetate) (44.0 mg, 0.129 mmol) in CH2Cl2 (1.5 ml) was added TEA (0.120 ml, 0.863 mmol) and HBTU (49.0 mg, 0.129 mmol) and stirred at r.t. for 80 min, diluted with MeOH, removed the solvent. The residue was dissolved in methanol, and purified by prep-HPLC to afford a TFA salt of compound 1 (0.0296 g, 45%). LC-MS retention time: 3.150; MS m/z 674 (M+H)]. 1H NMR (400 MHz, CHLOROFORM-D): δ ppm 1.12-1.57 (m, 7H) 1.23 (t, J=7.18 Hz, 6H) 1.81 (s, 2H) 1.87-2.17 (m, 5H) 2.64-2.79 (m, 1H) 2.83-3.02 (m, 2H) 3.10-3.23 (m, J=7.30, 4.78 Hz, 1H) 3.32-5.34 (m, 7H) 3.54 (q, J=7.05 Hz, 4H) 3.90 (s, 3H) 4.36 (s, 1H) 5.39-5.64 (m, 1H) 6.97 (dd, J=8.56, 2.77 Hz, 1H) 7.12 (d, J=2.52 Hz, 1H) 7.22-7.32 (m, 1H) 7.47 (d, J=8.31 Hz, 1H) 7.86-7.90 (m, 1H) 8.11 (s, 1H).

EXAMPLE 13

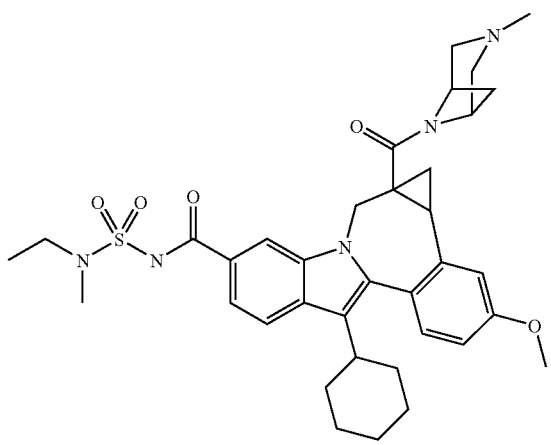

(+/−)-8-Cyclohexyl-N-(N-methyl-N-ethylaminosulfonyl)-1,1a,2,12b-tetrahydro-11-methoxy-1a-(1-(3-methyl-3,6-diazabicyclo[3.1.1]heptan-6-yl))-8-carbonyl)-cycloprop[d]indolo[2,1-a][2]benzazepine-5-carboxamide. A TFA salt of the product was prepared from the acid (0.0294 g, 55%). LC-MS retention time: 3.066; MS m/z 660(M+H). 1H NMR (400 MHz, CHLOROFORM-d): δ ppm 1.20-1.26 (m, 3H) 1.25-1.56 (m, 6H) 1.81 (s, 3H) 1.88-2.12 (m, 5H) 2.63-2.78 (m, 1H) 3.06 (s, 3H) 3.10-3.22 (m, J=7.18, 5.16 Hz, 1H) 3.42-3.50 (m, 5H) 3.55-3.76 (m, 1H) 3.90 (s, 3H) 3.93-4.40 (m, 5H) 4.33-4.39 (m, 1H) 5.38-5.53 (m, 1H) 6.97 (dd, J=8.69, 2.64 Hz, 1H) 7.12 (d, J=2.52 Hz, 1H) 7.24-7.32 (m, 1H) 7.49 (d, J=8.31 Hz, 1H) 7.85-7.90 (m, 1H) 8.12 (s, 1H).

EXAMPLE 14

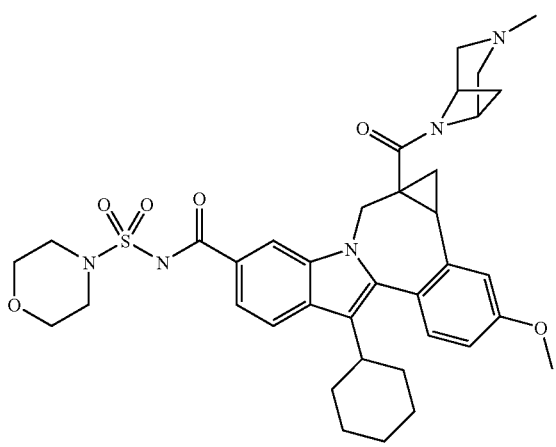

(+/−)-8-Cyclohexyl-N-(morpholinosulfonyl)-1,1a,2,12b-tetrahydro-11-methoxy-1a-(1-(3-methyl-3,6-diazabicyclo[3.1.1]heptan-6-yl))-8-carbonyl)-cycloprop[d]indolo[2,1-a][2]benzazepine-5-carboxamide. A TFA salt of the product was prepared (0.0323 g, 48%). LC-MS retention time: 2.955; MS m/z (M+H) 688. 1H NMR (400 MHz, CHLOROFORM-d): δ ppm 1.18-1.56 (m, 6H) 1.81 (t, J=12.84 Hz, 3H) 1.87-2.13 (m, 5H) 2.62-2.78 (m, 1H) 2.80-2.89 (m, J=18.51, 4.66 Hz, 1H) 2.90-3.01 (m, 1H) 3.08-3.20 (m, 1H) 3.40-3.55 (m, 6H) 3.56-3.69 (mm, 1H) 3.71-4.31 (m, 4H) 3.73-3.79 (m, 4H) 3.89 (s, 3H) 4.31-4.41 (m, 1H) 5.35-5.56 (mm, 1H) 6.97 (dd, J=8.69, 2.64 Hz, 1H) 7.11 (d, J=2.27 Hz, 1H) 7.20-7.33 (m, 1H) 7.46-7.56 (m, 1H) 7.87 (d, J=8.56 Hz, 1H) 8.12 (s, 1H).

EXAMPLE 15

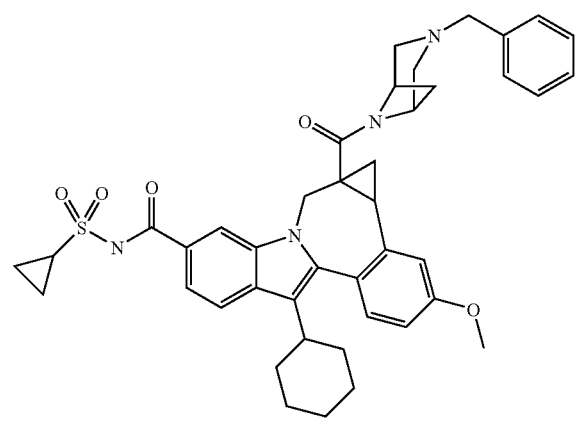

(+/−)-8-Cyclohexyl-N-(cyclopropylsulfonyl)-1,1a,2,12b-tetrahydro-11-methoxy-1a-(1-(3-benzyl-3,6-diazabicyclo[3.1.1]heptan-6-yl))-8-carbonyl)-cycloprop[d]indolo[2,1-a][2]benzazepine-5-carboxamide. A TFA salt of the product was prepared (0.056 g, 71%). LC-MS retention time: 3.11; MS m/z 719 (M+H). ¹H NMR (400 MHz, CHLOROFORM-d): δ ppm 1.02-1.60 (m, 9 1.69-2.17 (m, 9 2.48-3.03 (m, 3 3.06-3.34 (m, 3 3.46 (d, J=13.35 Hz, 1 3.62-4.06 (m, 4 3.90 (s, 3 4.28-4.68 (m, 2 6.88-7.02 (m, 2 7.13 (d, J=2.27 Hz, 2 7.23-7.30 (m, 1 7.35 (d, J=5.04 Hz, 2 7.38-7.54 (m, 2 7.87 (d, J=8.31 Hz, 1 8.32 (s, 1H).

EXAMPLE 16

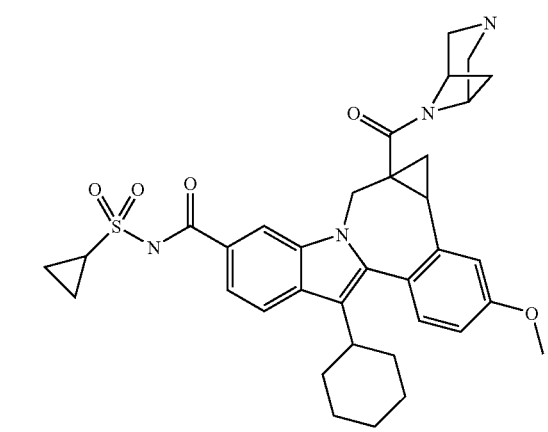

(+/−) 8-Cyclohexyl-N-(cyclopropylsulfonyl)-1,1a,2,12b-tetrahydro-11-methoxy-1a-(1-(3,6-diazabicyclo[3.1.1]heptan-6-yl))-8-carbonyl)-cycloprop[d]indolo[2,1-a][2]benzazepine-5-carboxamide. A mixture of the benzyl compound (0.052 g, 0.072 mmol) and Pd/C (w/w 10%, 0.05 g), in MeOH (8 mL) was degassed and stirred under $H_2$ balloon for overnight. Filtered off the solid and removed the solvent to afford the product as a yellow solid (0.042 g, 93%) in TFA salt form. LC-MS retention time: 2.976; MS m/z 629 (M+H). $^1$H NMR (400 MHz, CHLOROFORM-d): δ ppm 0.99-2.13 (m, 18 2.38-2.51 (m, 1 2.71-3.76(m, 7 3.88 (s, 3 4.09-4.26 (m, J=11.08 Hz, 1 4.50 (d, J=31.73 Hz, 1 4.90 (d, J=14.86 Hz, 1 6.89-6.98 (m, 1 7.05 (d, J=2.01 Hz, 1 7.21-7.31 (m, 1 7.69 (d, J=7.81 Hz, 1 7.82-7.92 (m, J=8.31 Hz, 1 8.24-8.33 (m, 1H).

Example 17 was analyzed by the following LC/MS method: Column: PHENOMENNEX-LUNA 3.0×50 mm S10; Mobile Phase:(A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

EXAMPLE 17

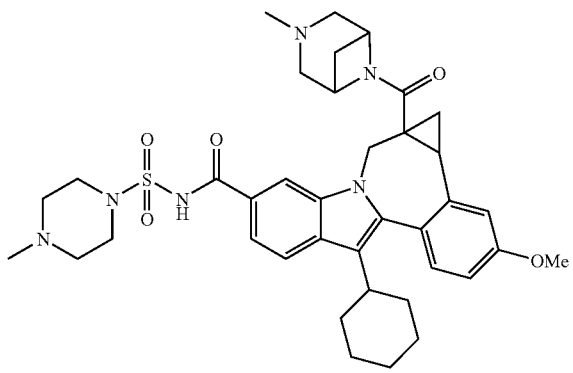

(+/−)-8-Cyclohexyl-N-4-(4-methylpiperazin-1-ylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The starting material was hydrolyzed with 1N NaOH in THF-MeOH to afford the corresponding acid in quantitative yield. The acid was coupled with amine using TBTU and TEA to afford the amide which purified by reverse phase prep HPLC and isolated in bis-TFA salt form as a beige solid. LC/MS: Retention time: 1.562 min; m/e 701 (MH$^+$). The product was observed to exist as inter-converting rotamers by 1H NMR (500 MHz, CHLOROFORM-D): δ ppm 1.14-1.52 (m, 7H), 1.70-2.11 (m, 9H), 2.75-3.11 (m, 10H), 3.11-3.23 (m, J=7.17, 4.73 Hz, 1H), 3.38-3.74 (m, 7H), 3.89 (s, 3H), 4.09 (s, 3H), 4.28-4.75 (m, 1H), 6.88-7.05 (m, 1H), 7.07-7.16 (m, 1H), 7.20-7.32 (m, 1H), 7.50-7.66 (m, 1H), 7.75-7.93 (m, 1H), 8.05-8.26 (m, 1H).

The general procedures below pertain to the experimental procedures that follow until noted. The acid (0.055 mmol, 1 eq.) was dissolved in dried DMF and followed by adding HATU (0.083 mmol, 1.5 eq.) and DIPEA(0.083. 1.5 eq.). The solution was stirred for 2 minutes and added into pre-weighted amine (0.083 mmol, 1.5 eq.) at room temperature. The mixture was stirred 14 h and purified by prep-HPLC. HPLC gradient methods: Method A: Column: Agilent SB CN4.6×100 mm 3.5 um; mobile phase: water, 10 mM $NH_4OH$, ACN; Method B: Column: Phenomenex Gemini 4.6×100 mm 5 um C18; mobile phase: water, 10 mM $NH_4OH$, ACN; Method C: Column: Waters x-Bidge C18 150×4.6 mm 5 micron; mobile phase: water, 10 mM $NH_4OH$, ACN; Method D: Column: Waters Xbridge 2.1×50 mm 5 um C18; mobile phase: water, 10 mM $NH_4OH$, ACN.

| Structure | HPLC Ret. Time [min] | HPLC Purity [%] | MS Reported Mass | HPLC Method |
|---|---|---|---|---|
| 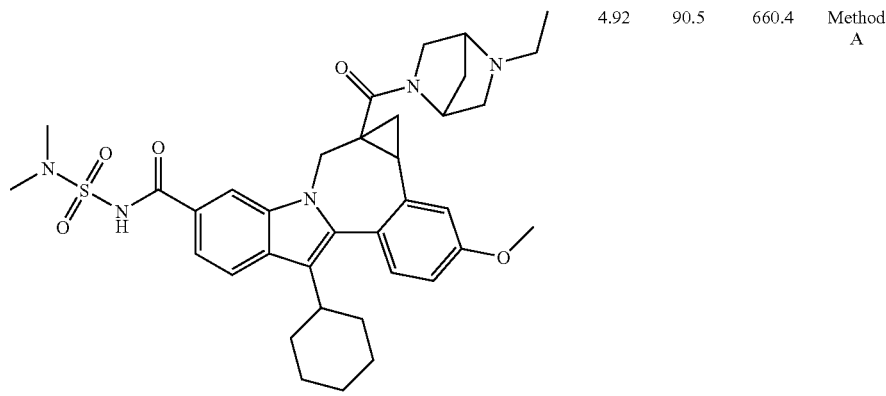 | 4.92 | 90.5 | 660.4 | Method A |

-continued

| Structure | HPLC Ret. Time [min] | HPLC Purity [%] | MS Reported Mass | HPLC Method |
|---|---|---|---|---|
| 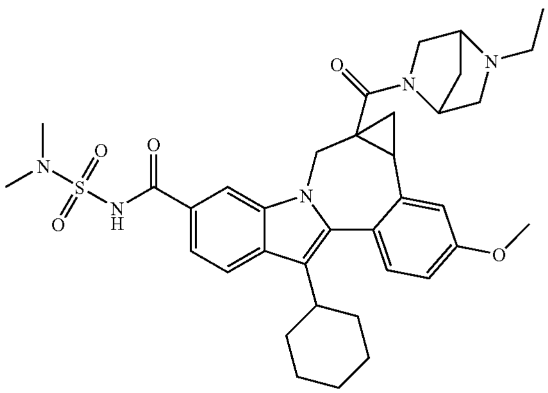 | 2.11 | 100 | 660.39 | Method D |
| 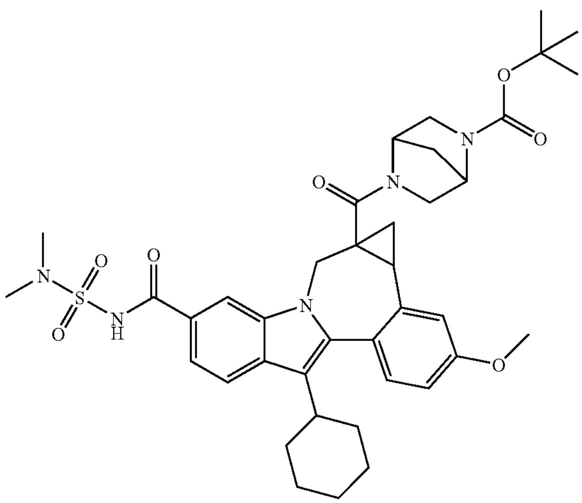 | 5.06 | 92.5 | 732.4 | Method A |
| 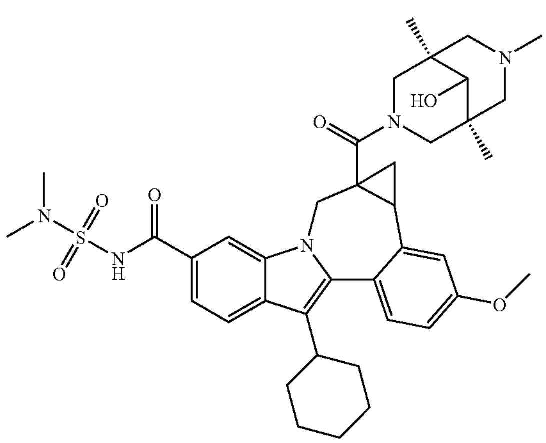 | 5.32 | 100 | 718.43 | Method A |

-continued

| Structure | HPLC Ret. Time [min] | HPLC Purity [%] | MS Reported Mass | HPLC Method |
|---|---|---|---|---|
| 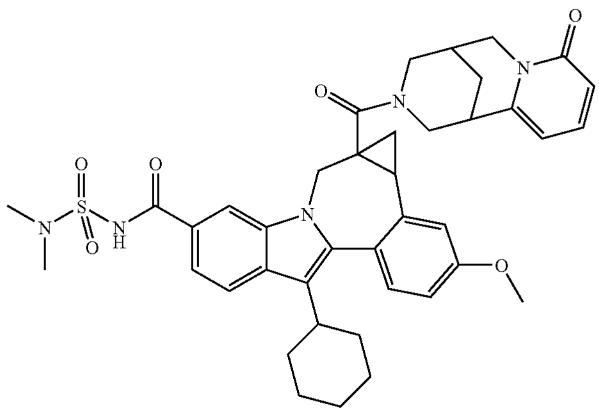 | 5.86 | 98.3 | 724.33 | Method B |
| 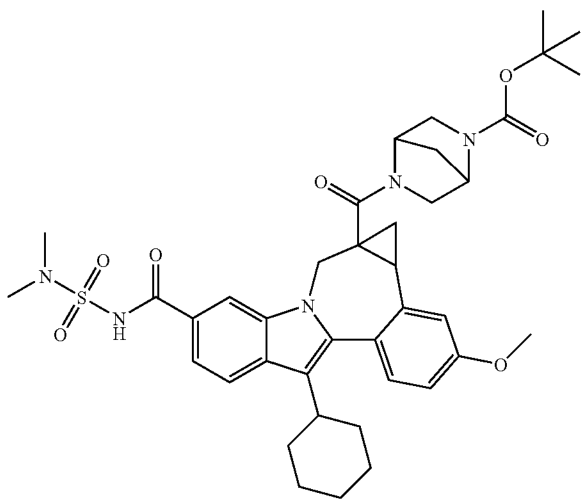 | 7.79 | 99.4 | 732.33 | Method B |
| 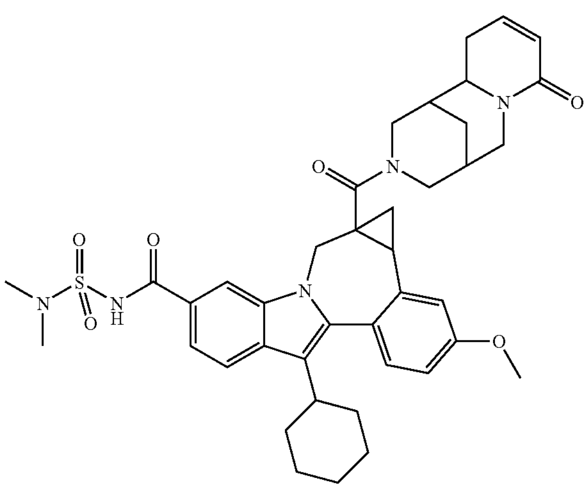 | 6.11 | 100 | 724.33 | Method B |

-continued

| Structure | HPLC Ret. Time [min] | HPLC Purity [%] | MS Reported Mass | HPLC Method |
|---|---|---|---|---|
| 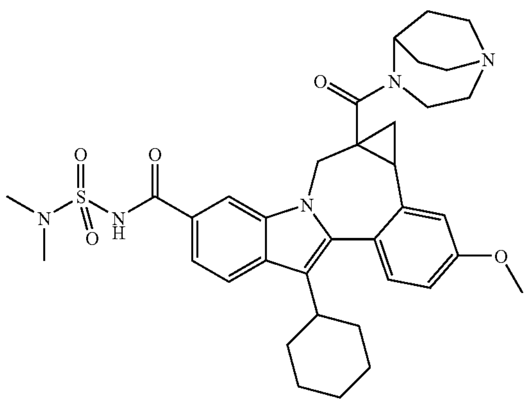 | 5.01 | 100 | 660.34 | Method B |
| 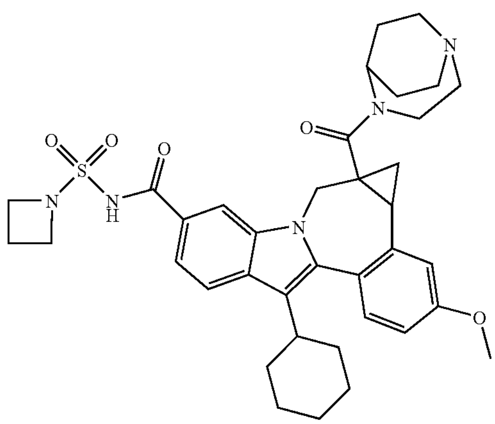 | 7.5 | 98.4 | 672.22 | Method C |
| 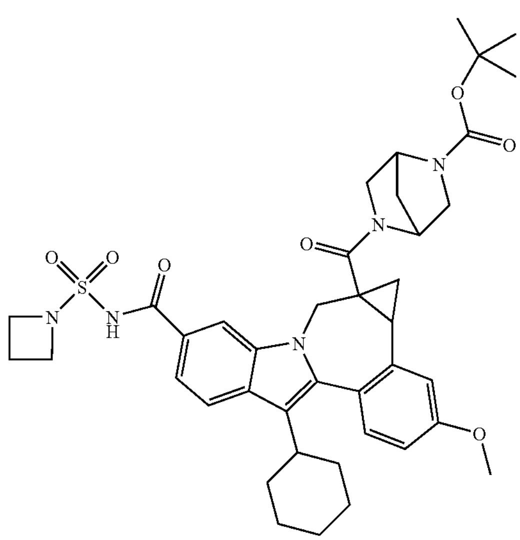 | 9.6 | 99.3 | 744.22 | Method C |

-continued
| Structure | HPLC Ret. Time [min] | HPLC Purity [%] | MS Reported Mass | HPLC Method |
|---|---|---|---|---|
| 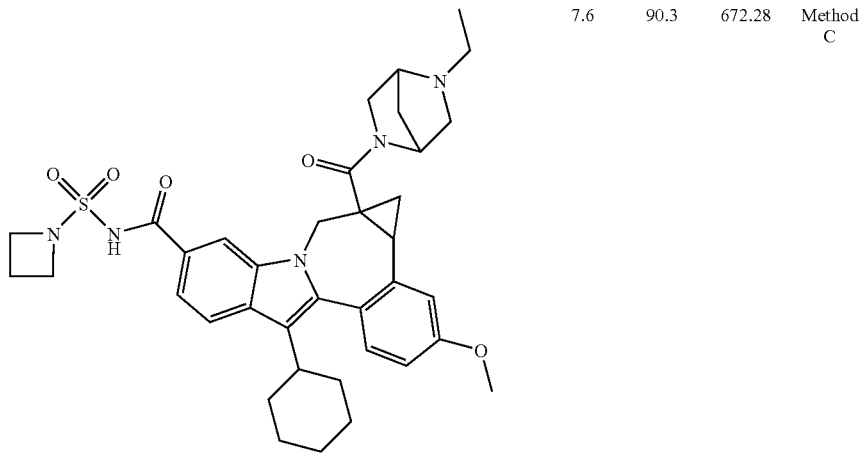 | 7.6 | 90.3 | 672.28 | Method C |
| 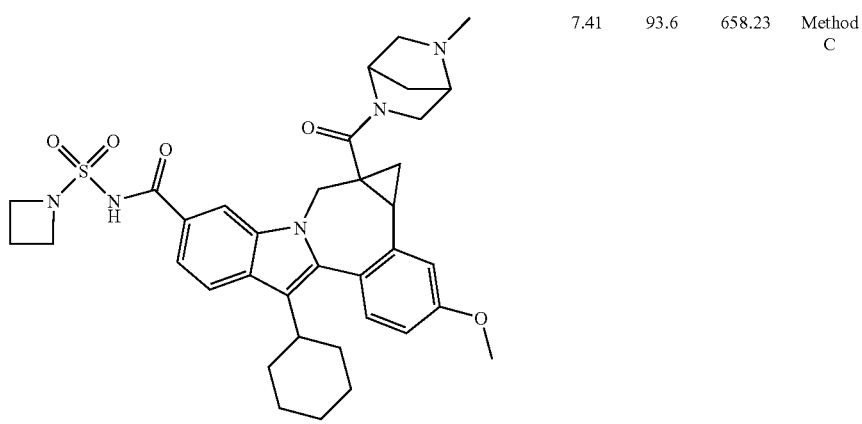 | 7.41 | 93.6 | 658.23 | Method C |
| 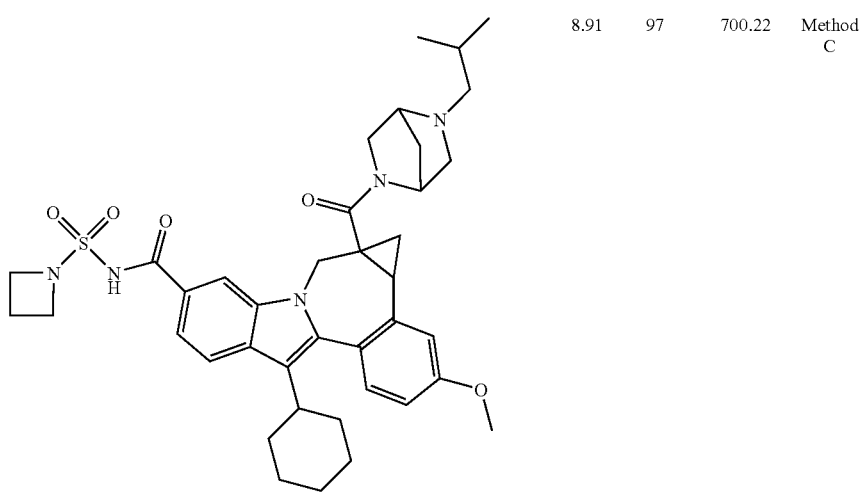 | 8.91 | 97 | 700.22 | Method C |

-continued

| Structure | HPLC Ret. Time [min] | HPLC Purity [%] | MS Reported Mass | HPLC Method |
|---|---|---|---|---|
| 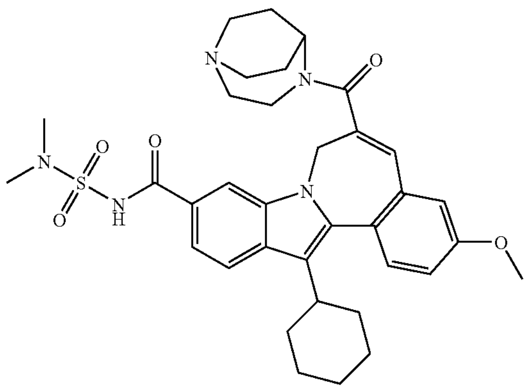 | 2.46 | 100 | 646.74 | Method D |
| 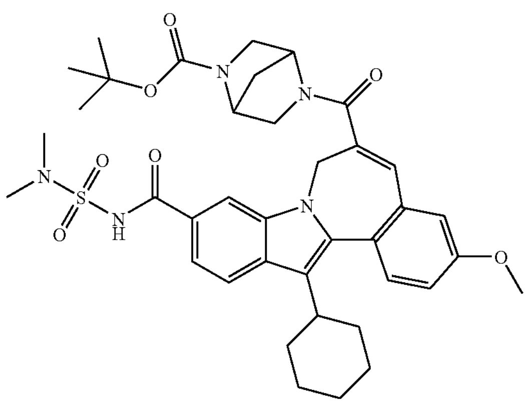 | 3.31 | 97 | 718.6 | Method D |
| 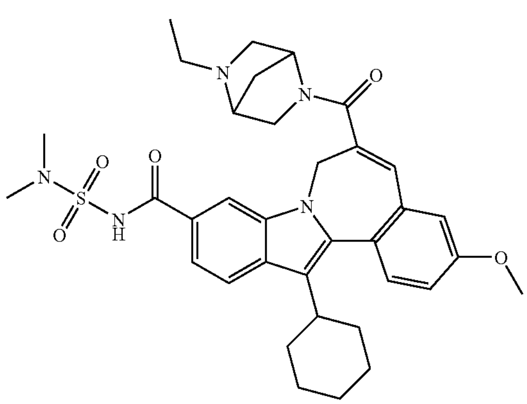 | 2.38 | 100 | 646.73 | Method D |

-continued

| Structure | HPLC Ret. Time [min] | HPLC Purity [%] | MS Reported Mass | HPLC Method |
|---|---|---|---|---|
| 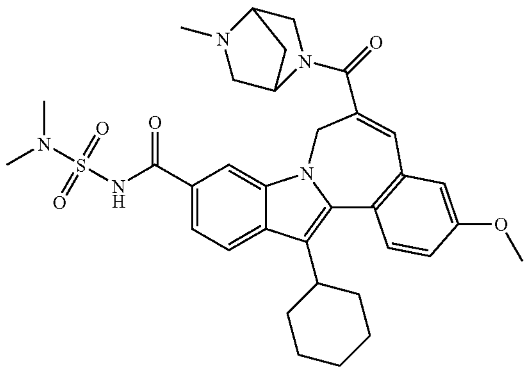 | 2.39 | 100 | 632.74 | Method D |
| 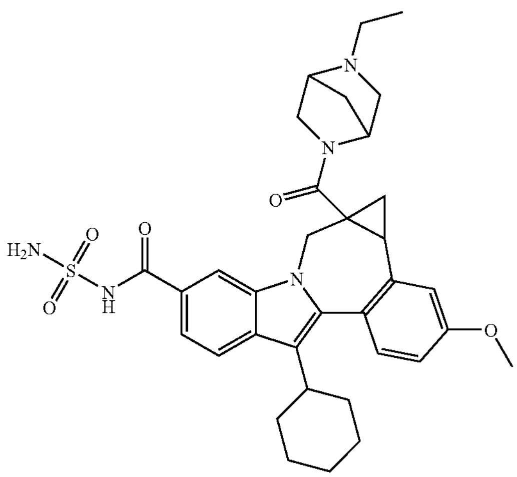 | 1.94 | 96.4 | 631.8 | Method D |
| 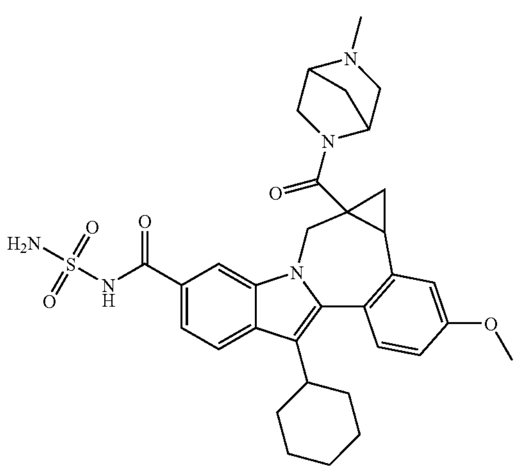 | 2.06 | 100 | 617.84 | Method D |

-continued
| Structure | HPLC Ret. Time [min] | HPLC Purity [%] | MS Reported Mass | HPLC Method |
|---|---|---|---|---|
| 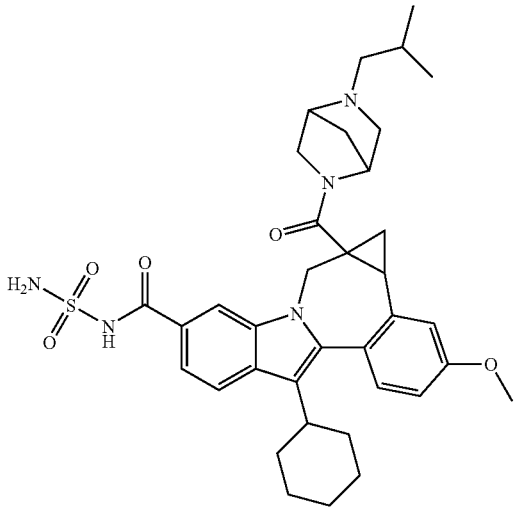 | 2.47 | 91.7 | 660.75 | Method D |
| 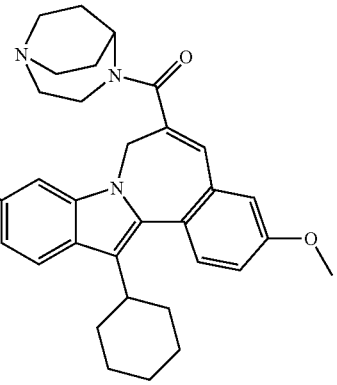 | 6.99 | 93 | 618.12 | Method D |
| 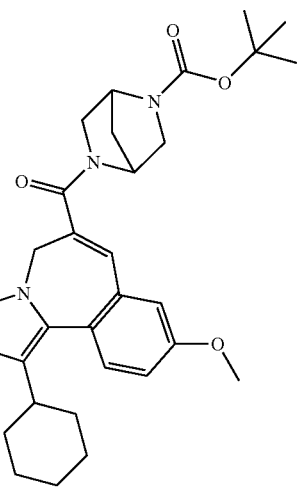 | 9.35 | 93.9 | 690.11 | Method D |

-continued
| Structure | HPLC Ret. Time [min] | HPLC Purity [%] | MS Reported Mass | HPLC Method |
|---|---|---|---|---|
| 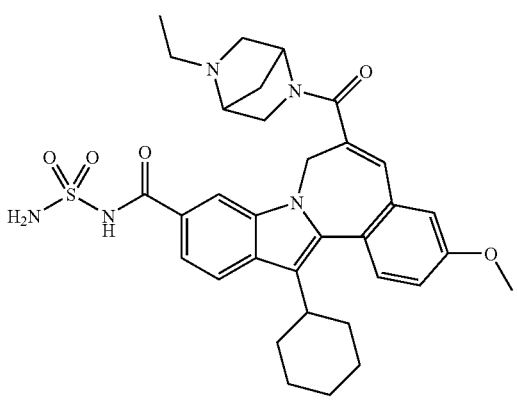 | 7.16 | 100 | 618.12 | Method D |
| 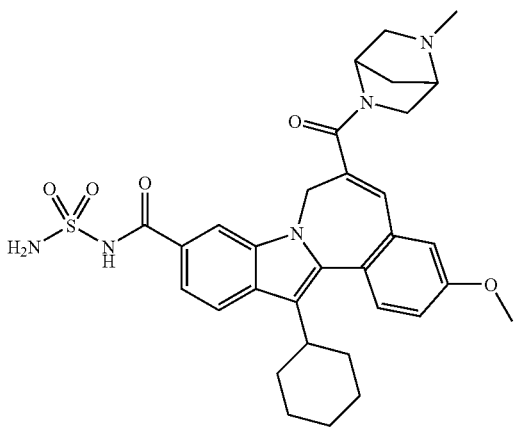 | 7.01 | 100 | 604.13 | Method D |
| 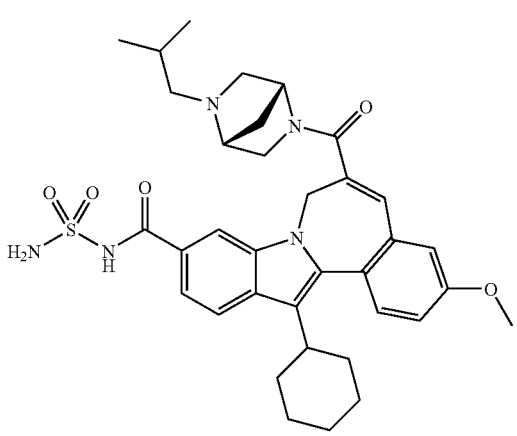 | 8.34 | 100 | 646.16 | Method D |

-continued

| Structure | HPLC Ret. Time [min] | HPLC Purity [%] | MS Reported Mass | HPLC Method |
|---|---|---|---|---|
| 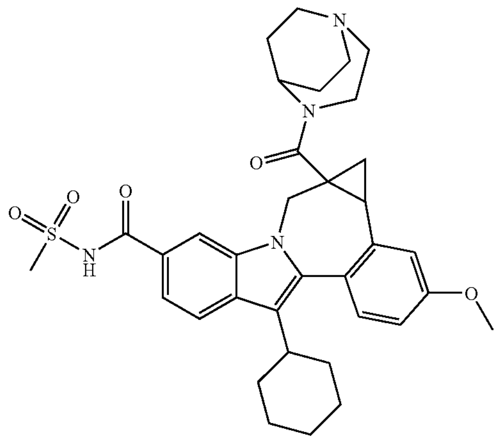 | 2.05 | 96.3 | 631.39 | Method D |
| 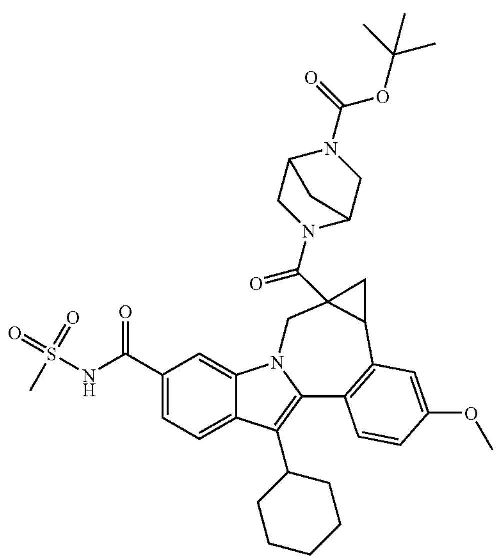 | 2.53 | 100 | 703.42 | Method D |
| 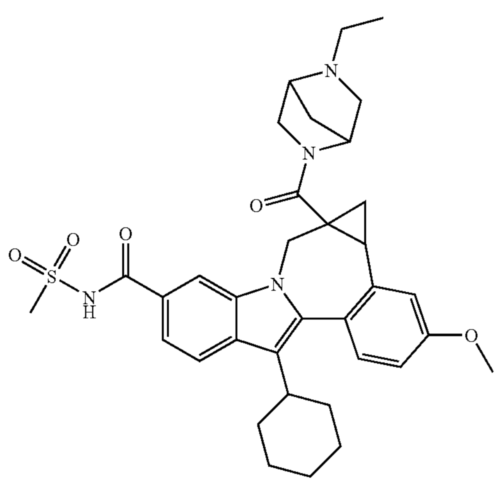 | 1.96 | 90.6 | 631.38 | Method D |

| Structure | HPLC Ret. Time [min] | HPLC Purity [%] | MS Reported Mass | HPLC Method |
|---|---|---|---|---|
| 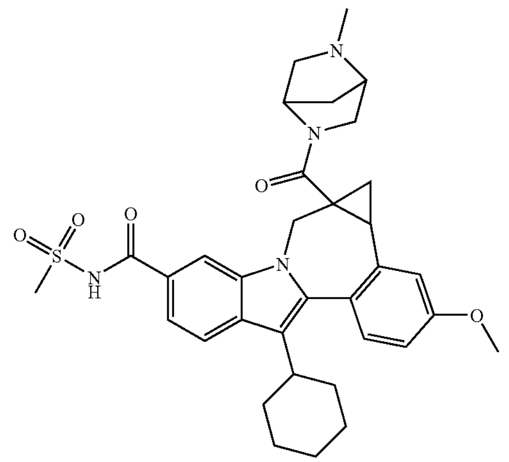 | 1.93 | 97.3 | 617.36 | Method D |
| 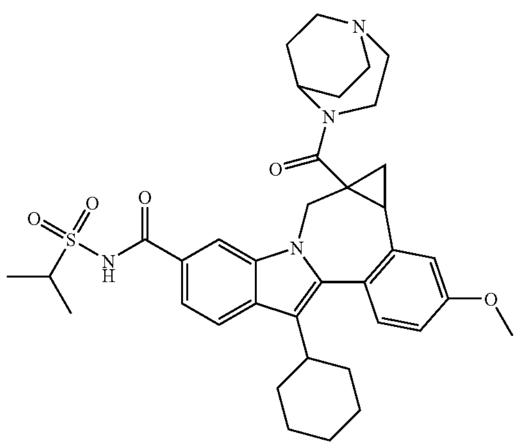 | 7.28 | 100 | 659.2 | Method D |
| 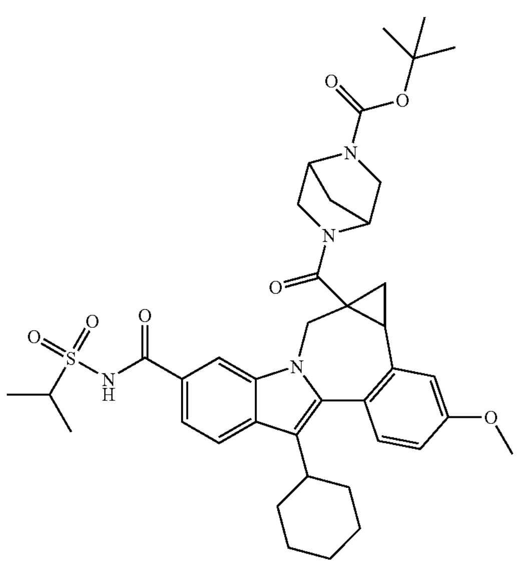 | 7.02 | 100 | 731.07 | Method D |

-continued
| Structure | HPLC Ret. Time [min] | HPLC Purity [%] | MS Reported Mass | HPLC Method |
|---|---|---|---|---|
| 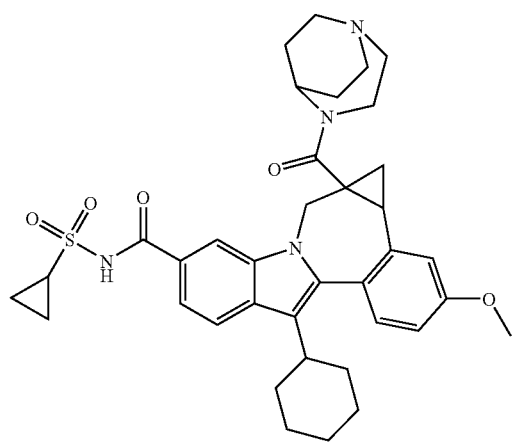 | 2.06 | 93.3 | 657.37 | Method D |
| 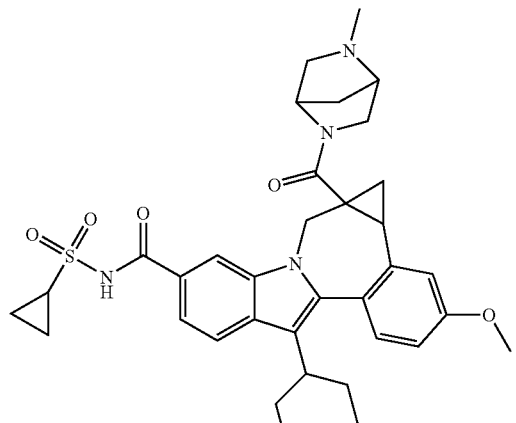 | 2.17 | 93.2 | 643.35 | Method D |
| 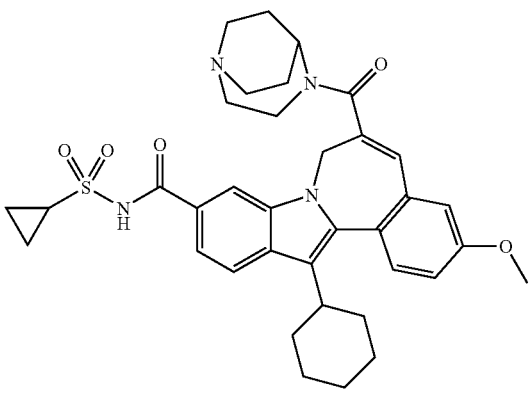 | 2.08 | 100 | 642.78 | Method D |

-continued
| Structure | HPLC Ret. Time [min] | HPLC Purity [%] | MS Reported Mass | HPLC Method |
|---|---|---|---|---|
| 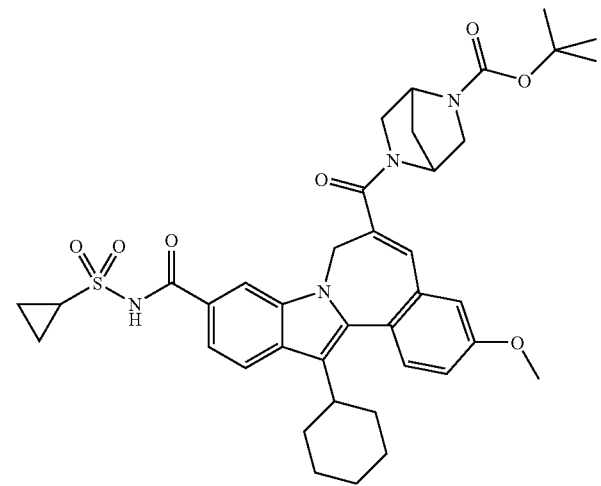 | 2.95 | 100 | 714.66 | Method D |
| 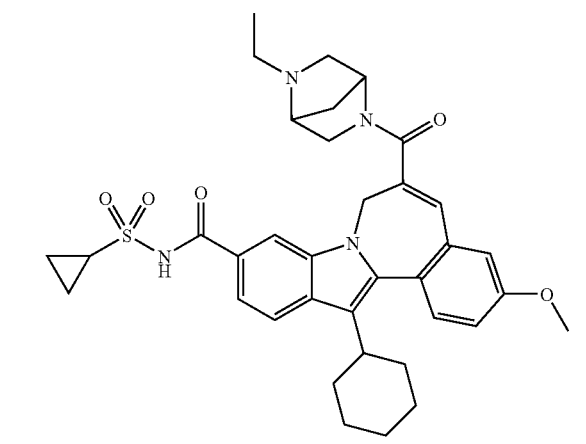 | 2.17 | 100 | 642.77 | Method D |
| 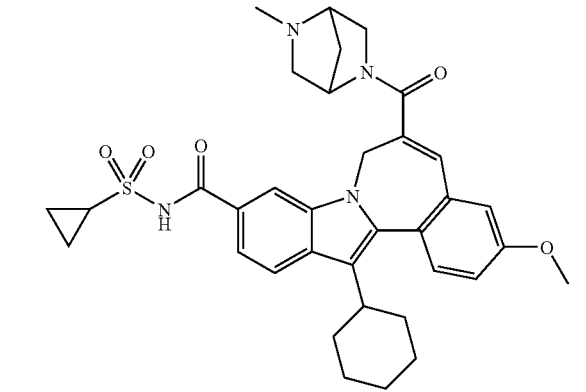 | 2.48 | 100 | 628.79 | Method D |

-continued

| Structure | HPLC Ret. Time [min] | HPLC Purity [%] | MS Reported Mass | HPLC Method |
|---|---|---|---|---|
| 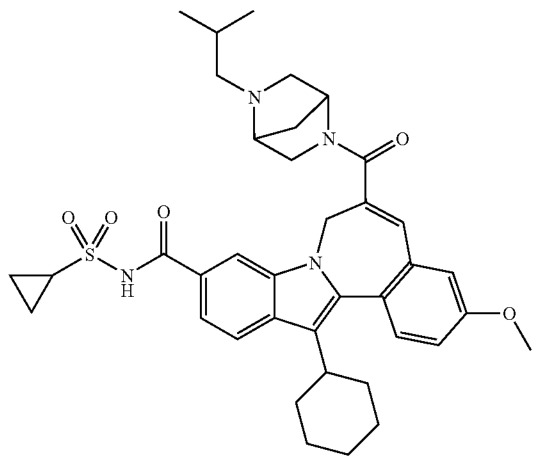 | 2.39 | 100 | 670.71 | Method D |
| 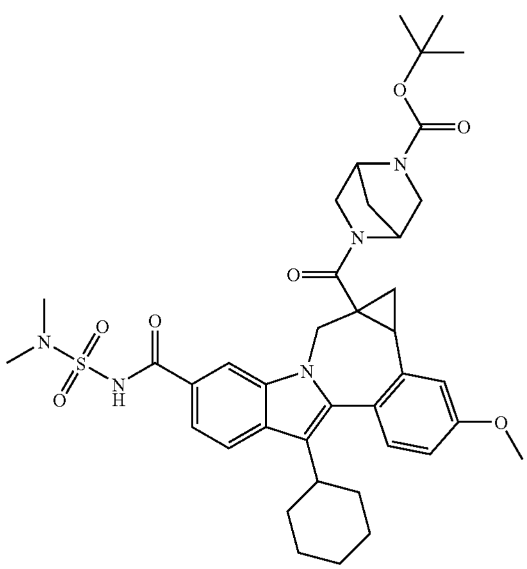 | 3.12 | 100.0 | 732.44 | Method D |
| 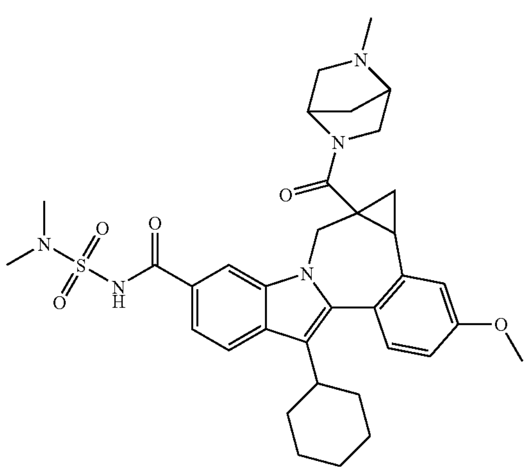 | 2.10 | 100.0 | 646.39 | Method D |

-continued

| Structure | HPLC Ret. Time [min] | HPLC Purity [%] | MS Reported Mass | HPLC Method |
|---|---|---|---|---|
| 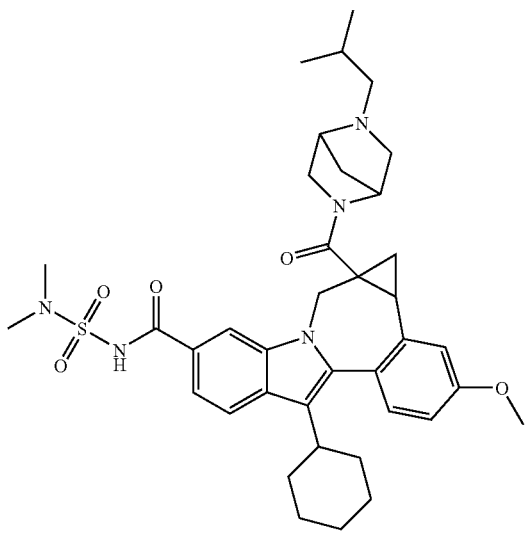 | 2.71 | 98.5 | 688.44 | Method D |

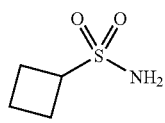

To a 250 mL RBF equipped with a stir bar was added bromocyclobutane (3.49 mL, 37.0 mmol) and 70 mL of diethyl ether. The flask was cooled to −78° C. (acetone/dry ice bath). To this solution was then added, via syringe, 2.0 eq. of a 1.7M solution of tert-butyllithium (43.6 mL, 74.1 mmol). The mixture was stirred for 60 minutes, then cannulated into a 500 mL flask containing sulfuryl chloride (6.00 mL, 74.1 mmol) in 30 mL of diethylether at −78° C. The suspension was warmed to room temperature overnight. The white mixture was diluted with 40 mL of diethylether, filtered and set aside. A 3 necked 500 mL RBF equipped with a stir bar and dry THF (10 mL) was cooled to −65° C. with the aid of a dry ice/isopropanol bath and gaseous ammonia was slowly sparged into the flask. Previously synthesized cyclobutanesulfonyl chloride (5.2 g, 33.6 mmol) was then dripped in via syringe (crude mixture in ~200 mL of ether/THF). Sparging of ammonia gas was continued for an additional 5 minutes. The mixture was kept at −65° C. for 4 hours then allowed to slowly warm to room temperature. The reaction mixture was filtered and washed with 100 mL of THF. The solvent was evaporated to give 2.1 g of the desired sulfonamide (46% yield) as a pale yellow oily solid. $^1$H NMR (500 MHz, DMSO-D6): δ ppm 1.81-1.89 (m, 2H), 2.16-2.22 (m, 2H), 2.23-2.31 (m, 2H), 3.66-3.74 (m, 1H), 6.68 (s, 2H).

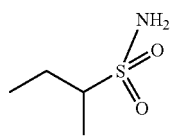

$^1$H NMR (500 MHz, DMSO-D6): δ ppm 0.94 (m, 3H), 1.20 (m, 3H), 1.30-1.45 (m, 1H), 1.90 (m, 1H), 2.76 (m, 1H), 6.59 (s, 2H).

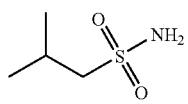

$^1$H NMR (500 MHz, DMSO-D6): δ ppm 1.02 (d, J=6.95 Hz, 6H), 2.11 (m, 1H), 2.86 (d, J=6.22 Hz, 2H), 6.71 (s, 2H).

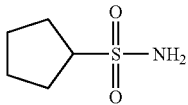

¹H NMR (500 MHz, DMSO-D6): δ ppm 1.51-1.66 (m, 4H), 1.86 (m, 4H), 3.37 (m, 1H), 6.65 (s, 2H).

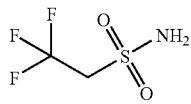

¹H NMR (500 MHz, DMSO-D6): δ ppm 4.24 (m, 2H), 7.46 (s, 2H).

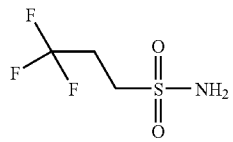

¹H NMR (500 MHz, DMSO-D6): δ ppm 2.70 (m, 2H), 3.20 (m, 2H), 7.01 (s, 2H).

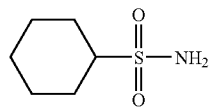

¹H NMR (500 MHz, DMSO-D6): δ ppm 1.07-1.17 (m, 1H), 1.22-1.38 (m, 4H), 1.62 (m, 1H), 1.78 (m, 2H), 2.05 (m, 2H), 2.68-2.77 (m, 1H), 6.57 (s, 2H).

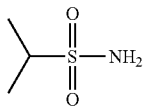

¹H NMR (300 MHz, DMSO-D6): δ ppm 1.22 (d, J=6.59 Hz, 6H), 3.00 (m, 1H), 6.59 (s, 2H).

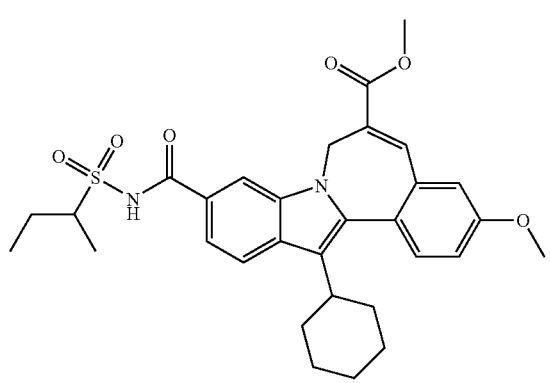

Methyl 10-((sec-butylsulfonyl)carbamoyl)-13-cyclohexyl-3-methoxy-7H-indolo[2,1-a][2]benzazepine-6-carboxylate. In a 100 mL round-bottomed flask (RBF) was added carboxylic acid 1 (575 mg, 1.291 mmol) and 1,1'-carbonyldiimidazole (460 mg, 2.84 mmol) in THF (15 mL) to give a yellow solution. The mixture was stirred at room temperature under nitrogen for 1 hour then heated to 70° C., in an oil bath, for 90 minutes. The mixture was cooled and sec-butyl sulfonamide (921 mg, 6.71 mmol) in 4 mL of THF was added along with neat DBU (0.389 mL, 2.58 mmol). The RBF was returned to the oil bath and heated overnight at 70° C. The reaction mixture was transferred to a separatory funnel, diluted with 100 mL of DCM, washed ×3 with 100 mL of 0.5 M HCl, then with 100 mL of H₂O, and finally saturated NaCl. The organic mixture was dried over MgSO4, filtered and concentrated to give 713 mgs of the desired acylsulfonamide 2 as a yellow solid (96% yield) which was placed under vacuum overnight. LC data was recorded on a Shimadzu LC-10AS liquid chromatograph equipped with a Phenomenex-Luna 10μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. 1H NMR (500 MHz, CD3OD): δ ppm 0.84-0.92 (m, 3H), 1.03 (t, J=7.32 Hz, 3H), 1.23 (m, 1H), 1.28-1.44 (m, 7H), 1.58 (m, 1H), 1.72 (m, 2H), 1.85 (m, 1H), 1.95-2.07 (m, 3H), 2.17 (m, 1H), 2.78 (m, 1H), 3.69 (m, 2H), 3.83-3.91 (m, 3H), 7.02 (s, 1H), 7.11 (m, 1H), 7.47 (d, J=7.63 Hz, 1H), 7.74 (m, 3H), 8.25 (s, 1H). LC/MS: m/z 565.22, Rf 2.192 min., 97.5% purity.

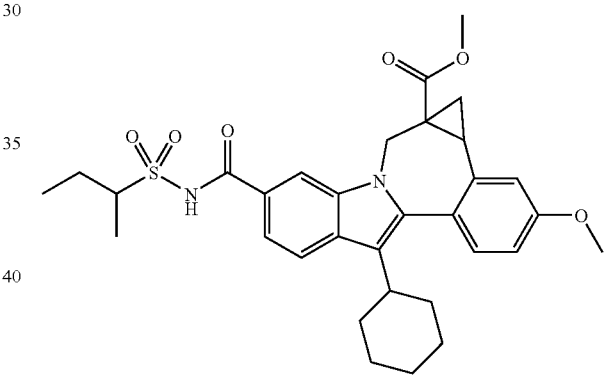

Methyl 5-((sec-butylsulfonyl)carbamoyl)-8-cyclohexyl-11-methoxy-1,12b-dihydro cyclopropa[d]indolo[2,1-a][2]benzazepine-1a(2H)-carboxylate. To 63.1 mgs of 95% NaH in 5 mL of dry DMF in a 100 mL RBF was added 629 mgs of trimethylsulfoxonium iodide at room temperature. The mixture was stirred at room temperature under nitrogen for 30 minutes. A solution of Intermediate 9 (in 7 mL of DMF) was added via syringe and the reaction was stirred for 15-20 minutes. The reaction mixture was quickly cooled to 0° C. with an ice bath, 1 mL of 1 M HCl was added followed by 60 mL of ice water. The heterogeneous mixture was stirred for 30 minutes. The mixture was filtered and the yellow solid was washed with ice water. The solid was taken up in 2% methanol/DCM and was purified using a Biotage Horizon MPLC employing a 40+M column with a solvent gradient of 2% methanol/DCM to 10% methanol/DCM. 450 mgs (62% yield) of the compound was obtained as a yellow solid after solvent evaporation. LC data was recorded on a Shimadzu LC-10AS liquid chromatograph equipped with a Phenomenex-Luna 10μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/ 90% H2O/0.1% trifluoroacetic acid and solvent B was 10% H2O/90% MeOH/0.1% trifluoroacetic acid. MS data was determined using a Micromass Platform for LC in electrospray mode. 1H NMR (300 MHz, CD3OD): δ ppm 0.19 (m, 0.35H), 1.03-1.14 (m, 3H), 1.19-1.34 (m, 2.65H), 1.43 (m, 5H), 1.55-1.66 (m, 2H), 1.74 (m, 2H), 1.89-1.94 (m, 2H), 1.99-2.14 (m, 3H), 2.64-2.95 (m, 2H), 3.35 (d, J=15.00 Hz, 0.65H), 3.48 (m, 2H), 3.67-3.81 (m, 2H), 3.85 (s, 3H), 3.90-3.98 (m, 0.35H), 5.17 (m, 0.35H), 5.36 (m, 0.65H), 6.91-6.98 (m, 1H), 7.09 (m, 0.35H), 7.16 (m, 0.65H), 7.19-7.27 (m, 1H), 7.52-7.65 (m, 1H), 7.83 (m, 1H), 8.09 (s, 0.35H), 8.29 (s, 0.65 H). LC/MS: m/z 579.31, Rf 2.167 min., 95.2% purity.

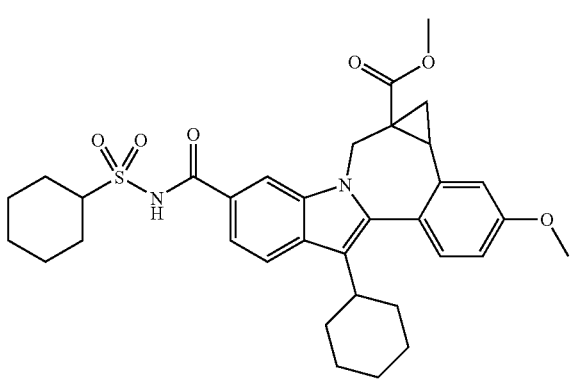

Methyl 8-cyclohexyl-5-((cyclohexylsulfonyl)carbamoyl)-11-methoxy-1,12b-dihydrocyclo propa[d]indolo[2,1-a][2]benzazepine-1a(2H)-carboxylate. 1H NMR (300 MHz, CD3OD): δ ppm 0.23 (m, 0.35H), 1.14-1.53 (m, 10H), 1.60-1.79 (m, 3H), 1.91 (m, 3H), 2.09 (m, 1.65H), 2.18 (m, 3H), 2.81-2.98 (m, 3H), 3.41-3.46 (m, 0.65H), 3.50 (m, 2H), 3.71-3.79 (m, 2H), 3.88 (s, 3H), 3.99-4.04 (m, 0.35H), 5.25 (m, 0.35H), 5.45 (m, 0.65H), 6.97-7.02 (m, 1H), 7.13 (m, 0.35H), 7.21 (m, 0.65H), 7.26-7.32 (m, 1H), 7.55-7.65 (m, 1H), 7.85-7.92 (m, 1H), 8.11 (s, 0.35H), 8.32 (s, 0.65 H). LC/MS: m/z 605.42, Rf 2.223 min., 99.2% purity.

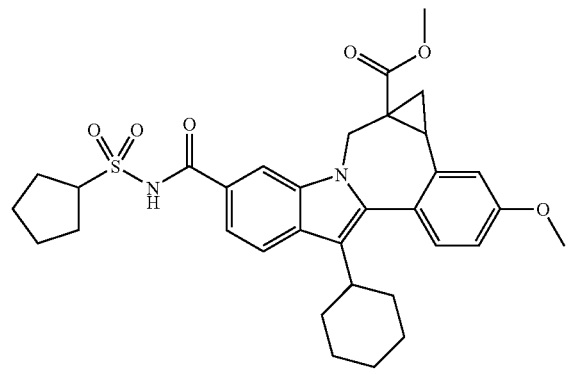

Methyl 8-cyclohexyl-5-((cyclopentylsulfonyl)carbamoyl)-11-methoxy-1,12b-dihydrocyclo propa[d]indolo[2,1-a][2]benzazepine-1a(2H)-carboxylate. 1H NMR (300 MHz, CD3OD): δ ppm 0.23 (m, 0.35H), 1.27 (m, 2.65H), 1.39 (m, 2H), 1.60-1.79 (m, 7H), 1.91-2.19 (m, 8H), 2.67-2.97 (m, 2H), 3.47 (m, 0.65H), 3.50 (m, 3H), 3.78-3.87 (m, 3H), 4.10 (m, 0.35H), 4.29 (m, 1H), 5.22 (m, 0.35H), 5.43 (m, 0.65H), 6.98-7.02 (m, 1H), 7.14 (m, 0.35H), 7.21 (m, 0.65H), 7.26-7.32 (m, 1H), 7.55-7.65 (m, 1H), 7.85-7.91 (m, 1H), 8.10 (s, 0.35H), 8.32 (s, 0.65H). LC/MS: m/z 591.33, Rf 2.200 min., 100% purity.

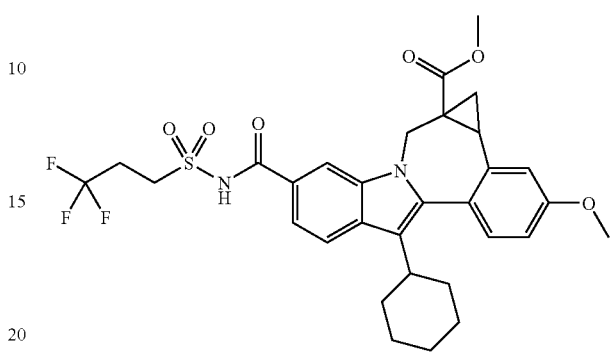

Methyl 8-cyclohexyl-11-methoxy-5-(((3,3,3-trifluoropropyl)sulfonyl)carbamoyl)-1,12b-dihydrocyclopropa[d]indolo[2,1-a][2]benzazepine-1a(2H)-carboxylate. 1H NMR (300 MHz, CD3OD): δ ppm 0.19 (m, 0.35H), 1.25 (m, 1.65H), 1.41 (m, 2H), 1.65 (m, 1H), 1.76 (m, 2H), 1.94 (m, 2H), 2.04 (m, 1H), 2.61-2.84 (m, 6H), 2.88-2.96 (m, 1H), 3.35-3.40 (m, 0.65H), 3.48 (m, 2H), 3.80 (m, 2H), 3.86 (m, 3H), 3.89-3.98 (m, 0.35H), 5.18 (m, 0.35H), 5.38 (m, 0.65H), 6.96-7.01 (m, 1H), 7.13 (m, 0.35H), 7.20 (m, 0.65H), 7.24-7.30 (m, 1H), 7.58-7.69 (m, 1H), 7.84-7.90 (m, 1H), 8.13 (s, 0.35H), 8.34 (s, 0.65H). LC/MS: m/z 619.32, Rf 2.188 min., 99.5% purity.

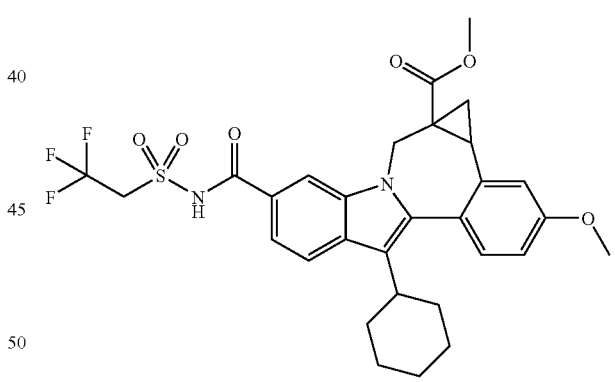

Methyl 8-cyclohexyl-11-methoxy-5-(((2,2,2-trifluoroethyl)sulfonyl)carbamoyl)-1,12b-dihydro cyclopropa[d]indolo[2,1-a][2]benzazepine-1a(2H)-carboxylate. 1H NMR (300 MHz, CD3OD): δ ppm 0.13 (m, 0.35H), 1.18 (m, 1.65H), 1.38 (m, 2H), 1.57-1.62 (m, 2H), 1.73 (m, 2H), 1.87 (m, 2H), 1.96-2.05 (m, 1H), 2.60-2.90 (m, 1.35H), 3.17-3.22 (m, 0.65H), 3.45 (m, 2H), 3.74 (m, 1H), 3.84 (m, 2H), 4.04-4.10 (m, 3H), 4.38-4.53 (m, 2 H), 5.06 (m, 0.35H), 5.18 (m, 0.65H), 6.90-6.96 (m, 1H), 7.06 (m, 0.35H), 7.13 (m, 0.65H), 7.16-7.22 (m, 1H), 7.63 (m, 0.65H), 7.70-7.80 (m, 1.35H), 8.14 (s, 0.35H), 8.33 (s, 0.65H). LC/MS: m/z 605.29, Rf 2.178 min., 96.5% purity.

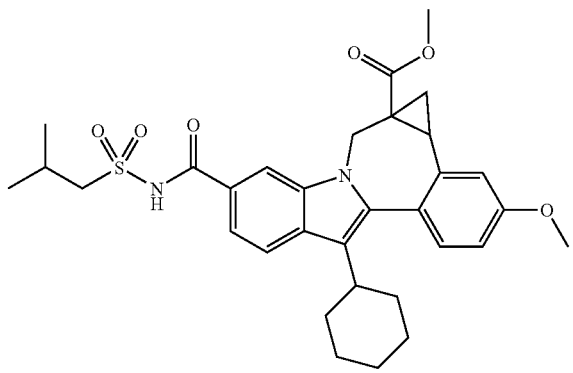

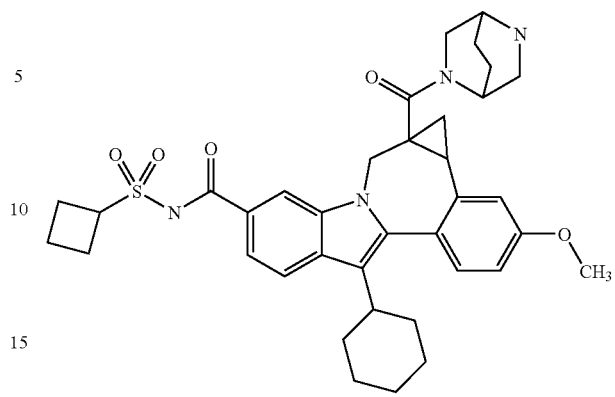

Methyl 8-cyclohexyl-5-((isobutylsulfonyl)carbamoyl)-11-methoxy-1,12b-dihydrocyclopropa [d]indolo[2,1-a][2]benzazepine-1a(2H)-carboxylate. 1H NMR (300 MHz, CD3OD): δ ppm 0.17 (m, 0.35H), 1.09 (m, 6H), 1.22 (m, 1.65H), 1.38 (m, 2H), 1.49-1.60 (m, 1H), 1.73 (m, 2H), 1.87 (m, 2H), 1.96-2.05 (m, 2H), 2.15-2.39 (m, 1H), 2.61-2.87 (m, 2H), 2.96 (d, J=6.22 Hz, 2H), 3.19 (m, 2H), 3.43 (m, 2H), 3.70 (m, 2H), 3.84 (m, 2H), 5.06-5.11 (m, 1H), 6.90-6.95 (m, 1H), 7.05-7.11 (m, 1H), 7.16-7.23 (m, 1H), 7.67-782 (m, 2H), 8.20 (s, 0.35H), 8.39 (s, 0.65H). LC/MS: m/z 579.30, Rf 2.190 min., 96.2% purity.

General procedure for the transformation of esters of formula 1 to corresponding amides. In a 100 mL round-bottomed flask was added 1 N sodium hydroxide (3 eq., 1.583 ml, 1.583 mmol) and bridged ester 1 (1 eq., 0.528 mmol) in methanol (4.00 ml) and THF (4.00 ml) to give a yellow solution. The mixture was stirred for 3 hours at room temperature. 3 equivalents of 1 N HCl was then added, the product diluted with ethyl acetate then extracted, washed with brine and dried over MgSO$_4$. Filtration and subsequent evaporation of volatiles gave the carboxylic acids 2 in near quantitative yield. To a 0.10 mmol solution of carboxylic acid 2 in 1 mL of anhydrous N,N-Dimethylformamide (DMF) in a 2 dram vial equipped with a Teflon™ lined screw cap was added 0.3 mmol (3 eq.) of 2-(1H-Benzotriazole-1-yl)-1,1,3,3,-Tetramethyluronium Tetrafluoroborate (TBTU) in 1.0 mL of anhydrous DMF followed by the addition of 0.2 mmol (2 eq.) of amine 3 in 1.0 mL of anhydrous DMF and 0.4 mmol of neat N,N-diisopropylethylamine. The reaction was shaken on a VWR Vortex-Genie 2 Mixer overnight at room temperature. The reaction volumes were then reduced in a Savant Speedvac and the crude products were taken up in 1.2 mL of methanol and purified using a Shimadzu preparative HPLC employing methanol/water and 0.1% trifluoroacetic acid buffer with a Phenomenex Luna, C18, 30 mm×100 mm, 10 µm column at a gradient of 40-100% B and a flow rate of 40 mL/min. over 10 minutes with a 5-10 minute hold, to give carboxamides 4 as yellow amorphous solids (65%-70% yield). Post-purification LC/MS data was obtained on a Shimadzu analytical LC/Micromass Platform LC (ESI+) at 220 nm using the following set of conditions: Column I (Phenomenex 10 µm C18, 4.6×30 mm), Solvent system I (gradient of 0-100% B where B=90% HPLC grade methanol/0.1% trifluoroacetic acid/10% HPLC grade water), in 2 minutes with a 1 minute hold at a flow rate of 5 mL/minute.

N-(cyclobutylsulfonyl)-8-cyclohexyl-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxamide. LC/MS: m/z 657.51, Rf 1.783 min., 96.5% purity.

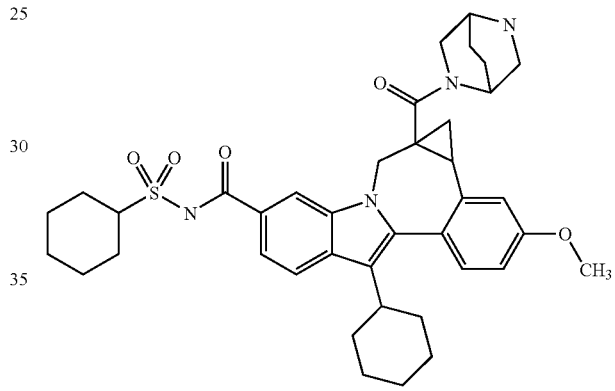

8-Cyclohexyl-N-(cyclohexylsulfonyl)-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxamide. LC/MS: m/z 685.52, Rf 1.872 min., 99.3% purity.

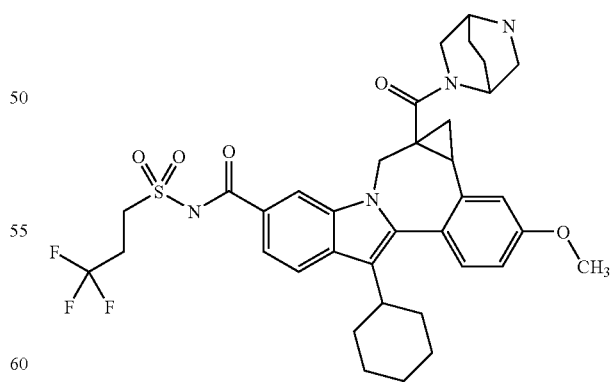

8-Cyclohexyl-1a-(2,5-diazabicyclo[2.2.2]oct-2-ylcarbonyl)-11-methoxy-N-((3,3,3-trifluoropropyl)sulfonyl)-1,1a,2,12b-tetrahydrocyclopropa[d]indolo[2,1-a][2]benzazepine-5-carboxamide. LC/MS: m/z 699.49, Rf 1.793 min., 98.0% purity.

201

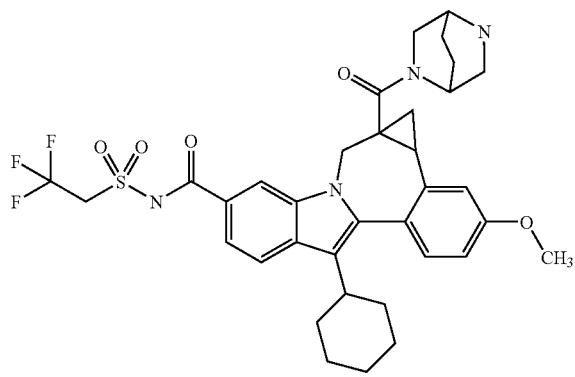

8-Cyclohexyl-1a-(2,5-diazabicyclo[2.2.2]oct-2-ylcarbonyl)-11-methoxy-N-((2,2,2-trifluoroethyl)sulfonyl)-1,1a,2,12b-tetrahydrocyclopropa[d]indolo[2,1-a][2]benzazepine-5-carboxamide. LC/MS: m/z 685.45, Rf 1.778 min., 96.5% purity.

8-Cyclohexyl-N-(cyclopentylsulfonyl)-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxamide. LC/MS: m/z 671.51, Rf 1.833 min., 99.3% purity.

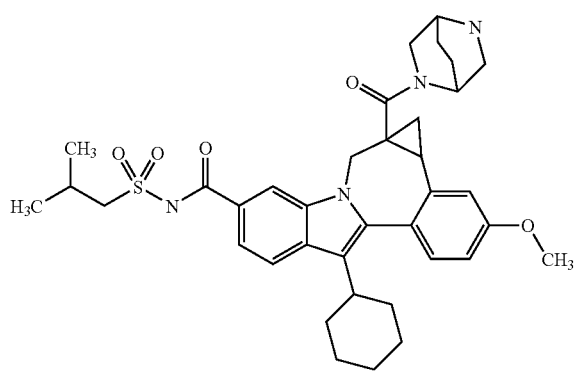

202

8-Cyclohexyl-1a-(2,5-diazabicyclo[2.2.2]oct-2-ylcarbonyl)-N-(isobutylsulfonyl)-11-methoxy-1,1a,2,12b-tetrahydrocyclopropa[d]indolo[2,1-a][2]benzazepine-5-carboxamide. LC/MS: m/z 659.52, Rf 1.808 min., 98.1% purity.

N-(sec-butylsulfonyl)-8-cyclohexyl-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxamide. LC/MS: m/z 659.52, Rf 1.805 min., 98.2% purity.

1a-((3-Benzyl-3,6-diazabicyclo[3.1.1]hept-6-yl)carbonyl)-N-(cyclobutylsulfonyl)-8-cyclohexyl-11-methoxy-1,1a,2,12b-tetrahydrocyclopropa[d]indolo[2,1-a][2]benzazepine-5-carboxamide. 1H NMR (300 MHz, CD3OD): δ ppm 0.16 (m, 0.35H), 1.27-1.37 (m, 2H), 1.41 (m, 1H), 1.45 (m, 1.65H), 1.62 (m, 1H), 2.05 (m, 2H), 2.06-2.15 (m, 7H) 2.39 (m, 2H), 2.59-2.68 (m, 2H), 2.81-2.90 (m, 1H), 3.02 (m, 1H), 3.19 (m, 1H), 3.36-3.45 (m, 1H), 3.47 (m, 1H), 3.53 (m, 1H), 3.62 (m, 1H), 3.90-3.97 (m, 3H), 4.15-4.33 (m, 1H), 4.50 (m, 1H), 4.59 (m, 1H), 4.77 (m, 2H), 5.39 (m, 2H), 7.06 (dd, J=8.55, 2.44 Hz, 1H), 7.24 (d, J=2.44 Hz, 1H), 7.32-7.41 (m, 2H), 7.45-7.52 (m, 3H), 7.55-7.64 (m, 2H), 7.92-8.00 (m, 1H), 8.21 (m, 1H). LC/MS: m/z 733.48, Rf 1.833 min., 98.5% purity.

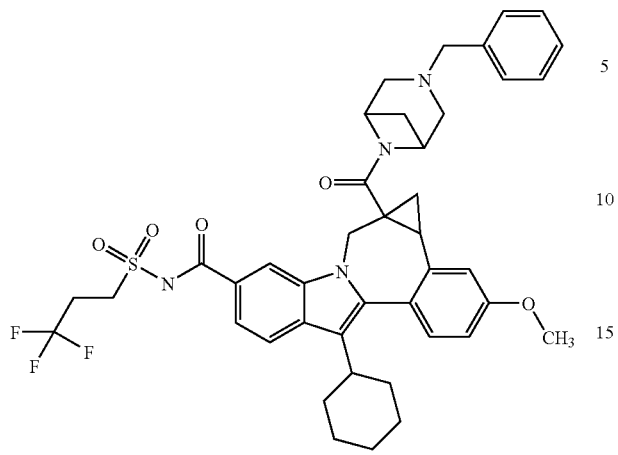

1a-((3-Benzyl-3,6-diazabicyclo[3.1.1]hept-6-yl)carbonyl)-8-cyclohexyl-11-methoxy-N-((3,3,3-trifluoropropyl)sulfonyl)-1,1a,2,12b-tetrahydrocyclopropa[d]indolo[2,1-a][2]benzazepine-5-carboxamide. 1H NMR (500 MHz, CD3OD): δ ppm 0.16 (m, 0.35H), 1.28-1.37 (m, 3H), 1.41 (m, 1.65H), 1.47 (m, 2H), 1.70 (m, 1H), 1.83 (m, 2H), 1.98-2.14 (m, 5H), 2.59 (m, 1H), 2.78-2.86 (m, 4H), 3.03 (m, 1H), 3.16-3.24 (m, 1H), 3.44-3.58 (m, 2H), 3.85-3.96 (m, 6H), 4.18 (m, 1H), 4.47 (m, 1H), 5.47 (m' 7.07 (m, 1H), 7.20-7.26 (m, 1H), 7.32-7.39 (m, 2H), 7.46 (m, 3H), 7.59-7.67 (m, 2H), 7.94-7.98 (m, 1H), 8.15-8.29 (m, 1H). LC/MS: m/z 775.45, Rf 1.888 min., 95.7% purity.

1a-((3-Benzyl-3,6-diazabicyclo[3.1.1]hept-6-yl)carbonyl)-8-cyclohexyl-N-(cyclohexylsulfonyl)-11-methoxy-1,1a,2,12b-tetrahydrocyclopropa[d]indolo[2,1-a][2]benzazepine-5-carboxamide. 1H NMR (500 MHz, CD3 OD): δ ppm 0.14 (m, 0.35H), 1.21-1.48 (m, 9.65H), 1.63 (m, 3H), 1.68 (m, 1H), 1.80 (m, 3H), 1.93 (m, 4H), 1.98-2.08-2.17 (m, 5H), 2.60-2.87 (m, 1H), 2.99 (m, 1H), 3.18 (m, 1H), 3.44 (m, 1H), 3.55 (m, 2H), 3.68-3.77 (m, 2H), 3.86-3.94 (m, 3H), 4.16 (m, 1H), 4.58 (m, 1H), 5.36 (m, 1H), 7.04 (dd, J=8.55, 2.75 Hz, 1H), 7.18-7.27 (m, 1H), 7.30-7.38 (m, 2H), 7.42-7.50 (m, 3H), 7.53-7.60 (m, 2H), 7.92 (m, 1H), 8.12-8.22 (m, 1H). LC/MS: m/z 761.54, Rf 1.922 min., 98.6% purity.

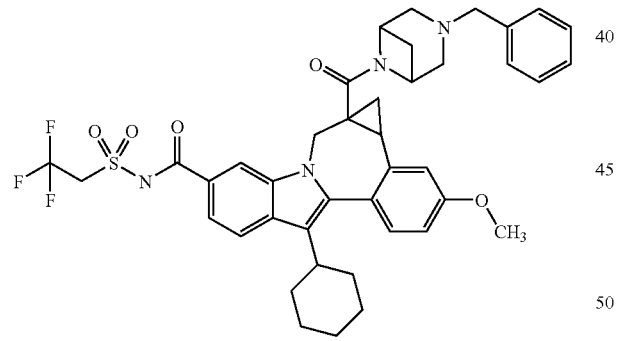

1a-((3-Benzyl-3,6-diazabicyclo[3.1.1]hept-6-yl)carbonyl)-8-cyclohexyl-11-methoxy-N-((2,2,2-trifluoroethyl)sulfonyl)-1,1a,2,12b-tetrahydrocyclopropa[d]indolo[2,1-a][2]benzazepine-5-carboxamide. 1H NMR (300 MHz, CD3OD): δ ppm 0.10 (m, 0.35H), 1.28 (m, 2H), 1.35 (m, 3H), 1.51 (m, 0.65H), 1.68-1.84 (m, 3H), 1.87-2.10 (m, 5H), 2.53 (m, 1H), 2.71-2.86 (m, 1H), 2.89-3.04 (m, 1H), 3.43-3.58 (m, 3H), 3.67-3.80 (m, 1H), 3.87 (s, 3H), 4.13 (m, 1H), 4.32 (m, 1H), 4.49-4.74 (m, 3H), 4.90-5.04 (m, 1H), 5.30 (m, 1H), 7.00 (m, 1H), 7.15-7.23 (m, 1H), 7.25-7.33 (m, 2H), 7.36-7.46 (m, 3H), 7.48-7.61 (m, 2H), 7.89 (m, 1H), 8.09-8.18 (m, 1H). LC/MS: m/z 761.47, Rf 1.850 min., 97.0% purity.

1a-((3-Benzyl-3,6-diazabicyclo[3.1.1]hept-6-yl)carbonyl)-8-cyclohexyl-N-(cyclopentylsulfonyl)-11-methoxy-1,1a,2,12b-tetrahydrocyclopropa[d]indolo[2,1-a][2]benzazepine-5-carboxamide. 1H NMR (500 MHz, CD3OD): δ ppm 0.012 (m, 0.35), 1.33 (m, 2H), 1.39 (m, 1.65H), 1.45 (m, 3H), 1.65 (m, 1H), 1.79 (m, 3H), 1.83 (m, 4H), 1.91 (m, 2H), 1.94-2.14 (m, 6H), 2.58-2.89 (m, 2H), 2.99 (m, 2H), 3.16 (m, 1H), 3.36 (m, 2H), 3.40-3.56 (m, 2H), 3.89 (m, 3H), 4.30 (m, 1H), 4.50 (m, 1H), 5.38 (m, 1H), 7.04 (dd, J=8.39, 2.59 Hz, 1H), 7.18-7.22 (m, 1H), 7.32-7.37 (m, 2H), 7.44 (m, 3H), 7.57 (m, 2H), 7.91-7.95 (m, 1H), 8.10-8.21 (m, 1H). LC/MS: m/z 747.50, Rf 1.868 min., 96.3% purity.

205

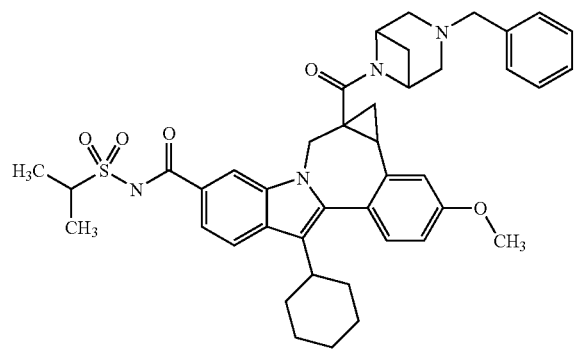

1a-((3-Benzyl-3,6-diazabicyclo[3.1.1]hept-6-yl)carbonyl)-8-cyclohexyl-N-(isopropyl sulfonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.12 (m, 0.35H), 1.34 (m, 6.65H), 1.43 (m, 6H), 1.59 (m, 1H), 1.79 (m, 3H), 1.97 (m, 5H), 2.56-2.85 (m, 1H), 2.92-3.07 (m, 1H), 3.45-3.60 (m, 3H), 3.85 (m, 1H), 3.88-4.00 (m, 6H), 4.52 (m, 1H), 5.32 (m, 1H), 7.03 (dd, J=8.78, 2.56 Hz, 1H), 7.17-7.23 (m, 1H), 7.29-7.36 (m, 2H), 7.41-7.49 (m, 3H), 7.51-7.65 (m, 2H), 7.88-7.96 (m, 1H), 8.08-8.19 (m, 1H). LC/MS: m/z 721.50, Rf 1.828 min., 97.0% purity.

206

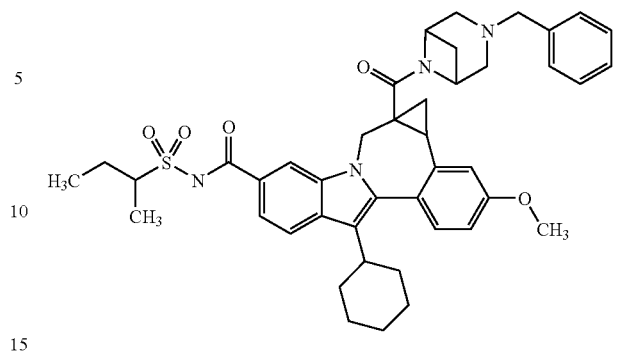

1a-((3-Benzyl-3,6-diazabicyclo[3.1.1]hept-6-yl)carbonyl)-N-(sec-butylsulfonyl)-8-cyclohexyl-11-methoxy-1,1a,2,12b-tetrahydrocyclopropa[d]indolo[2,1-a][2]benzazepine-5-carboxamide. 1H NMR (300 MHz, CD3OD): δ ppm 0.13 (m, 0.35H), 1.01-1.13 (m, 3.65H), 1.21 (m, 3H), 1.30-1.45 (m, 6H), 1.50-1.80 (m, 6H), 1.80-2.12 (m, 4H), 2.57-2.86 (m, 2H), 3.00 (m, 1H), 3.55 (m, 3H), 3.76 (m, 2H), 3.84-3.94 (m, 3H), 4.11 (m, 2H), 4.56 (m, 1H), 5.36 (m, 1H), 7.03-7.09 (m, 1H), 7.23 (m, 1H), 7.27-7.40 (m, 3H), 7.45-7.86 (m, 4H), 7.92-8.00 (m, 1H), 8.13-8.23 (m, 1H). LC/MS: m/z 735.60, Rf 1.865 min., 95.2% purity.

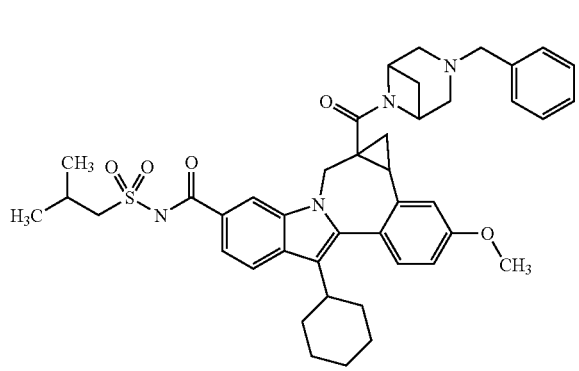

1a-((3-Benzyl-3,6-diazabicyclo[3.1.1]hept-6-yl)carbonyl)-8-cyclohexyl-N-(isobutylsulfonyl)-11-methoxy-1,1a,2,12b-tetrahydrocyclopropa[d]indolo[2,1-a][2]benzazepine-5-carboxamide. 1H NMR (500 MHz, CD3OD): δ ppm 0.14 (m, 0.35H), 1.13 (m, 6.65H), 1.23 (m, 1H), 1.26-1.35 (m, 2H), 1.39 (m, 2H), 1.42 (m, 2H), 1.59 (m, 1H), 1.81 (m, 2H), 1.95 (m, 2H), 2.02 (m, 1H), 2.12 (m, 2H), 2.27-2.36 (m, 2H), 2.87 (m, 1H), 3.01 (m, 1H), 3.13-3.22 (m, 1H), 3.39-3.44 (m, 2H), 3.47-3.53 (m, 3H), 3.88-3.95 (m, 4H), 4.58 (m, 1H), 5.36 (m, 1H), 7.04 (dd, J=8.55, 2.44 Hz, 1H), 7.17-7.24 (m, 1H), 7.30-7.38 (m, 2H), 7.45 (m, 3H), 7.55-7.64 (m, 2H), 7.92-8.00 (m, 1H), 8.10-8.21 (m, 1H). LC/MS: m/z 735.51, Rf 1.895 min., 95.0% purity.

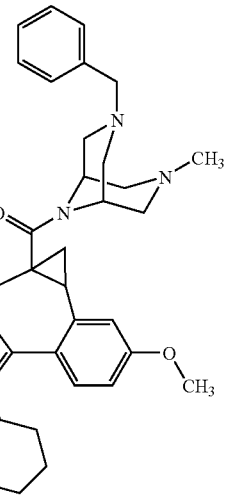

1a-((3-Benzyl-7-methyl-3,7,9-triazabicyclo[3.3.1]non-9-yl)carbonyl)-N-(sec-butyl sulfonyl)-8-cyclohexyl-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.20H), 1.06-1.14 (m, 3H), 1.20-1.36 (m, 2.80H), 1.42 (m, 6H), 1.72 (m, 4H), 1.98-2.13 (m, 6H), 2.62 (m, 2H), 2.85 (m, 4H), 3.15 (m, 1H), 3.52 (m, 2H), 3.63 (m, 2H), 3.76 (m, 2H), 3.87 (m, 4H), 4.11 (m, 1H), 4.38 (m, 1H), 4.55 (m, 1H), 5.06 (m, 1H), 6.97-7.05 (m, 1H), 7.11-7.17 (m, 1H), 7.27-7.42 (m, 5H), 7.59 (m, 2H), 7.90 (m, 1H), 8.01-8.09 (m, 1H). LC/MS: m/z 779.48, Rf 1.897 min., 95.3% purity.

7.29-7.37 (m, 1H), 7.51-7.63 (m, 1H), 7.89 (m, 1H), 7.99-8.10 (m, 1H). LC/MS: m/z 689.50, Rf 1.813 min., 98.3% purity.

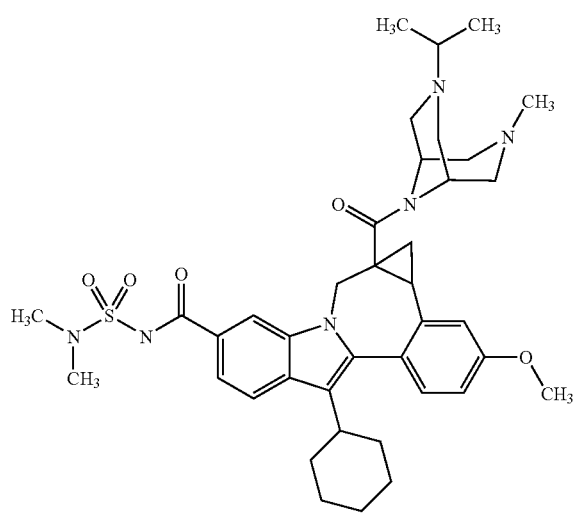

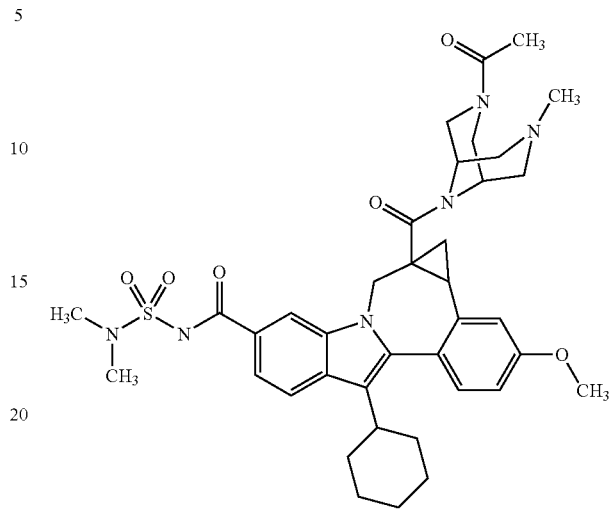

8-Cyclohexyl-N-(dimethylsulfamoyl)-1a-((3-isopropyl-7-methyl-3,7,9-triazabicyclo[3.3.1]non-9-yl)carbonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.19 (m, 0.35H), 1.12 (m, 3.65H), 1.20-1.35 (m, 4H), 1.39 (m, 2H), 1.45-1.58 (m, 2H), 1.64 (m, 2H), 1.78 (m, 3H), 2.00 (m, 6H), 2.61 (m, 3H), 2.74-2.90 (m, 2H), 2.90-3.05 (m, 6H), 3.48 (m, 1H), 3.61 (m, 2H), 3.84-3.91 (m, 4H), 4.15 (m, 1H), 4.45 (m, 1H), 5.07 (m, 1H), 7.01 (m, 1H), 7.11-7.20 (m, 1H), 7.26-7.35 (m, 1H), 7.50-7.63 (m, 1H), 7.88 (m, 1H), 8.00-8.09 (m, 1H). LC/MS: m/z 717.52, Rf 1.762 min., 97.8% purity.

1a-((3-Acetyl-7-methyl-3,7,9-triazabicyclo[3.3.1]non-9-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (300 MHz, CD3OD): δ ppm 0.51 (m, 0.20H), 1.68 (m, 4.80H), 1.98 (m, 2H), 2.12 (m, 2H), 2.41 (m, 7H), 2.98 (m, 1H), 3.19 (m, 2H), 3.56-3.65 (m, 13H), 3.94-4.10 (m, 2H), 4.14-4.29 (m, 4H), 4.95 (m, 2H), 5.40 (m, 1H), 7.35 (m, 1H), 7.47-7.53 (m, 1H), 7.60-7.67 (m, 1H), 7.85 (m, 1H), 8.16-8.25 (m, 1H), 8.36 (s, 1H). LC/MS: m/z 717.47, Rf 1.710 min., 97.1% purity.

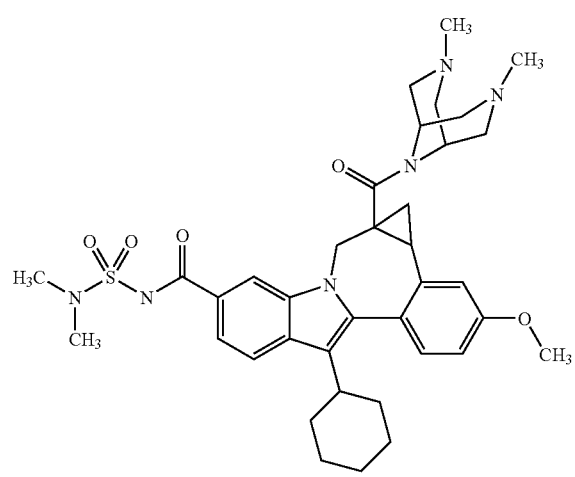

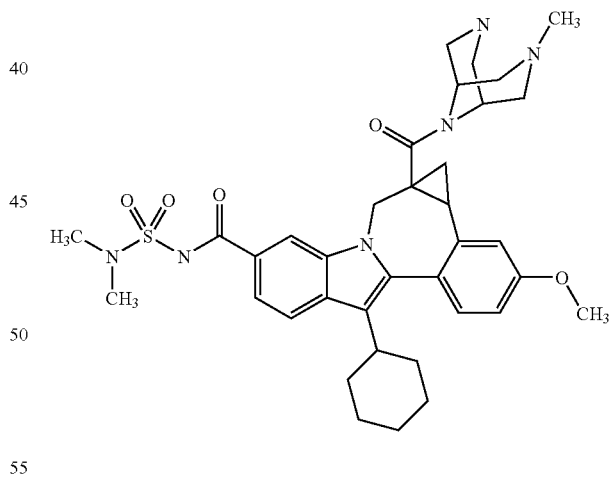

8-Cyclohexyl-N-(dimethylsulfamoyl)-1a-((3,7-dimethyl-3,7,9-triazabicyclo[3.3.1]non-9-yl)carbonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.24 (m, 0.20H), 1.24-1.38 (m, 2.80H), 1.45 (m, 4H), 1.56 (m, 1H), 1.83 (m, 2H), 2.04 (m, 4H), 2.65 (m, 1H), 2.82-2.91 (m, 1H), 2.93-3.05 (m, 9H), 3.17 (m, 3H), 3.49 (m, 1H), 3.64 (m, 2H), 3.78 (m, 1H), 3.86-3.95 (m, 4H), 4.03 (m, 1H), 4.18 (m, 1H), 4.37 (m, 1H), 4.51 (m, 1H), 5.08 (d, J=15.37 Hz, 1H), 6.99-7.07 (m, 1H), 7.13-7.22 (m, 1H), 8-Cyclohexyl-N-(dimethylsulfamoyl)-11-methoxy-1a-((3-methyl-3,7,9-triazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.20 (m, 0.20H), 1.24-1.36 (m, 1.80H), 1.45 (m, 2H), 1.55 (m, 3H), 1.64 (m, 1H), 1.80 (m, 1H) 1.86 (m, 2H) 2.08 (m, 6H), 2.36 (m, 1H), 2.48 (m, 1H), 2.62 (m, 2H), 2.86 (m, 1H), 3.00 (m, 3H), 3.16 (m, 1H), 3.45 (m, 2H) 3.66 (m, 4H), 3.85-3.96 (m, 3H), 4.18 (m, 1H), 4.34 (m, 1H), 4.46 (m, 1H), 5.05 (m, 1H), 7.01 (m, 1H), 7.13-7.20 (m, 1H), 7.32 (m, 1H), 7.52-7.61 (m, 1H), 7.89 (m, 1H), 8.00-8.07 (m, 1H). LC/MS: m/z 675.37, Rf 1.772 min., 95.3% purity.

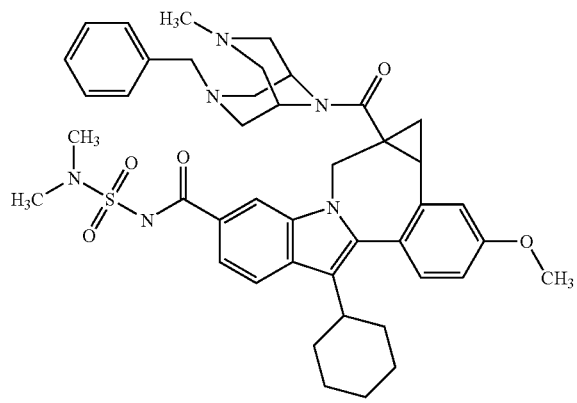

1a-((3-Benzyl-7-methyl-3,7,9-triazabicyclo[3.3.1]non-9-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.20H), 1.32 (m, 2.80H), 1.43 (m, 4H), 1.77 (m, 2H), 2.01 (m, 5H), 2.59-2.72 (m, 2H), 2.78 (m, 1H), 2.87 (m, 1H), 2.90-3.05 (m, 8H), 3.25 (m, 2H), 3.59 (m, 4H), 3.75 (m, 1H), 3.84-3.93 (m, 3H), 4.15 (m, 1H), 4.38 (m, 1H), 4.56 (m, 1H), 5.08 (d, J=15.00 Hz, 1H), 6.97-7.04 (m, 1H), 7.07-7.17 (m, 1H), 7.28-7.42 (m, 6H), 7.53-7.61 (m, 1H), 7.85-7.92 (m, 1H), 7.99-8.13 (m, 1H). LC/MS: m/z 765.45, Rf 1.840 min., 99.7% purity.

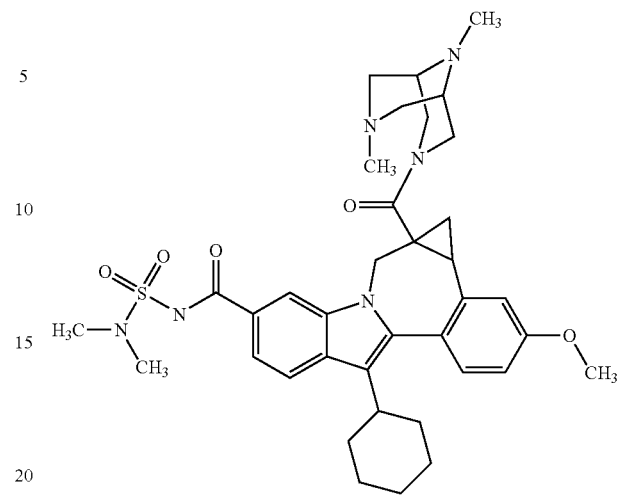

8-Cyclohexyl-N-(dimethylsulfamoyl)-1a-((7,9-dimethyl-3,7,9-triazabicyclo[3.3.1]non-3-yl)carbonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.24 (m, 0.35H), 1.24 (m, 0.65H), 1.29-1.49 (m, 5H), 1.62 (m, 1H), 1.79 (m, 2H), 1.98 (m, 4H), 2.42 (m, 1H), 2.53 (m, 1H), 2.62 (m, 1H), 2.75 (m, 1H), 2.87 (m, 2H), 2.93-3.07 (m, 8H), 3.12-3.22 (m, 2H), 3.42 (m, 2H), 3.51-3.66 (m, 1H), 3.88 (m, 3H), 4.13 (m, 3H), 4.27 (m, 1H), 4.60 (m, 1H), 5.00 (m, 1H), 6.97-7.04 (m, 1H), 7.14-7.20 (m, 1H), 7.31 (m, 1H), 7.49-7.61 (m, 1H), 7.81-7.92 (m, 1.65H), 8.06 (m, 0.35H). LC/MS: m/z 689.86, Rf 1.785 min., 96.2% purity.

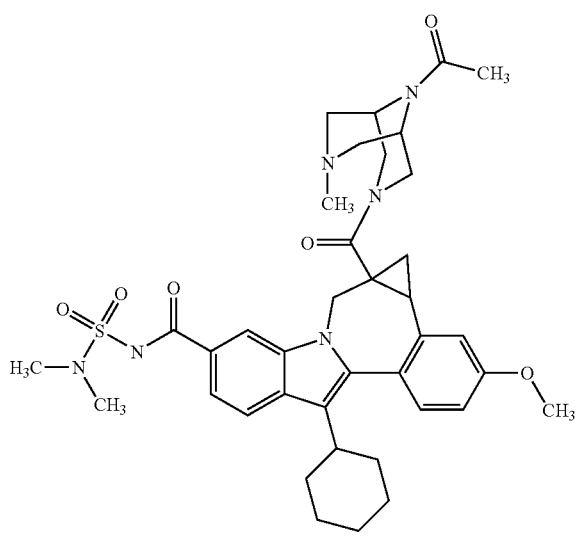

1a-((9-Acetyl-7-methyl-3,7,9-triazabicyclo[3.3.1]non-3-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.35H), 1.01-1.30 (m, 0.65H), 1.38 (m, 5H), 1.79 (m, 3H), 1.93-2.21 (m, 13H), 2.62 (m, 1H), 2.82 (m, 2H), 2.99 (s, 6H), 3.56 (m, 1H), 3.90 (m, 3H), 4.04-4.18 (m, 3H), 4.53 (m, 1H), 4.63 (m, 1H), 4.99 (m, 1H), 6.95-7.01 (m, 1H), 7.19 (m, 1H), 7.31 (m, 1H), 7.50-7.60 (m, 1H), 7.80 (m, 1H), 7.88-8.07 (m, 1H). LC/MS: m/z 717.92, Rf 1.760 min., 97.6% purity.

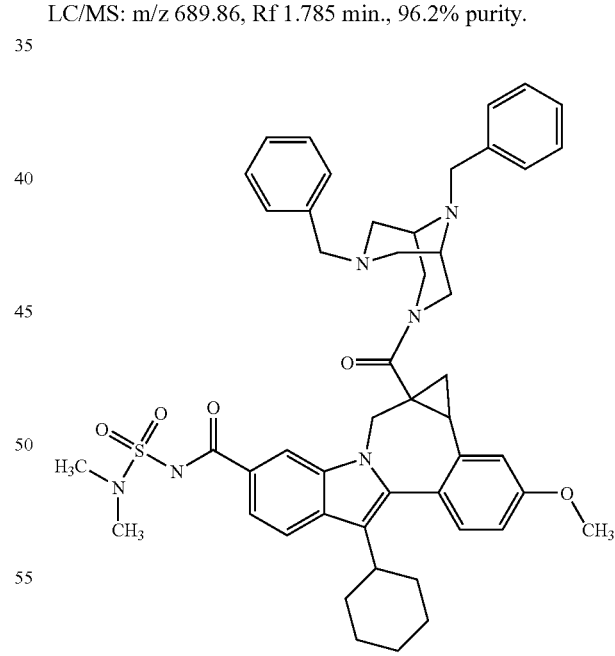

8-Cyclohexyl-1a-((7,9-dibenzyl-3,7,9-triazabicyclo[3.3.1]non-3-yl)carbonyl)-N-(dimethylsulfamoyl)-11-methoxy-1,1a,2,12b-tetrahydrocyclopropa[d]indolo[2,1-a][2]benzazepine-5-carboxamide. 1H NMR (500 MHz, CD3OD): δ ppm 0.22 (m, 0.25H), 0.90 (m, 1H), 1.19-1.28 (m, 1.75H), 1.38-1.46 (m, 3H), 1.76 (m, 3H), 1.95 (m, 2H), 2.00 (m, 2H), 2.07 (m, 2H), 2.54 (m, 1H), 2.86 (m, 1H), 2.99 (m, 9H), 3.16 (m, 1H), 3.43 (m, 1H), 3.47 (m, 3H), 3.84-3.91 (m, 4H), 4.01-4.09 (m, 2H), 4.75 (m, 1H), 4.99 (d, J=15.26 Hz, 1H), 6.94-7.02 (m, 1H), 7.08-7.17 (m, 1H), 7.27-7.56 (m, 11H), 7.70 (m, 1H), 7.86-8.07 (m, 2H). LC/MS: m/z 842.66, Rf 2.010 min., 98.0% purity.

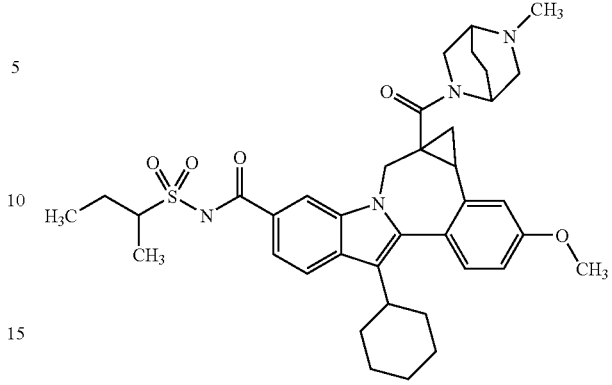

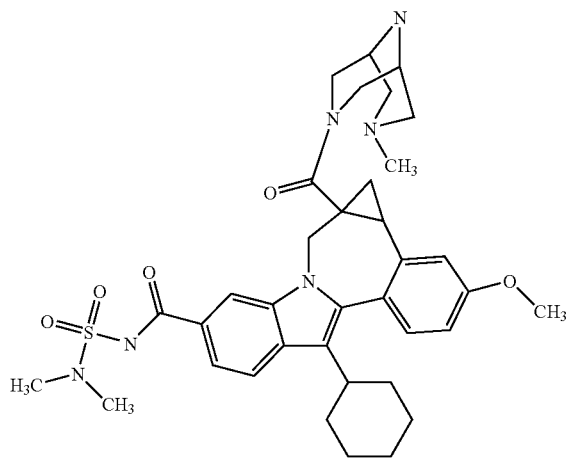

Cycloprop[d]indolo[2,1-a][2]benzazepine-5-carboxamide, 8-cyclohexyl-1,1a,2,12b-tetrahydro-11-methoxy-1a-[(5-methyl-2,5-diazabicyclo[2.2.2]oct-2-yl)carbonyl]-N-[(1-methylpropyl)sulfonyl]-. 1H NMR (500 MHz, CD3OD): δ ppm 0.13 (m, 0.20H), 0.98-1.14 (m, 3H), 1.17-1.35 (m, 1.80H), 1.35-1.59 (m, 7H), 1.60-1.73 (m, 2H), 1.72-1.85 (m, 2H), 1.87-2.16 (m, 6H), 2.20-2.45 (m, 1H), 2.56 (m, 1H), 2.73-2.92 (m, 3H), 2.97-3.17 (m, 3H), 3.27-3.35 (m, 1H), 3.45-3.69 (m, 2H), 3.69-3.81 (m, 2H), 3.83-3.94 (m, 3H), 3.93-4.20 (m, 1H), 4.16-4.52 (m, 1H), 4.92-5.26 (m, 1H), 6.97-7.04 (m, 1H), 7.18 (m, 1H), 7.26-7.31 (m, 1H), 7.47-7.61 (m, 1H), 7.85-7.91 (m, 1H), 7.93-8.17 (m, 1H). LC/MS: m/z 673.35, Rf 1.823 min., 98.4% purity.

8-Cyclohexyl-N-(dimethylsulfamoyl)-11-methoxy-1a-((7-methyl-3,7,9-triazabicyclo[3.3.1]non-3-yl)carbonyl)-1,1a,2,12b-tetrahydrocyclopropa[d]indolo[2,1-a][2]benzazepine-5-carboxamide. 1H NMR (500 MHz, CD3OD): δ ppm 0.23 (m, 0.30H), 1.07-1.29 (m, 0.70H), 1.36-1.45 (m, 5H), 1.60 (m, 1H), 1.73-1.82 (m, 2H), 1.90-2.07 (m, 4H), 2.17 (m, 1H), 2.35 (m, 1H), 2.54-2.70 (m, 3H), 2.86 (m, 1H), 3.00 (m, 8H), 3.20 (m, 2H), 3.59 (m, 1H), 3.71-3.80 (m, 1H), 3.84-3.91 (m, 3H), 4.14 m, 1H), 4.43 (m, 1H), 4.65 (m, 1H), 4.98 (m, 1H), 6.98-7.01 (m, 1H), 7.15-7.20 (m, 1H), 7.28-7.32 (m, 1H), 7.50-7.60 (m, 1H), 7.85-8.05 (m, 2H). LC/MS: m/z 675.61, Rf 1.783 min., 98.7% purity.

General procedure for reductive alkylation. To a 2 dram vial was added 0.05 mmol of piperidine carboxamide in 600 μL of methanol and 60 μL of water, along with 1.0 eq. of 1H-benzo[d][1,2,3]triazole, 2.0 eq. of aqueous formaldehyde and 2.0 equivalents of neat triethylamine. The vials were capped and shaken over night at room temperature on an orbital shaker. The reaction mixtures were then diluted with 2 mL of methanol and dry sodium borohydride was slowly added (2 eq). When effervescence ceased, the vials were recapped and heated at 65° C. with shaking in a dry block for ~90 min. After returning to room temperature the crude products were purified using a Shimadzu preparative HPLC employing methanol/water/0.1% TFA buffer where solvent A was 10% MeOH/90% H2O/0.1% trifluoroacetic acid and solvent B was 10% H2O/90% MeOH/0.1% trifluoroacetic acid with a Phenomenex-Luna 10u C18 30×100 mm column at a gradient of 30-100% B and a flow rate of 40 mL/min. over 10 minutes with a 8 minute hold. The products were evaporated to dryness overnight in a Savant Speedvac yielding methylpiperidines as yellow amorphous solids (63% average yield).

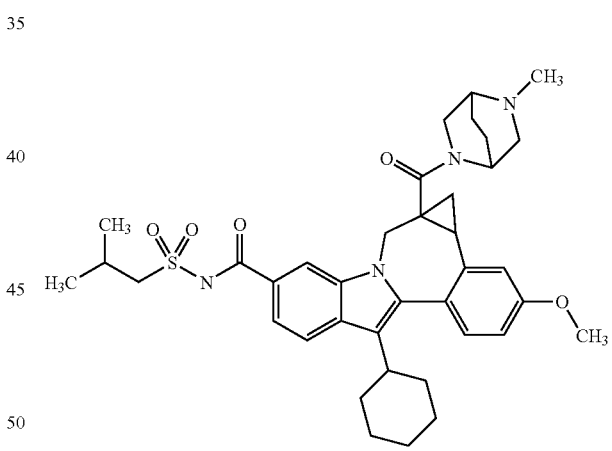

Cycloprop[d]indolo[2,1-a][2]benzazepine-5-carboxamide, 8-cyclohexyl-1,1a,2,12b-tetrahydro-11-methoxy-1a-[(5-methyl-2,5-diazabicyclo[2.2.2]oct-2-yl)carbonyl]-N-[(2-methylpropyl)sulfonyl]-. 1H NMR (500 MHz, CD3OD): δ ppm 0.13 (m, 0.20H), 1.14 (d, J=6.71 Hz, 6H), 1.24-1.32 (m, 1.80H), 1.39-1.49 (m, 4H), 1.50 (m, 1H), 1.80 (m, 3H), 1.93-2.08 (m, 5H), 2.31 (m, 2H), 2.52 (m, 1H), 2.88 (m, 2H), 2.97 (m, 2H), 3.10 (m, 1H), 3.33 (m, 1H), 3.49 (m, 2H), 3.67 (m, 3H), 3.82-3.90 (m, 3H), 4.03 (m, 1H), 4.32 (m, 1H), 5.05 (m, 1H), 7.01 (m,1H), 7.21 (m,1H), 7.26-7.34 (m, 1H), 7.55-7.64 (m, 1H), 7.90 (m, 1H), 7.93 -8.02 (m, 1H). LC/MS: m/z 673.45, Rf 1.827 min., 98.5% purity.

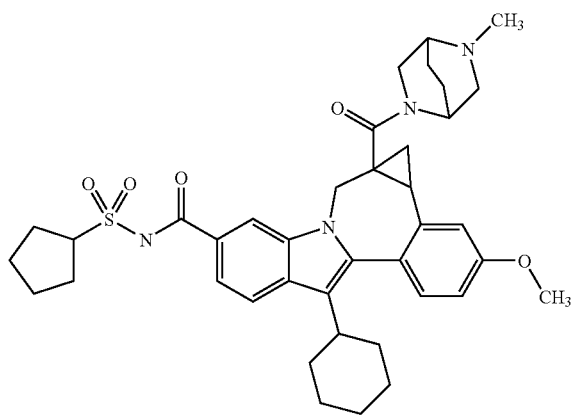
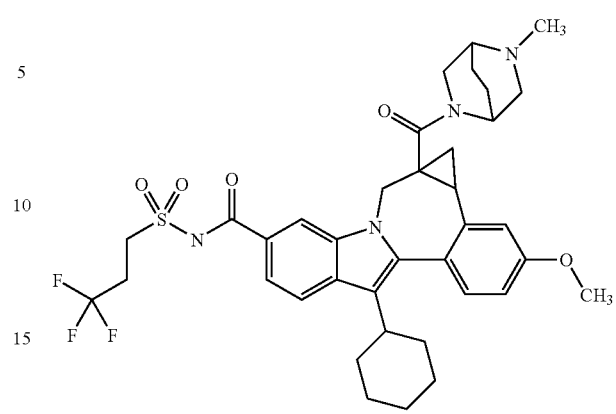

Cycloprop[d]indolo[2,1-a][2]benzazepine-5-carboxamide, 8-cyclohexyl-N-(cyclopentylsulfonyl)-1,1a,2,12b-tetrahydro-11-methoxy-1a-[(5-methyl-2,5-diazabicyclo[2.2.2]oct-2-yl)carbonyl]-. 1H NMR (500 MHz, CD3OD): δ ppm 0.13 (m, 0.20H), 1.17-1.32 (m, 2H), 1.39-1.48 (m, 3.80H), 1.65-1.75 (m, 3H), 1.76-1.85 (m, 4H), 1.90-2.17 (m, 9H), 2.40 (m, 1H), 2.57 (m, 2H), 2.83-2.92 (m, 2H), 2.92-3.01 (m, 3H), 3.34 (m, 1H), 3.62 (m, 3H), 3.82-3.90 (m, 3H), 4.02 (m, 1H), 4.22-4.31 (m, 2H), 5.02 (m, 1H), 7.00 (m, 1H), 7.17 (m, 1H), 7.27-7.32 (m, 1H), 7.52-7.61 (m, 1H), 7.84-8.20 (m, 2H). LC/MS: m/z 685.47, Rf 1.827 min., 99.2% purity.

Cycloprop[d]indolo[2,1-a][2]benzazepine-5-carboxamide, 8-cyclohexyl-1,1a,2,12b-tetrahydro-11-methoxy-1a-[(5-methyl-2,5-diazabicyclo[2.2.2]oct-2-yl)carbonyl]-N-[(3,3,3-trifluoropropyl)sulfonyl]-. 1H NMR (500 MHz, CD3OD): δ ppm 0.12 (m, 0.20H), 1.06-1.33 (m, 2H), 1.36-1.70 (m, 4.80H), 1.78 (m, 2H), 1.93-2.09 (m, 5H), 2.30 (m, 1H), 2.56 (m, 2H), 2.7-3.19 (m, 7H), 3.34 (m, 1H), 3.59 (m, 3H), 3.88 (m, 5H), 4.02 (m, 1H), 4.28 (m, 1H), 5.04 (m, 1H), 7.00-7.07 (m, 1H), 7.17-7.22 (m, 1H), 7.23-7.34 (m, 1H), 7.54-7.64 (m, 1H), 7.84-8.02 (m, 2H). LC/MS: m/z 713.30, Rf 1.818 min., 98.6% purity.

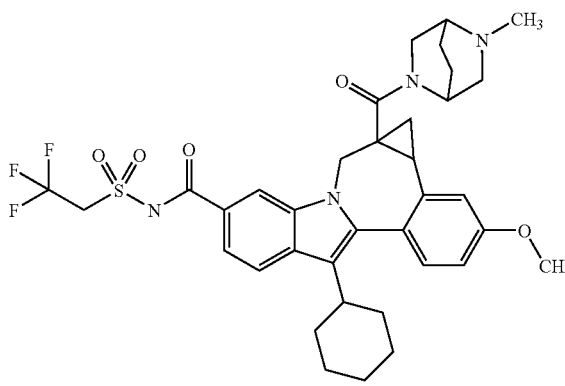
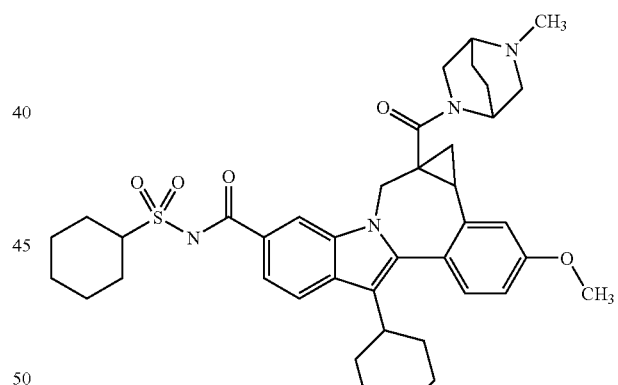

Cycloprop[d]indolo[2,1-a][2]benzazepine-5-carboxamide, 8-cyclohexyl-1,1a,2,12b-tetrahydro-11-methoxy-1a-[(5-methyl-2,5-diazabicyclo[2.2.2]oct-2-yl)carbonyl]-N-[(2,2,2-trifluoroethyl)sulfonyl]-. 1H NMR (500 MHz, CD3OD): δ ppm 0.15 (m, 0.20H), 1.23-1.32 (m, 3H), 1.39-1.49 (m, 3.80H), 1.80 (m, 3H), 1.94-2.30 (m, 4H), 2.69 (m, 1H), 2.84-2.93 (m, 2H), 2.94-3.03 (m, 2H), 3.14-3.21 (m, 2H), 3.34 (m, 1H), 3.58 (m, 2H), 3.70 (m, 2H), 3.75 (m 1H), 3.85-3.91 (m, 3H), 4.10 (m, 1H), 4.36 (m, 1H), 4.61-4.70 (m, 1H), 5.08 (m, 1H), 6.98-7.07 (m, 1H), 7.15-7.24 (m, 1H), 7.32 (m, 1H), 7.47-7.64 (m, 1H), 7.85-7.96 (m, 1H), 8.02 (m, 1H). LC/MS: m/z 699.25, Rf 1.813 min., 98.3% purity.

Cycloprop[d]indolo[2,1-a][2]benzazepine-5-carboxamide, 8-cyclohexyl-N-(cyclohexylsulfonyl)-1,1a,2,12b-tetrahydro-11-methoxy-1a-[(5-methyl-2,5-diazabicyclo[2.2.2]oct-2-yl)carbonyl]-. 1H NMR (500 MHz, CD3OD): δ ppm 0.19 (m, 0.20H), 1.14-1.50 (m, 8.80H), 1.66 (m, 3H), 1.80 (m, 3H), 1.96 (m, 3H), 2.01-2.20 (m, 6H), 2.40 (m, 1H), 2.61 (m, 2H), 2.89 (m, 2H), 3.00 (m, 3H), 3.37 (m, 1H), 3.73 (m, 4H), 3.91 (m, 3H), 4.06 (m, 1H), 4.32 (m, 1H), 5.09 (m, 1H), 7.02-7.08 (m, 1H), 7.21-7.24 (m, 1H), 7.33 (m, 1H), 7.56-7.66 (m, 1H), 7.88-8.02 (m, 2H). LC/MS: m/z 699.46, Rf 1.895 min., 100% purity.

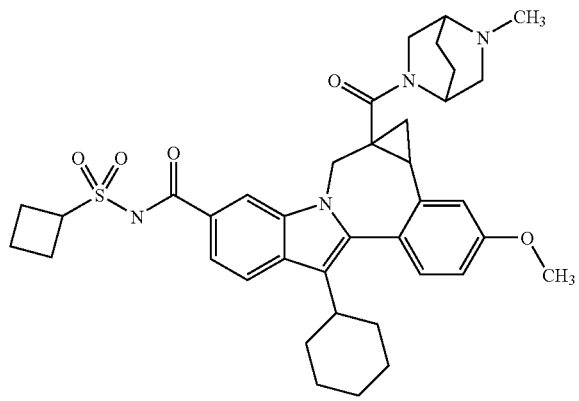

Cycloprop[d]indolo[2,1-a][2]benzazepine-5-carboxamide, N-(cyclobutylsulfonyl)-8-cyclohexyl-1,1a,2,12b-tetrahydro-11-methoxy-1a-[(5-methyl-2,5-diazabicyclo[2.2.2]oct-2-yl)carbonyl]-. 1H NMR (500 MHz, CD3OD): δ ppm 0.12 (m, 0.20H), 1.21-1.31 (m, 3H), 1.38-1.61 (m, 4.80H), 1.99 (m, 3H), 1.73-1.82 (m, 3H), 1.90-2.09 (m, 4H), 2.31-2.40 (m, 3H), 2.54-2.63 (m, 3H), 2.90 (m, 1H), 2.93-3.17 (m, 4H), 3.55 (m, 3H), 3.89 (m, 3H), 4.00 (m, 1H), 4.29 (m, 1H), 4.50-4.59 (m, 1H), 5.05 (m, 1H), 7.04 (m, 1H), 7.20 (m, 1H), 7.29-7.33 (m, 1H), 7.54-7.61 (m, 1H), 7.88-8.09 (m, 2H). LC/MS: m/z 671.34, Rf 1.886 min., 100% purity.

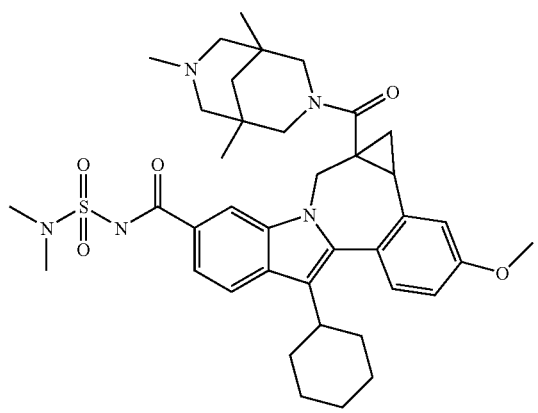

8-Cyclohexyl-N-(dimethylsulfamoyl)-11-methoxy-1a-((1,5,7-trimethyl-3,7-diazabicyclo[3.3.1]non-3-yl)carbonyl)-1,1a,2,12b-tetrahydrocyclopropa[d]indolo[2,1-a][2]benzazepine-5-carboxamide. HATU (36 mg, 0.094 mmol) was added to a stirring solution of the starting acid (40 mg, 0.073 mmol) and 1,3,5-trimethyl-3,7-diazabicyclo[3.3.1]nonane (25 mg, 0.15 mmol) in DMF (0.5 mL) and TEA (0.06 mL, 0.4 mmol) and the reaction was stirred at rt for 1 h. The reaction mixture was diluted with MeOH (~1 mL), filtered and purified by preparative HPLC (Xterra Prep MS C18 5u 30×100 mm, Eluent A: 5% acetonitrile/water with 10 mM ammonium acetate, Eluent B: 95% acetonitrile/water with 10 mM ammonium acetate, Flow Rate: 42 mL/min, linear gradient from 15% Eluent B to 100% Eluent B over 15 min) to yield 8-cyclohexyl-N-(dimethylsulfamoyl)-11-methoxy-1a-((1,5,7-trimethyl-3,7-diazabicyclo[3.3.1]non-3-yl)carbonyl)-1,1a,2,12b-tetrahydrocyclopropa[d]indolo[2,1-a][2]benzazepine-5-carboxamide (37.5 mg, 0.053 mmol, 74% yield) as a off-white solid. The compound was isolated as a mixture of enantiomers. Presents as a 1:1 mixture of rotamers or atrope isomers. $^1$HNMR (300 MHz, CDCl$_3$) δ 0.17-3.20 (m, 31H), 3.02 (s, 6H), 3.77-5.05 (m, 4H), 3.87 (s, 3H), 6.84-6.95 (m, 1H), 6.99-7.11 (m, 1H), 7.26 (d, J=8.8 Hz, 1H), 7.42-8.01 (m, 1.5H), 7.85 (d, J=8.4 Hz, 1H), 8.04 (br s, 0.5H). LC-MS retention time: 3.45 min; m/z 700 (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 4 min, a hold time of 1 min, and an analysis time of 5 min where solvent A was 5% acetonitrile/95% H$_2$O/10 mM ammonium acetate and solvent B was 5% H$_2$O/95% acetonitrile/10 mM ammonium acetate. MS data was determined using a Micromass Platform for LC in electrospray mode.

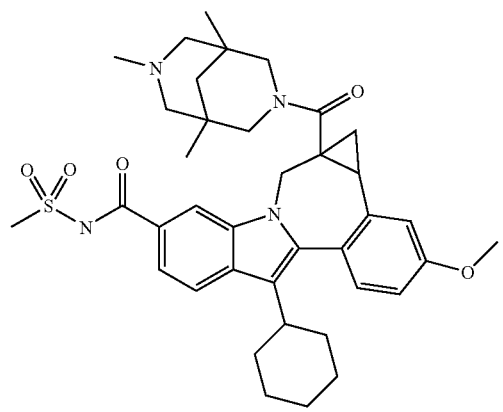

8-Cyclohexyl-11-methoxy-N-(methylsulfonyl)-1a-((1,5,7-trimethyl-3,7-diazabicyclo[3.3.1]non-3-yl)carbonyl)-1,1a,2,12b-tetrahydrocyclopropa[d]indolo[2,1-a][2]benzazepine-5-carboxamide. HATU (38 mg, 0.10 mmol) was added to a stirring solution of the starting acid (40 mg, 0.077 mmol) and 1,3,5-trimethyl-3,7-diazabicyclo[3.3.1]nonane (26 mg, 0.15 mmol) in DMF (0.5 mL) and TEA (0.06 mL, 0.4 mmol) and the reaction was stirred at rt for 3 h. The reaction mixture was diluted with MeOH (~1 mL), filtered and purified by preparative HPLC (Xterra Prep MS C18 5u 30×100 mm, Eluent A: 5% acetonitrile/water with 10 mM ammonium acetate, Eluent B: 95% acetonitrile/water with 10 mM ammonium acetate, Flow Rate: 42 mL/min, linear gradient from 15% Eluent B to 100% Eluent B over 15 min) to yield 8-cyclohexyl-11-methoxy-N-(methylsulfonyl)-1a-((1,5,7-trimethyl-3,7-diazabicyclo[3.3.1]non-3-yl)carbonyl)-1,1a,2,12b-tetrahydrocyclopropa[d]indolo[2,1-a][2]benzazepine-5-carboxamide (40.2 mg, 0.060 mmol, 78% yield) as a white solid. The compound was isolated as a mixture of enantiomers. 1HNMR (300 MHz, CDCl3) δ ppm 0.07-3.15 (m, 24H), 3.40 (s, 3H), 3.46-4.12 (m, 3H), 3.87 (s, 3H), 4.34-5.05 (m, 3H), 6.85-6.96 (m, 1H), 6.99-7.12 (m, 1H), 7.24-7.33 (m, 1H), 7.49-7.65 (m, 1H), 7.80-7.90 (m, 1H), 7.92-8.08 (m, 1H). LC-MS retention time: 2.43 min; m/z 671 (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 4 min, a hold time of 1 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

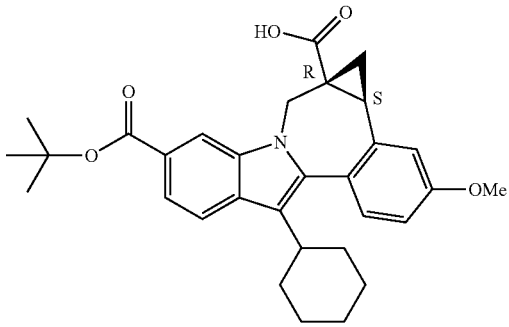

(1aR,12bS)-5-(tert-butoxycarbonyl)-8-cyclohexyl-11-methoxy-1,12b-dihydrocyclopropa[d]indolo[2,1-a][2]benzazepine-1a(2H)-carboxylic acid. Sodium hydroxide (aq. 1M, 31 mL) was added to a cooled solution (0° C., ice bath) containing 5-tert-butyl 1a-ethyl (1aR,12bS)-8-cyclohexyl-11-methoxy-1,12b-dihydrocyclopropa[d]indolo[2,1-a][2]benzazepine-1a,5 (2H)-dicarboxylate (4.0 g, 7.76 mmol), THF (35 mL), and methanol (35 mL). After 20 min, the solution was removed from the cooling bath and maintained at ambient temperature for 3 h. The solution was cooled again (0° C., ice bath) and the pH reduced to just below 4 by slow addition of 1N HCL (aq., 33 mL). The mixture was immediately extracted with ethyl acetate (2×30 mL). The combined organic portions were washed with brine, (20 mL), dried (magnesium sulfate), filtered and concentrated to afford a white solid which was used without further purification in the next step. LCMS: retention time: 3.162 min. LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 502 (MH$^+$).

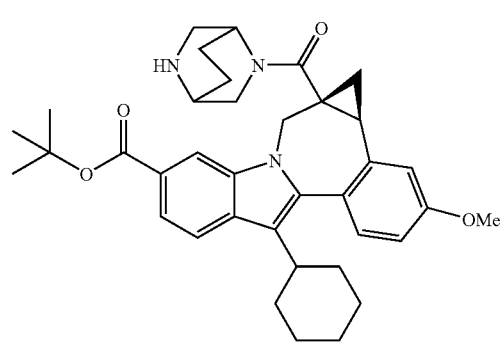

Tert-butyl (1aR,12bS)-8-cyclohexyl-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxylate. TBTU (691 mg, 2.15 mmol) was added in one portion to a cooled solution (0° C., ice bath) containing (1aR,12bS)-5-(tert-butoxycarbonyl)-8-cyclohexyl-11-methoxy-1,12b-dihydrocyclopropa[d]indolo[2,1-a][2]benzazepine-1a(2H)-carboxylic acid(900 mg, 1.79 mmol), DIEA (1.88 mL, 10.77 mmol), 2,5-diazabicyclo[2.2.2]octane (1:1) dihydrochloride ((498 mg, 2.69 mmol), (H. Newman, *J. Het. Chem.* 449 (1974 ); P. E. Thompson, J. B. Zeigler, J. W. McCall, *J. Med. Chem.*, 17, 481 (1974 )), and dichloromethane (36 mL). The solution was maintained for 1.5 h and diluted with additional dichloromethane (20 mL). The solution was washed with water (3×20 mL), washed with brine (15 mL), dried (magnesium sulfate), filtered and concentrated to afford a white, tacky residue which was triturated with n-pentane (2×20 mL) to afford a white solid which was used without further purification in the next step. LCMS: retention time 3.841 min LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode., m/z 596 (MH$^+$).

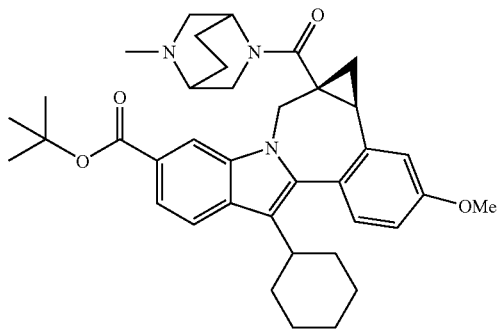

Tert-butyl (1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylate. A suspension containing tert-butyl (1aR,12bS)-8-cyclohexyl-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxylate (904 mg, 1.51 mmol), formaldehyde (37% in water, 40 mL, 531 mmol), 10% palladium on carbon (323 mg, 0.303 mmol Pd), and ethanol (76 mL) was stirred under a hydrogen gas balloon for 26 hrs. The mixture was filtered through celite and the filtrate concentrated to dryness. The resultant solid was triturated with n-pentane (2×25 mL) and used without further purification. LCMS: retention time 4.123 min LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$ CN/95% H$_2$O/10 mM ammonium acetate and solvent B was 5% H₂O/95% CH₃CN/10 mM ammonium acetate. MS data was determined using a Micromass Platform for LC in electrospray mode. m/z 610 (MH⁺).

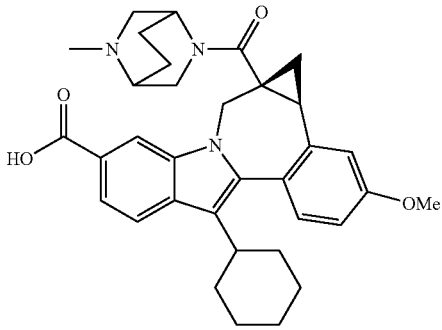

(1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylic acid. TFA (11.6 mL, 1.164 mmol) was added to a solution containing tert-butyl (1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylate (710 mg, 1.164 mmol) and DCM (11.6 mL). The solution was maintained at rt for 3 h and then concentrated to dryness. The resultant residue was charged with 1:1 methanol/water (20 mL) and the pH increased to above 8 by slow addition of aqueous, saturated, sodium bicarbonate (10 mL). The solution was concentrated to remove methanol and extracted with dichloromethane (6×10 mL). The combined organic portions were washed with brine (20 mL), dried (magnesium sulfate), filtered and concentrated to afford a yellow solid which was used without further purification. LC/MS shows separate diastereomers under basic conditions at retention times 2.047 min and 2.178 min LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH₃CN/95% H₂O/10 mM ammonium acetate and solvent B was 5% H₂O/95% CH₃CN/10 mM ammonium acetate. MS data was determined using a Micromass Platform for LC in electrospray mode.; m/z 554 (MH⁺).

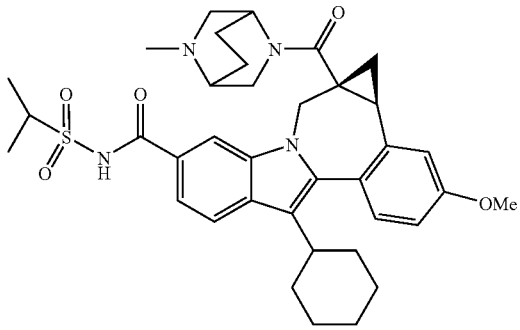

(1aR,12bS)-8-cyclohexyl-N-(isopropylsulfonyl)-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxamide. EDCI (208 mg, 1.084 mmol) was added at rt, in one portion, to a solution containing (1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylic acid (300 mg, 0.542 mmol), DMAP (50 mg, 0.406 mmol), 2-isopropyl sulfonamide (100 mg, 0.813 mmol), and dichloromethane (6 mL). The solution was maintained at rt for 24 h, diluted with additional dichloromethane (20 mL), washed with aqueous, saturated sodium bicarbonate (2×20 mL), washed with water (20 mL), dried (magnesium sulfate), filtered and concentrated. The resultant yellow residue was purified by preparative, reverse phase HPLC under basic conditions using a Phenomenex, luna, 10 micron, 30×100 mm column. This separates two diastereomers, each as a white solid. LC/MS shows separate diastereomers under basic conditions at retention times 2.160 min and 2.292 min LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH₃CN/95% H₂O/10 mM ammonium acetate and solvent B was 5% H₂O/95% CH₃CN/10 mM ammonium acetate. MS data was determined using a Micromass Platform for LC in electrospray mode m/z 659 (MH⁺).

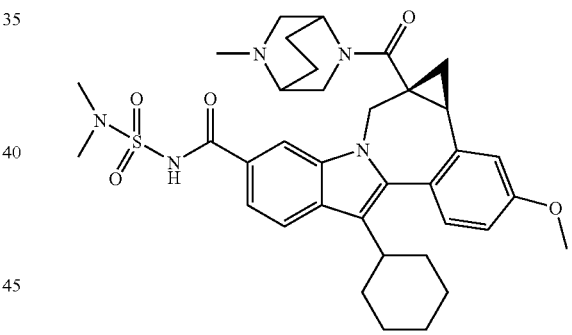

(1aR,12bS)-8-cyclohexyl-N-(dimethylsulfamoyl)-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxamide. The title compound was prepared from (1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylic acid under similar conditions to those described for (1aR,12bS)-8-cyclohexyl-N-(isopropylsulfonyl)-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxamide. The resultant yellow residue was purified by preparative, reverse phase HPLC under basic conditions using a Phenomenex, luna, 10 micron, 30×100 mm column. This separates two diastereomers, each as a white solid. LC/MS shows separate diastereomers under basic conditions at retention time 2.285 min and 2.437 min LC data was recorded on a Shimadzu LC-10AS liquid chromatograph equipped with a Phenomenex-Luna 10u C18 4.6×

50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode.; m/z 660 (MH$^+$).

Compounds described in the following procedures were analyzed by using the following LC/MS method: Analysis Conditions: Column: PHENOMENNEX-LUNA 3.0×50 mm S10; Mobile Phase: (A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

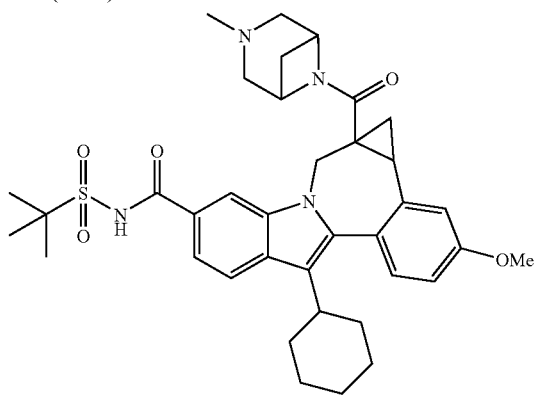

(+/-)-8-cyclohexyl-N-(tert-butylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.867 min; m/e 659 (MH$^+$). The product was observed to exist as inter-converting rotamers by 1H NMR (400 MHz, CHLOROFORM-D) δ ppm 1.09-1.69 (m, 16H), 1.81 (s, 3H), 2.01 (s, 5H), 2.70 (s, 1H), 2.95 (d, J=3.53 Hz, 2H), 3.17 (s, 1H), 3.24-3.77 (m, 6H), 3.87-3.98 (m, 3H), 4.07 (s, 1H), 4.38 (s, 1H), 5.44 (s, 1H), 6.98 (dd, J=8.56, 2.52 Hz, 1H), 7.12 (d, J=2.52 Hz, 1H), 7.19-7.37 (m, 1H), 7.57 (d, J=8.31 Hz, 1H), 7.89 (d, J=8.31 Hz, 1H), 8.11 (s, 1H).

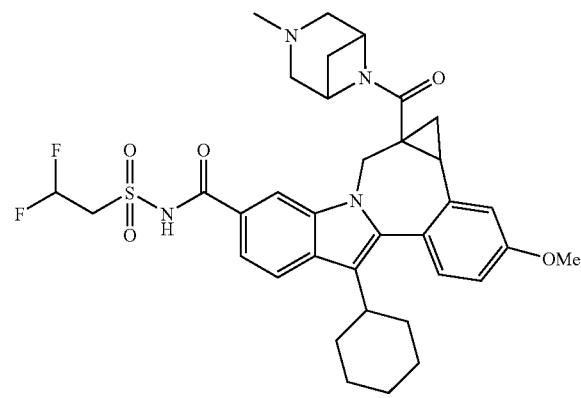

(+/-)-8-cyclohexyl-N-(2,2-difluoroethylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.837 min; m/e 667 (MH$^+$). The product was observed to exist as inter-converting rotamers by 1H NMR (400 MHz, CHLOROFORM-D) δ ppm 0.73-1.59 (m, 6H), 1.59-2.11 (m, 14H), 2.59-2.87 (m, 1H), 2.87-3.22 (m, 2H), 3.26-3.65 (m, 3H), 3.78-3.94 (m, 3H), 3.98-4.46 (m, 3H), 5.29-5.55 (m, 1H), 6.08-6.48 (m, 1H), 6.89-7.06 (m, 1H), 7.04-7.19 (m, J=2.77 Hz, 1H), 7.18-7.34 (m, 1H), 7.60-7.77 (m, J=9.82 Hz, 1H), 7.84-7.98 (m, J=8.56 Hz, 1H), 8.01-8.12 (m, 1H).

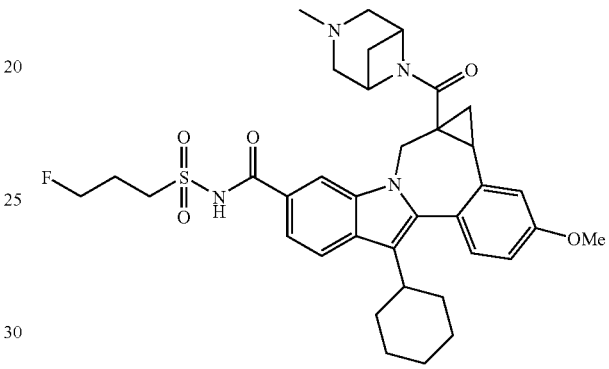

(+/-)-8-cyclohexyl-N-(3-fluoropropylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.811 min; m/e 663 (MH$^+$). The product was observed to exist as inter-converting rotamers by 1H NMR (400 MHz, CHLOROFORM-D) δ ppm 0.71-0.97 (m, 1H), 1.09-1.59 (m, 5H), 1.68-2.11 (m, J=74.28 Hz, 6H), 2.16-2.49 (m, 2H), 2.60-3.31 (m, 8H), 3.35-3.56 (m, 4H), 3.68-3.82 (m, 4H), 3.84 -3.95 (m, 3H), 4.30-4.43 (m, 1H), 4.46-4.56 (m, 1H), 4.57-4.73 (m, 1H), 5.31-5.57 (m, 1H), 6.87-7.04 (m, J=8.56, 2.52 Hz, 1H), 7.04-7.19 (m, J=2.27 Hz, 1H), 7.18-7.34 (m, 1H), 7.57-7.74 (m, J=8.81 Hz, 1H), 7.80-7.95 (m, J=8.69, 8.69 Hz, 1H), 8.04-8.19 (m, 1H).

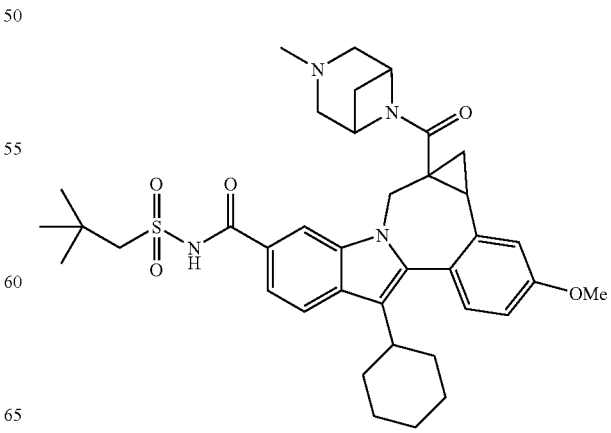

(+/−)-8-cyclohexyl-N-(neopentylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.935 min; m/e 673 (MH+). The product was observed to exist as inter-converting rotamers by 1H NMR (500 MHz, CHLOROFORM-D) δ ppm 0.26-1.01 (m, 2H), 0.97-1.65 (m, 14H), 1.65-2.31 (m, 7H), 2.50-3.35 (m, 9H), 3.31-3.71 (m, 4H), 3.80-3.95 (m, 3H), 3.93-4.45 (m, 1H), 4.44-5.01 (m, 1H), 5.31-5.58 (m, 1H), 6.87-7.06 (m, 1H), 7.01-7.20 (m, J=2.14 Hz, 1H), 7.16-7.34 (m, 1H), 7.43-7.72 (m, J=8.24 Hz, 1H), 7.80-8.00 (m, J=8.39, 8.39 Hz, 1H), 8.01-8.20 (m, 1H).

benzazepine-5-carboxamide. The product was purified by prep HPLC and isolated as a beige solid in mono TFA salt form. LC/MS: Retention time: 1.850 min; m/e 657 (MH+). The product was observed to exist as inter-converting rotamers by 1H NMR (500 MHz, CHLOROFORM-D) δ ppm 1.07-1.67 (m, 6H), 1.71-2.17 (m, 7H), 2.27-2.53 (m, 3H), 2.51-3.31 (m, 11H), 3.31-3.78 (m, 4H), 3.80-3.95 (m, 3H), 3.95-4.25 (m, J=53.41 Hz, 1H), 4.26-4.48 (m, 1H), 4.49-4.72 (m, 1H), 5.33-5.63 (m, 1H), 6.87-7.05 (m, 1H), 7.05-7.19 (m, J=2.44 Hz, 1H), 7.18-7.36 (m, 1H), 7.52-7.80 (m, 1H), 7.81-7.96 (m, 1H), 8.04-8.36 (m, 1H).

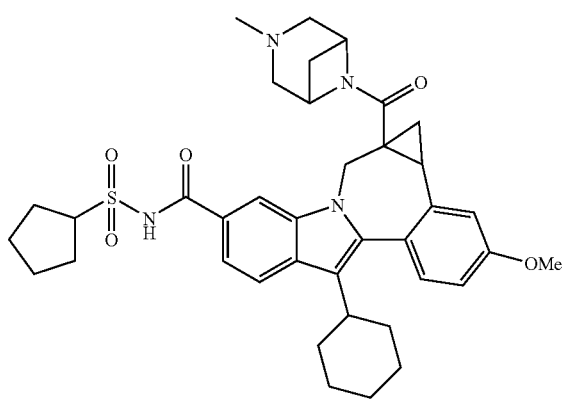

(+/−)-8-cyclohexyl-N-(cyclopentylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.895 min; m/e 671 (MH+). The product was observed to exist as inter-converting rotamers by 1H NMR (500 MHz, CHLOROFORM-D) δ ppm 0.32-0.96 (m, 1H), 1.17-1.60 (m, 5H), 1.62-2.33 (m, 8H), 2.38-2.82 (m, 10H), 2.77-3.27 (m, 5H), 3.32-3.75 (m, 3H), 3.82-3.98 (m, 3H), 3.93-4.22 (m, 1H), 4.25-4.45 (m, 2H), 4.50-4.90 (m, 1H), 5.28-5.58 (m, 1H), 6.90-7.05 (m, 1H), 7.04-7.18 (m, 1H), 7.17-7.37 (m, 1H), 7.39-7.69 (m, 1H), 7.72-7.96 (m, 1H), 8.05-8.32 (m, 1H).ppm.

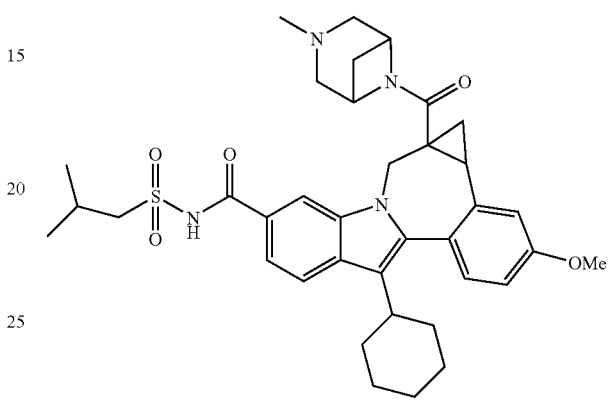

(+/−)-8-cyclohexyl-N-(isobutylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.935 min; m/e 659 (MH+). The product was observed to exist as inter-converting rotamers by 1H NMR (500 MHz, CHLOROFORM-D) δ ppm 0.29-0.93 (m, J=272.84 Hz, 1H), 1.07-1.19 (m, J=6.71, 6.71 Hz, 4H), 1.17-1.66 (m, 7H), 1.70-2.21 (m, 7H), 2.25-2.55 (m, 2H), 2.58-3.25 (m, 4H), 3.29-3.75 (m, 8H), 3.81-3.96 (m, 3H), 3.94-4.27 (m, 1H), 4.28-4.47 (m, 1H), 4.52-4.97 (m, 1 ), 5.31-5.59 (m, 1H), 6.87-7.05 (m, 1H), 7.04-7.18 (m, J=1.83 Hz, 1H), 7.18-7.34 (m, 1H), 7.52-7.78 (m, 1H), 7.81-7.97 (m, 1H), 8.10-8.36 (m, 1H).

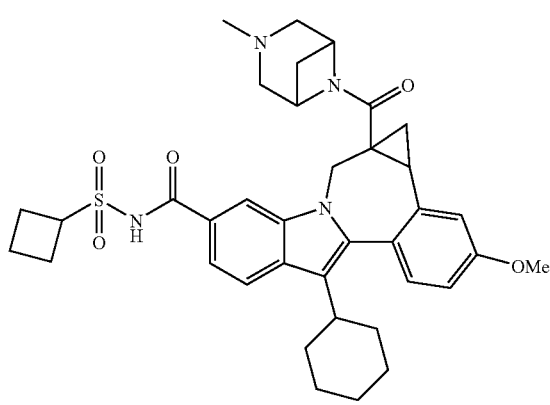

(+/−)-8-cyclohexyl-N-(cyclobutylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]

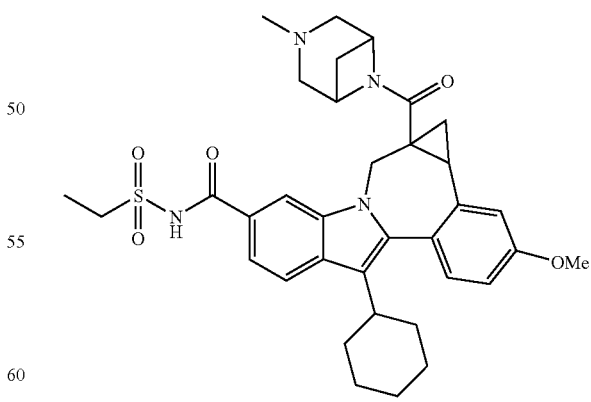

(+/−)-8-cyclohexyl-N-(ethylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS:

Retention time: 1.778 min; m/e 631 (MH+). The product was observed to exist as inter-converting rotamers by 1H NMR (400 MHz, CHLOROFORM-D) δ ppm 0.30-0.97 (m, J=222.34 Hz, 1H), 1.09-1.64 (m, 8H), 1.66-2.24 (m, 1H), 2.54-3.21 (m, 4H), 3.21-3.76 (m, 10H), 3.81-3.95 (m, 3H), 3.92-4.26 (m, 1H), 4.28-4.50 (m, 1H), 4.51-5.01 (m, J=126.15 Hz, 1H), 5.23-5.57 (m, 1H), 6.90-7.02 (m, 1H), 7.05-7.18 (m, J=2.52 Hz, 1H), 7.19-7.35 (m, 1H), 7.57-7.71 (m, J=8.31 Hz, 1H), 7.80-7.99 (m, J=7.81, 7.81 Hz, 1H), 8.02-8.22 (m, 1H).

product was observed to exist as inter-converting rotamers by 1H NMR (400 MHz, CHLOROFORM-D) δ ppm 0.27-0.88 (m, 1H), 0.97-1.15 (m, J=7.64, 7.64, 7.64 Hz, 3H), 1.14-1.62 (m, 4H), 1.69-2.23 (m, 8H), 2.53-3.22 (m, 5H), 3.22-3.79 (m, 10H), 3.81-3.94 (m, 3H), 3.94-4.25 (m, 1H), 4.26-4.51 (m, 1H), 4.53-4.97 (m, 1H), 5.25-5.54 (m, 1H), 6.89-7.05 (m, 1H), 7.06-7.18 (m, J=2.27 Hz, 1H), 7.19-7.33 (m, 1H), 7.51-7.71 (m, J=8.31 Hz, 1H), 7.79-7.95 (m, 1H), 8.05-8.22 (m, 1H).

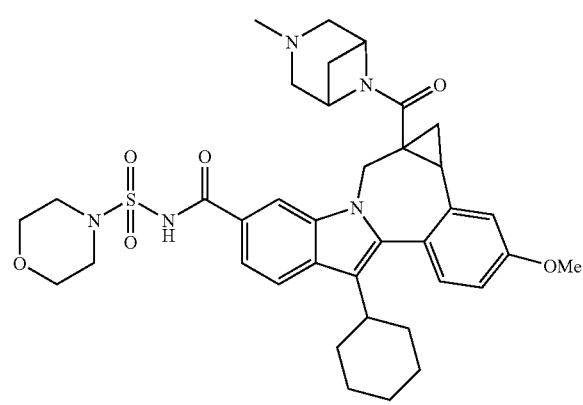

(+/−)-8-cyclohexyl-N-(morpholinosulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.847 min; m/e 688 (MH+). The product was observed to exist as inter-converting rotamers by 1H NMR (400 MHz, CHLOROFORM-D) δ ppm 0.32-1.06 (m, 1H), 1.13-1.67 (m, 6H), 1.67-2.13 (m, 6H), 2.14-2.78 (m, 9H), 2.80-3.27 (m, 3H), 3.36-3.70 (m, 5H), 3.69-3.84 (m, J=4.28 Hz, 3H), 3.84-3.93 (m, 3H), 3.93-4.17 (m, 1H), 4.25-4.49 (m, 1H), 4.50-4.93 (m, J=112.56 Hz, 1H), 5.26-5.54 (m, 1H), 6.90-7.05 (m, J=8.44, 2.64 Hz, 1H), 7.05-7.19 (m, J=2.52 Hz, 1H), 7.17-7.34 (m, 1H), 7.50-7.65 (m, 1H), 7.79-7.95 (m, 1H), 8.02-8.15 (m, 1H).

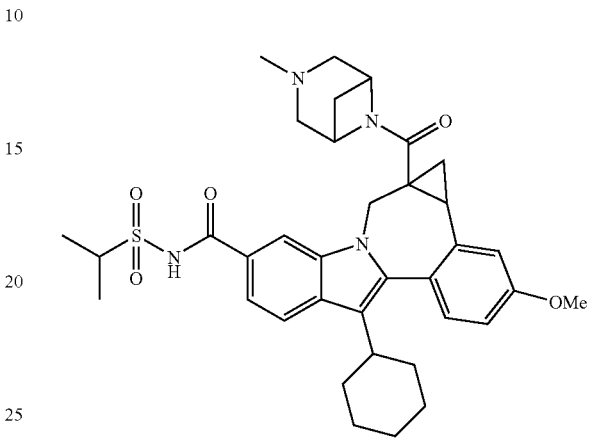

(+/−)-8-cyclohexyl-N-(isopropylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.871 min; m/e 645 (MH+). The product was observed to exist as inter-converting rotamers by 1H NMR (400 MHz, CHLOROFORM-D) δ ppm 1.05-1.57 (m, 9H), 1.69-2.08 (m, J=79.57 Hz, 4H), 2.08-2.42 (m, 9H), 2.58-3.25 (m, 5H), 3.35-3.75 (m, 4H), 3.82-3.95 (m, 3H), 3.95-4.18 (m, 2H), 4.26-4.45 (m, 1H), 5.26-5.52 (m, 1H), 6.89-7.03 (m, J=8.18, 2.90 Hz, 1H), 7.04-7.17 (m, J=2.27 Hz, 1H), 7.21-7.34 (m, 1H), 7.49-7.68 (m, J=34.75 Hz, 1H), 7.81-7.96 (m, J=8.56 Hz, 1H), 8.05-8.19 (m, 1H).

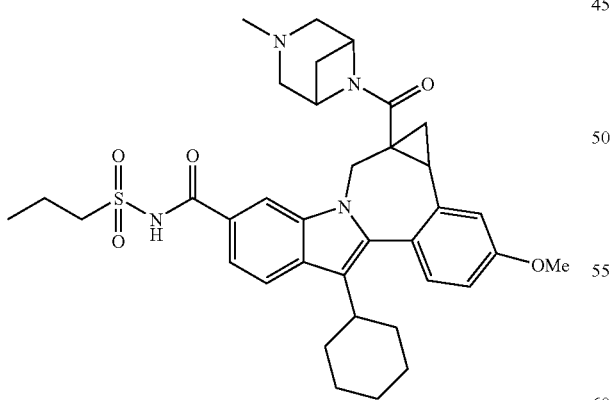

(+/−)-8-cyclohexyl-N-(propylsulfonyl)-1,1a,2,12b-tetrahydro-11-methoxy-1a-(3-methyl-3,6-diazabicyclo[3.1.1]heptane-6-carbonyl) cycloprop[d]indolo[2,1-a][2]benzazepine-5-carboxamide. The product was purified by prep HPLC and isolated as a beige solid in mono TFA salt form. LC/MS: Retention time: 1.888 min; m/e 645 (MH+). The

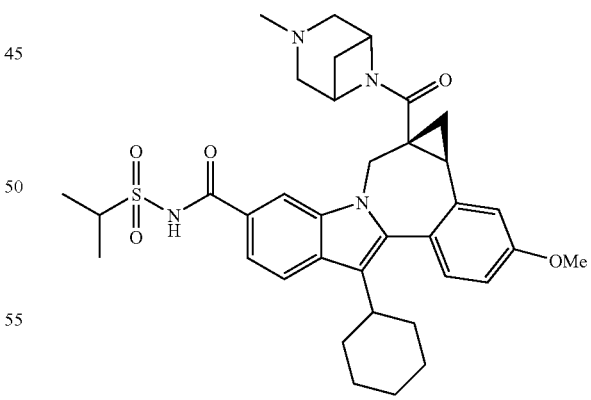

8-cyclohexyl-N-(isopropylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.855 min; m/e 645 (MH+). The product was observed to exist as inter-converting rotamers by 1H NMR (400 MHz, CHLOROFORM-D) δ ppm 1.11-1.62 (m, 11H), 1.68-2.16 (m, J=74.53 Hz, 6H), 2.42-2.82 (m, 7H), 2.78-3.23 (m, 4H), 3.38-3.68 (m, 4H), 3.81-3.94 (m, 3H), 3.95-4.16 (m, 1H), 4.55-4.92 (m, J=94.43 Hz, 1H), 5.34-5.54 (m, 1H), 6.87-7.04 (m, J=8.81, 2.27 Hz, 1H), 7.04-7.19 (m, J=2.27 Hz, 1H), 7.20-7.33 (m, 1H), 7.50-7.67 (m, 1H), 7.82-7.97 (m, J=8.31 Hz, 1H), 8.05-8.23 (m, 1H).

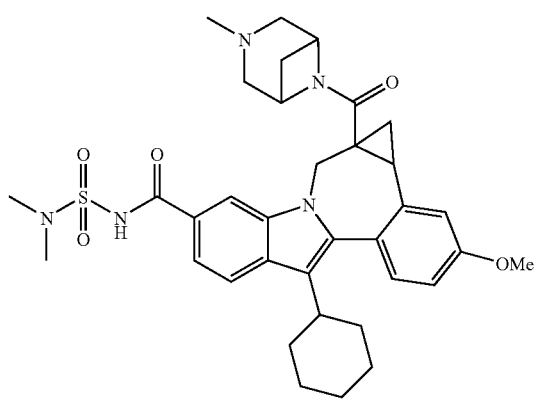

(+/−)-8-cyclohexyl-N-(N,N-dimethylsulfamoyl)-1,1a,2,12b-tetrahydro-11-methoxy-1a-(6-methyl-3,6-diazabicyclo[3.1.1]heptane-3-carbonyl)cycloprop[d]indolo[2,1-a][2]benzazepine-5-carboxamide. The product was purified by prep HPLC and isolated as a beige solid in mono TFA salt form. LC/MS: Retention time: 1.545 min; m/e 646 (MH⁺). The product was observed to exist as inter-converting rotamers by 1H NMR (400 MHz, CHLOROFORM-D) δ ppm 0.38-1.08 (m, 1H), 1.09-1.64 (m, 5H), 1.66-2.21 (m, 6H), 2.40-2.68 (m, J=50.86 Hz, 1H), 2.75-3.04 (m, 11H), 3.07-3.32 (m, 3H), 3.47-3.84 (m, 2), 3.82-3.97 (m, 3H), 3.98-4.37 (m, 2H), 4.74-5.17 (m, 1H), 5.22-5.70 (m, 2H), 6.85-7.06 (m, 1H), 7.04-7.19 (m, 1H), 7.21-7.38 (m, 1H), 7.47-7.85 (m, 1H), 7.85-7.99 (m, 1H), 8.26-8.71 (m, 1H).

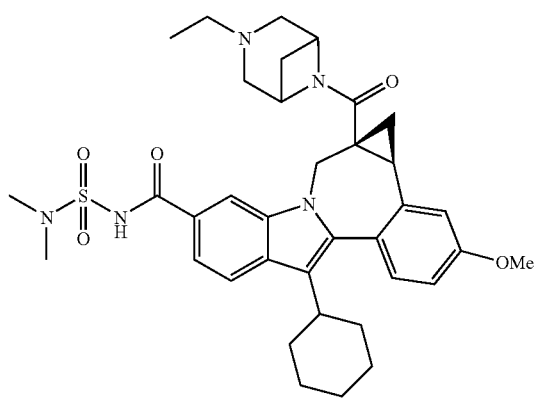

8-cyclohexyl-N-(N,N-dimethylsulfamoyl)-1,1a,2,12b-tetrahydro-11-methoxy-1a-(3-ethyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.823 min; m/e 660 (MH⁺). The product was observed to exist as inter-converting rotamers by 1H NMR (400 MHz, CHLOROFORM-D) δ ppm 0.74-1.04 (m, J=19.89 Hz, 2H), 1.09-1.60 (m, 6H), 1.65-2.19 (m, 6H), 2.61-3.22 (m, 14H), 3.25-3.75 (m, 4H), 3.82-3.95 (m, 3H), 3.94-4.28 (m, 1H), 4.27-4.46 (m, 1H), 4.43-4.95 (m, 1H), 5.33-5.60 (m, 1H), 6.83-7.04 (m, 1H), 7.05-7.18 (m, J=2.52 Hz, 1H), 7.18-7.35 (m, 1H), 7.47-7.65 (m, 1H), 7.81-7.96 (m, 1H), 8.03-8.21 (m, 1H).

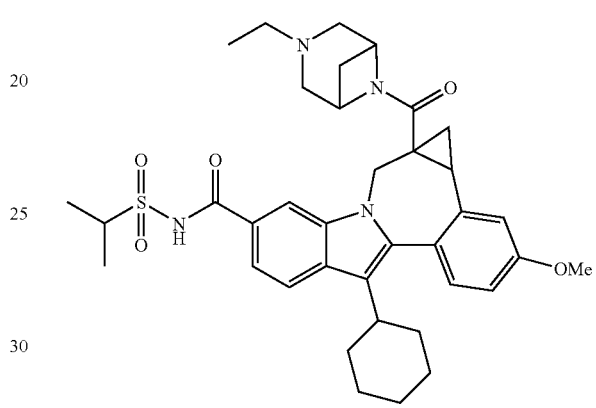

(+/−)-8-cyclohexyl-N-(isopropylsulfonyl)-1,1a,2,12b-tetrahydro-11-methoxy-1a-(3-ethyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.863 min; m/e 659 (MH⁺). The product was observed to exist as inter-converting rotamers by 1H NMR (400 MHz, CHLOROFORM-D) δ ppm 0.70-1.09 (m, 3H), 1.10-1.63 (m, 11H), 1.69-2.12 (m, 5H), 2.57-3.05 (m, J=4.28 Hz, 9H), 3.04-3.24 (m, 1H), 3.26-3.76 (m, 4H), 3.80-3.95 (m, 3H), 3.96-4.24 (m, 2H), 4.27-4.48 (m, 1H), 5.34-5.56 (m, 1H), 6.87-7.04 (m, J=8.56, 2.52 Hz, 1H), 7.04-7.19 (m, J=2.52 Hz, 1H), 7.18-7.35 (m, 1H), 7.54-7.71 (m, J=8.56 Hz, 1H), 7.81-7.94 (m, J=9.06, 9.06 Hz, 1H), 8.03-8.18 (m, 1H).

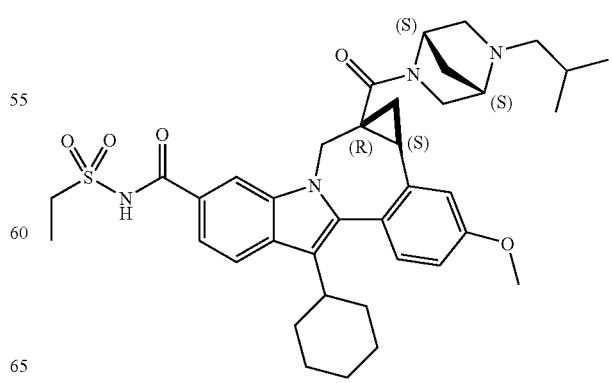

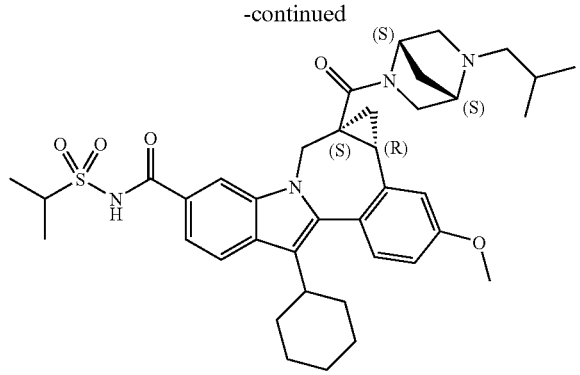

8-cyclohexyl-N-(isopropylsulfonyl)-1,1a,2,12b-tetrahydro-11-methoxy-1a-[(1S,4S)-5-isobutyl-2,5-diazabicyclo[2.2.1]heptane-2-carbonyl]cycloprop[d]indolo[2,1-a][2]benzazepine-5-carboxamide. Step 1: To a mixture of compound acid (50 mg, 0.091 mmol) and (1S,4S)-2-isobutyl-2,5-diazabicyclo[2.2.1]heptane, 2TFA (52 mg, 0.136 mmol) in dichloromethane (1.5 ml) was added TEA (0.127 ml, 0.908 mmol) and HBTU (48 mg, 0.127 mmol). The mixture was stirred at room temperature for 2 h. Diluted with MeOH (1 ml), removed the solvents, the residue was dissolved in MeOH, filtered and purified by prep-HPLC and isolated as TFA salts to afford the products (0.0094 g, 26%) and (0.0099 g, 27%). First peak: LC-MS retention time: 3.138; MS m/z (M+H) 687; observed to exist as inter-converting rotamers 1H NMR (400 MHz, CHLOROFORM-d) δ ppm 0.93 (6H, m), 1.35(10H, m), 1.74(11H, m), 2.45(1H, br. s.), 2.80 (4H, m), 3.14 (2H, br. s.), 3.64 (3H, m), 3.90 (3H, s), 3.98 (1H, m), 4.15 (1H, br. s.), 5.20 (1H, d, J=15.11 Hz), 6.98 (1H, dd, J=8.44, 2.64 Hz), 7.11 (1H, d, J=2.01 Hz), 7.28 (1H, m), 7.82 (1H, br. s.), 7.96 (1H, d, J=8.31 Hz), 8.53 (1H, br. s.). Second peak: LC-MS retention time: 3.170; MS m/z (M+H) 687; observed to exist as inter-converting rotamers by 1H NMR.

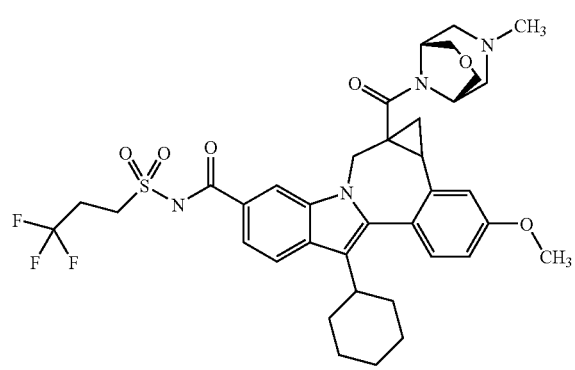

8-Cyclohexyl-11-methoxy-1a-(((1R,5S)-7-methyl-3-oxa-7,9-diazabicyclo[3.3.1]non-9-yl)carbonyl)-N-((3,3,3-trifluoropropyl)sulfonyl)-1,1a,2,12b-tetrahydrocyclopropa[d]indolo[2,1-a][2]benzazepine-5-carboxamide. 1H NMR (300 MHz, CD3OD): δ ppm 0.20 (m, 0.35H), 1.21 (m, 1H), 1.35 (m, 1.65H), 1.45 (m, 2H), 1.58 (m, 2H), 1.79 (m, 2H), 1.91-2.07 (m, 4H), 2.62 (m, 1H), 2.74-2.90 (m, 4H), 2.90-3.06 (m, 3H), 3.34 (m, 1H), 3.62 (d, J=15.37 Hz, 2H), 3.72 (m, 1H), 3.80-3.93 (m, 6H), 4.00 (m, 2H), 4.15 (d, J=15.00 Hz, 1H), 4.38 (m, 2H), 4.90-5.09 (m, 1H), 7.02 (m, 1H), 7.12-7.20 (m, 1H), 7.27-7.33 (m, 1H), 7.53-7.63 (m, 1H), 7.89 (m, 1H), 8.04-8.11 (m, 1H). LC/MS: m/z 729.42, Rf 1.793 min., 95.7% purity.

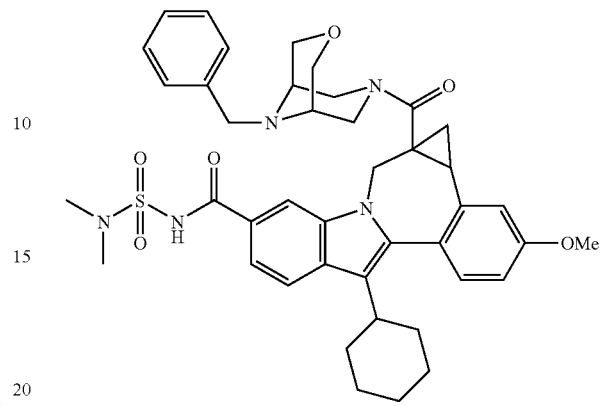

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[9-(phenylmethyl)-3-oxa-7,9-diazabicyclo[3.3.1]non-7-yl]carbonyl]-. was prepared from the coupling between the racemic acid and 9-benzyl-3-oxa-7,9-diazabicyclo[3.3.1]nonane hydrochloride in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Flow Rate=30 mL/min, Column: Xterra Prep MS C18 5u 30×50 mm, Fraction Collection: 8.31-8.91 min. (UV detection at 220 nm); LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; (ES+) m/z (M+H)$^+$=752.91, HPLC R$_t$=1.752 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; (ES+) m/z (M+H)$^+$=752.48, HPLC R$_t$=1.633 min.

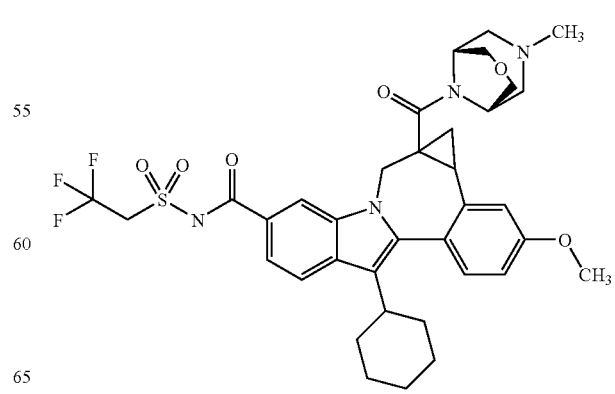

8-Cyclohexyl-11-methoxy-1a-(((1R,5S)-7-methyl-3-oxa-7,9-diazabicyclo[3.3.1]non-9-yl)carbonyl)-N-((2,2,2-trifluoroethyl)sulfonyl)-1,1a,2,12b-tetrahydrocyclopropa[d]indolo[2,1-a][2]benzazepine-5-carboxamide. 1H NMR (300 MHz, CD3OD): δ ppm 0.22 (m, 0.35H), 1.19 (m, 1H), 1.25-1.41 (m, 2H), 1.44 (m, 2H), 1.58 (m, 1.65H), 1.79 (m, 2H), 1.92-2.04 (m, 4H), 2.63 (m, 2H), 2.86 (m, 2H), 2.90-3.04 (m, 2H), 3.60 (m, 2H), 3.66 (m, 1H), 3.85-3.98 (m, 6H), 4.16 (m, 1H), 4.27-4.42 (m, 2H), 4.67 (m, 2H), 5.08 (d, J=15.00 Hz, 1H), 6.98-7.06 (m, 1H), 7.13-7.21 (m, 1H), 7.27-7.35 (m, 1H), 7.53-7.64 (m, 1H), 7.90 (m, 1H), 8.04-8.13 (m, 1H). LC/MS: m/z 715.41, Rf 1.783 min., 98.0% purity.

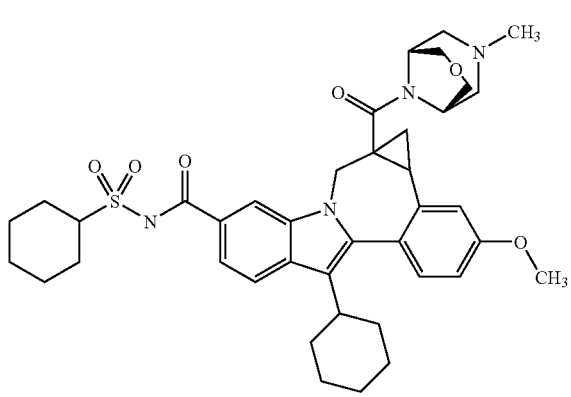

8-Cyclohexyl-N-(cyclohexylsulfonyl)-11-methoxy-1a-(((1R,5S)-7-methyl-3-oxa-7,9-diazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.24 (m, 0.35H), 1.31-1.52 (m, 7.65H), 1.59-1.74 (m, 4H), 1.80 (m, 3H), 1.95 (m, 4H), 2.11 (m, 2H), 2.21 (m, 2H), 2.68 (m, 2H), 2.89 (m, 2H), 2.97 (m, 2H), 3.64-3.79 (m, 4H), 3.83-3.98 (m, 4H), 4.10 (m, 3H), 4.41 (m, 2H), 5.12 (d, J=15.37 Hz, 1H), 7.05 (m,1H), 7.16-7.25 (m, 1H), 7.34 (m, 1H), 7.56-7.69 (m, 1H), 7.93 (m, 1H), 8.04-8.19 (m, 1H). LC/MS: m/z 715.51, Rf 1.840 min., 97.1% purity.

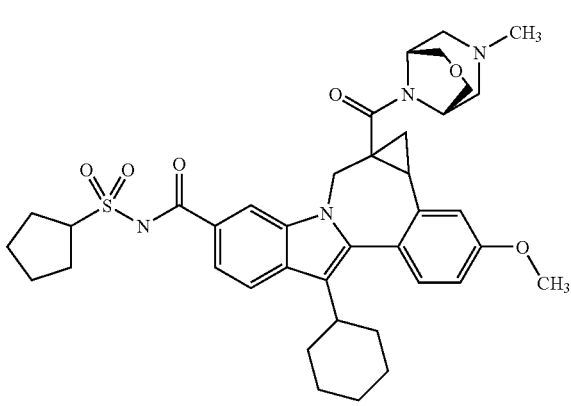

8-Cyclohexyl-N-(cyclopentylsulfonyl)-11-methoxy-1a-(((1R,5S)-7-methyl-3-oxa-7,9-diazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.21 (m, 0.35H), 1.15-1.26 (m, 1.65H) 1.32-1.37 (m, 1H), 1.41 (m, 2H), 1.58 (m, 1H), 1.69-1.74 (m, 3H), 1.76-1.86 (m, 4H), 2.00-2.16 (m, 8H), 2.63 (m, 1H), 2.86-3.06 (m, 5H), 3.63 (m, 3H), 3.81-3.95 (m, 5H), 4.01 (m, 1H), 4.16 (m, 1H), 4.23-4.38 (m, 3H), 4.84-5.10 (m, 1H), 6.95-7.06 (m, 1H), 7.12-7.22 (m, 1H), 7.26-7.34 (m, 1H), 7.52-7.62 (m, 1H), 7.83-7.93 (m, 1H), 8.01-8.09 (m, 1H). LC/MS: m/z 701.49, Rf 1.778 min., 97.0% purity.

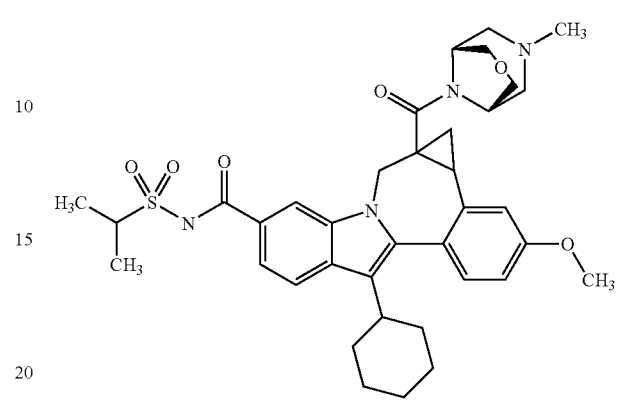

8-cyclohexyl-N-(isopropylsulfonyl)-11-methoxy-1a-(((1R,5S)-7-methyl-3-oxa-7,9-diazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.19 (m, 0.35H), 1.28 (m, 1.65H), 1.31-1.38 (m, 1H), 1.38-1.48 (m, 6H), 1.57 (m, 2H), 1.78 (m, 2H), 1.91-2.09 (m, 4H), 2.64 (m, 1H), 2.81 (m, 1H), 2.89-3.02 (m, 4H), 3.64 (m, 4H), 3.85-3.99 (m, 7H), 4.01 (m, 2H), 4.37 (m, 2H), 4.85-5.08 (m, 1H), 7.02-7.07 (m, 1H), 7.17-7.22 (m, 1H), 7.32-7.36 (m, 1H), 7.57-7.64 (m, 1H), 7.90-7.94 (m, 1H), 8.05-8.10 (m, 1H). LCAMS: m/z 675.44, Rf 1.743 min., 97.2% purity.

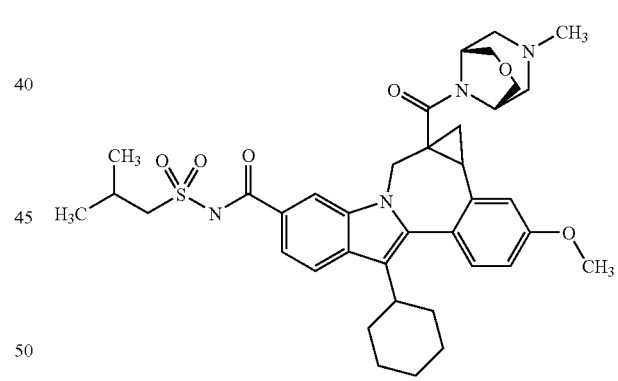

8-Cyclohexyl-N-(isobutylsulfonyl)-11-methoxy-1a-(((1R,5S)-7-methyl-3-oxa-7,9-diazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): 0.19 (m, 0.35 ), 1.07 (td, J=7.50, 2.56 Hz, 3H), 1.23-1.37 (m, 2.65H), 1.37-1.49 (m, 5H), 1.57-1.68 (m, 2H), 1.70-1.82 (m, 3H), 1.94-2.13 (m, 6H), 2.61 (m, 2H), 2.85 (m, 1H), 2.89-3.03 (m, 3H), 3.10-3.24 (m, 1H), 3.61 (d, J=15.37 Hz, 1H), 3.67-3.82 (m, 3H), 3.83-3.91 (m, 3H), 3.96 (m, 1H), 4.15 (m, 1H), 4.37 (m, 2H), 4.90-5.08 (m, 1H), 6.97-7.04 (m, 1H), 7.13 (d, J=2.56 Hz, 0.35H), 7.17 (d, J=2.56 Hz, 0.65H), 7.26-7.33 (m, 1H), 7.53-7.60 (m, 1H), 7.84-7.92 (m, 1H), 8.02-8.07 (s, 1H). LC/MS: m/z 689.49, Rf 1.788 min., 97.0% purity.

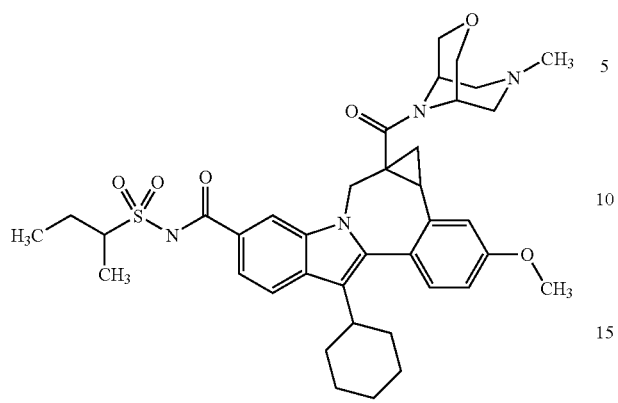

N-(sec-butylsulfonyl)-8-cyclohexyl-11-methoxy-1a-((7-methyl-3-oxa-7,9-diazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.21 (m, 0.20H), 1.09 (m, 3H), 1.30 (m, 1.80H), 1.44 (m, 7H), 1.56-1.79 (m, 5H), 1.72-2.12 (m, 5H), 2.65 (m, 1H), 2.97 (m, 5H), 3.63 (d, J=15.37 Hz, 1H), 3.69-3.83 (m, 3H), 3.84-3.97 (m, 4H), 4.14 (m, 2H), 4.39 (m, 2H), 5.07 (m, 1H), 6.98-7.06 (m, 1H), 7.14-7.21 (m, 1H), 7.28-7.34 (m, 1H), 7.53-7.63 (m, 1H), 7.85-7.93 (m, 1H), 8.02-8.11 (m, 1H). LC/MS: m/z 689.46, Rf 1.797 min., 96.0% purity.

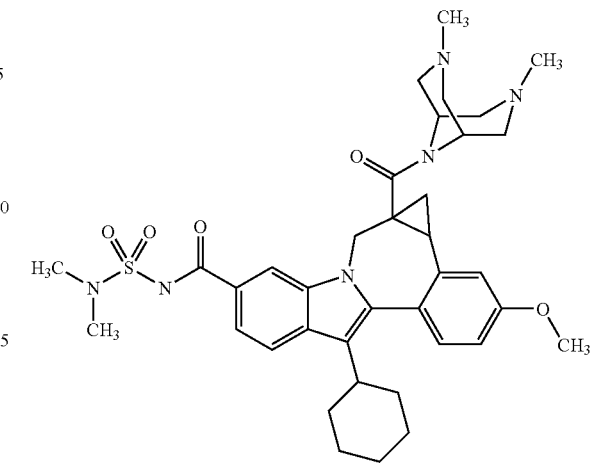

8-Cyclohexyl-N-(dimethylsulfamoyl)-1a-((3,7-dimethyl-3,7,9-triazabicyclo[3.3.1]non-9-yl)carbonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.24 (m, 0.20H), 1.24-1.38 (m, 2.80H), 1.45 (m, 4H), 1.56 (m, 1H), 1.83 (m, 2H), 2.04 (m, 4H), 2.65 (m, 1H), 2.82-2.91 (m, 1H), 2.93-3.05 (m, 9H), 3.17 (m, 3H), 3.49 (m, 1H), 3.64 (m, 2H), 3.78 (m, 1H), 3.86-3.95 (m, 4H), 4.03 (m, 1H), 4.18 (m, 1H), 4.37 (m, 1H), 4.51 (m, 1H), 5.08 (d, J=15.37 Hz, 1H), 6.99-7.07 (m, 1H), 7.13-7.22 (m, 1H), 7.29-7.37 (m, 1H), 7.51-7.63 (m, 1H), 7.89 (m, 1H), 7.99-8.10 (m, 1H). LC/MS: m/z 689.50, Rf 1.813 min., 98.3% purity.

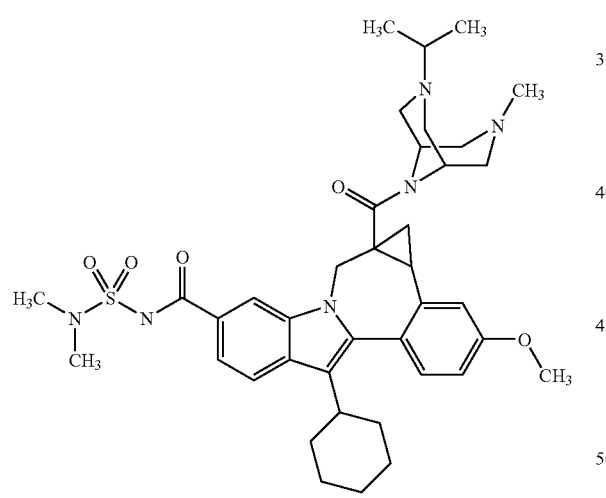

8-Cyclohexyl-N-(dimethylsulfamoyl)-1a-((3-isopropyl-7-methyl-3,7,9-triazabicyclo[3.3.1]non-9-yl)carbonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.19 (m, 0.35H), 1.12 (m, 3.65H), 1.20-1.35 (m, 4H), 1.39 (m, 2H), 1.45-1.58 (m, 2H), 1.64 (m, 2H), 1.78 (m, 3H), 2.00 (m, 6H), 2.61 (m, 3H), 2.74-2.90 (m, 2H), 2.90-3.05 (m, 6H), 3.48 (m, 1H), 3.61 (m, 2H), 3.84-3.91 (m, 4H), 4.15 (m, 1H), 4.45 (m, 1H), 5.07 (m, 1H), 7.01 (m, 1H), 7.11-7.20 (m, 1H), 7.26-7.35 (m, 1H), 7.50-7.63 (m, 1H), 7.88 (m, 1H), 8.00-8.09 (m, 1H). LC/MS: m/z 717.52, Rf 1.762 min., 97.8% purity.

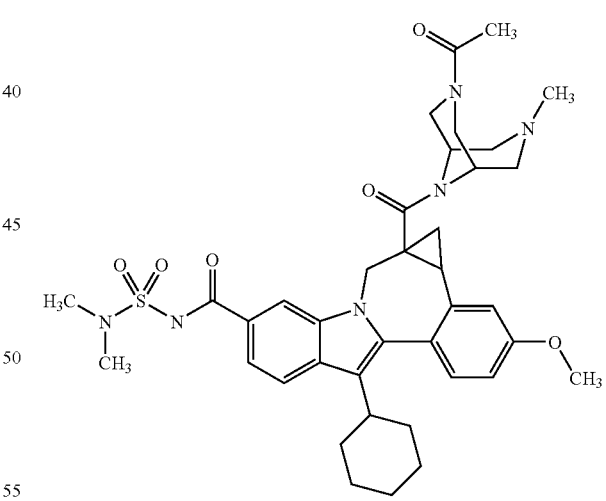

1a-((3-Acetyl-7-methyl-3,7,9-triazabicyclo [3.3.1]non-9-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (300 MHz, CD3OD): δ ppm 0.51 (m, 0.20H), 1.68 (m, 4.80H), 1.98 (m, 2H), 2.12 (m, 2H), 2.41 (m, 7H), 2.98 (m, 1H), 3.19 (m, 2H), 3.56-3.65 (m, 13H), 3.94-4.10 (m, 2H), 4.14-4.29 (m, 4H), 4.95 (m, 2H), 5.40 (m, 1H), 7.35 (m, 1H), 7.47-7.53 (m, 1H), 7.60-7.67 (m, 1H), 7.85 (m, 1H), 8.16-8.25 (m, 1H), 8.36 (s, 1H). LC/MS: m/z 717.47, Rf 1.710 min., 97.1% purity.

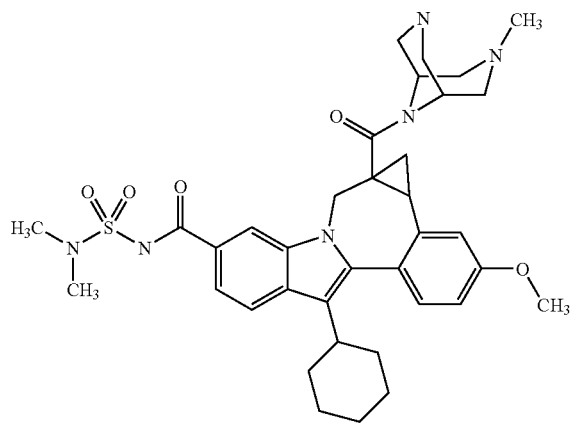

8-Cyclohexyl-N-(dimethylsulfamoyl)-11-methoxy-1a-((3-methyl-3,7,9-triazabicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.20 (m, 0.20H), 1.24-1.36 (m, 1.80H), 1.45 (m, 2H), 1.55 (m, 3H), 1.64 (m, 1H), 1.80 (m, 1H) 1.86 (m, 2H) 2.08 (m, 6H), 2.36 (m, 1H), 2.48 (m, 1H), 2.62 (m, 2H), 2.86 (m, 1H), 3.00 (m, 3H), 3.16 (m, 1H), 3.45 (m, 2H) 3.66 (m, 4H), 3.85-3.96 (m, 3H), 4.18 (m, 1H), 4.34 (m, 1H), 4.46 (m, 1H), 5.05 (m, 1H), 7.01 (m, 1H), 7.13-7.20 (m, 1H), 7.32 (m, 1H), 7.52-7.61 (m, 1H), 7.89 (m, 1H), 8.00-8.07 (m, 1H). LC/MS: m/z 675.37, Rf 1.772 min., 95.3% purity.

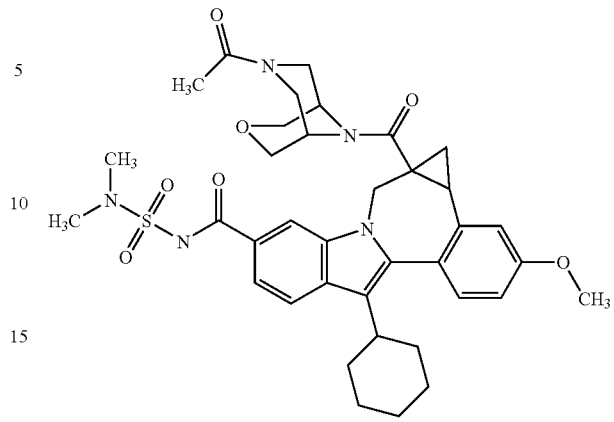

1a-((7-Acetyl-3-oxa-7,9-diazabicyclo[3.3.1]non-9-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (500 MHz, CD3OD): δ ppm 0.17 (m, 0.25H), 1.12 (m, 0.75H), 1.33 (m, 2H), 1.51 (m, 3H), 1.70 (m, 1H), 1.80 (m, 2H), 2.00-2.15 (m, 7H), 2.55-2.65 (m, 1H), 2.85 (m, 1H), 2.94-3.02 (m, 6H), 3.16 (m, 1H), 3.34 (m, 1H), 3.63 (m, 1H), 3.75 (m, 1H), 3.88 (m, 3H), 4.12 (m, 3H), 4.26 (m, 1H), 4.78 (m, 1H), 4.90 (m, 1H), 5.06 (m, 1H), 6.96-7.03 (m, 1H), 7.11-7.20 (m, 1H), 7.26-7.34 (m, 1H), 7.51-7.57 (m, 1H), 7.84-7.91 (m, 1H), 8.04-8.12 (s, 1H). LC/MS: m/z 704.34, Rf 1.938 min., 98.1% purity.

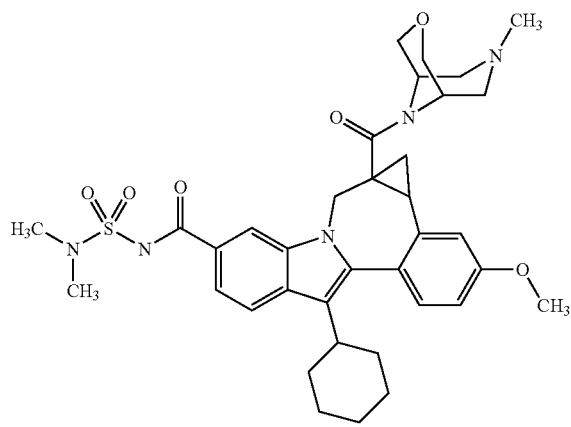

8-Cyclohexyl-N-(dimethylsulfamoyl)-11-methoxy-1a-((7-methyl-3-oxa-7,9-diaza bicyclo[3.3.1]non-9-yl)carbonyl)-1,1a,2,12b-tetrahydrocyclopropa[d]indolo[2,1-a][2]benzazepine-5-carboxamide. 1H NMR (300 MHz, CD3OD): δ ppm 0.22 (m, 0.20H), 1.30-1.38 (m, 1.80H), 1.44 (m, 2H), 1.56 (m, 2H), 1.70 (m, 1H), 1.80 (m, 2H), 2.02 (m, 4H), 2.66 (m, 1H), 2.86 (m, 2H), 2.92-3.07 (m, 9H), 3.66 (m, 3H), 3.81-3.94 (m, 4H), 4.02 (m, 2H), 4.17 (m, 1H), 4.36 (m, 2H), 5.10 (m, 1H), 7.03 (m, 1H), 7.13-7.22 (m, 1H), 7.32 (m, 1H), 7.56 (m, 1H), 7.86-7.95 (m, 1H), 8.01-8.11 (m, 1H). LC/MS: m/z 676.40, Rf 1.703 min., 98.2% purity.

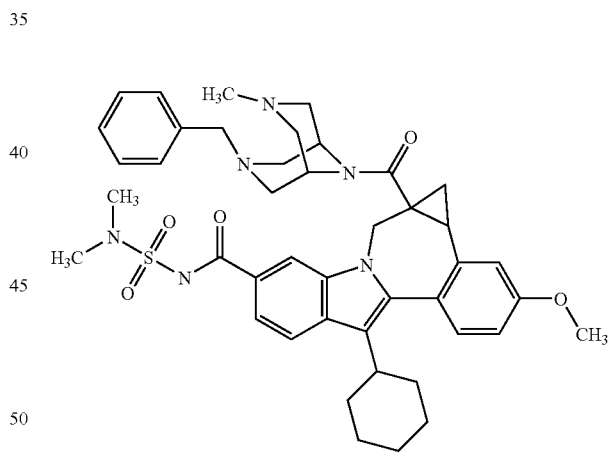

1a-((3-Benzyl-7-methyl-3,7,9-triazabicyclo[3.3.1]non-9-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.20H), 1.32 (m, 2.80H), 1.43 (m, 4H), 1.77 (m, 2H), 2.01 (m, 5H), 2.59-2.72 (m, 2H), 2.78 (m, 1H), 2.87 (m, 1H), 2.90-3.05 (m, 8H), 3.25 (m, 2H), 3.59 (m, 4H), 3.75 (m, 1H), 3.84-3.93 (m, 3H), 4.15 (m, 1H), 4.38 (m, 1H), 4.56 (m, 1H), 5.08 (d, J=15.00 Hz, 1H), 6.97-7.04 (m, 1H), 7.07-7.17 (m, 1H), 7.28-7.42 (m, 6H), 7.53-7.61 (m, 1H), 7.85-7.92 (m, 1H), 7.99-8.13 (m, 1H). LCAMS: m/z 765.45, Rf 1.840 min., 99.7% purity.

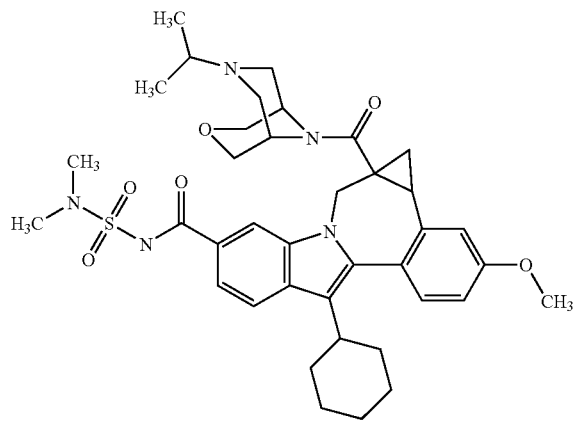

8-Cyclohexyl-N-(dimethylsulfamoyl)-1a-((7-isopropyl-3-oxa-7,9-diazabicyclo[3.3.1]non-9-yl)carbonyl)-11-methoxy-1,1a,2,12b-tetrahydrocyclopropa[d]indolo[2,1-a][2]benzazepine-5-carboxamide. 1H NMR (500 MHz, CD3OD): δ ppm 0.24 (m, 0.25H), 1.23 (m, 0.75H), 1.36 (m, 2H), 1.38(m, 1H), 1.49 (m, 6H), 1.61 (m, 1H), 1.70 (m, 1H), 1.84 (m, 2H), 1.96-2.14 (m, 4H), 2.64-2.71 (m, 1H), 2.89 (m, 1H), 2.98-3.07 (m, 6H), 3.20 (m, 1H), 3.29 (m, 2H), 3.37 (m, 1H), 3.41 (m, 1H), 3.50 (m, 1H), 3.69 (m, 1H), 3.92 (m, 4H), 4.00 (m, 2H), 4.18 (m, 1H), 4.43 (m, 1H), 5.14 (m, 1H), 7.05 (m, 1H), 7.16-7.24 (m, 1H), 7.35 (m, 1H), 7.55-7.64 (m, 1H), 7.93(m, 1H), 8.05-8.12 (m, 1H). LC/MS: m/z 704.40, Rf 1.755 min., 99.2% purity.

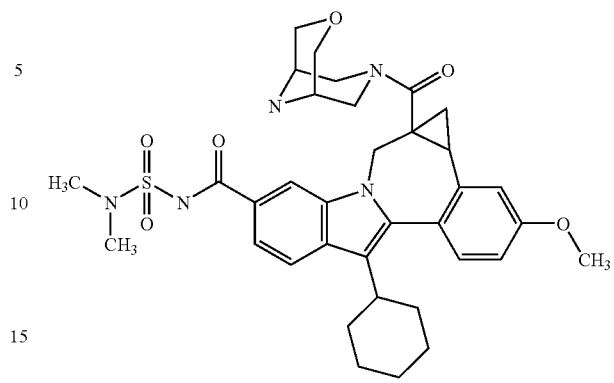

8-Cyclohexyl-N-(dimethylsulfamoyl)-11-methoxy-1a-(3-oxa-7,9-diazabicyclo[3.3.1]non-7-ylcarbonyl)-1,1a,2,12b-tetrahydrocyclopropa[d]indolo[2,1-a][2]benzazepine-5-carboxamide. 1H NMR (300 MHz, CD3OD): δ ppm 0.25 (m, 0.20H), 1.08-1.32 (m, 1.80H), 1.44 (m, 4H), 1.78 (m, 3H), 1.99 (m, 4H), 2.57 (m, 1H), 2.77 (m, 1H), 2.90-3.02 (m, 7H), 3.62 (m, 3H), 3.85-3.94 (m, 3H), 4.00-4.15 (m, 4H), 4.57 (m, 2H), 5.00 (d, J=15.37 Hz, 1H), 7.00 (dd, J=8.60, 2.38 Hz, 1H), 7.17 (d, J=2.38 Hz, 1H), 7.24-7.34 (m, 1 H), 7.50-7.61 (m, 1H), 7.82-8.06 (m, 2H). LC/MS: m/z 662.46, Rf 1.760 min., 98.2% purity.

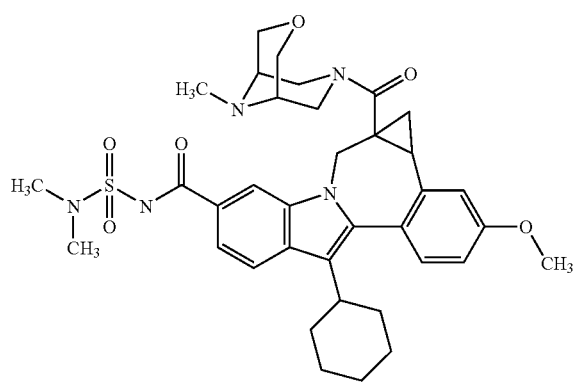

8-cyclohexyl-N-(dimethylsulfamoyl)-11-methoxy-1a-((9-methyl-3-oxa-7,9-diaza bicyclo[3.3.1]non-7-yl)carbonyl)-1,1a,2,12b-tetrahydrocyclopropa[d]indolo[2,1-a][2]benzazepine-5-carboxamide. 1H NMR (300 MHz, CD3OD): δ ppm 0.24 (m, 0.25H), 1.32 (m, 1.75H), 1.43 (m, 4H), 1.78 (m, 3H), 1.98 (m, 4H), 2.55 (m, 1H), 2.77-2.90 (m, 1H), 3.00 (s, 6H), 3.11-3.26 (m, 4H), 3.55 (m, 3H), 3.88 (m, 3H), 4.13 (m, 4H), 4.54 (m, 2H), 5.00 (d, J=15.00 Hz, 1H), 7.00 (dd, J=8.42, 2.56 Hz, 1H), 7.16 (m, 1H), 7.21-7.33 (m, 1H), 7.49-7.60 (m, 1H), 7.81-7.88 (m, 1H), 7.91-8.06 (m, 1H). LC/MS: m/z 676.35, Rf 1.747 min., 98.2% purity.

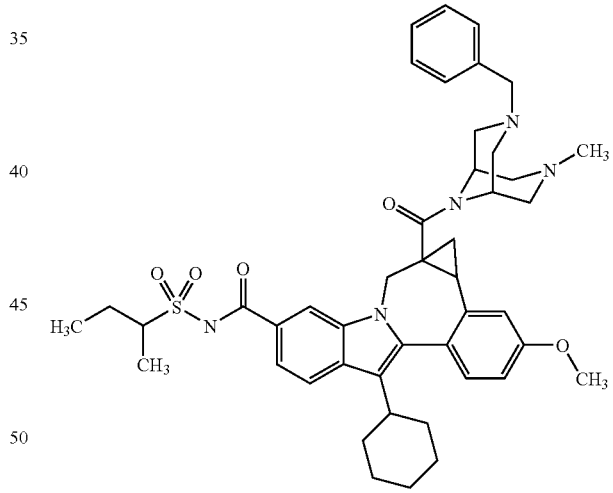

1a-((3-Benzyl-7-methyl-3,7,9-triazabicyclo[3.3.1]non-9-yl)carbonyl)-N-(sec-butyl sulfonyl)-8-cyclohexyl-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.20H), 1.06-1.14 (m, 3H), 1.20-1.36 (m, 2.80H), 1.42 (m, 6H), 1.72 (m, 4H), 1.98-2.13 (m, 6H), 2.62 (m, 2H), 2.85 (m, 4H), 3.15 (m, 1H), 3.52 (m, 2H), 3.63 (m, 2H), 3.76 (m, 2H), 3.87 (m, 4H), 4.11 (m, 1H), 4.38 (m, 1H), 4.55 (m, 1H), 5.06 (m, 1H), 6.97-7.05 (m, 1H), 7.11-7.17 (m, 1H), 7.27-7.42 (m, 5H), 7.59 (m, 2H), 7.90 (m, 1H), 8.01-8.09 (m, 1H). LC/MS: m/z 779.48, Rf 1.897 min., 95.3% purity.

7.49-7.61 (m, 1H), 7.81-7.92 (m, 1.65H), 8.06 (m, 0.35H). LC/MS: m/z 689.86, Rf 1.785 min., 96.2% purity.

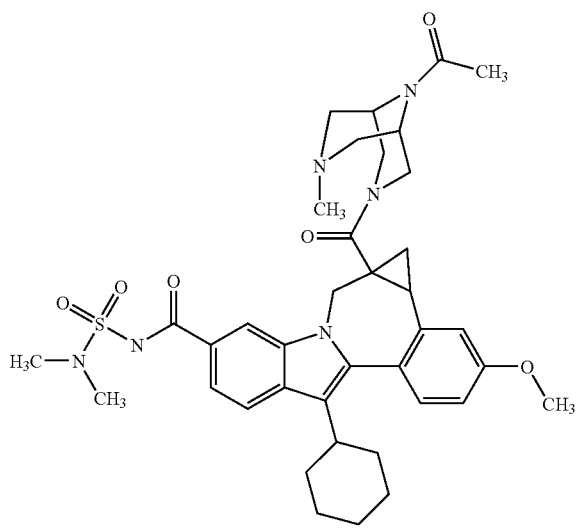

1a-((9-Acetyl-7-methyl-3,7,9-triazabicyclo[3.3.1]non-3-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.35H), 1.01-1.30 (m, 0.65H), 1.38 (m, 5H), 1.79 (m, 3H), 1.93-2.21 (m, 13H), 2.62 (m, 1H), 2.82 (m, 2H), 2.99 (s, 6H), 3.56 (m, 1H), 3.90 (m, 3H), 4.04-4.18 (m, 3H), 4.53 (m, 1H), 4.63 (m, 1H), 4.99 (m, 1H), 6.95-7.01 (m, 1H), 7.19 (m, 1H), 7.31 (m, 1H), 7.50-7.60 (m, 1H), 7.80 (m, 1H), 7.88-8.07 (m, 1H). LC/MS: m/z 717.92, Rf 1.760 min., 97.6% purity.

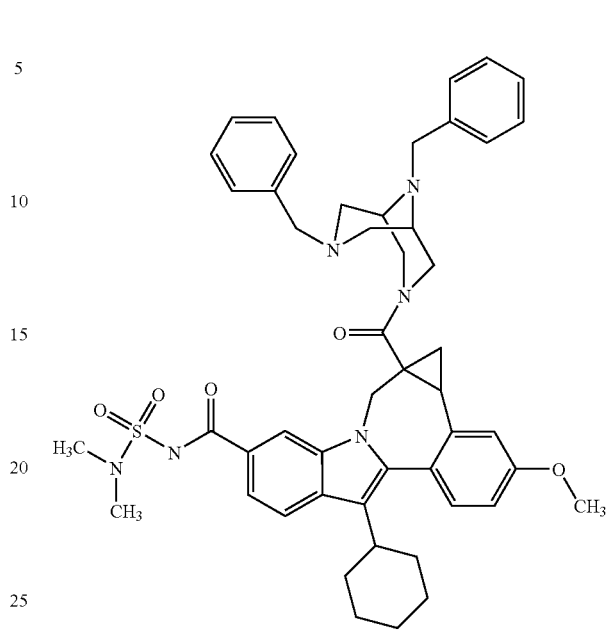

8-Cyclohexyl-1a-((7,9-dibenzyl-3,7,9-triazabicyclo[3.3.1]non-3-yl)carbonyl)-N-(dimethylsulfamoyl)-11-methoxy-1,1a,2,12b-tetrahydrocyclopropa[d]indolo[2,1-a][2]benzazepine-5-carboxamide. 1H NMR (500 MHz, CD3OD): δ ppm 0.22 (m, 0.25H), 0.90 (m, 1H), 1.19-1.28 (m, 1.75H), 1.38-1.46 (m, 3H), 1.76 (m, 3H), 1.95 (m, 2H), 2.00 (m, 2H), 2.07 (m, 2H), 2.54 (m, 1H), 2.86 (m, 1H), 2.99 (m, 9H), 3.16 (m, 1H), 3.43 (m, 1H), 3.47 (m, 3H), 3.84-3.91 (m, 4H), 4.01-4.09 (m, 2H), 4.75 (m, 1H), 4.99 (d, J=15.26 Hz, 1H), 6.94-7.02 (m, 1H), 7.08-7.17 (m, 1H), 7.27-7.56 (m, 11H), 7.70 (m, 1H), 7.86-8.07 (m, 2H). LC/MS: m/z 842.66, Rf 2.010 min., 98.0% purity.

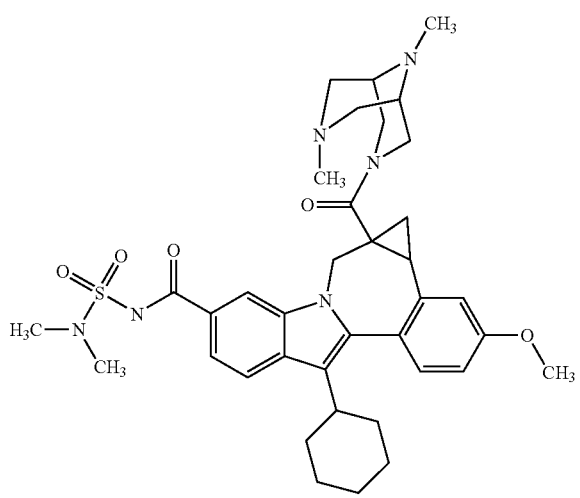

8-Cyclohexyl-N-(dimethylsulfamoyl)-1a-((7,9-dimethyl-3,7,9-triazabicyclo[3.3.1]non-3-yl)carbonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.24 (m, 0.35H), 1.24 (m, 0.65H), 1.29-1.49 (m, 5H), 1.62 (m, 1H), 1.79 (m, 2H), 1.98 (m, 4H), 2.42 (m, 1H), 2.53 (m, 1H), 2.62 (m, 1H), 2.75 (m, 1H), 2.87 (m, 2H), 2.93-3.07 (m, 8H), 3.12-3.22 (m, 2H), 3.42 (m, 2H), 3.51-3.66 (m, 1H), 3.88 (m, 3H), 4.13 (m, 3H), 4.27 (m, 1H), 4.60 (m, 1H), 5.00 (m, 1H), 6.97-7.04 (m, 1H), 7.14-7.20 (m, 1H), 7.31 (m, 1H),

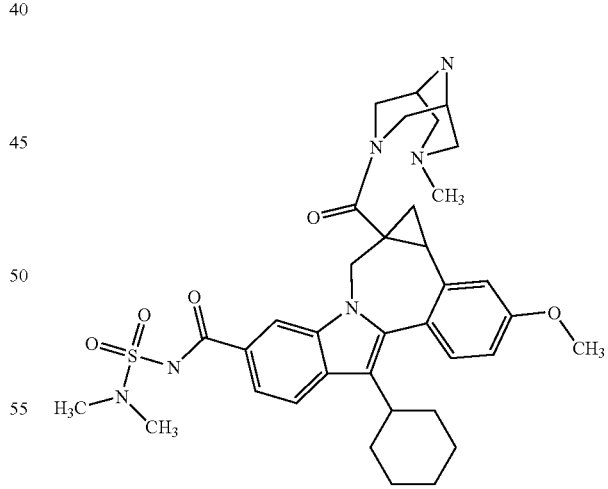

8-Cyclohexyl-N-(dimethylsulfamoyl)-11-methoxy-1a-((7-methyl-3,7,9-triazabicyclo[3.3.1]non-3-yl)carbonyl)-1,1a,2,12b-tetrahydrocyclopropa[d]indolo[2,1-a][2]benzazepine-5-carboxamide. 1H NMR (500 MHz, CD3OD): δ ppm 0.23 (m, 0.30H), 1.07-1.29 (m, 0.70H), 1.36-1.45 (m, 5H), 1.60 (m, 1H), 1.73-1.82 (m, 2H), 1.90-2.07 (m, 4H), 2.17 (m, 1H), 2.35 (m, 1H), 2.54-2.70 (m, 3H), 2.86 (m, 1H), 3.00 (m, 8H), 3.20 (m, 2H), 3.59 (m, 1H), 3.71-3.80 (m, 1H), 3.84-3.91 (m, 3H), 4.14 m, 1H), 4.43 (m, 1H), 4.65 (m, 1H), 4.98 (m,1H), 6.98-7.01 (m, 1H), 7.15-7.20 (m,1H), 7.28-7.32 (m, 1H), 7.50-7.60 (m, 1H), 7.85-8.05 (m, 2H). LC/MS: m/z 675.61, Rf 1.783 min., 98.7% purity.

All compounds described in the procedures and examples that follow were analyzed by using the following LC/MS method until noted: Analysis Conditions: Column: PHENOMENNEX-LUNA 3.0×50 mm S10 ; Mobile Phase: (A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

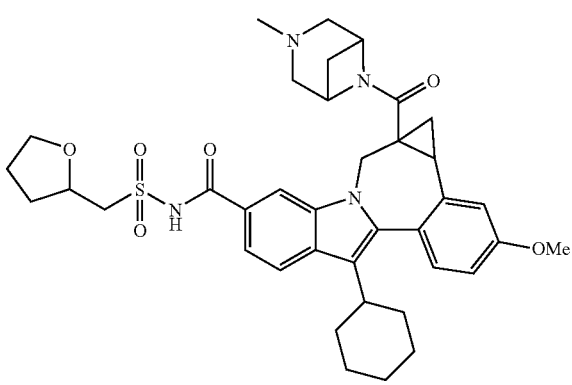

8-cyclohexyl-N-((tetrahydrofuran-2-yl)methylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a mixture of diastereomers in mono TFA salt form. LC/MS: Retention time: 1.832 min; m/e 687 (MH+). The product was observed to exist as inter-converting rotamers by 1H NMR (400 MHz, CHLOROFORM-D) δ ppm 1.07-1.58 (m, 6H), 1.61-2.10 (m, 6H), 2.11-2.51 (m, 8H), 2.58-2.88 (m, 2H), 2.89-3.04 (m, 2H), 3.06-3.25 (m, 1H), 3.38-3.82 (m, 7H), 3.83-3.97 (m, 5H), 4.31-4.52 (m, J=25.94 Hz, 2H), 5.34-5.57 (m, 1H), 6.91-7.02 (m, J=8.69, 2.64 Hz, 1H), 7.05-7.18 (m, J=2.52 Hz, 1H), 7.21-7.35 (m, 1H), 7.54-7.69 (m, 1H), 7.79-7.98 (m, 1H), 8.04-8.23 (m, 1H).

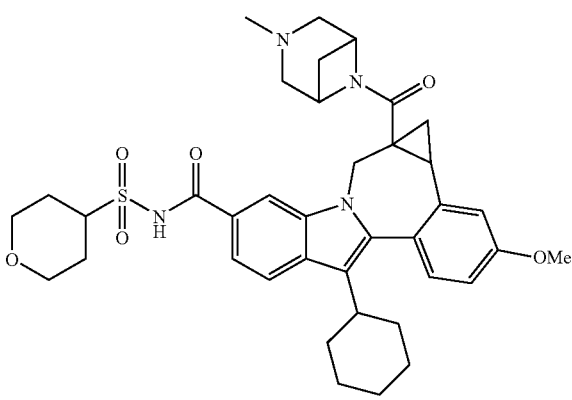

(+/−)-8-cyclohexyl-N-(tetrahydro-2H-pyran-4-ylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.810 min; m/e 687 (MH+). The product was observed to exist as inter-converting rotamers by 1H NMR (400 MHz, CHLOROFORM-D) δ ppm 1.08-1.63 (m, 7H), 1.72-1.86 (m, 2H), 1.88-2.15 (m, 7H), 2.15-2.60 (m, 7H), 2.60-3.19 (m, 4H), 3.34-3.52 (m, 3H), 3.52-3.68 (m, 1H), 3.83-3.94 (m, 3H), 3.97-4.20 (m, 4H), 4.28-4.49 (m, 1H), 5.33-5.56 (m, 1H), 6.87-7.04 (m, J=8.56, 2.77 Hz, 1H), 7.05-7.17 (m, J=2.52 Hz, 1H), 7.24-7.35 (m, 1H), 7.55-7.73 (m, J=8.31 Hz, 1H), 7.81-7.96 (m, J=8.56 Hz, 1H), 8.02-8.21 (m, 1H).

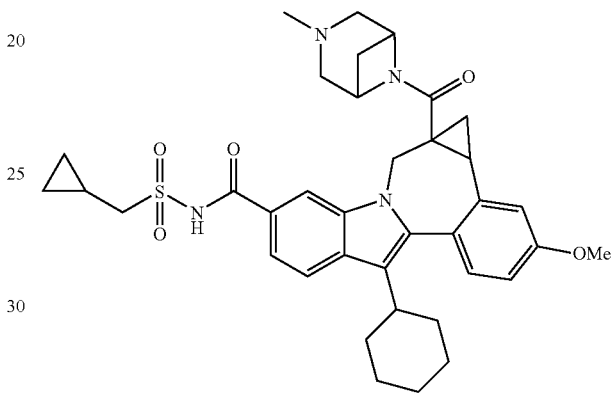

(+/−)-8-cyclohexyl-N-(cyclopropylmethylsulfonyl)-1,1a,2,12b-tetrahydro-11-methoxy-1a-(3-methyl-3,6-diazabicyclo[3.1.1]heptane-6-carbonyl)cycloprop[d]indolo[2,1-a][2]benzazepine-5-carboxamide. The product was purified by prep HPLC and isolated as a beige solid in mono TFA salt form. LC/MS: Retention time: 1.848 min; m/e 657 (MH+). The product was observed to exist as inter-converting rotamers by 1H NMR (400 MHz, CHLOROFORM-D) δ ppm 0.29-0.48 (m, 2H), 0.59-0.78 (m, 2H), 1.10-1.61 (m, 6H), 1.68-2.19 (m, J=81.58 Hz, 6H), 2.21-2.78 (m, 10H), 2.79-3.28 (m, 2H), 3.31-3.72 (m, 4H), 3.78-3.97 (m, 3H), 3.97-4.70 (m, 2H), 5.33-5.59 (m, 1H), 6.86-7.04 (m, J=8.56, 2.52 Hz, 1 H), 7.05-7.18 (m, J=2.27 Hz, 1H), 7.18-7.37 (m, 1H), 7.47-7.70 (m, 1H), 7.79-8.01 (m, 1H), 8.03-8.35 (m, 1H).

9-methyl-9,10-diazatricyclo[4.2.1.1$^{2,5}$]decane. To a cold (0° C.) solution of 9-benzyl-9,10-diazatricyclo[4.2.1.1$^{2,5}$]decane (*J. Med. Chem.* 2000, 43, 2115-2123) and TEA in an DMF (1-2 ml) was added MeI. The mixture was allowed to warm to rt and stirred for 2-3 h. The rxn mixture was evaporated to dryness and partitioned between ether and satd. NaHCO3 and ether layer separated, washed with brine and dried (Na2SO4). Evaporation of ether afforded 9-benzyl-10-methyl-9,10-diazatricyclo[4.2.1.1$^{2,5}$]decane as a light-brown oil. A stirred suspension of 9-benzyl-10-methyl-9,10-diazatricyclo[4.2.1.1$^{2,5}$]decane in EtOH containing conc. HCl (0.5 ml) and 10% Pd—C was hydrogenated under balloon pressure of hydrogen overnight. The suspension was filtered and filtrate was added dry toluene (10-15 ml) and evaporated to dryness to afford the 9-methyl-9,10-diazatricyclo[4.2.1.1$^{2,5}$]decane and isolated as bis-HCl salt.

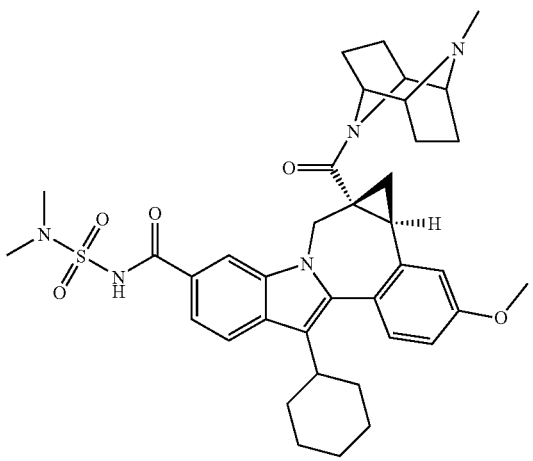

8-cyclohexyl-N-(N,N-dimethylsulfamoyl)-1,1a,2,12b-tetrahydro-11-methoxy-1a-(9-methyl-9,10-diazatricyclo[4.2.1.1$^{2,5}$]decane-10-carbonyl)cycloprop[d]indolo[2,1-a][2]benzazepine-5-carboxamide. Neat 2-(1H-enzotriazol-1-yl)-1,1,3,3-tetramethyluroniumtetrafluoroborate (12.52 mg, 0.039 mmol) was added to a stirred solution of the acid (17 mg, 0.03 mmol), 9-methyl-9,10-diazatricyclo[4.2.1.1$^{2,5}$]decane (9 mg, 0.036 mmol) and TEA (0.025 ml, 0.180 mmol) in an DCM (1 ml). The mixture stirred at rt overnight and then evaporated to dryness. The crude product was purified by reverse-phase prep. HPLC to afford the product and isolated as mono TFA salt: LC/MS: Retention time: 2.810 min; m/e 686 (MH$^+$). The product was observed to exist as inter-converting rotamers by 1H NMR (400 MHz, CHLOROFORM-D) δ ppm 0.18-0.35 (m, J=6.17, 6.17 Hz, 1H), 1.10-1.28 (m, 2H), 1.30-1.43 (m, 3H), 1.43-1.61 (m, J=24.93 Hz, 1H), 1.69-1.85 (m, 2H), 1.83-2.08 (m, 4H), 2.10-2.34 (m, 2H), 2.37-2.55 (m, 2H), 2.58-2.72 (m, 2H), 2.73-2.94 (m, 3H), 2.95-3.08 (m, 6H), 3.37-3.61 (m, 3H), 3.65-3.81 (m, J=18.63 Hz, 2H), 3.82-3.94 (m, J=3.02 Hz, 3H), 3.94-4.06 (m, J=14.60 Hz, 1H), 4.09-4.25 (m, J=14.10 Hz, 1H), 4.34-4.63 (m, 1H), 4.73-4.88 (m, 1H), 5.15-5.27 (m, 1H), 6.91-6.99 (m, 1H), 6.97-7.14 (m, 1H), 7.26-7.35 (m, 1H), 7.46-7.55 (m, J=9.32, 9.32 Hz, 1H), 7.83-7.90 (m, J=8.18, 8.18 Hz, 1H), 7.90-8.00 (m, 1H).

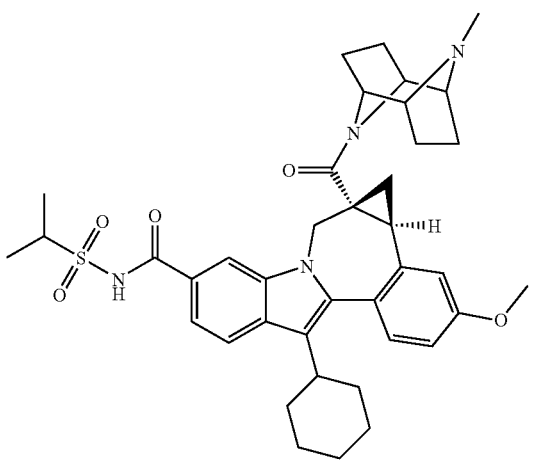

8-cyclohexyl-N-(isopropylsulfonyl)-1,1a,2,12b-tetrahydro-11-methoxy-1a-(9-methyl-9,10-diazatricyclo[4.2.1.1$^{2,5}$]decane-10-carbonyl)cycloprop[d]indolo[2,1-a][2]benzazepine-5-carboxamide. Neat 2-(1H-benzotriazol-1-yl)-1,1,3,3-tetramethyluronium tetrafluoroborate (12.52 mg, 0.039 mmol) was added to a stirred solution of the acid (17 mg, 0.03 mmol), 9-methyl-9,10-diazatricyclo[4.2.1.1$^{2,5}$]decane (9 mg, 0.036 mmol) and TEA (0.025 ml, 0.180 mmol) in an DCM (1 ml). The mixture stirred at rt overnight and then evaporated to dryness. The crude product was purified by reverse-phase prep. HPLC to afford the product and isolated as mono TFA salt: LC/MS: Retention time: 2.855 min; m/e 685 (MH$^+$). The product was observed to exist as inter-converting rotamers by 1H NMR (400 MHz, CHLOROFORM-D) δ ppm 0.16-0.36 (m, 1H), 1.03-1.28 (m, 2H), 1.29-1.57 (m, 8H), 1.65-1.85 (m, 2H), 1.84-2.06 (m, 4H), 2.09-2.33 (m, 2H), 2.36-2.54 (m, 1H), 2.59-2.79 (m, 2H), 2.80-2.89 (m, 2H), 2.89-3.20 (m, 2H), 3.41-3.63 (m, 3H), 3.62-3.82 (m, 4H), 3.83-3.93 (m, J=3.78 Hz, 3H), 3.96-4.09 (m, 2H), 4.10-4.25 (m, J=14.60 Hz, 1H), 4.43-4.56 (m, 1H), 4.71-4.85 (m, 1H), 5.12-5.26 (m, 1H), 6.91-6.98 (m, 1H), 6.97-7.12 (m, 1H), 7.27-7.34 (m, 1H), 7.49-7.58 (m, J=8.31 Hz, 1H), 7.84-7.90 (m, J=8.44, 6.17 Hz, 1H), 7.90-7.99 (m, 1H).

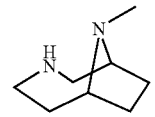

9-methyl-3,9-diazabicyclo[4.2.1]nonane. 9-Methyl-3,9-diazabicyclo[4.2.1]nonane (*J. Org. Chem.*, 1960, 637). Conc. H$_2$SO$_4$ (6.25 ml, 0.117 mol) was added dropwise to a stirred cold (−5° C.) solution of 8-methyl-8-azabicyclo[3.2.1]octan-3-one (2.78 g, 0.02 mol) in CHCl$_3$ (25 ml) while keeping the temperature below 15° C. After cooling to 0-5° C., neat sodium azide (2.60 g, 0.040 mol) was added in small portions while maintaining pot temperature below 35° C. The mixture stirred at rt for 2 h and then heated at 50° C. for 2 h. Rxn mixture was poured into ice and neutralized with Na$_2$CO$_3$ and then basify with 50% NaOH. Organic layer separated and the aq. layer re-extracted with CHCl$_3$ (2×25 ml). Combined organic layers were washed with water (10 ml), brine and dried (MgSO$_4$). Evaporation of CHCl$_3$ gave 9-methyl-3,9-diazabicyclo[4.2.1]nonan-4-one as a off-white solid (1.15 g, 37%). 1H NMR (400 MHz, CHLOROFORM-D) ppm 1.67-1.75 (m, 1H) 1.77-1.85 (m, 1H) 2.05-2.16 (m, 2H) 2.42 (s, 3H) 2.46 (ddd, J=16.05, 6.23, 2.14 Hz, 1H) 2.80-2.90 (m, 2H) 3.17 (t, J=6.42 Hz, 1H) 3.24 (t, J=6.30 Hz, 1H) 3.60 d), J=14.60 Hz, 1H) 5.90 (s, 1H).

Neat LAH (0.5 g, 13.17 mmol) was added in small portions to a stirred solution of 9-methyl-3,9-diazabicyclo[4.2.1]nonan-4-one (1.0 g, 6.48 mmol) in THF (40 ml) and the mixture was heated at reflux under nitrogen for 3-4 h. Reaction mixture was cooled in ace bath and quenched by consecutive addition of water (0.5 ml), 15% NaOH (1.5 ml) and water (0.5 ml) and then stirred for 30 min. Precipitated sodium aluminate was filtered off and the filtrate was dried over MgSO4, filtered and evaporated to dryness to afford 9-methyl-3,9-diazabicyclo[4.2.1]nonane as a light yellow oil. 1H NMR (400 MHz, CHLOROFORM-D) δ ppm 1.08-1.67 (m, 4H) 1.74-1.92 (m, 1H) 2.01-2.31 (m, 2H) 2.41-2.46 (m, 3H) 2.66 (dd, J=13.09, 2.01 Hz, 1H) 2.77-3.00 (m,2H) 3.07-3.36 (m, 2H) 3.50-4.06 (m, 1H).

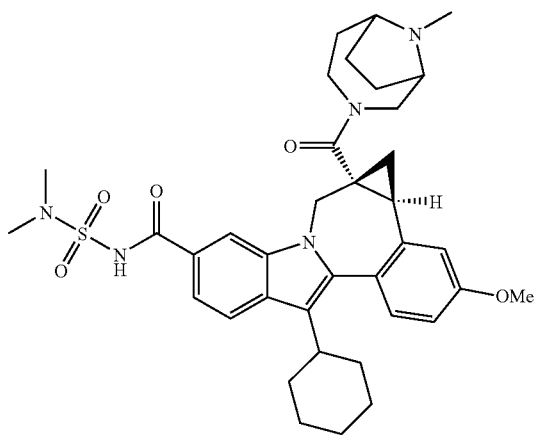

8-cyclohexyl-N-(N,N-dimethylsulfamoyl)-1,1a,2,12b-tetrahydro-11-methoxy-1a-(9-methyl-3,9-diazabicyclo[4.2.1]nonane-3-carbonyl)cycloprop[d]indolo[2,1-a][2]benzazepine-5-carboxamide. Neat 2-(1H-benzotriazol-1-yl)-1,1,3,3-tetramethyluronium tetrafluoroborate (22 mg, 0.069 mmol) was added to a stirred solution of the acid (28 mg, 0.051 mmol), 9-methyl-3,9-diazabicyclo[4.2.1]nonane (15 mg, 0.102 mmol) and TEA (0.021 ml, 0.152 mmol) in an DCM (1 ml). The mixture stirred at rt for 30-45 min and then evaporated to dryness. The crude product was purified by reverse-phase prep. HPLC to afford the product as a mixture of diastereomers and isolated in mono TFA salt: LC/MS: Retention time: 1.788 min; m/e 674 (MH+). The product was observed to exist as inter-converting rotamers by 1H NMR (400 MHz, CHLOROFORM-D) δ ppm 0.22-0.50 (m, 1H), 1.13-1.46 (m, J=54.89 Hz, 4H), 1.46-1.61 (m, 1H), 1.63-1.84 (m, 3H), 1.85-2.22 (m, 5H), 2.28-2.69 (m, 7H), 2.69-2.98 (m, 4H), 2.98-3.12 (m, 6H), 3.43-3.56 (m, 1H), 3.55-3.82 (m, 2H), 3.84-3.91 (m, J=4.28 Hz, 3H), 3.92-4.08 (m, 2H), 4.10-4.24 (m, 1H), 4.64-5.10 (m, J=132.95 Hz, 1H), 6.87-7.00 (m, 1H), 7.01-7.12 (m, 1H), 7.27-7.35 (m, 1H), 7.40-7.63 (m, 1H), 7.82-7.93 (m, 2H).

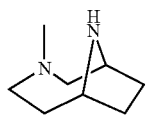

3-methyl-3,9-diazabicyclo[4.2.1]nonane. 3-Methyl-3,9-diazabicyclo[4.2.1]nonane was prepared by following the procedure described in reference: J. Org. Chem., 1960, 637. Conc. H2SO4 (3.25 ml, 0.061 mol) was added dropwise to a stirred cold (−5° C.) solution of 8-benzyl-8-azabicyclo[3.2.1]octan-3-one (2.153 g, 0.01 mol) in CHCl3 (15 ml) while keeping the temperature below 15° C. After cooling to 0-5° C., neat sodium azide (1.30 g, 0.020 mol) was added in small portions while maintaining pot temperature below 35° C. The mixture was stirred at rt overnight and then heated at 50° C. for 2 h. Rxn mixture was poured into ice and neutralized with Na2CO3 and then basify with 50% NaOH. Organic layer separated and the aq. layer re-extracted with CHCl3 (2×25 ml). Combined organic lyers were washed with water (10 ml), brine and dried (MgSO4). Evaporation of CHCl3 gave 9-benzyl-3,9-diazabicyclo[4.2.1]nonan-4-one as a beige semisolid. LC/MS: m/e 231 (MH+).

Neat LAH (0.4 g, 10.54 mmol) was added in small portions to a stirred solution of 9-benzyl-3,9-diazabicyclo[4.2.1]nonan-4-one (1.2 g, 5.21 mmol) in THF (40 ml) and the mixture was stirred under nitrogen overnight. Reaction mixture was cooled in ace bath and quenched by consecutive addition of water (0.4 ml), 15% NaOH (1.2 ml) and water (0.4 ml) and then stirred for 30 min. Precipitated sodium aluminate was filtered off and the filtrate was dried over MgSO4, filtered and evaporated to dryness to afford 9-benzyl-3,9-diazabicyclo[4.2.1]nonane as a light yellow oil. LC/MS: m/e 217 (MH+).

Neat Iodomethane (0.173 ml, 2.77 mmol) was added dropwise to a stirred solution of 9-benzyl-3,9-diazabicyclo[4.2.1]nonane (0.4 g, 1.849 mmol) and TEA (2.58 ml, 18.49 mmol) in THF (5 ml). The resultant suspension was stirred at rt for 3 hrs and diluted with ether and then filtered. The filtrate was evaporated to dryness to afford 9-benzyl-3-methyl-3,9-diazabicyclo[4.2.1]nonane as a light yellow oil. LC/MS: m/e 231 (MH+).

Neat ammonium formate (2 g, 31.7 mmol) was added to stirred suspension of 9-benzyl-3-methyl-3,9-diazabicyclo[4.2.1]nonane (250 mg, 1.085 mmol) and 10% Pd-C (150 mg, 0.141 mmol) in abs. ethanol (50 ml). The mixture was heated to reflux for 2-3 h. The suspension was filtered and to the filtrate TFA (0.5 ml) was added and evaporated to dryness to afford 3-methyl-3,9-diazabicyclo[4.2.1]nonane and isolated as the bis-TFA salt. LC/MS: m/e 141 (MH+).

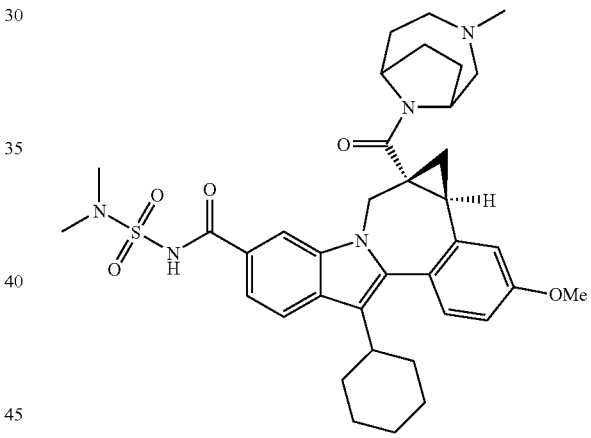

8-cyclohexyl-N-(N,N-dimethylsulfamoyl)-1,1a,2,12b-tetrahydro-11-methoxy-1a-(3-methyl-3,9-diazabicyclo[4.2.1]nonane-9-carbonyl)cycloprop[d]indolo[2,1-a][2]benzazepine-5-carboxamide. Neat 2-(1H-benzotriazol-1-yl)-1,1,3,3-tetramethyluronium tetrafluoroborate (22 mg, 0.069 mmol) was added to a stirred solution of the acid (28 mg, 0.051 mmol), 3-methyl-3,9-diazabicyclo[4.2.1]nonane, 2TFA (37.4 mg, 0.102 mmol) and TEA (0.035 ml, 0.254 mmol) in an. DCM (1 ml). The mixture stirred at rt for 30-45 min and then evaporated to dryness. The crude product was purified by reverse-phase prep. HPLC to afford the product as a mixture of diastereomers and isolated in mono TFA salt: LC/MS: Retention time: 1.830 min; m/e 674 (MH+). The product was observed to exist as inter-converting rotamers by 1H NMR (500 MHz, CHLOROFORM-D) δ ppm 0.09-0.66 (m, 1H), 0.72-1.14 (m, 1H), 1.13-1.47 (m, 5H), 1.48-1.65 (m, 1H), 1.65-1.83 (m, 3H), 1.83-2.14 (m, 4H), 2.14-2.40 (m, 2H), 2.38-2.69 (m, 2H), 2.70-2.87 (m, 3H), 2.86-3.08 (m, 6H), 3.09-3.42 (m, 2H), 3.43-3.55 (m, 1H), 3.56-3.73 (m, J=16.48 Hz, 1H), 3.74-3.98 (m, 4H), 3.95-4.26 (m, 1H), 4.22-4.61 (m, 2H), 4.61-4.87 (m, J=35.10 Hz, 1H), 4.95-5.21 (m, J=64.39 Hz, 1H), 6.86-7.01 (m, 1H), 7.02-7.14 (m, 1H), 7.25-7.34 (m, 1H), 7.34-7.58 (m, 1H), 7.78-8.00 (m, 2H).

The following compounds were analyzed by the following method until noted: Analysis Conditions: Column: PHE-NOMENNEX-LUNA 3.0×50 mm S10; Mobile Phase: (A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

General procedure for the preparation of 3-alkyl-3,9-diazabicyclo[3.3.1]nonane. A suspension of pyridine-2,6-dicarboxylic acid (6.68 g, 40.0 mmol) and Platinum(IV) oxide (0.23 g, 1.013 mmol) in Acetic Acid (200 ml) was hydrogenated in a Parr shaker under 50 psi of hydrogen pressure for 4-5 h. The suspension was filtered and the filtrate was acidified with conc. HCl (50 ml) to the piperidine-2,6-dicarboxylic acid hydrochloride as a white solid (5.9 g, 70%). LCMS: m/e 174 (MH+).

To a cold (0-5° C.) solution of piperidine-2,6-dicarboxylic acid hydrochloride (1.05 g, 5.01 mmol) in 1 N NaOH (10.02 mL, 10.02 mmol) Benzyl chloroformate (1.430 mL, 10.02 mmol) was added at a rate that kept reaction temp. below 5° C. Reaction mixture was allowed to warm to rt and stirred overnight. Excess benzyl chloroformate was removed by washing the rxn mixture with ether (2×10 ml). Aqueous layer was cooled in a ice bath and acidified with 6 N HCl (4 ml) and white precipitate was extracted with EtOAc (2×25 ml), dried (MgSO4), evaporated to afford 1-(benzyloxycarbonyl)-piperidine-2,6-dicarboxylic acid as a white solid (1.35 g, 88%). LCMS: m/e 264 (M–CO2H)+.

Neat acetic anhydride (0.453 ml, 4.80 mmol) was added to a stirred suspension of 1-(benzyloxycarbonyl)piperidine-2,6-dicarboxylic acid (1.23 g, 4.00 mmol) in toluene (20 ml) and the mixture was heated to reflux for 1 h. Resultant clear solution was evaporated to dryness to afford the corresponding anhydride as a colorless viscous oil (1.2 g, 100%). A THF solution of methylamine (5.00 ml, 10.01 mmol) and TEA (0.558 ml, 4.00 mmol) were added to a cold (−20° C.) solution of the crude anhydride in an THF (4 ml) and the mixture was allowed to warm to rt and stirred for 1-2 h. Rxn was diluted with ether (25 ml) and 2N HCl (10 ml) was added and organic layer separated, washed with water, brine and dried (MgSO4). Evaporation of solvents gave a viscous oil (1.13 g) which was dissolved in an toluene (10 ml) and treated with acetic anhydride (0.453 ml, 4.80 mmol). The mixture was heated to reflux to for 2 h and then evaporated to dryness to afford an oil (1.32 g) which was purified by flash column chromatography (silica gel, 3% MeOH in DCM) to afford benzyl 3-methyl-2,4-dioxo-3,9-diazabicyclo[3.3.1]nonane-9-carboxylate as a colorless oil (0.805 g, 66.5%). LC/MS: m/e 303 (MH+).

A stirred suspension of benzyl 3-methyl-2,4-dioxo-3,9-diazabicyclo[3.3.1]nonane-9-carboxylate (742 mg, 2.454 mmol) and 10% Pd—C (100 mg) in ethyl acetate (40 ml) was hydrogenated under balloon pressure of hydrogen overnight. The suspension was filtered to remove the catalyst and the filtrate was evaporated to dryness to afford 3-methyl-3,9-diazabicyclo[3.3.1]nonane-2,4-dione as a white solid (377 mg). MS: m/e 169 (MH+).

To a stirred cold (0-5° C.) suspension of LAH (205 mg, 5.40 mmol) in an THF (15 ml) a solution of 3-methyl-3,9-diazabicyclo[3.3.1]nonane-2,4-dione (375 mg) in THF (5 ml) was added and the mixture was heated to reflux for 1-2 h. Rxn was cooled in a ice bath and quenched by addition of water (0.2 ml), 15% NaOH (0.6 ml) and water (0.2 ml) and the suspension was vigorously stirred and filtered and dried over Na2SO4. Evaporation of solvents gave light-brown oil which was dissolved in ether and treated with 1N HCl in ether to afford 3-methyl-3,9-diazabicyclo[3.3.1]nonane and isolated as bis-HCl salt. MS: m/e 141 (MH+). 1H NMR (500 MHz, CD3OD): δ ppm 1.34-1.59 (5H, m), 2.02-2.32 (6H, m), 2.57-2.97 (4H, m).

General procedure for the preparation of amides from corresponding acids via amide coupling using 3-methyl-3,9-diazabicyclo[3.3.1]nonane. A mixture of acid (1 eq), amine (1.2-1.5 eq), TBTU (1.3 eq) and TEA (4 eq) in an. DCM was stirred for 1-2 h at rt. to afford the amide which were purified by reverse phase prep HPLC and isolated as TFA salt.

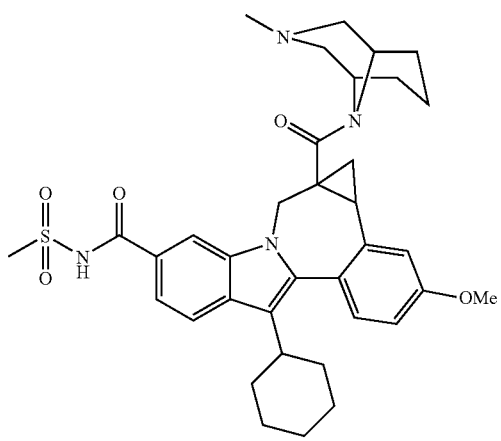

(+/−)-8-cyclohexyl-N-(methylsulfonyl)-1,1a,2,12b-tetrahydro-11-methoxy-1a-(3-methyl-3,9-diazabicyclo[3.3.1]nonane-9-carbonyl) cycloprop[d]indolo[2,1-a][2]benzazepine-5-carboxamide. The product was purified by prep HPLC and isolated as a beige solid. LC/MS: Retention time: 2.776 min; m/e 645 (MH+). The product was observed to exist as inter-converting rotamers by 1H NMR (400 MHz, CHLOROFORM-D) δ ppm 0.17-0.49 (m, 1H), 1.06-1.48 (m, 5H), 1.48-2.16 (m, J=80.83 Hz, 10H), 2.19-2.45 (m, 1H), 2.48-3.17 (m, 10H), 3.32-3.53 (m, 3H), 3.54-3.76 (m, J=15.36 Hz, 2H), 3.77-4.04 (m, 4H), 4.54-4.77 (m, 1H), 4.81-5.27 (m, J=119.61 Hz, 1H), 6.86-7.05 (m, 1H), 7.03-7.16 (m, J=2.52 Hz, 1H), 7.19-7.34 (m, 1H), 7.48-7.75 (m, 1H), 7.80-8.16 (m, 2H).

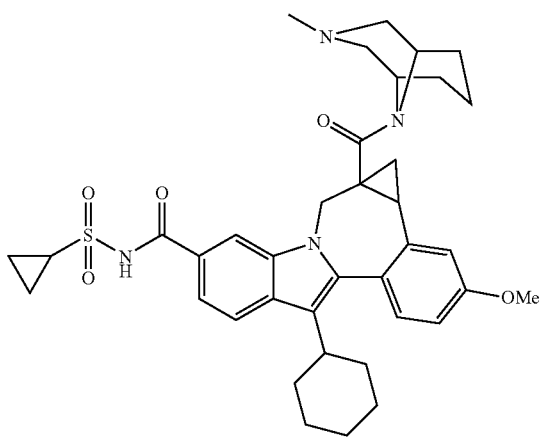

(+/−)-8-cyclohexyl-N-(cyclopropylsulfonyl)-1,1a,2,12b-tetrahydro-11-methoxy-1a-(3-methyl-3,9-diazabicyclo[3.3.1]nonane-9-carbonyl)cycloprop[d]indolo[2,1-a][2]benzazepine-5-carboxamide. The product was purified by prep HPLC and isolated as a beige solid. LC/MS: Retention time: 2.846 min; m/e 671 (MH$^+$). The product was observed to exist as inter-converting rotamers by 1H NMR (400 MHz, CHLOROFORM-D) δ ppm 1.04-1.57 (m, 6H), 1.60-1.86 (m, J=44.57 Hz, 4H), 1.85-2.29 (m, 18H), 2.49-3.26 (m, 4H), 3.52-3.74 (m, J=14.60 Hz, 2H), 3.80-3.99 (m, 4H), 4.54-4.77 (m, 1H), 4.97-5.31 (m, 1H), 6.88-7.04 (m, 1H), 7.06-7.18 (m, J=2.77 Hz, 1H), 7.18-7.35 (m, 2H), 7.81-8.01 (m, 2H).

zepine-5-carboxamide. The product was purified by prep HPLC and isolated as a beige solid. LC/MS: Retention time: 2.846 min; m/e 659 (MH$^+$). The product was observed to exist as inter-converting rotamers by 1H NMR (400 MHz, CHLOROFORM-D) δ ppm 0.14-0.52 (m, 1H), 1.10-1.49 (m, 7H), 1.48-2.19 (m, 11H), 2.18-2.39 (m, 1H), 2.50-3.21 (m, 5H), 3.28-3.75 (m, 7H), 3.83-3.92 (m, 4H), 3.92-4.34 (m, 2H), 4.53-4.79 (m, 1H), 4.86-5.24 (m, J=82.59 Hz, 1H), 6.91-7.02 (m, 1H), 7.08-7.15 (m, J=2.52 Hz, 1H), 7.26-7.33 (m, 1H), 7.48-7.73 (m, J=76.80 Hz, 1H), 7.87-7.96 (m, J=8.56 Hz, 1H), 7.96-8.17 (m, 1H).

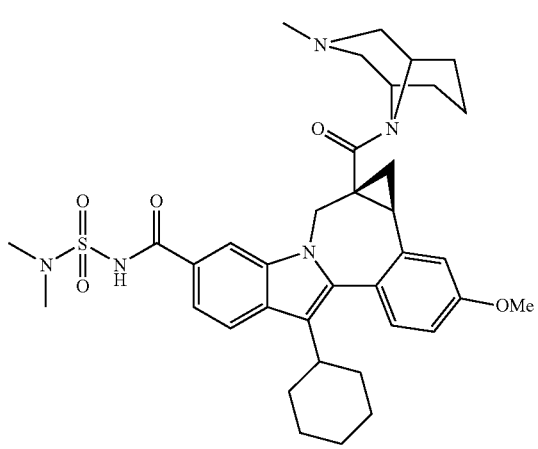

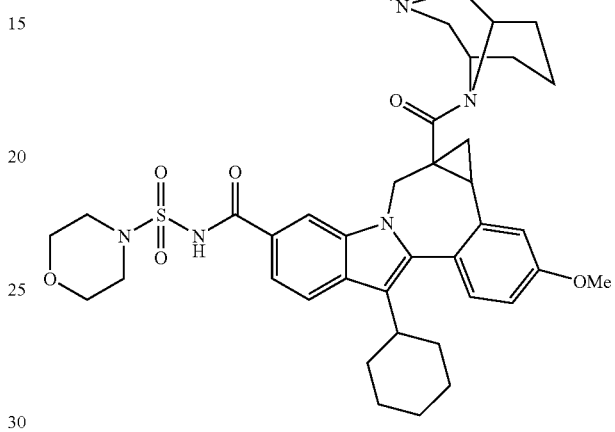

8-cyclohexyl-N-(N,N-dimethylsulfamoyl)-1,1a,2,12b-tetrahydro-11-methoxy-1a-(3-methyl-3,9-diazabicyclo[3.3.1]nonane-9-carbonyl)cycloprop[d]indolo[2,1-a][2]benzazepine-5-carboxamide. The product was purified by prep HPLC and isolated as a beige solid. LC/MS: Retention time: 2.890 min; m/e 674 (MH$^+$). The product was observed to exist as inter-converting rotamers by 1H NMR (400 MHz, CHLOROFORM-D) δ ppm 1.01-1.59 (m, 7H), 1.58-2.36 (m, 9H), 2.37-3.30 (m, 15H), 3.42-3.74 (m, 2H), 3.77-3.93 (m, J=3.02 Hz, 4H), 3.93-4.22 (m, 1H), 4.55-4.73 (m, 1H), 4.71-5.20 (m, 1H), 6.85-7.04 (m, 1H), 7.02-7.17 (m, J=2.27 Hz, 1H), 7.16-7.34 (m, 1H), 7.41-7.66 (m, 1H), 7.76-8.15 (m, 2H).

(+/−)-8-cyclohexyl-N-(morpholinosulfonyl)-1,1a,2,12b-tetrahydro-11-methoxy-1a-(3-methyl-3,9-diazabicyclo[3.3.1]nonane-9-carbonyl)cycloprop[d]indolo[2,1-a][2]benzazepine-5-carboxamide. The product was purified by prep HPLC and isolated as a beige solid. LC/MS: Retention time: 2.828 min; m/e 716 (MH$^+$). The product was observed to exist as inter-converting rotamers by 1H NMR (400 MHz, CHLOROFORM-D) δ ppm 0.14-0.57 (m, 1H), 1.01-1.47 (m, 6H), 1.47-1.88 (m, 6H), 1.87-2.21 (m, 7H), 2.24-3.13 (m, 11H), 3.38-3.56 (m, 4H), 3.57-3.69 (m, J=15.11 Hz, 2H), 3.84-3.94 (m, 4H), 4.56-4.74 (m, 1H), 4.76-5.25 (m, 1H), 6.93-7.03 (m, 1H), 7.07-7.15 (m, J=2.52 Hz, 1H), 7.29 (d, J=8.56 Hz, 1H), 7.49-7.71 (m, 1H), 7.84-8.00 (m, 2H).

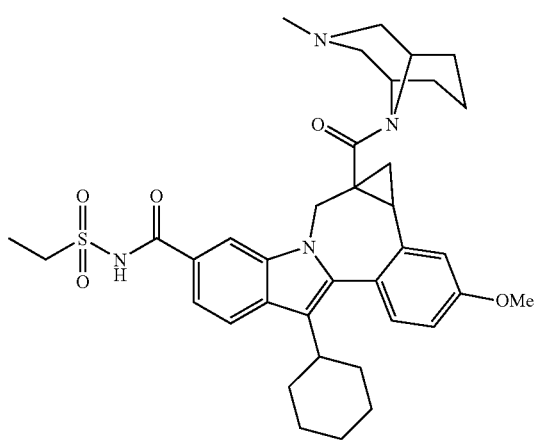

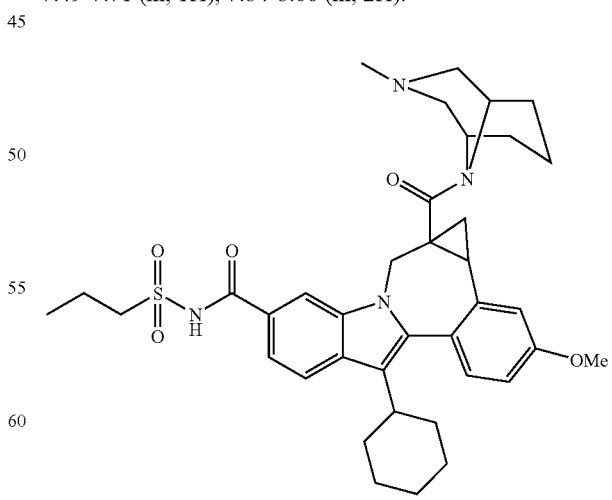

(+/−)-8-cyclohexyl-N-(ethylsulfonyl)-1,1a,2,12b-tetrahydro-11-methoxy-1a-(3-methyl-3,9-diazabicyclo[3.3.1]nonane-9-carbonyl) cycloprop[d]indolo[2,1-a][2]benza- (+/−)-8-cyclohexyl-N-(propylsulfonyl)-1,1a,2,12b-tetrahydro-11-methoxy-1a-(3-methyl-3,9-diazabicyclo[3.3.1]nonane-9-carbonyl)cycloprop[d]indolo[2,1-a][2]benzazepine-5-carboxamide. The product was purified by prep HPLC and isolated as a beige solid. LC/MS: Retention time: 2.918 min; m/e 673 (MH+). The product was observed to exist as inter-converting rotamers by 1H NMR (400 MHz, CHLOROFORM-D) δ ppm 0.12-0.53 (m, 1H), 0.76-1.14 (m, 4H), 1.14-1.52 (m, 5H), 1.49-2.16 (m, 12H), 2.20-2.46 (m, 1H), 2.48-3.05 (m, 4H), 3.05-3.71 (m, 9H), 3.82-4.01 (m,4H), 4.55-4.79 (m, 1H), 4.82-5.22 (m, J=86.12 Hz, 1H), 6.91-7.02 (m, 1H), 7.07-7.15 (m, J=2.52 Hz, 1H), 7.26-7.33 (m, 1H), 7.56-7.76 (m, 1H), 7.85-7.96 (m, J=8.56 Hz, 1H), 7.95-8.19 (m, 1H).

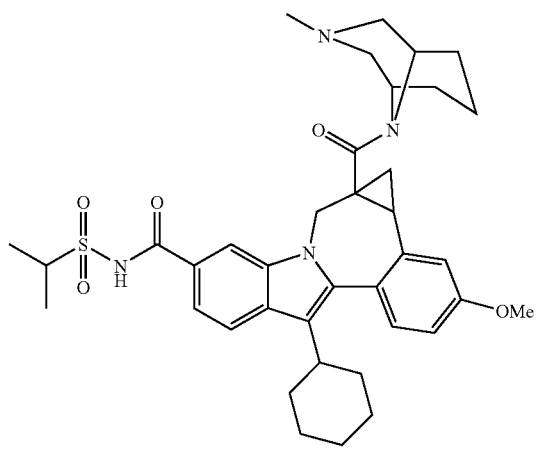

(+/−)-8-cyclohexyl-N-(isopropylsulfonyl)-1,1a,2,12b-tetrahydro-11-methoxy-1a-(3-methyl-3,9-diazabicyclo[3.3.1]nonane-9-carbonyl)cycloprop[d]indolo[2,1-a][2]benzazepine-5-carboxamide. The product was purified by prep HPLC and isolated as a beige solid. LC/MS: Retention time: 3.120 min; m/e 673 (MH+). The product was observed to exist as inter-converting rotamers by 1H NMR (400 MHz, CHLOROFORM-D) δ ppm 0.14-0.53 (m, 1H), 1.12-1.51 (m, 9H), 1.50-2.19 (m, 12H), 2.20-2.46 (m, 1H), 2.48-3.27 (m, 8H), 3.40-3.70 (m, 3H), 3.81-3.95 (m, 4H), 3.93-4.12 (m, J=22.66 Hz, 1H), 4.52-4.76 (m, 1H), 4.79-5.24 (m, J=105.76 Hz, 1H), 6.91-7.03 (m, 1H), 7.07-7.14 (m, J=2.52 Hz, 1H), 7.26-7.32 (m, J=8.56 Hz, 1H), 7.51-7.70 (m, 1H), 7.85-8.00 (m, J=8.56 Hz, 2H).

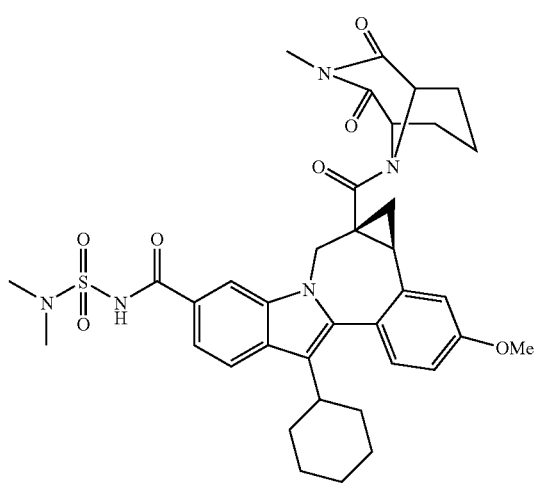

(+/−)-8-cyclohexyl-N-(N,N-dimethylsulfamoyl)-1,1a,2,12b-tetrahydro-11-methoxy-1a-(3-methyl-2,4-dioxo-3,9-diazabicyclo[3.3.1]nonane-9-carbonyl)cycloprop[d]indolo[2,1-a][2]benzazepine-5-carboxamide. The product was purified by prep HPLC and isolated as a beige solid. LC/MS: Retention time: 3.306 min; m/e 702 (MH+). The product was observed to exist as inter-converting rotamers by 1H NMR (500 MHz, CHLOROFORM-D) δ ppm 0.29-0.77 (m, 1H), 0.98-1.64 (m, 4H), 1.64-2.23 (m, 9H), 2.44-2.97 (m, 2H), 2.98-3.16 (m, 9H), 3.31-3.67 (m, 6H), 3.79-3.96 (m, 4H), 3.96-4.54 (m, 1H), 5.03-5.52 (m, 1H), 6.83-6.96 (m, 1H), 6.97-7.14 (m, 1H), 7.17-7.33 (m, 1H), 7.44-7.71 (m, 1H), 7.73-7.90 (m, 1H), 7.90-8.30 (m, 1H).

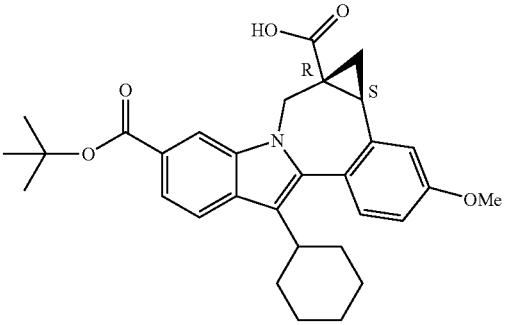

(1aR,12bS)-5-(tert-butoxycarbonyl)-8-cyclohexyl-11-methoxy-1,12b-dihydrocyclopropa[d]indolo[2,1-a][2]benzazepine-1a(2H)-carboxylic acid. Sodium hydroxide (aq. 1M, 31 mL) was added to a cooled solution (0° C., ice bath) containing 5-tert-butyl 1a-ethyl (1aR,12bS)-8-cyclohexyl-11-methoxy-1,12b-dihydrocyclopropa[d]indolo[2,1-a][2]benzazepine-1a,5(2H)-dicarboxylate (4.0 g, 7.76 mmol), THF (35 mL), and methanol (35 mL). After 20 min, the solution was removed from the cooling bath and maintained at ambient temperature for 3 h. The solution was cooled again (0° C., ice bath) and the pH reduced to just below 4 by slow addition of 1N HCl (aq., 33 mL). The mixture was immediately extracted with ethyl acetate (2×30 mL). The combined organic portions were washed with brine, (20 mL), dried (magnesium sulfate), filtered and concentrated to afford a white solid which was used without further purification in the next step. LCMS: retention time: 3.162 min. LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 502 (MH+).

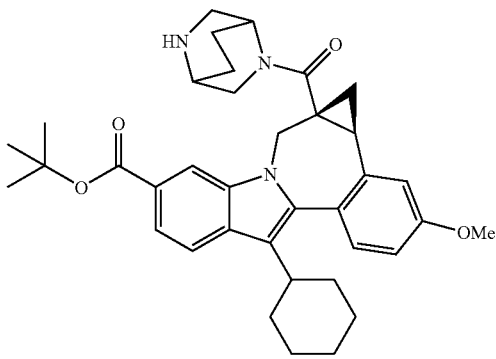

Tert-butyl (1aR,12bS)-8-cyclohexyl-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxylate. TBTU (691 mg, 2.15 mmol) was added in one portion to a cooled solution (0° C., ice bath) containing (1aR,12bS)-5-(tert-butoxycarbonyl)-8-cyclohexyl-11-methoxy-1,12b-dihydrocyclopropa[d]indolo[2,1-a][2]benzazepine-1a(2H)-carboxylic acid(900 mg, 1.79 mmol), DIEA (1.88 mL, 10.77 mmol), 2,5-diazabicyclo[2.2.2]octane (1:1) dihydrochloride ((498 mg, 2.69 mmol), (H. Newman, *J. Het. Chem.* 449 (1974 ); P. E. Thompson, J. B. Zeigler, J. W. McCall, *J. Med. Chem.*, 17, 481 (1974 )), and dichloromethane (36 mL). The solution was maintained for 1.5 h and diluted with additional dichloromethane (20 mL). The solution was washed with water (3×20 mL), washed with brine (15 mL), dried (magnesium sulfate), filtered and concentrated to afford a white, tacky residue which was triturated with n-pentane (2×20 mL) to afford a white solid which was used without further purification in the next step. LCMS: retention time 3.841 min LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 596 ($MH^+$).

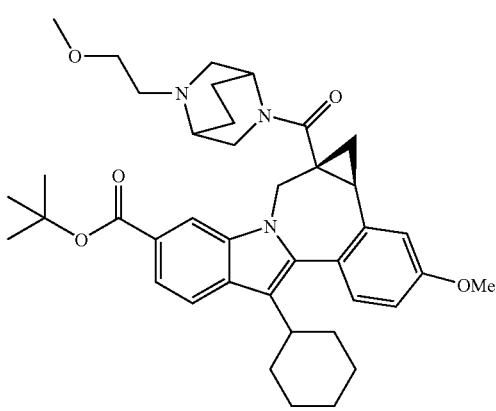

Tert-butyl (1aR,12bS)-8-cyclohexyl-11-methoxy-1a-((5-(2-methoxyethyl)-2,5-diazabicyclo[2.2.2]oct-2-yl)carbonyl)-1,1a,2,12b-tetrahydrocyclopropa[d]indolo[2,1-a][2]benzazepine-5-carboxylate. A suspension containing tert-butyl (1aR,12bS)-8-cyclohexyl-1a-(2,5-diazabicyclo[2.2.2]oct-2-ylcarbonyl)-11-methoxy-1,1a,2,12b-tetrahydrocyclopropa[d]indolo[2,1-a][2]benzazepine-5-carboxylate (400 mg, 0.671 mmol), 1-bromo-2-methoxyethane (373 mg, 2.69 mmol), potassium carbonate (978 mg, 6.71 mmol), and THF (7.0 mL) was stirred with rigor at 70° C. for 20 hrs. The mixture was filtered and the filtrate concentrated to dryness. The resultant solid was triturated with n-pentane (2×5 mL) and used without further purification. LCMS: retention time 4.073 min. LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 654 ($MH^+$).

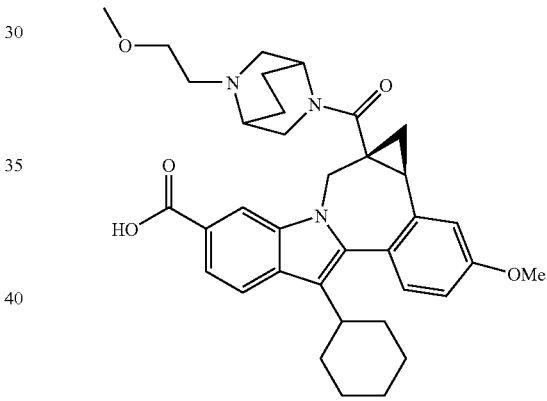

(1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylic acid. TFA (8.4 mL) was added to a solution containing tert-butyl (1aR,12bS)-8-cyclohexyl-11-methoxy-1a-((5-methyl-2,5-diazabicyclo[2.2.2]oct-2-yl)carbonyl)-1,1a,2,12b-tetrahydrocyclopropa[d]indolo[2,1-a][2]benzazepine-5-carboxylate (550 mg, 0.841 mmol) and DCM (8.4 mL). The solution was maintained at rt for 3 h and then concentrated to dryness. The resultant residue was charged with 1:1 methanol/water (20 mL) and the pH increased to above 8 by slow addition of aqueous, saturated, sodium bicarbonate (10 mL). The solution was concentrated to remove methanol and extracted with dichloromethane (6×10 mL). The combined organic portions were washed with brine (20 mL), dried (magnesium sulfate), filtered and concentrated to afford a light yellow solid which was used without further purification. LC/MS shows overlapping peaks at retention time 2.385 min. LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode.; m/z 598 (MH+).

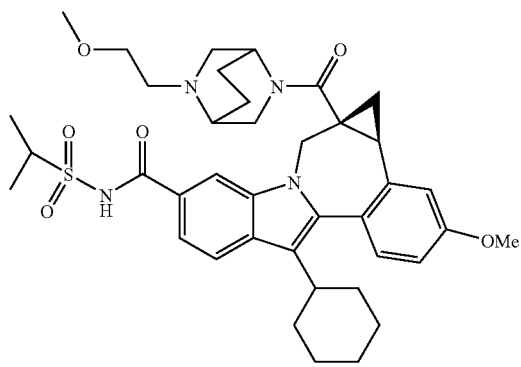

(1aR,12bS)-8-cyclohexyl-N-(isopropylsulfonyl)-11-methoxy-1a-((5-(2-methoxyethyl)-2,5-diazabicyclo[2.2.2]oct-2-yl)carbonyl)-1,1a,2,12b-tetrahydrocyclopropa[d]indolo[2,1-a][2]benzazepine-5-carboxamide. EDCI (178 mg, 928 mmol) was added at rt, in one portion, to a solution containing (1aR,12bS)-8-cyclohexyl-11-methoxy-1a-((5-(2-methoxyethyl)-2,5-diazabicyclo[2.2.2]oct-2-yl)carbonyl)-1,1a,2,12b-tetrahydrocyclopropa[d]indolo[2,1-a][2]benzazepine-5-carboxylic acid (378 mg, 0.619 mmol), DMAP (38 mg, 0.309 mmol), 2-isopropyl sulfonamide (191 mg, 1.547 mmol), and dichloromethane (7 mL). The solution was maintained at rt for 24 h, diluted with additional dichloromethane (20 mL), washed with aqueous, saturated sodium bicarbonate (2×20 mL), washed with water (20 mL), dried (magnesium sulfate), filtered and concentrated. The resultant light yellow residue was purified by preparative, reverse phase HPLC under basic conditions using a Phenomenex, luna, 10 micron, 30×100 mm column. Diastereomers were not seperable under these conditions. Product was a white solid. LC/MS shows separate diastereomers as overlapping peaks at retention times 2.288 min and 2.372 min. LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode m/z 703 (MH+).

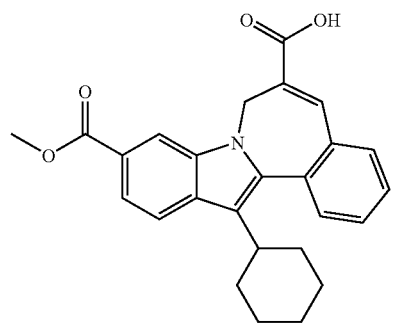

13-cyclohexyl-10-(methoxycarbonyl)-7 H-indolo[2,1-a][2]benzazepine-6-carboxylic acid. Tetrabutylammoniumhydroxide (9.1 mL, 40% solution in water) was added dropwise to a cooled solution (0° C., ice bath) containing dimethyl 13-cyclohexyl-7H-indolo[2,1-a][2]benzazepine-6,10-dicarboxylate (Prepared as described in US Patent App. Publication US20070184024A1, Intermediate 9) and THF (463 mL). The solution was maintained with continued cooling for 50 min. and then concentrated to a volume of about 50 mL. The resultant solution was diluted with ethyl acetate (250 mL), washed with aq. HCl (0.5 N, 3×150 mL), washed with brine (150 mL), dried (magnesium sulfate), filtered, and concentrated to afford a yellow solid. LCMS: retention time: 1.698 min. LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode: m/z 416 (MH+). $^1$H NMR (300 MHz, DMSO-D6) δ ppm: 12.97 (s, 1H), 8.17 (m, 1H), 7.91(m, 2H), 7.63 (m, 5H), 5.56 (s, 1H), 4.51 (m, 1H), 3.89 (m, 3H), 2.80 (m, 1H), 1.99 (m, 6H), 1.30 (m, 4H).

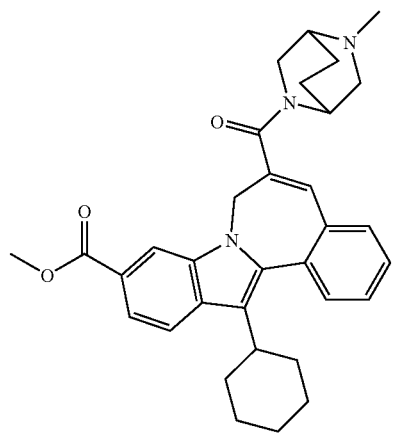

Prepared from the acid above via standard coupling between acid and diamine and then reductive methylation of diamine. Coupling of the N-monomethyldiamine could have been utilized. Standard cyclopropanation, esterhydrolysis, and coupling of the acid to an appropriate sulfamide or sulfonamide as detailed in the procedures and schemes would provide final compounds of the invention. The remaining steps could be carried out in the order described or the ester hydrolysis and coupling to the sulfonamide or sulfamide could be carried out prior to the cyclopropanation. 1H NMR (500 MHz, CD$_3$OD): δ ppm 0.92-2.69 (series of multiplets, 19H), 2.90-3.19, (series of multiplets, 3H), 3.41-3.85 (series of multiplets, 3H), 3.96-3.98 (m, 2H), (m, 1H), 4.37-4.45 (m, 1H), 5.19-5.28 (m, 1H), 6.98 (m, 0.7H), 7.17 (m, 0.3H), 6.98-7.07 (m, 1H), 7.56-7.58 (m, 3H), 7.64-7.65 (m, 1H), 7.73-7.75 (m, 1H), 7.92-7.94 (m, 1H), 8.23 (m, 1H). LCMS: retention time 4.008 min LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 524 (MH$^+$).

The following compounds were prepared using procedures analogous to those described above.

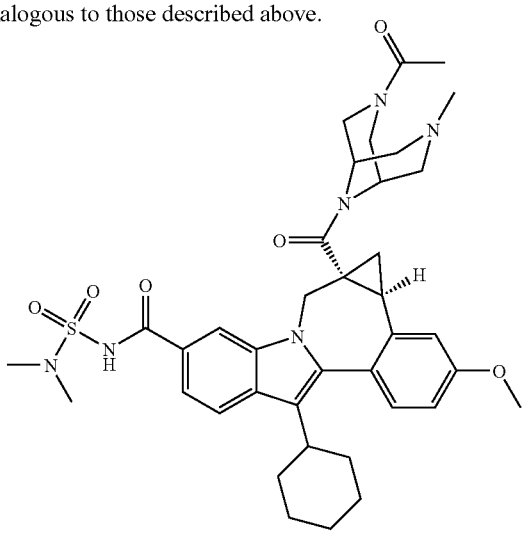

1a-((3-Acetyl-7-methyl-3,7,9-triazabicyclo[3.3.1]non-9-yl)carbonyl)-8-cyclohexyl-N-(dimethylsulfamoyl)-11-methoxy-1,1a,2,12b-tetrahydrocyclopropa[d]indolo[2,1-a][2]benzazepine-5-carboxamide, (1aR, 12bS)-. $^1$H NMR (500 MHz, CD3OD): δ ppm 0.21 (m, 0.25H), 1.19-1.33 (m, 1H), 1.43 (m, 3H), 1.70 (m, 1.75H), 1.80 (m, 2H), 1.95 (m, 2H), 2.25 (m, 5H), 2.64 (m, 1H), 2.83 (m, 2H), 3.01 (m, 9H), 3.16 (m, 1H), 3.39 (m, 1H), 3.44 (m, 1H), 3.74 (m, 3H), 3.91 (m, 4H), 4.19 (m, 0.25H), 5.54 (m, 2H), 5.00 (m, 1.75H), 7.03 (m, 1H), 7.18 (m, 1H), 7.28 (d, J=8.55, 0.75H), 7.34 (d, J=8.55, 0.25H), 7.53 (m, 0.75H), 7.60 (m, 0.25H), 7.86 (d, J=8.24, 0.75H), 7.91 (d, J=8.24, 0.25H), 8.05 (m, 1H). LC/MS: m/z 717.43, Rf 1.705 min., 97.7% purity. LC data was recorded on a Shimadzu LC-10AS liquid chromatograph equipped with a Phenomenex-Luna 10μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

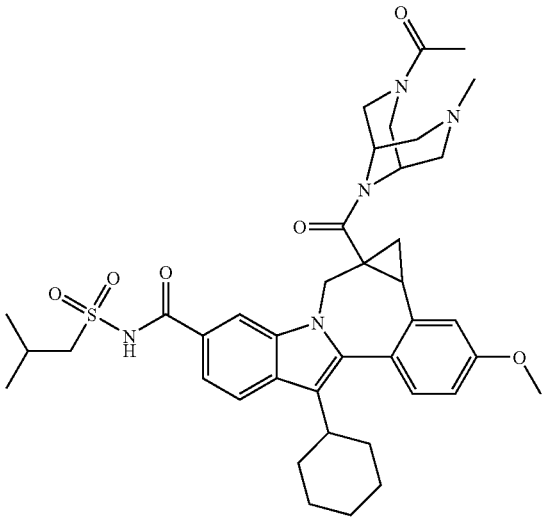

1a-((3-Acetyl-7-methyl-3,7,9-triazabicyclo[3.3.1]non-9-yl)carbonyl)-8-cyclohexyl-N-(isobutylsulfonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.25H), 1. 14 (m, 6H), 1.36 (m, 4H), 1.64 (m, 1H), 1.78 (m, 2.75H), 1.99 (m, 4H), 2.29 (m, 4H), 2.63 (m, 2H), 2.84 (m, 4H), 2.97 (m, 3H), 3.18 (m, 1H), 3.47 (m, 2H), 3.66 (m, 2H), 3.88 (m, 4H), 4.19 (m, 1H), 4.50 (m, 2H), 5.05 (m, 1H), 7.01 (m, 1H), 7.17 (m, 1H), 7.29 (m, 1H), 7.51-7.61 (m, 1H), 7.88 (m, 1H), 7.96-8.06 (m, 1H). LC/MS: m/z 730.30, Rf 1.787 min., 96.0% purity. LC data was recorded on a Shimadzu LC-10AS liquid chromatograph equipped with a Phenomenex-Luna 10 μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

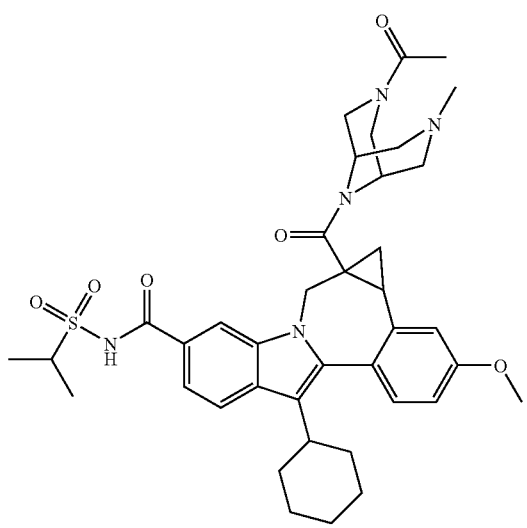

1a-((3-Acetyl-7-methyl-3,7,9-triazabicyclo[3.3.1]non-9-yl)carbonyl)-8-cyclohexyl-N-(isopropylsulfonyl)-11-methoxy-1,1a,2,12b-tetrahydrocyclopropa[d]indolo[2,1-a][2]benzazepine-5-carboxamide. 1H NMR (300 MHz, CD3OD): δ ppm 0.20 (m, 0.25H), 0.98 (m, 2H), 1.13 (m, 1H), 1.24-1.49 (m, 9H), 1.65 (m, 0.75H), 1.83 (m, 2H), 2.04 (m, 4H), 2.50 (m, 4H), 2.67 (m, 1H), 2.83 (m, 1H), 2.88 (m, 3H), 3.01 (m, 3H), 3.10 (m, 1H), 3.17 (m, 2H), 3.72 (m, 2H), 3.92 (m, 3H), 3.98 (m, 1H), 4.50 (m, 1H), 5.03 (m, 1H), 7.06 (m, 1H), 7.21 (m, 1H), 7.35 (m, 1H), 7.57-7.70 (m, 1H), 7.92 (m, 1H), 8.00-8.09 (m, 1H). LC/MS: m/z 716.23, Rf 1.740 min., 98.0% purity. LC data was recorded on a Shimadzu LC-10AS liquid chromatograph equipped with a Phenomenex-Luna 10μ, C18, 4.6×30 mm column, using a SPD-10AV UV-Vis detector at a detector wave length of 220 nM. The elution conditions employed a flow rate of 5 ml/min., a gradient of 100% solvent A/0% solvent B to 0% solvent A/100% solvent B, a gradient time of 2 min., a hold time of 1 min., and an analysis time of 3 min. where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

We claim:

1. A compound of formula I

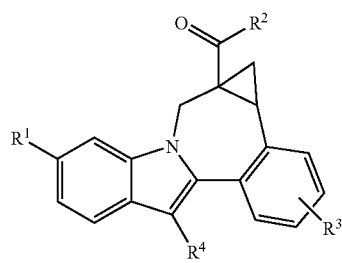

where:

$R^1$ is $CO_2R^5$ or $CONR^6R^7$;

$R^2$ is

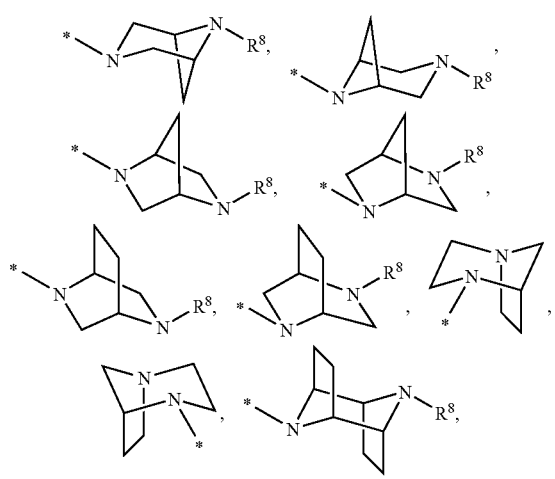

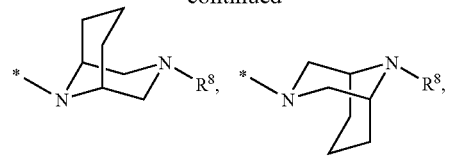

-continued

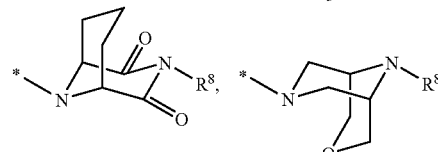

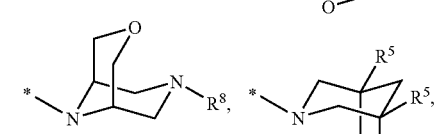

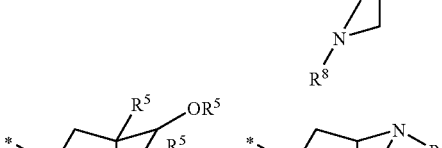

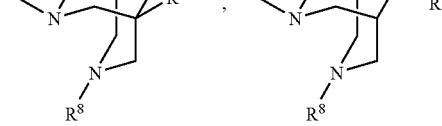

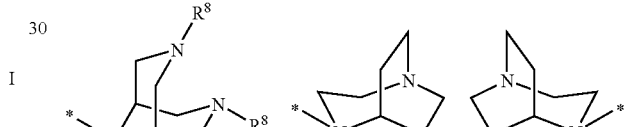

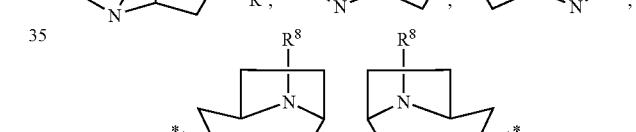

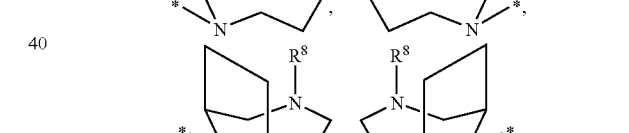

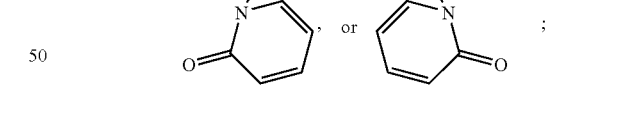

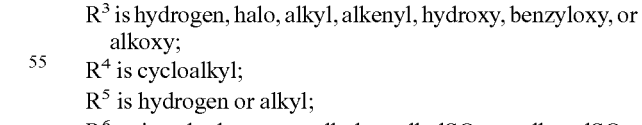

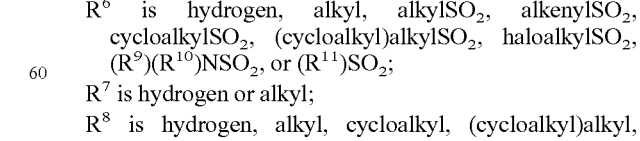

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, alkenylSO$_2$, cycloalkylSO$_2$, (cycloalkyl)alkylSO$_2$, haloalkylSO$_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, hydroxyalkyl, alkoxyalkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, N-$(R^{12})$piperazinyl, morpholinyl, thiomorpholinyl, homopiperidinyl, homomorpholinyl, tetrahydrofuranyl, tetrahydropyranyl, (tetrahydrofuranyl)alkyl, or (tetrahydropyranyl)alkyl; and $R^{12}$ is hydrogen or alkyl;

or a pharmaceutically acceptable salt thereof.

2. A compound of claim 1 where $R^1$ is $CO_2R^5$ or $CONR^6R^7$;

$R^2$ is

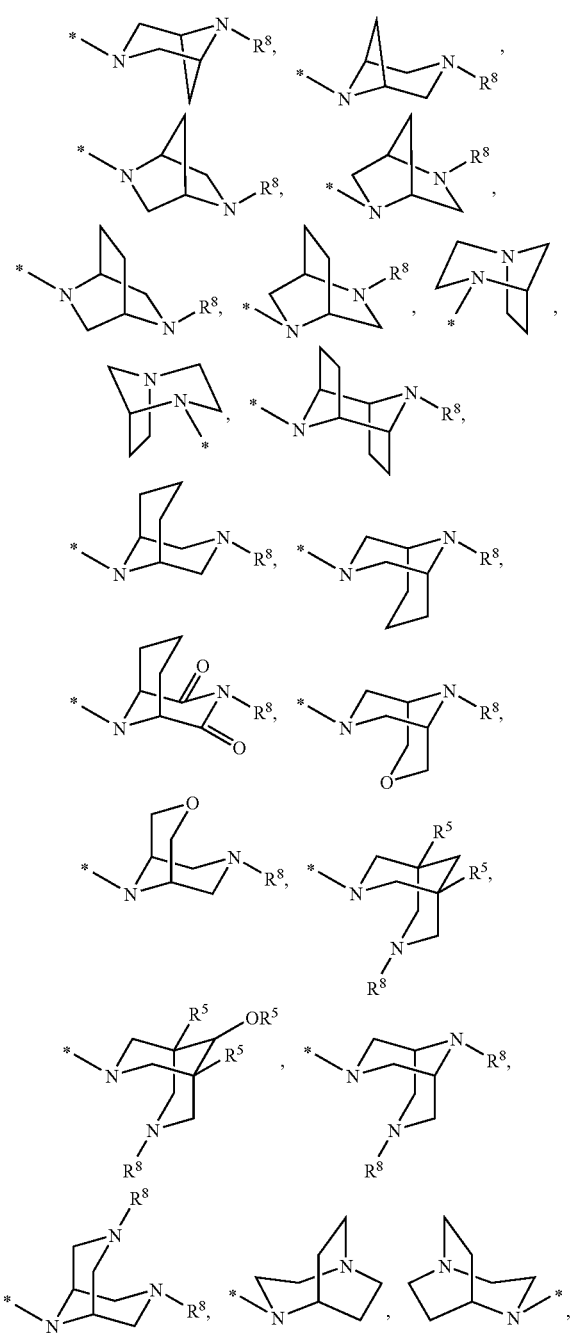

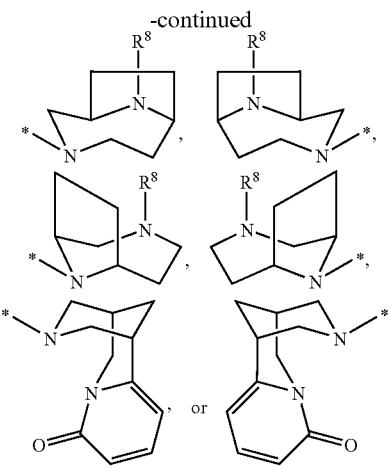

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkyl$SO_2$, alkenyl$SO_2$, , cycloalkyl$SO_2$, (cycloalkyl)alkyl$SO_2$, haloalkyl$SO_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkyl$SO_2$, cycloalkyl$SO_2$, haloalkyl$SO_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, N-$(R^{12})$piperazinyl, morpholinyl, thiomorpholinyl, homopiperidinyl, homomorpholinyl, tetrahydrofuranyl, tetrahydropyranyl, (tetrahydrofuranyl)alkyl, or (tetrahydropyranyl)alkyl; and $R^{12}$ is hydrogen or alkyl;

or a pharmaceutically acceptable salt thereof.

3. A compound of claim 1 where $R^1$ is $CO_2R^5$ or $CONR^6R^7$;

$R^2$ is

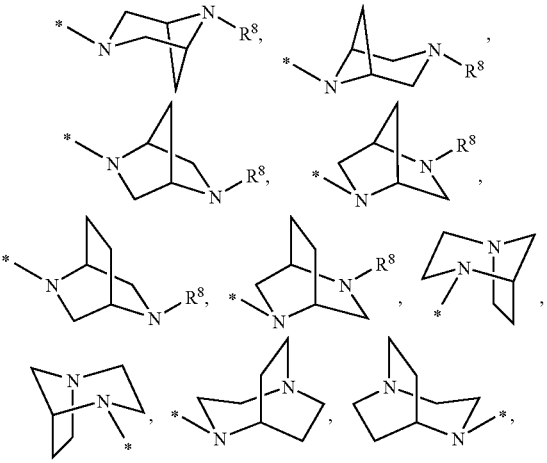

-continued

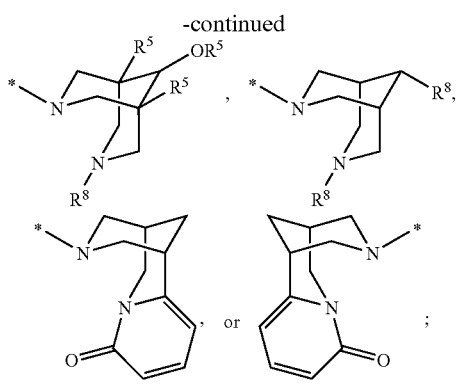, 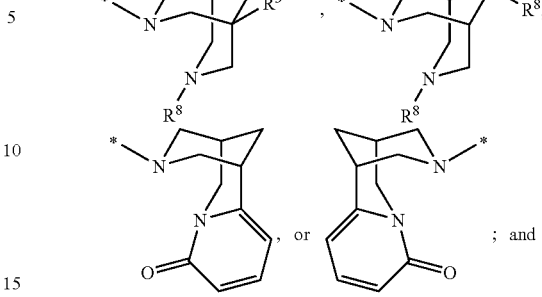

R³ is hydrogen, halo, alkyl, alkenyl, hydroxy, benzyloxy, or alkoxy;

R⁴ is cycloalkyl;

R⁵ is hydrogen or alkyl;

R⁶ is hydrogen, alkyl, alkylSO₂, cycloalkylSO₂, haloalkylSO₂, (R⁹)(R¹⁰)NSO₂, or (R¹¹)SO₂;

R⁷ is hydrogen or alkyl;

R⁸ is hydrogen, alkyl, cycloalkyl, (cycloalkyl)alkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, benzyl, benzyloxycarbonyl, or pyridinyl;

R⁹ is hydrogen or alkyl;

R¹⁰ is hydrogen or alkyl;

R¹¹ is azetidinyl, pyrrolidinyl, piperidinyl, N-(R¹²)piperazinyl, morpholinyl, thiomorpholinyl, homopiperidinyl, or homomorpholinyl; and R¹² is hydrogen or alkyl;

or a pharmaceutically acceptable salt thereof.

4. A compound of claim 1 where R¹ is CONR⁶R⁷; R⁶ is alkylSO₂, cycloalkylSO₂, haloalkylSO₂, (R⁹)(R¹⁰)NSO₂, or (R¹¹)SO₂; and R⁷ is hydrogen.

5. A compound of claim 1 where R² is

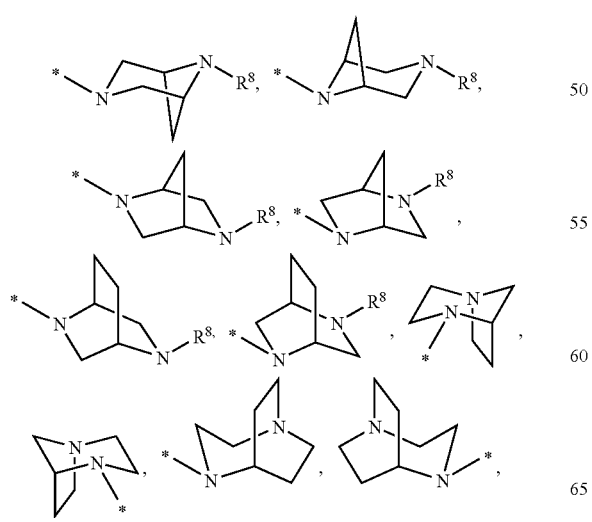

R¹¹ is azetidinyl, pyrrolidinyl, piperidinyl, N-(R¹²)piperazinyl, morpholinyl, thiomorpholinyl, homopiperidinyl, or homomorpholinyl.

6. A compound of claim 1 where R³ is hydrogen.

7. A compound of claim 1 where R³ is methoxy.

8. A compound of claim 1 where R⁴ is cyclohexyl.

9. A compound of claim 1 where R⁶ is (R⁹)(R¹⁰)NSO₂ or (R¹¹)SO₂.

10. A compound of claim 1 where R⁸ is alkyl or alkoxyalkyl.

11. A compound of claim 1 selected from the group consisting of

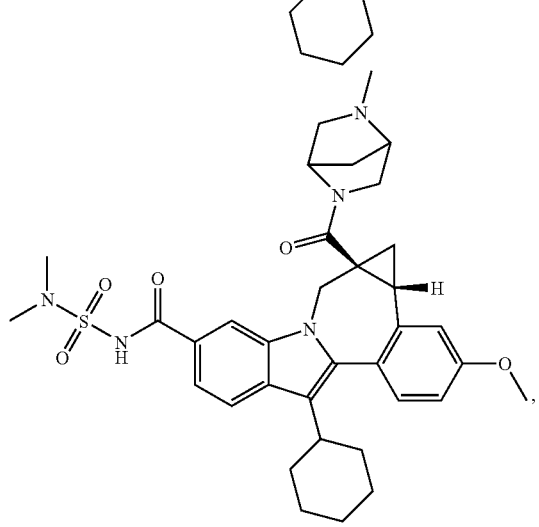

265
-continued
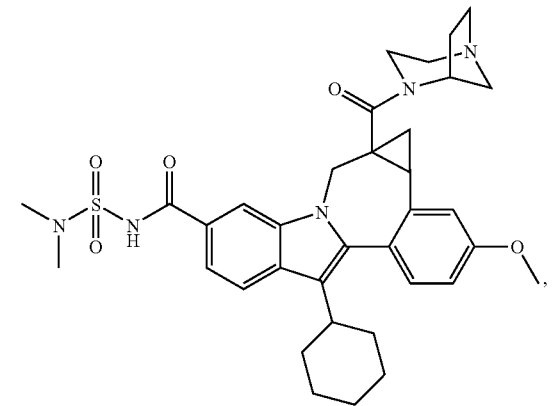
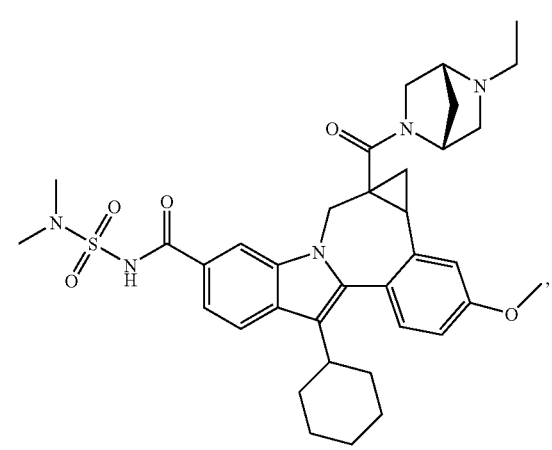
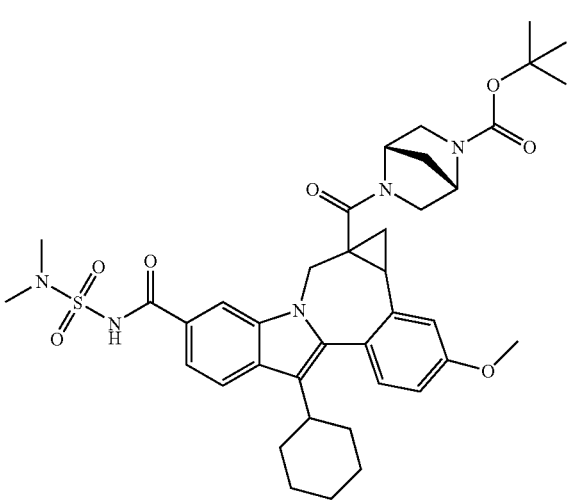
266
-continued
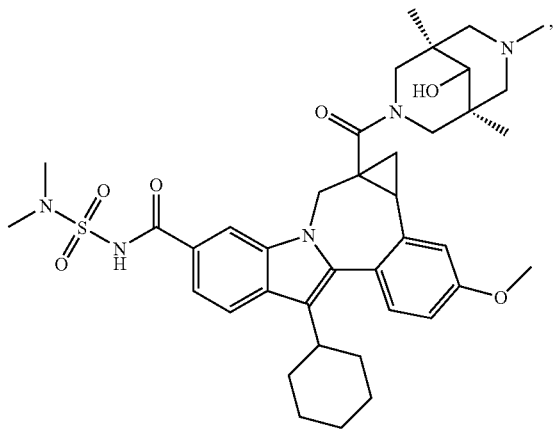
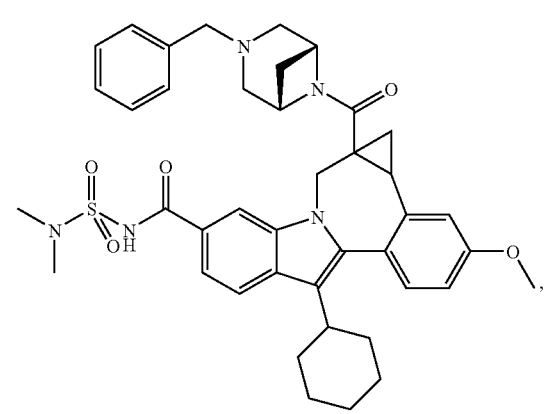
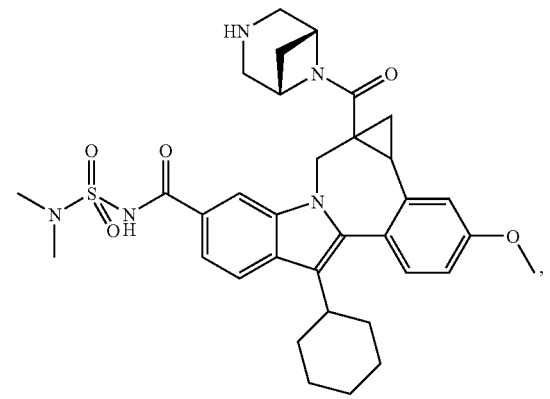
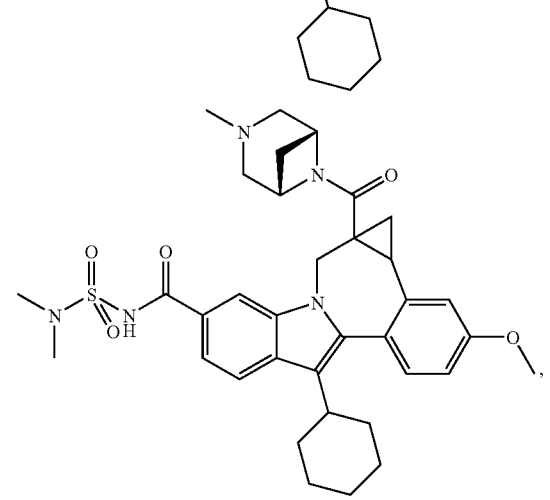

267
-continued
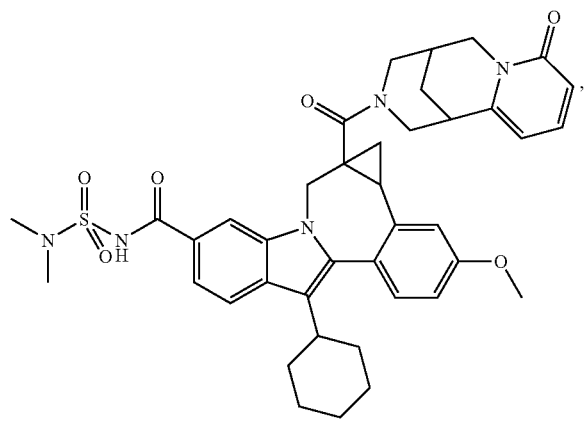
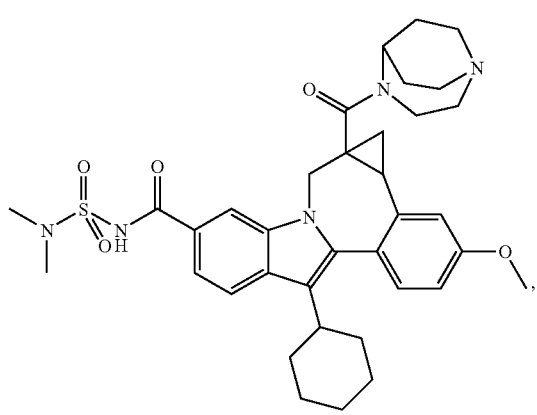
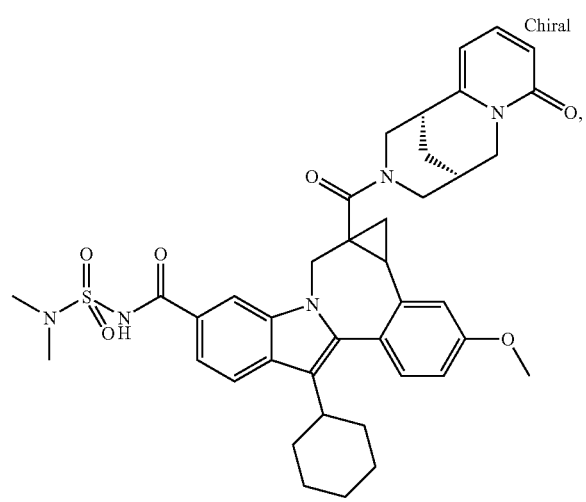
268
-continued
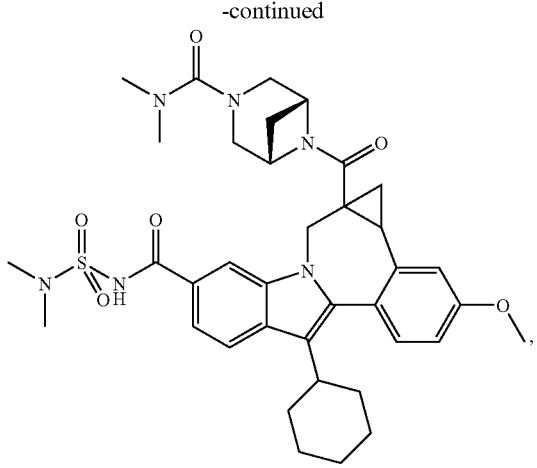
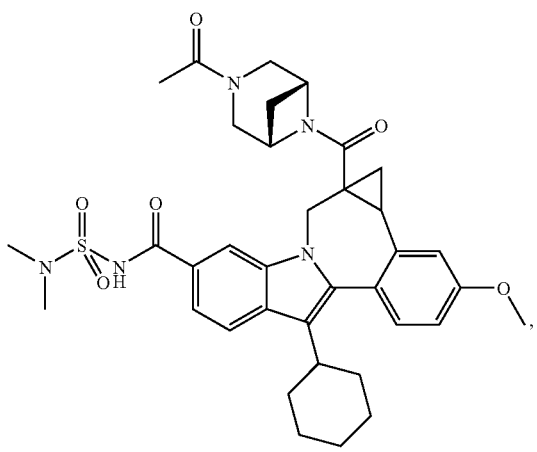
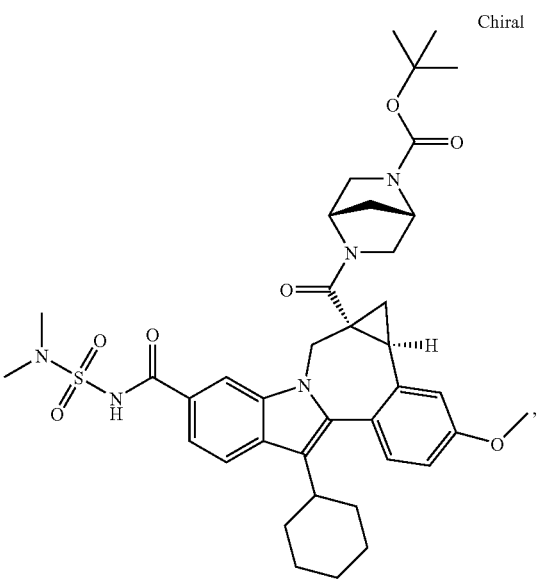

269
-continued
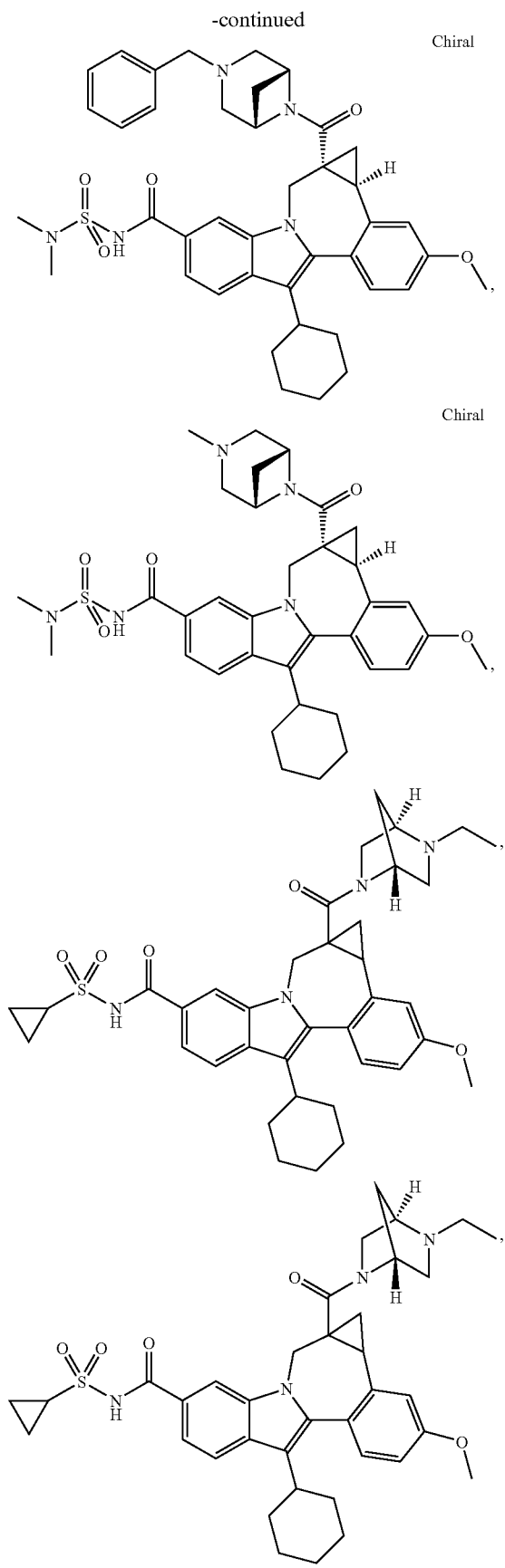
270
-continued
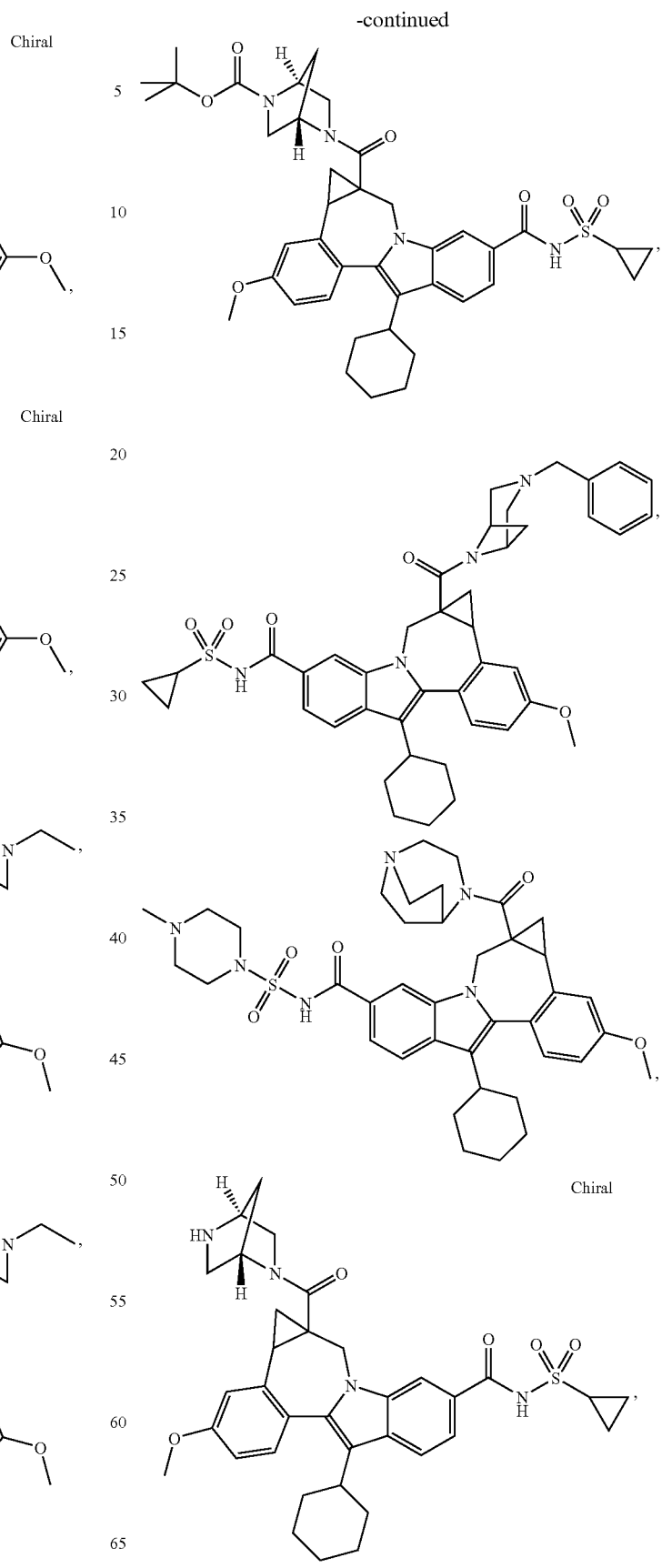

271 272
-continued -continued
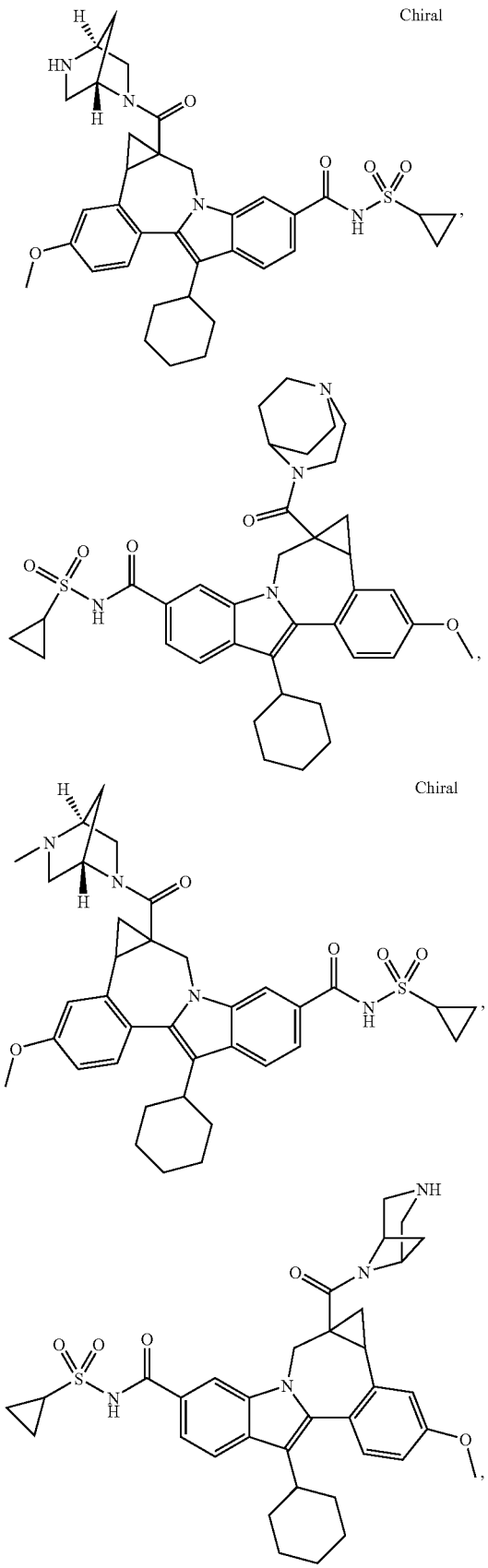
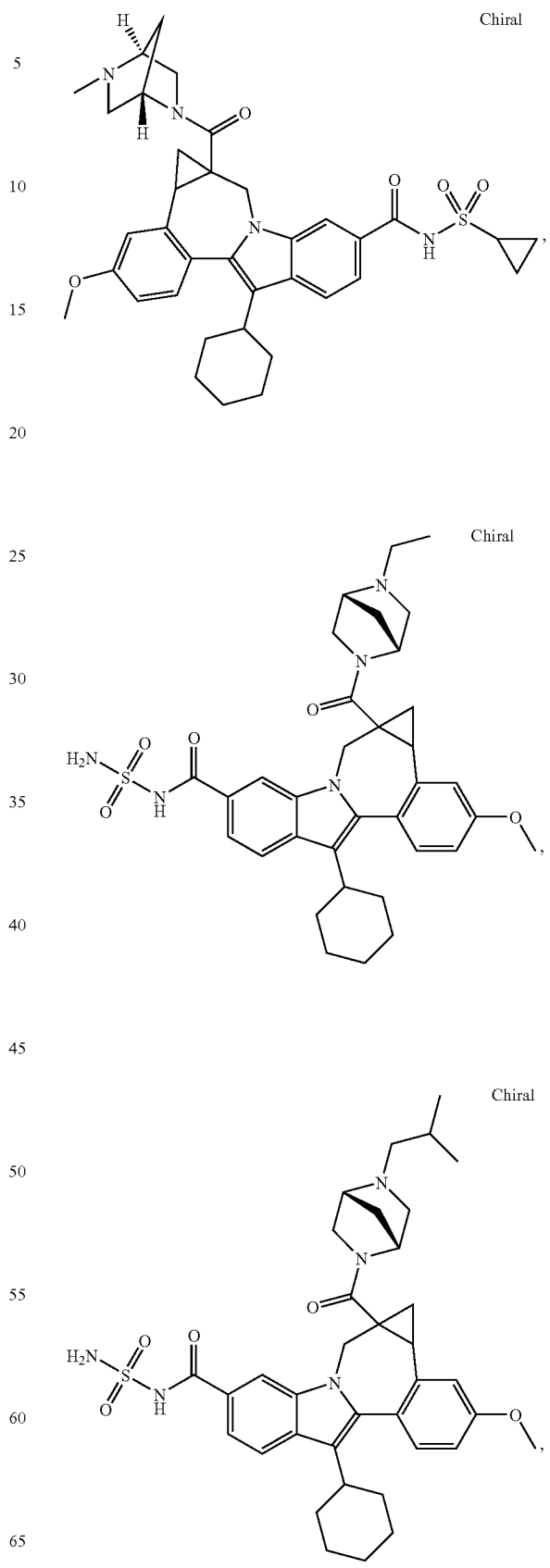

273
-continued
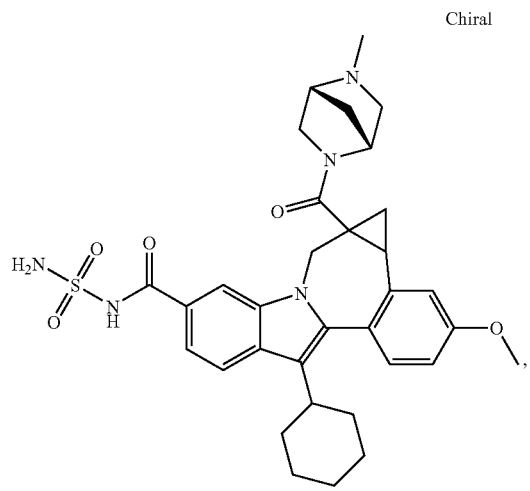
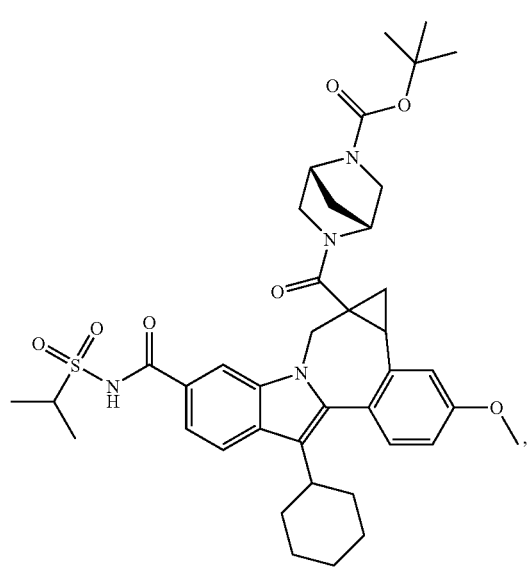
274
-continued
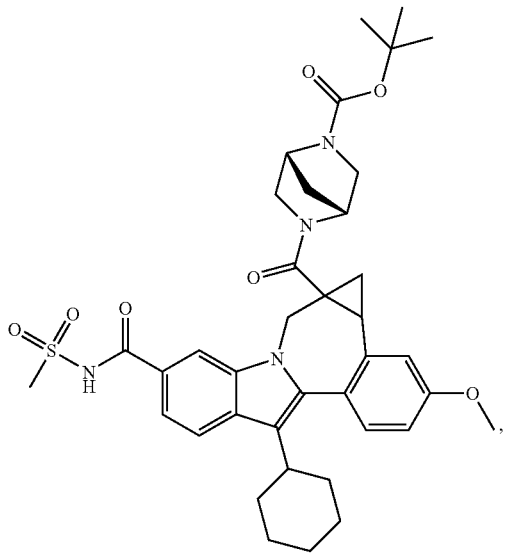
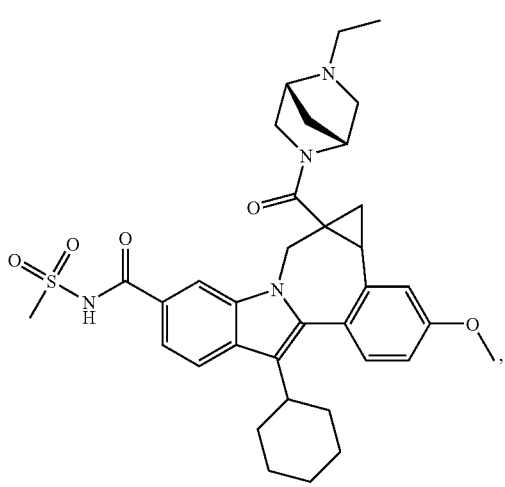

275
-continued
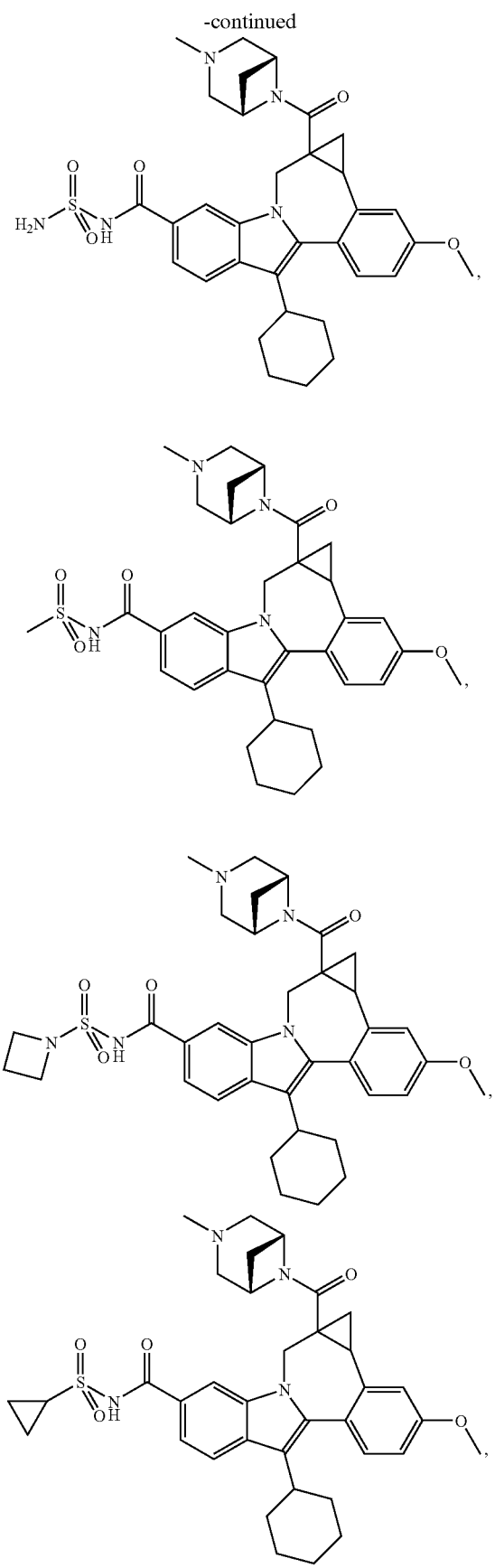
276
-continued
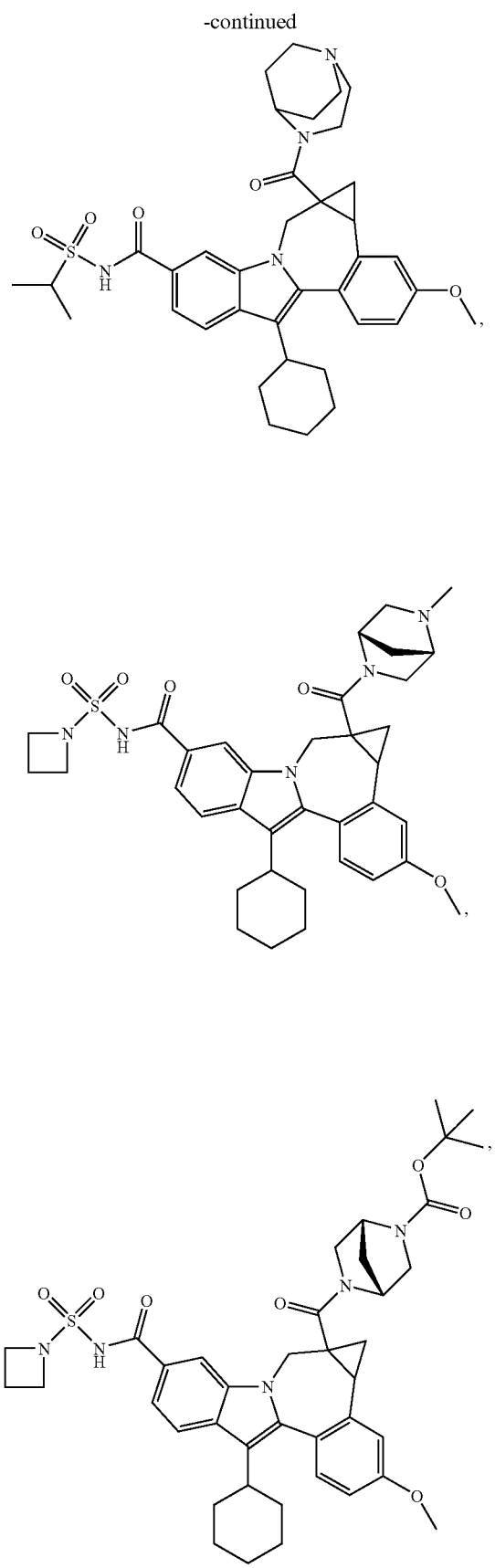

277
-continued
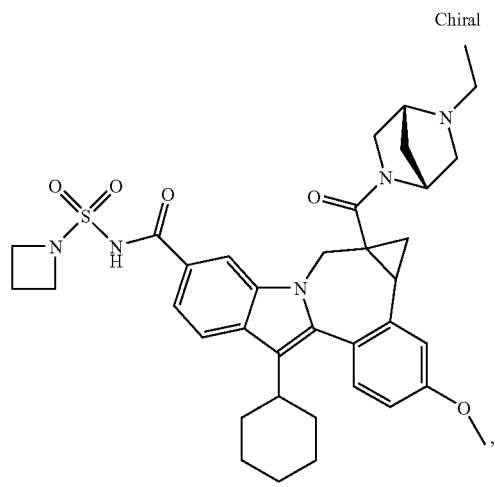
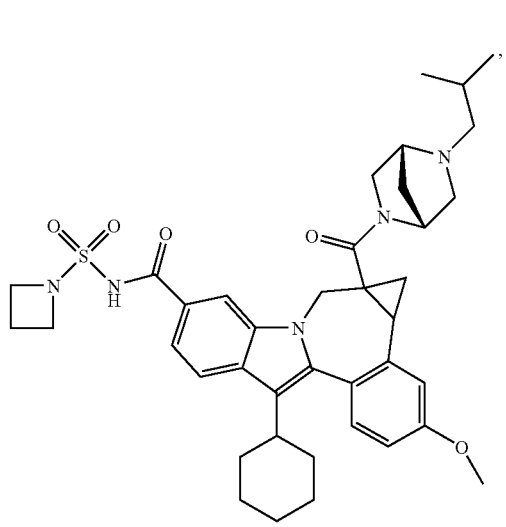
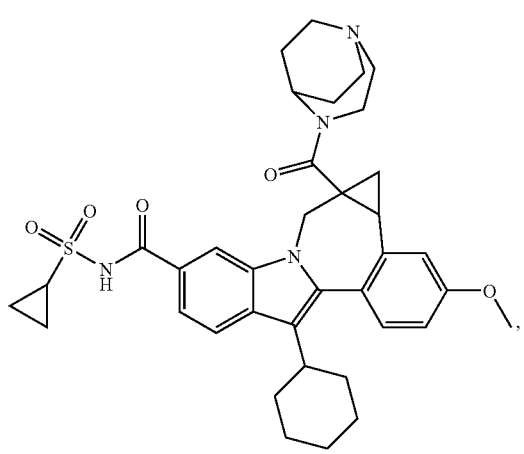
278
-continued
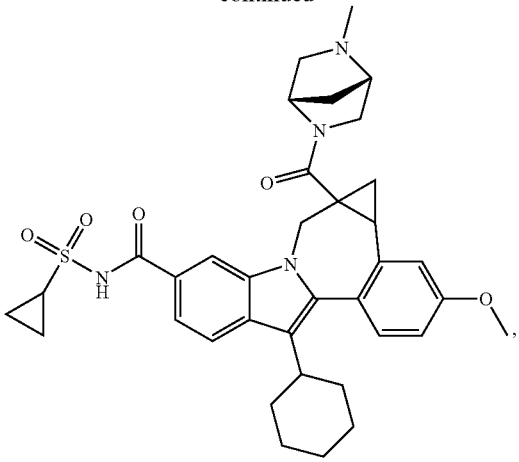
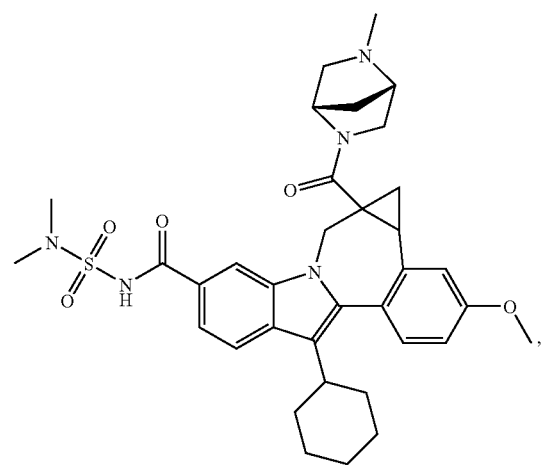
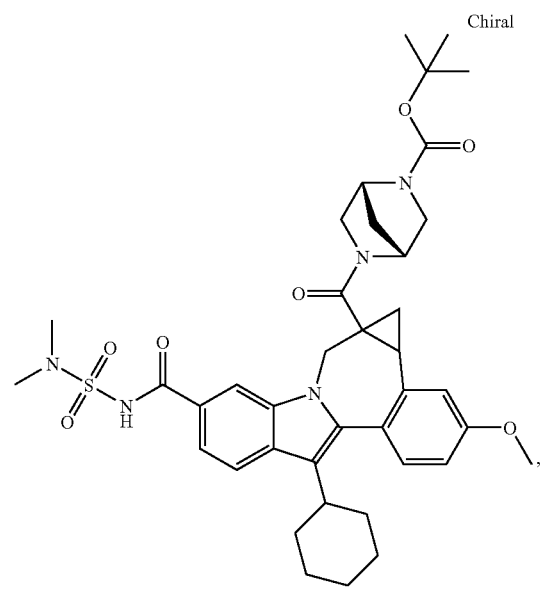

-continued
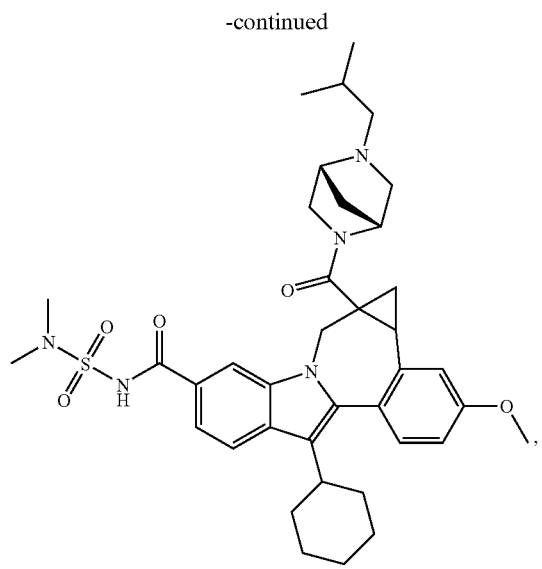
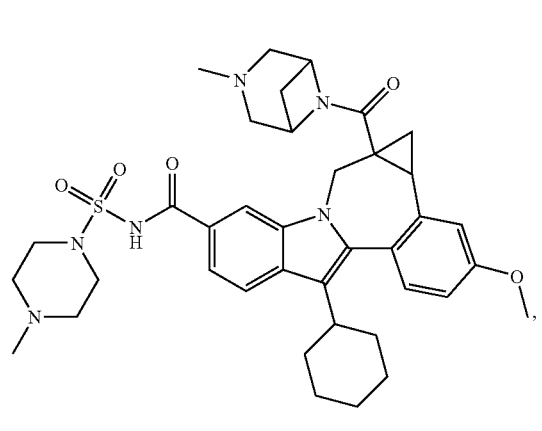
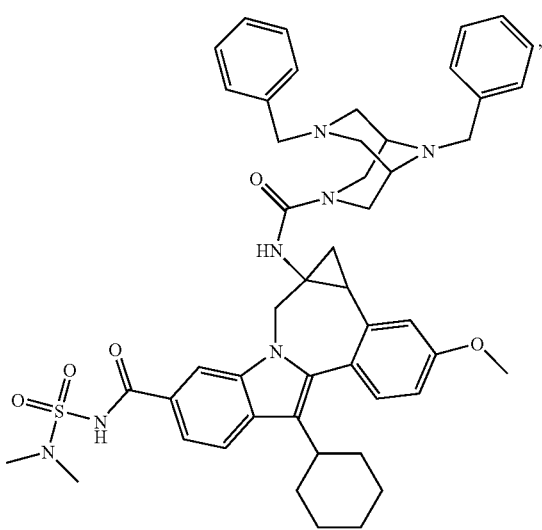
-continued
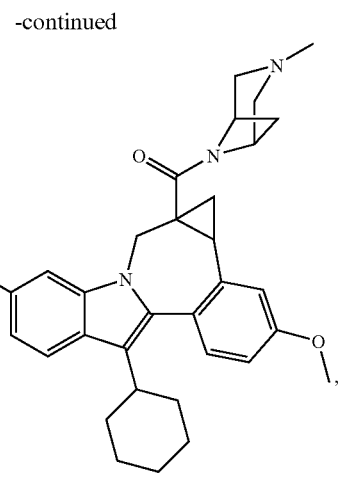
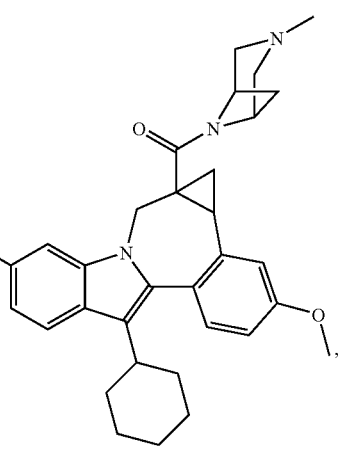
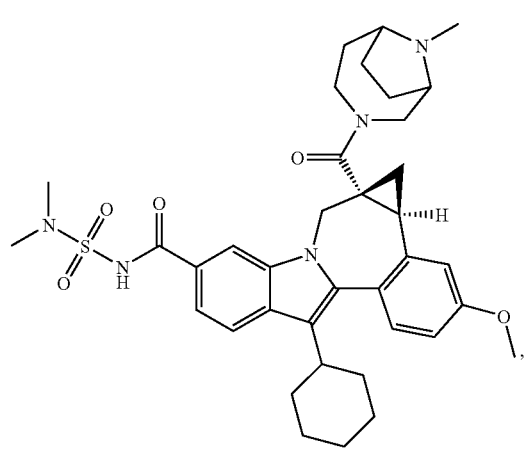

281
-continued
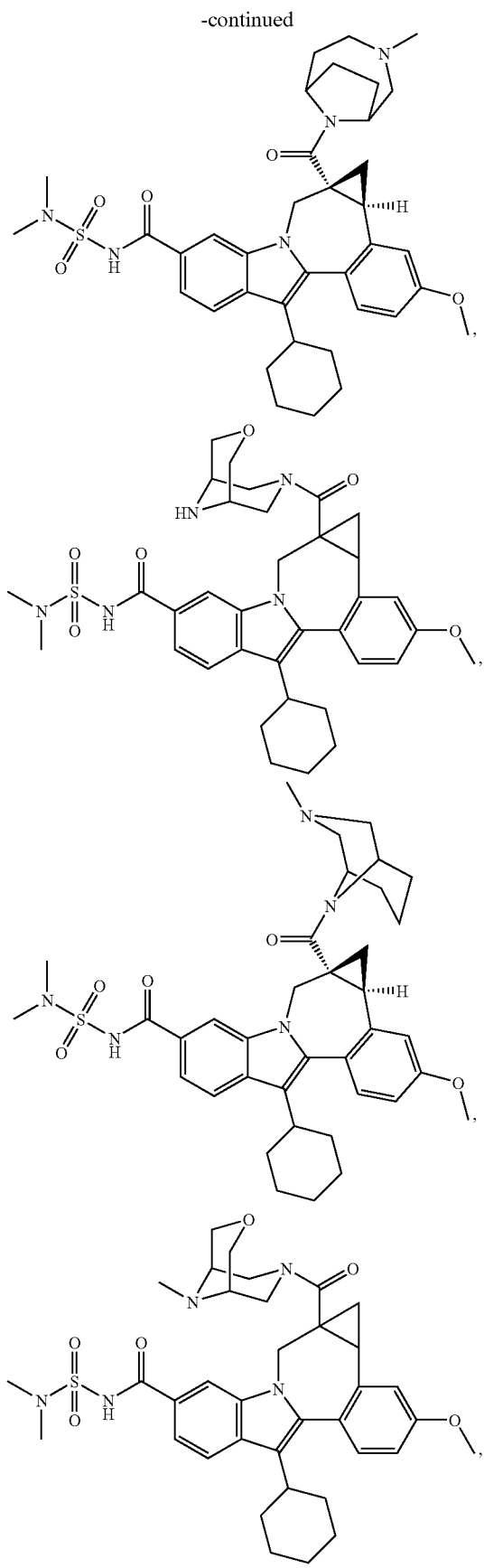
282
-continued
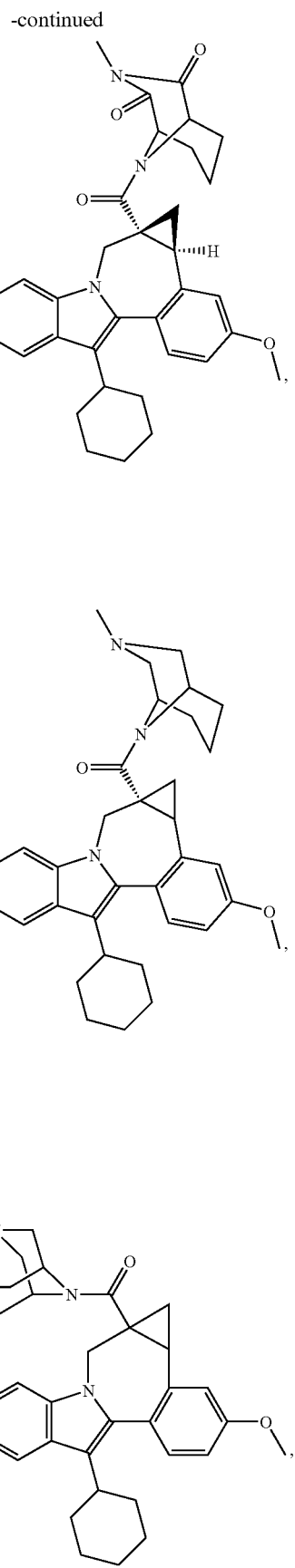

283
-continued
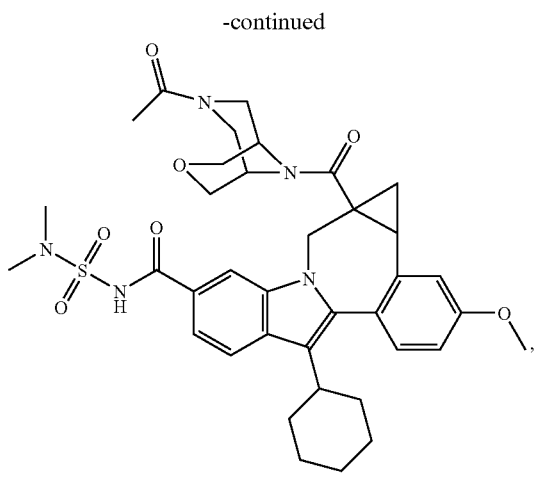
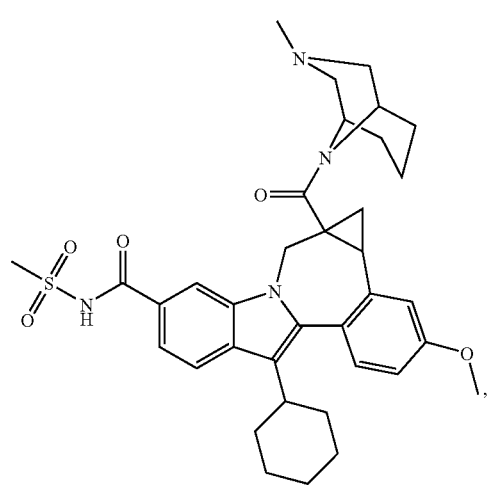
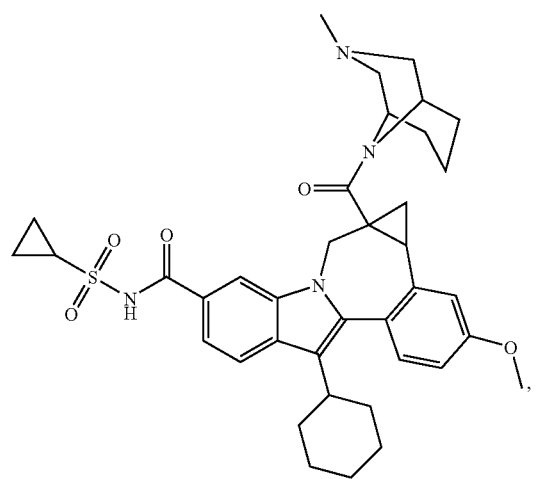
284
-continued
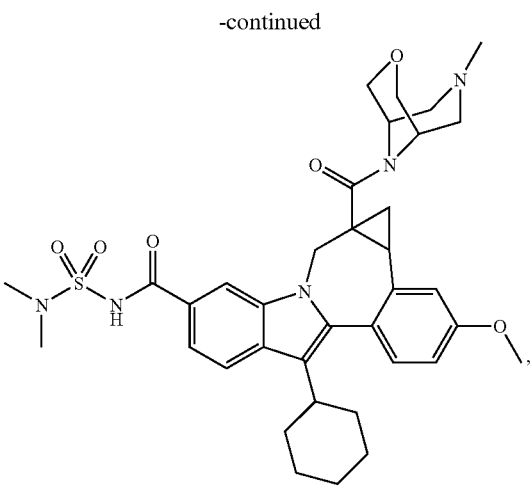
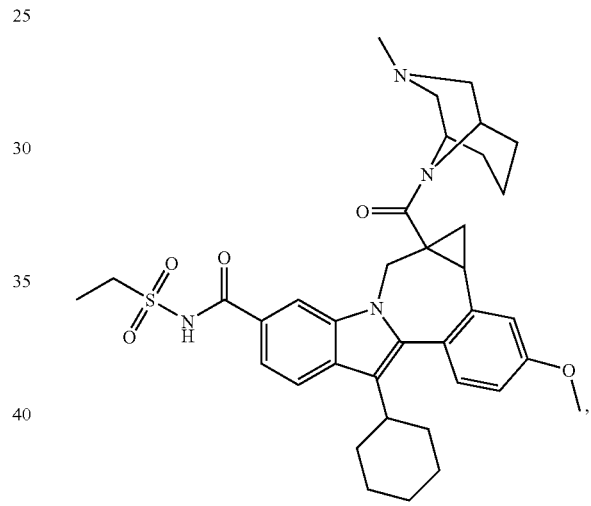
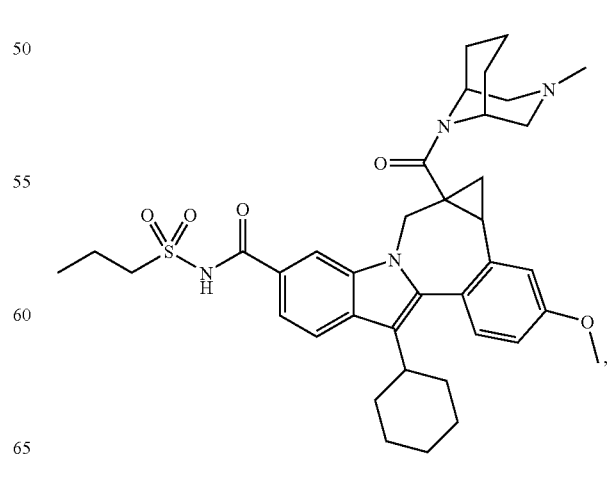

-continued
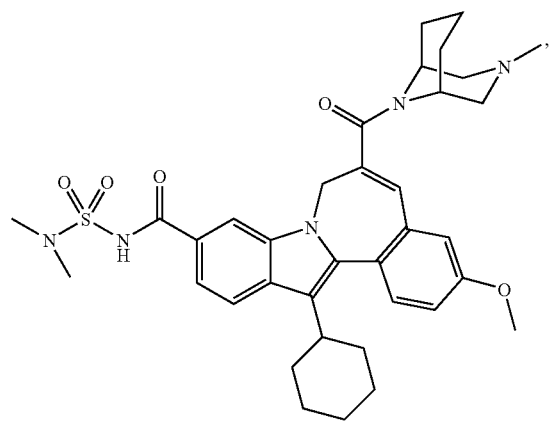
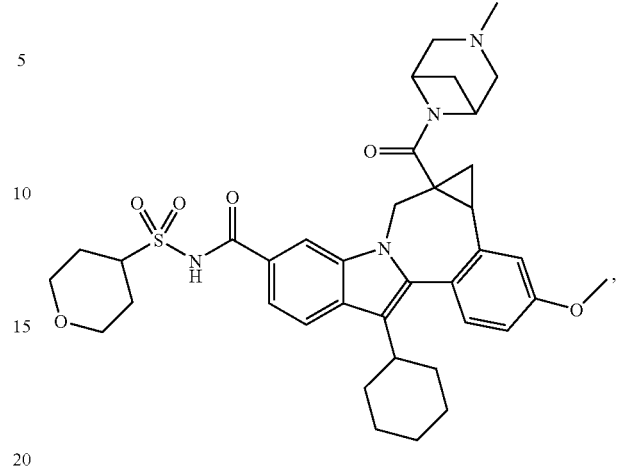
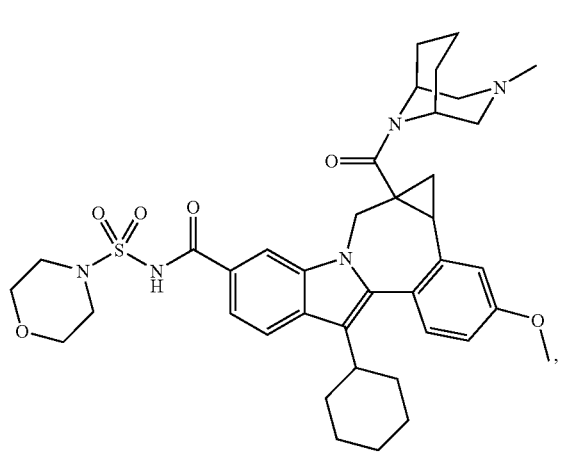
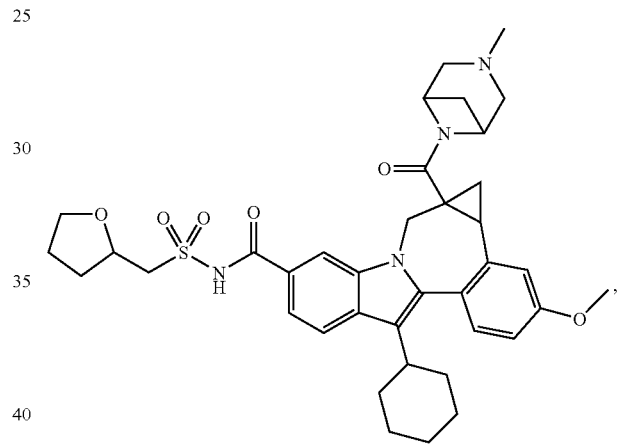
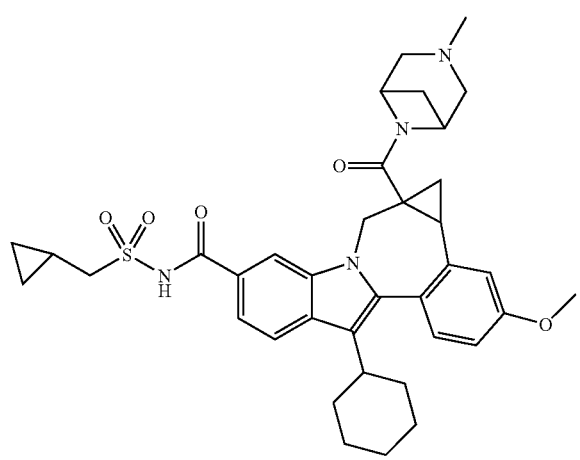
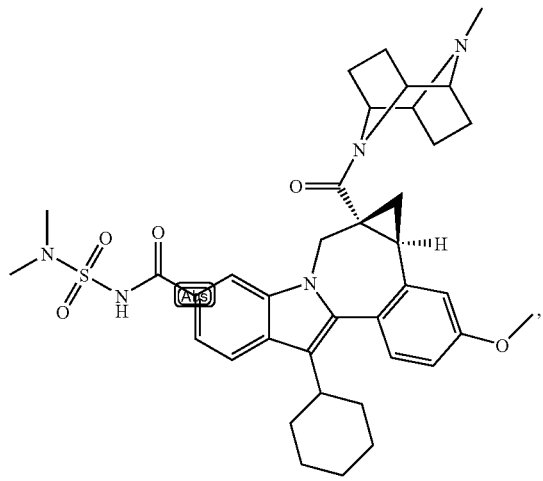

287 288
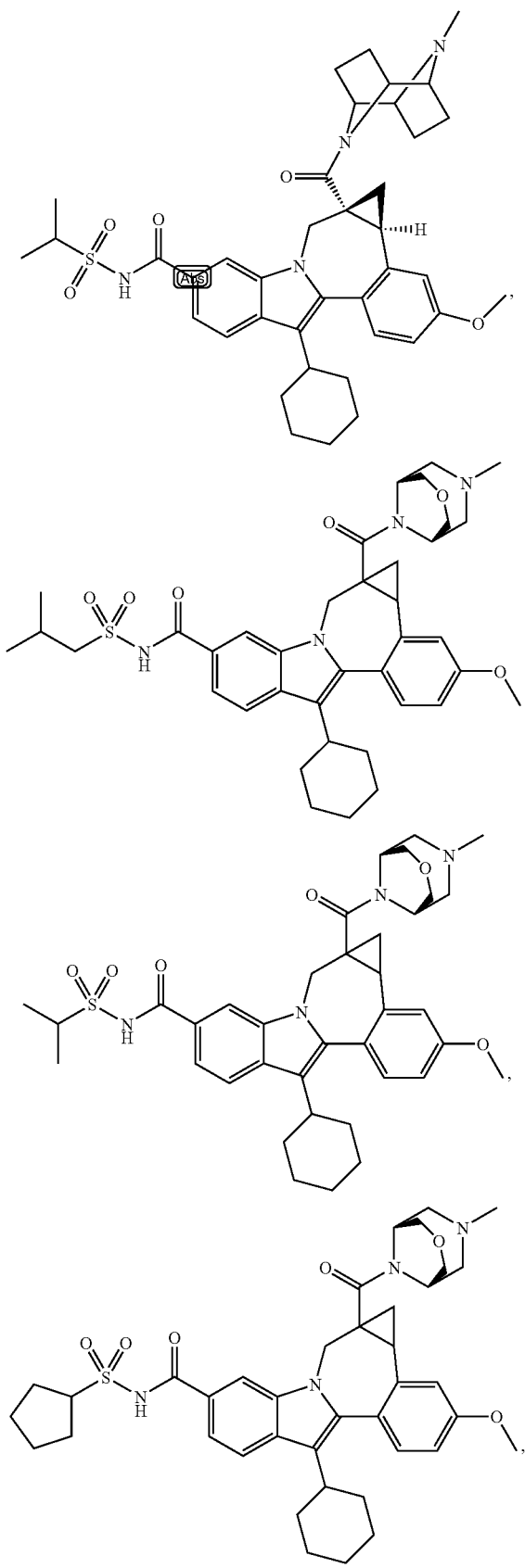
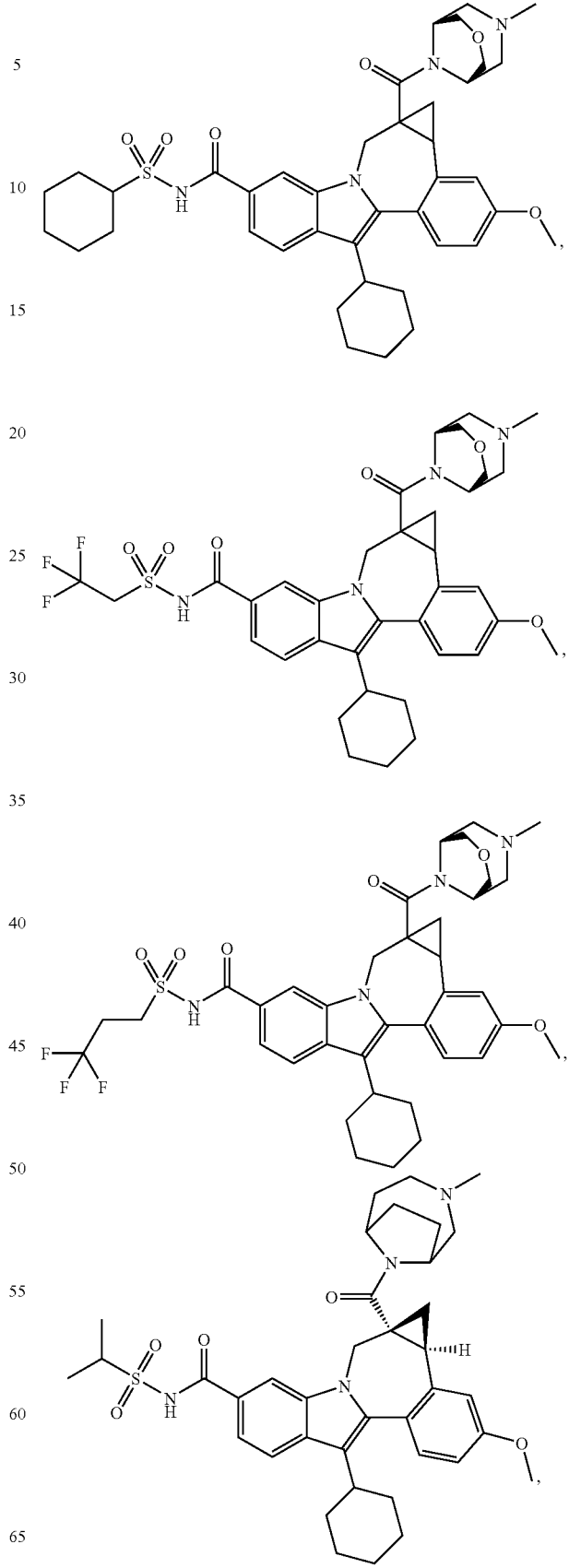

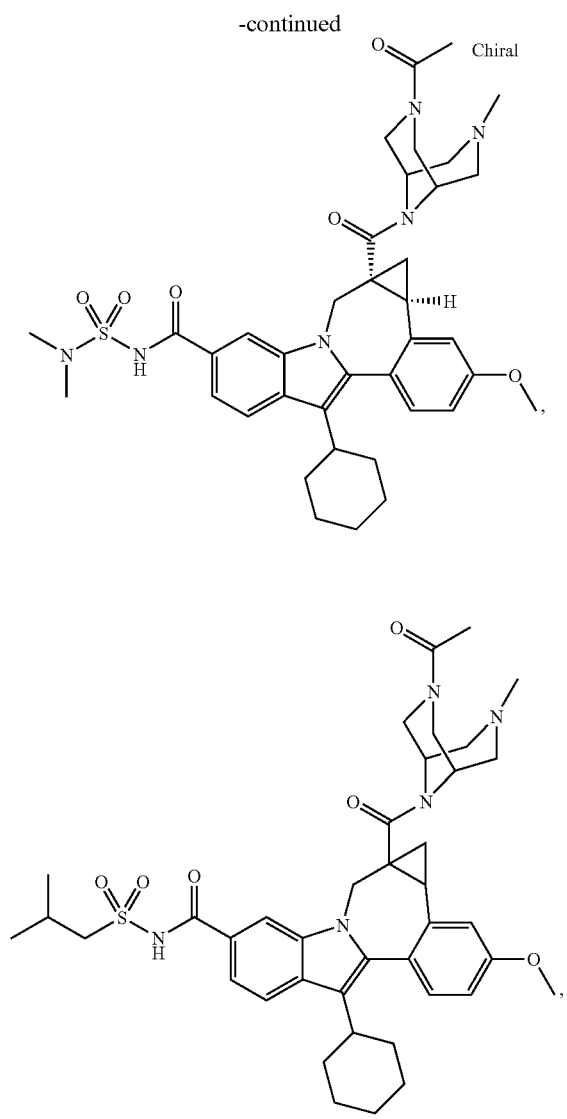
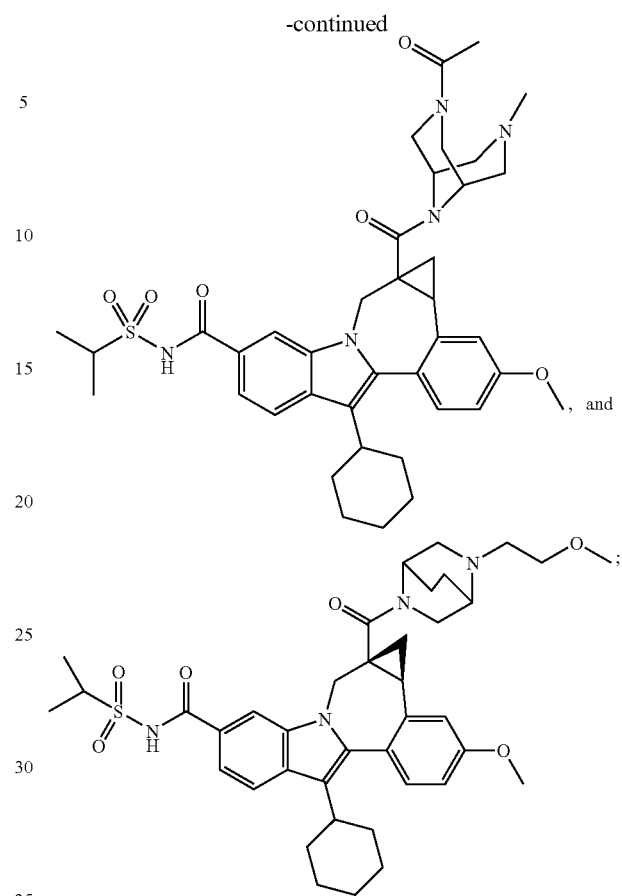
or a pharmaceutically acceptable salt thereof.
12. A composition comprising a compound of claim 1, or a pharmaceutically acceptable salt thereof, and a pharmaceutically acceptable carrier.
13. A method of treating hepatitis C infection comprising administering a therapeutically effective amount of a compound of claim 1 to a patient.
* * * * *

UNITED STATES PATENT AND TRADEMARK OFFICE
CERTIFICATE OF CORRECTION

PATENT NO.         : 7,547,690 B2                                                Page 1 of 1
APPLICATION NO.    : 12/039239
DATED              : June 16, 2009
INVENTOR(S)        : Robert G. Gentles et al.

It is certified that error appears in the above-identified patent and that said Letters Patent is hereby corrected as shown below:

In the Claims:

Claim 2:
Column 262, line 25, change "alkenylSO$_2$, ," to -- alkenylSO$_2$, --.

Claim 3:
Column 263, lines 4 to 9, change "  " to -- , --.

Claim 11:
Column 279, lines 46 to 65, delete " 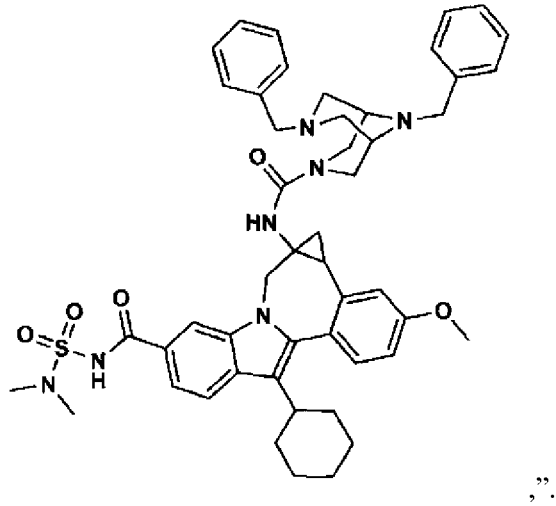 ,".

Signed and Sealed this
First Day of May, 2012

David J. Kappos
*Director of the United States Patent and Trademark Office*